US012655429B2

(12) United States Patent
Kortylewski et al.

(10) Patent No.: US 12,655,429 B2
(45) Date of Patent: Jun. 16, 2026

(54) MICRORNA AS A THERAPEUTIC AGENT

(71) Applicant: City of Hope, Duarte, CA (US)

(72) Inventors: Marcin Tomasz Kortylewski, Monrovia, CA (US); Guido Marcucci, Azusa, CA (US); Yu-Lin Su, Duarte, CA (US); Piotr Marek Swiderski, San Dimas, CA (US)

(73) Assignee: CITY OF HOPE, Duarte, CA (US)

( * ) Notice: Subject to any disclaimer, the term of this patent is extended or adjusted under 35 U.S.C. 154(b) by 937 days.

(21) Appl. No.: 17/779,293

(22) PCT Filed: Nov. 25, 2020

(86) PCT No.: PCT/US2020/062413

§ 371 (c)(1),
(2) Date: May 24, 2022

(87) PCT Pub. No.: WO2021/108702

PCT Pub. Date: Jun. 3, 2021

(65) Prior Publication Data

US 2023/0220385 A1 Jul. 13, 2023

Related U.S. Application Data

(60) Provisional application No. 62/940,723, filed on Nov. 26, 2019.

(51) Int. Cl.

*C12N 15/113* (2010.01)
*A61P 35/00* (2006.01)
*A61P 35/02* (2006.01)

(52) U.S. Cl.

CPC ............ *C12N 15/113* (2013.01); *A61P 35/00* (2018.01); *A61P 35/02* (2018.01); *C12N 2310/141* (2013.01); *C12N 2310/3519* (2013.01); *C12N 2320/30* (2013.01)

(58) Field of Classification Search

None
See application file for complete search history.

(56) References Cited

U.S. PATENT DOCUMENTS

| | | | | |
|---|---|---|---|---|
| 8,748,405 | B2 | 6/2014 | Yu et al. | |
| 9,200,279 | B2 | 12/2015 | Yu et al. | |
| 9,200,280 | B2 | 12/2015 | Yu et al. | |
| 9,688,982 | B2 | 6/2017 | Yu et al. | |
| 9,976,147 | B2 | 5/2018 | Kortylewski et al. | |
| 10,253,318 | B2 | 4/2019 | Yu et al. | |
| 10,711,272 | B2 | 7/2020 | Yu et al. | |
| 10,801,026 | B2 * | 10/2020 | Kortylewski ........ | C12N 15/113 |
| 10,829,765 | B2 | 11/2020 | Kortylewski et al. | |
| 11,186,840 | B2 | 11/2021 | Yu et al. | |
| 11,208,654 | B2 | 12/2021 | Yu et al. | |
| 11,591,596 | B2 * | 2/2023 | Kortylewski ........ | A61K 31/704 |
| 11,801,266 | B2 * | 10/2023 | Marcucci ............. | C07K 16/289 |
| 12,227,745 | B2 * | 2/2025 | Kortylewski ........ | A61K 31/704 |
| 2008/0214436 | A1 | 9/2008 | Yu et al. | |
| 2018/0312837 | A1 | 11/2018 | Kortylewski et al. | |
| 2019/0330632 | A1 | 10/2019 | Anand et al. | |
| 2020/0281982 | A1 | 9/2020 | Marcucci et al. | |
| 2021/0077535 | A1 | 3/2021 | Kortylewski et al. | |

FOREIGN PATENT DOCUMENTS

| | | | |
|---|---|---|---|
| WO | WO-2012/145729 | A2 | 10/2012 |
| WO | WO-2012/145729 | A3 | 10/2012 |
| WO | WO-2017/004357 | A1 | 1/2017 |
| WO | WO-2017/066639 | A1 | 4/2017 |
| WO | WO-2019/241766 | A1 | 12/2019 |
| WO | WO-2020/041691 | A1 | 2/2020 |
| WO | WO-2020/041691 | A9 | 2/2020 |

OTHER PUBLICATIONS

Ziegler et al. Nucleic acid therapeutics vol. 23, pp. 1-14 (Year: 2013).*

Garzon, R. et al. (Oct. 2010). "Targeting microRNAs in cancer: rationale, strategies and challenges," *Nat Rev Drug Discov.* 9(10):775-789.

International Search Report mailed on Apr. 22, 2021, for PCT Application No. PCT/US2020/062413, filed Nov. 25, 2020, 5 pages.

Kortylewski, M. et al. (Oct. 2009, e-published Sep. 13, 2009). "In vivo delivery of siRNA to immune cells by conjugation to a TLR9 agonist enhances antitumor immune responses," *Nat Biotechnol.* 27(10):925-932.

Su, Y-L. et al. (2019). "Targeted Delivery of miRNA Antagonists to Myeloid Cells In Vitro and In Vivo," *Methods Mol Biol.* 1974:141-150.

Trissal, M.C. et al. (Jul. 1, 2018, e-published May 3, 2018). "MIR142 Loss-of-Function Mutations Derepress ASH1L to Increase HOXA Gene Expression and Promote Leukemogenesis," *Cancer Res* 78(13):3510-3521.

Written Opinion mailed on Apr. 22, 2021, for PCT Application No. PCT/US2020/062413, filed Nov. 25, 2020, 8 pages.

Chernikov, I.V. et al. (Apr. 26, 2019). "Current Development of siRNA Bioconjugates: From Research to the Clinic," *Frontiers in Pharmacology* 10:444.

Extended European Search Report mailed on Feb. 20, 2024, for EP Patent Application No. 20893875.3, 19 pages.

(Continued)

*Primary Examiner* — Brian Whiteman

(74) *Attorney, Agent, or Firm* — Mintz, Levin, Cohn, Ferris, Glovsky and Popeo, P.C.

(57) ABSTRACT

The disclosure provides, inter alia, hybridized nucleic acid sequences and compounds comprising Toll-like receptor 9-binding nucleic acid sequences and nucleic acid sequences comprising a microRNA passenger strand sequence hybridized to a microRNA guide strand sequence; pharmaceutical compositions comprising the hybridized nucleic acid sequences and compounds; and the use of the hybridized nucleic acid sequences, compounds, and pharmaceutical compositions to treat medical conditions, such as cancer and inflammatory diseases.

21 Claims, 39 Drawing Sheets

Specification includes a Sequence Listing.

(56) References Cited

OTHER PUBLICATIONS

Kalashnikova, I. et al. (Apr. 2015). "Nanoceria-Mirna as a Modulator of Inflammation in Diabetic Wounds," Poster-Society for Biomaterials Annual Meeting Charlotte.
Nechaev, S. et al. (Sep. 28, 2013, e-published Jun. 15, 2013). "Intracellular processing of immunostimulatory CpG-siRNA: Toll-like receptor 9 facilitates siRNA dicing and endosomal escape," *Journal of Controlled Release* 170(3):307-315.
Su, Y-L et al. (May 2018). "Targeted Delivery of miR-146a Mimic or Antisense Oligonucleotides as a Potential Therapeutic Approach to Modulate DC Activity in Cancer and Autoimmune Diseases," *European Journal of Immunology* 48(S1):1-193.
Su, Y-L et al. (Aug. 2018). "Targeted Delivery of miR-146a Mimic Oligonucleotides as a Potential Therapeutic Approach to Modulate NF-kB Signaling in Myeloid Leukemia and Myeloproliferative Diseases," *Experimental Hematology* 64, Supplement S42.
Su, Y-L et al. (Nov. 29, 2018). "Targeted Delivery of CpG-Mir-146a Mimic Oligonucleotides As a Therapeutic Strategy to Reduce NF-Kb-Mediated Pathogenic Inflammation and Myeloid Leukemia Progression," *Blood* 132(Supplement 1):3501.
Su, Y-L et al. (Jan. 16, 2020). "Myeloid cell-targeted miR-146a mimic inhibits NF-kB—driven inflammation and leukemia progression in vivo," *Blood* 135(3):167-180.
Zhang, Q. et al. (Feb. 21, 2013, e-published Jan. 3, 2013). "TLR9-mediated siRNA delivery for targeting of normal and malignant human hematopoietic cells in vivo," *Blood* 121(8):1304-1315.

* cited by examiner

SEQUENCE LISTING

<160> NUMBER OF SEQ ID NOS: 49

<210> SEQ ID NO 1
<211> LENGTH: 20
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: miR146a passenger strand

<400> SEQUENCE: 1
cccauggaau ucaguucuca 20

<210> SEQ ID NO 2
<211> LENGTH: 22
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: miR146a passenger strand
<220> FEATURE:
<221> NAME/KEY: modified_base
<222> LOCATION: (21)..(21)
<223> OTHER INFORMATION: 2'O-methyl-adenosine

<400> SEQUENCE: 2
cccauggaau ucaguucuca aa 22

<210> SEQ ID NO 3
<211> LENGTH: 22
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: miR146a passenger strand
<220> FEATURE:
<221> NAME/KEY: modified_base
<222> LOCATION: (21)..(21)
<223> OTHER INFORMATION: 2'-O-methyl-adenosine
<220> FEATURE:
<221> NAME/KEY: misc_feature
<222> LOCATION: (22)..(22)
<223> OTHER INFORMATION: phosphorothioation

<400> SEQUENCE: 3
cccauggaau ucaguucuca aa 22

<210> SEQ ID NO 4
<211> LENGTH: 22
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: miR146a passenger strand
<220> FEATURE:
<221> NAME/KEY: modified_base
<222> LOCATION: (1)..(3)
<223> OTHER INFORMATION: 2'-fluoro-cytosine
<220> FEATURE:
<221> NAME/KEY: modified_base
<222> LOCATION: (5)..(5)
<223> OTHER INFORMATION: 2'-fluoro-uracil
<220> FEATURE:
<221> NAME/KEY: modified_base
<222> LOCATION: (10)..(11)
<223> OTHER INFORMATION: 2'-fluoro-uracil
<220> FEATURE:
<221> NAME/KEY: modified_base
<222> LOCATION: (12)..(12)
<223> OTHER INFORMATION: 2'-fluoro-cytosine
<220> FEATURE:
<221> NAME/KEY: modified_base
<222> LOCATION: (15)..(16)
<223> OTHER INFORMATION: 2'-fluoro-uracil
<220> FEATURE:
<221> NAME/KEY: modified_base
<222> LOCATION: (17)..(17)
<223> OTHER INFORMATION: 2'-fluoro-cytosine
<220> FEATURE:
<221> NAME/KEY: modified_base
<222> LOCATION: (18)..(18)
<223> OTHER INFORMATION: 2'-fluoro-uracil
<220> FEATURE:
<221> NAME/KEY: modified_base
<222> LOCATION: (19)..(19)
<223> OTHER INFORMATION: 2'-fluoro-cytosine

<400> SEQUENCE: 4
cccauggaau ucaguucuca aa 22

<210> SEQ ID NO 5
<211> LENGTH: 22
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: miR146a passenger strand
<220> FEATURE:
<221> NAME/KEY: misc_feature
<222> LOCATION: (1)..(22)
<223> OTHER INFORMATION: phosphorothioation
<220> FEATURE:
<221> NAME/KEY: modified_base
<222> LOCATION: (1)..(3)
<223> OTHER INFORMATION: cm
<220> FEATURE:
<221> NAME/KEY: modified_base
<222> LOCATION: (4)..(4)
<223> OTHER INFORMATION: 2'-O-methyl-adenosine
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(7)
<223> OTHER INFORMATION: gm
<220> FEATURE:
<221> NAME/KEY: modified_base
<222> LOCATION: (8)..(9)
<223> OTHER INFORMATION: 2'-O-methyl-adenosine
<220> FEATURE:
<221> NAME/KEY: modified_base
<222> LOCATION: (10)..(11)

-continued

```
<223> OTHER INFORMATION: um
<220> FEATURE:
<221> NAME/KEY: modified_base
<222> LOCATION: (12)..(12)
<223> OTHER INFORMATION: cm
<220> FEATURE:
<221> NAME/KEY: modified_base
<222> LOCATION: (13)..(13)
<223> OTHER INFORMATION: 2'-O-methyl-adenosine
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(16)
<223> OTHER INFORMATION: um
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (18)..(18)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (20)..(22)
<223> OTHER INFORMATION: 2'-O-methyl-adenosine

<400> SEQUENCE: 5

cccauggaau ucaguucuca aa                                              22


<210> SEQ ID NO 6
<211> LENGTH: 20
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: miR146a passenger strand

<400> SEQUENCE: 6

ugagaacuga auuccauggg                                                 20


<210> SEQ ID NO 7
<211> LENGTH: 22
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: miR146a passenger strand 898

<400> SEQUENCE: 7

ugagaacuga auuccauggg uu                                              22


<210> SEQ ID NO 8
<211> LENGTH: 22
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: miR146a passenger strand 1024
<220> FEATURE:
```

<221> NAME/KEY: misc_feature
<222> LOCATION: (1)..(1)
<223> OTHER INFORMATION: nucleic acid with a single phosphate group
<220> FEATURE:
<221> NAME/KEY: modified_base
<222> LOCATION: (21)..(21)
<223> OTHER INFORMATION: um
<220> FEATURE:
<221> NAME/KEY: misc_feature
<222> LOCATION: (22)..(22)
<223> OTHER INFORMATION: phosphorothioation

<400> SEQUENCE: 8
ugagaacuga auuccauggg uu 22

<210> SEQ ID NO 9
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: phosphorothioation
<220> FEATURE:
<221> NAME/KEY: misc_feature
<222> LOCATION: (16)..(20)
<223> OTHER INFORMATION: phosphorothioation

<400> SEQUENCE: 9
ggtgcatcga tgcagggggg 20

<210> SEQ ID NO 10
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: phosphorothioation
<220> FEATURE:
<221> NAME/KEY: misc_feature
<222> LOCATION: (16)..(19)
<223> OTHER INFORMATION: phosphorothioation

<400> SEQUENCE: 10
ggtgcatgca tgcagggggg 20

<210> SEQ ID NO 11
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: phosphorothioation

<400> SEQUENCE: 11
ggtgcatcga tgcagggggg 20

<210> SEQ ID NO 12
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: phosphorothioation

<400> SEQUENCE: 12
tccatgacgt tcctgatgct 20

<210> SEQ ID NO 13
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: phosphorothioation
<220> FEATURE:
<221> NAME/KEY: misc_feature
<222> LOCATION: (15)..(19)
<223> OTHER INFORMATION: phosphorothioation

<400> SEQUENCE: 13
ggggtcaacg ttgagggggg 20

<210> SEQ ID NO 14
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: phosphorothioation
<220> FEATURE:
<221> NAME/KEY: misc_feature
<222> LOCATION: (15)..(19)
<223> OTHER INFORMATION: phosphorothioation

<400> SEQUENCE: 14
ggggtcaacg ttgagggggg 20

<210> SEQ ID NO 15
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: phosphorothioation
<220> FEATURE:
<221> NAME/KEY: misc_feature
<222> LOCATION: (15)..(19)
<223> OTHER INFORMATION: phosphorothioation

<400> SEQUENCE: 15
gggggacgat cgtcgggggg 20

<210> SEQ ID NO 16
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)

<223> OTHER INFORMATION: phosphorothioation
<220> FEATURE:
<221> NAME/KEY: misc_feature
<222> LOCATION: (15)..(19)
<223> OTHER INFORMATION: phosphorothioation

<400> SEQUENCE: 16
gggggacgat cgtcgggggg 20

<210> SEQ ID NO 17
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: phosphorothioation
<220> FEATURE:
<221> NAME/KEY: misc_feature
<222> LOCATION: (16)..(19)
<223> OTHER INFORMATION: phosphorothioation

<400> SEQUENCE: 17
ggtgcatcga tgcagggggg 20

<210> SEQ ID NO 18
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: phosphorothioation
<220> FEATURE:
<221> NAME/KEY: misc_feature
<222> LOCATION: (16)..(20)
<223> OTHER INFORMATION: phosphorothioation

<400> SEQUENCE: 18
ggtgcatcga tgcagggggg 20

<210> SEQ ID NO 19
<211> LENGTH: 23
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: anti-miR155 passenger strand sequence

<400> SEQUENCE: 19
accccuauca caauuagcau uaa 23

<210> SEQ ID NO 20
<211> LENGTH: 23
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: anti-miR155 guide strand sequence

<400> SEQUENCE: 20
uuaaugcuaa uugugauagg ggu 23

<210> SEQ ID NO 21
<211> LENGTH: 23
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: miR142 passenger strand sequence

<400> SEQUENCE: 21
uccauaaagu aggaaacacu aca 23

<210> SEQ ID NO 22
<211> LENGTH: 23
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: miR142 guide strand sequence

<400> SEQUENCE: 22
uguaguguuu ccuacuuuau gga 23

<210> SEQ ID NO 23
<211> LENGTH: 22
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: miR125b passenger strand sequence

<400> SEQUENCE: 23
ucacaaguua gggucucagg ga 22

<210> SEQ ID NO 24
<211> LENGTH: 22
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: miR-125b (or miR125-5p) guide strand sequence

<400> SEQUENCE: 24
ucccugagac ccuaacuugu ga 22

<210> SEQ ID NO 25
<211> LENGTH: 22
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: miR203b passenger strand sequence

<400> SEQUENCE: 25
ugugaaaugu uuaggaccac ua 22

<210> SEQ ID NO 26
<211> LENGTH: 22

```
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: miR203b (or miR203b-5p) guide strand sequence

<400> SEQUENCE: 26

uaguggucu aaacauuuca ca                                              22


<210> SEQ ID NO 27
<211> LENGTH: 23
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: miR221 passenger strand sequence

<400> SEQUENCE: 27

gaaacccagc agacaaugua gcu                                            23


<210> SEQ ID NO 28
<211> LENGTH: 23
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: miR221 (or miR221-3p) passenger sequence

<400> SEQUENCE: 28

agcuacauug ucugcugggu uuc                                            23


<210> SEQ ID NO 29
<211> LENGTH: 21
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: miR222 passenger strand sequence

<400> SEQUENCE: 29

acccaguagc cagauguagc u                                              21


<210> SEQ ID NO 30
<211> LENGTH: 21
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: miR222 (or miR222-3p) guide strand sequence

<400> SEQUENCE: 30

agcuacaucu ggcuacuggg u                                              21


<210> SEQ ID NO 31
<211> LENGTH: 24
<212> TYPE: RNA
<213> ORGANISM: Artificial sequence
<220> FEATURE:
<223> OTHER INFORMATION: Synthetic polynucleotide
```

<220> FEATURE:
<221> NAME/KEY: misc_feature
<223> OTHER INFORMATION: miR29b passenger strand sequence

<400> SEQUENCE: 31
ucuaaaccac cauaugaaac cagc 24

<210> SEQ ID NO 32
<211> LENGTH: 24
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: miR29b (or miR29b-5p) guide strand sequence

<400> SEQUENCE: 32
gcugguuuca uauggugguu uaga 24

<210> SEQ ID NO 33
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(3)
<223> OTHER INFORMATION: phosphorothioation
<220> FEATURE:
<221> NAME/KEY: misc_feature
<222> LOCATION: (16)..(20)
<223> OTHER INFORMATION: phosphorothioation

<400> SEQUENCE: 33
ggggacgacg tcgtgggggg g 21

<210> SEQ ID NO 34
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: phosphorothioation
<220> FEATURE:
<221> NAME/KEY: misc_feature
<222> LOCATION: (16)..(20)
<223> OTHER INFORMATION: phosphorothioation

<400> SEQUENCE: 34
ggggacgacg tcgtgggggg g 21

<210> SEQ ID NO 35
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: phosphorothioation

<400> SEQUENCE: 35
tccatgacgt tcctgatgct 20

<210> SEQ ID NO 36
<211> LENGTH: 23
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: miR-146a-2Ome-2F-pPS-21-23 guide
<220> FEATURE:
<221> NAME/KEY: misc_feature
<222> LOCATION: (1)..(2)
<223> OTHER INFORMATION: phosphorothioation
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (2)..(2)
<223> OTHER INFORMATION: 2'-fluoro-uracil
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(4)
<223> OTHER INFORMATION: 2'-O-methyl-adenosine
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (6)..(6)
<223> OTHER INFORMATION: 2'-fluoro-adenine
<220> FEATURE:
<221> NAME/KEY: modified_base
<222> LOCATION: (7)..(7)
<223> OTHER INFORMATION: 2'-O-methyl-adenosine
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(10)
<223> OTHER INFORMATION: gm
<220> FEATURE:
<221> NAME/KEY: modified_base
<222> LOCATION: (11)..(12)
<223> OTHER INFORMATION: 2'-O-methyl-adenosine
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (14)..(14)
<223> OTHER INFORMATION: 2'-fluoro-uracil
<220> FEATURE:
<221> NAME/KEY: modified_base
<222> LOCATION: (16)..(16)
<223> OTHER INFORMATION: 2'-fluoro-cytosine
<220> FEATURE:
<221> NAME/KEY: modified_base
<222> LOCATION: (17)..(17)
<223> OTHER INFORMATION: 2'-O-methyl-adenosine
<220> FEATURE:
<221> NAME/KEY: modified_base
<222> LOCATION: (18)..(18)
<223> OTHER INFORMATION: um
<220> FEATURE:
<221> NAME/KEY: modified_base
<222> LOCATION: (19)..(21)
<223> OTHER INFORMATION: gm
<220> FEATURE:

<221> NAME/KEY: misc_feature
<222> LOCATION: (21)..(22)
<223> OTHER INFORMATION: phosphorothioation
<220> FEATURE:
<221> NAME/KEY: modified_base
<222> LOCATION: (22)..(23)
<223> OTHER INFORMATION: um

<400> SEQUENCE: 36
uugagaacug aauuccaugg guu 23

<210> SEQ ID NO 37
<211> LENGTH: 21
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: miR-146a-2OMe-2F-pPS-21-23 passenger
<220> FEATURE:
<221> NAME/KEY: misc_feature
<222> LOCATION: (1)..(2)
<223> OTHER INFORMATION: phosphorothioation
<220> FEATURE:
<221> NAME/KEY: modified_base
<222> LOCATION: (1)..(3)
<223> OTHER INFORMATION: cm
<220> FEATURE:
<221> NAME/KEY: modified_base
<222> LOCATION: (4)..(4)
<223> OTHER INFORMATION: 2'-O-Methyl-adenosine
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (7)..(7)
<223> OTHER INFORMATION: 2'-fluoro-guanine
<220> FEATURE:
<221> NAME/KEY: modified_base
<222> LOCATION: (8)..(8)
<223> OTHER INFORMATION: 2'-O-Methyl-adenosine
<220> FEATURE:
<221> NAME/KEY: modified_base
<222> LOCATION: (9)..(9)
<223> OTHER INFORMATION: 2'-fluoro-adenine
<220> FEATURE:
<221> NAME/KEY: modified_base
<222> LOCATION: (10)..(11)
<223> OTHER INFORMATION: 2'-fluoro-uracil
<220> FEATURE:
<221> NAME/KEY: modified_base
<222> LOCATION: (13)..(13)
<223> OTHER INFORMATION: 2'-O-Methyl-adenosine
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(16)
<223> OTHER INFORMATION: um
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (18)..(18)
<223> OTHER INFORMATION: um
<220> FEATURE:

<221> NAME/KEY: modified_base
<222> LOCATION: (19)..(19)
<223> OTHER INFORMATION: cm
<220> FEATURE:
<221> NAME/KEY: modified_base
<222> LOCATION: (20)..(21)
<223> OTHER INFORMATION: 2'-O-Methyl-adenosine

<400> SEQUENCE: 37
cccauggaau ucaguucuca a 21

<210> SEQ ID NO 38
<211> LENGTH: 22
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: miR-146a-2OMe-2F-pPS-20-22 guide
<220> FEATURE:
<221> NAME/KEY: misc_feature
<222> LOCATION: (1)..(2)
<223> OTHER INFORMATION: phosphorothioation
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (2)..(2)
<223> OTHER INFORMATION: 2'-fluoro-guanine
<220> FEATURE:
<221> NAME/KEY: modified_base
<222> LOCATION: (3)..(3)
<223> OTHER INFORMATION: 2'-O-Methyl-adenosine
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(5)
<223> OTHER INFORMATION: 2'-O-Methyl-adenosine
<220> FEATURE:
<221> NAME/KEY: modified_base
<222> LOCATION: (6)..(6)
<223> OTHER INFORMATION: 2'-fluoro-adenine
<220> FEATURE:
<221> NAME/KEY: modified_base
<222> LOCATION: (7)..(7)
<223> OTHER INFORMATION: cm
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (10)..(11)
<223> OTHER INFORMATION: 2'-O-Methyl-adenosine
<220> FEATURE:
<221> NAME/KEY: modified_base
<222> LOCATION: (12)..(13)
<223> OTHER INFORMATION: um
<220> FEATURE:
<221> NAME/KEY: modified_base
<222> LOCATION: (14)..(14)
<223> OTHER INFORMATION: 2'-fluoro-cytosine
<220> FEATURE:
<221> NAME/KEY: modified_base
<222> LOCATION: (15)..(15)
<223> OTHER INFORMATION: cm
<220> FEATURE:

<221> NAME/KEY: modified_base
<222> LOCATION: (16)..(16)
<223> OTHER INFORMATION: 2'-fluoro-adenine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(20)
<223> OTHER INFORMATION: gm
<220> FEATURE:
<221> NAME/KEY: misc_feature
<222> LOCATION: (20)..(21)
<223> OTHER INFORMATION: phosphorothioation
<220> FEATURE:
<221> NAME/KEY: modified_base
<222> LOCATION: (21)..(22)
<223> OTHER INFORMATION: um

<400> SEQUENCE: 38
ugagaacuga auuccauggg uu 22

<210> SEQ ID NO 39
<211> LENGTH: 20
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: miR-146a-2OMe-2F-pPS-20-22 passenger
<220> FEATURE:
<221> NAME/KEY: misc_feature
<222> LOCATION: (1)..(2)
<223> OTHER INFORMATION: phosphorothioation
<220> FEATURE:
<221> NAME/KEY: modified_base
<222> LOCATION: (1)..(3)
<223> OTHER INFORMATION: cm
<220> FEATURE:
<221> NAME/KEY: modified_base
<222> LOCATION: (4)..(4)
<223> OTHER INFORMATION: 2'-O-Methyl-adenosine
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: 2'-fluoro-guanine
<220> FEATURE:
<221> NAME/KEY: modified_base
<222> LOCATION: (7)..(7)
<223> OTHER INFORMATION: gm
<220> FEATURE:
<221> NAME/KEY: modified_base
<222> LOCATION: (8)..(9)
<223> OTHER INFORMATION: 2'-fluoro-adenine
<220> FEATURE:
<221> NAME/KEY: modified_base
<222> LOCATION: (10)..(10)
<223> OTHER INFORMATION: 2'-fluoro-uracil
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: cm
<220> FEATURE:
<221> NAME/KEY: modified_base
<222> LOCATION: (13)..(13)
<223> OTHER INFORMATION: 2'-O-Methyl-adenosine
<220> FEATURE:

-continued

<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(16)
<223> OTHER INFORMATION: um
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (18)..(18)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (20)..(20)
<223> OTHER INFORMATION: 2'-O-Methyl-adenosine

<400> SEQUENCE: 39
cccauggaau ucaguucuca 20

<210> SEQ ID NO 40
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: phosphorothioation

<400> SEQUENCE: 40
tccatgacgt tcctgacgtt 20

<210> SEQ ID NO 41
<211> LENGTH: 24
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(23)
<223> OTHER INFORMATION: phosphorothioation

<400> SEQUENCE: 41
tcgtcgtttt gtcgttttgt cgtt 24

<210> SEQ ID NO 42
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(21)
<223> OTHER INFORMATION: phosphorothioation

<400> SEQUENCE: 42
tcgtcgttgt cgttttgtcg tt 22

<210> SEQ ID NO 43
<211> LENGTH: 22

<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(21)
<223> OTHER INFORMATION: phosphorothioation

<400> SEQUENCE: 43
tcgtcgtttt cggcgcgcgc cg 22

<210> SEQ ID NO 44
<211> LENGTH: 25
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(24)
<223> OTHER INFORMATION: phosphorothioation

<400> SEQUENCE: 44
tcgtcgtcgt tcgaacgacg ttgat 25

<210> SEQ ID NO 45
<211> LENGTH: 22
<212> TYPE: RNA
<213> ORGANISM: Artificial sequence
<220> FEATURE:
<223> OTHER INFORMATION: Synthetic polynucleotide
<220> FEATURE:
<221> NAME/KEY: modified_base
<222> LOCATION: (21)..(21)
<223> OTHER INFORMATION: 2'-O-Methyl-adenosine

<400> SEQUENCE: 45
auuuagccuu aauacacgcc aa 22

<210> SEQ ID NO 46
<211> LENGTH: 22
<212> TYPE: RNA
<213> ORGANISM: Artificial sequence
<220> FEATURE:
<223> OTHER INFORMATION: Synthetic polynucleotide

<400> SEQUENCE: 46
ggcguguauu aaggcuaaau cu 22

<210> SEQ ID NO 47
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: modified_base
<222> LOCATION: (1)..(3)
<223> OTHER INFORMATION: cm
<220> FEATURE:
<221> NAME/KEY: modified_base
<222> LOCATION: (4)..(4)
<223> OTHER INFORMATION: 2'-O-Methyl-adenosine
<220> FEATURE:
<221> NAME/KEY: modified_base
<222> LOCATION: (5)..(5)
<223> OTHER INFORMATION: tm
<220> FEATURE:
<221> NAME/KEY: modified_base
<222> LOCATION: (6)..(7)

-continued

<223> OTHER INFORMATION: gm
<220> FEATURE:
<221> NAME/KEY: modified_base
<222> LOCATION: (8)..(9)
<223> OTHER INFORMATION: 2'-O-Methyl-adenosine
<220> FEATURE:
<221> NAME/KEY: modified_base
<222> LOCATION: (10)..(11)
<223> OTHER INFORMATION: tm
<220> FEATURE:
<221> NAME/KEY: modified_base
<222> LOCATION: (12)..(12)
<223> OTHER INFORMATION: cm
<220> FEATURE:
<221> NAME/KEY: modified_base
<222> LOCATION: (13)..(13)
<223> OTHER INFORMATION: 2'-O-Methyl-adenosine
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(16)
<223> OTHER INFORMATION: tm
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (18)..(18)
<223> OTHER INFORMATION: tm
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (20)..(20)
<223> OTHER INFORMATION: 2'-O-Methyl-adenosine

<400> SEQUENCE: 47
cccatggaat tcagttctca 20

<210> SEQ ID NO 48
<211> LENGTH: 23
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: miR142 mimic guide strand
<220> FEATURE:
<221> NAME/KEY: misc_feature
<222> LOCATION: (1)..(2)
<223> OTHER INFORMATION: phosphorothioation
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (2)..(2)
<223> OTHER INFORMATION: 2'-fluoro-guanine
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (4)..(4)
<223> OTHER INFORMATION: 2'-O-Methyl-adenosine
<220> FEATURE:
<221> NAME/KEY: modified_base
<222> LOCATION: (5)..(5)

<223> OTHER INFORMATION: gm
<220> FEATURE:
<221> NAME/KEY: modified_base
<222> LOCATION: (6)..(6)
<223> OTHER INFORMATION: 2'-fluoro-uracil
<220> FEATURE:
<221> NAME/KEY: modified_base
<222> LOCATION: (7)..(7)
<223> OTHER INFORMATION: gm
<220> FEATURE:
<221> NAME/KEY: modified_base
<222> LOCATION: (8)..(10)
<223> OTHER INFORMATION: um
<220> FEATURE:
<221> NAME/KEY: modified_base
<222> LOCATION: (11)..(12)
<223> OTHER INFORMATION: cm
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (14)..(14)
<223> OTHER INFORMATION: 2'-fluoro-adenine
<220> FEATURE:
<221> NAME/KEY: modified_base
<222> LOCATION: (15)..(15)
<223> OTHER INFORMATION: cm
<220> FEATURE:
<221> NAME/KEY: modified_base
<222> LOCATION: (16)..(16)
<223> OTHER INFORMATION: 2'-fluoro-uracil
<220> FEATURE:
<221> NAME/KEY: modified_base
<222> LOCATION: (17)..(18)
<223> OTHER INFORMATION: um
<220> FEATURE:
<221> NAME/KEY: modified_base
<222> LOCATION: (19)..(19)
<223> OTHER INFORMATION: 2'-O-Methyl-adenosine
<220> FEATURE:
<221> NAME/KEY: modified_base
<222> LOCATION: (20)..(20)
<223> OTHER INFORMATION: um
<220> FEATURE:
<221> NAME/KEY: misc_feature
<222> LOCATION: (21)..(22)
<223> OTHER INFORMATION: phosphorothioation
<220> FEATURE:
<221> NAME/KEY: modified_base
<222> LOCATION: (21)..(22)
<223> OTHER INFORMATION: gm
<220> FEATURE:
<221> NAME/KEY: modified_base
<222> LOCATION: (23)..(23)
<223> OTHER INFORMATION: 2'-O-Methyl-adenosine

<400> SEQUENCE: 48
uguaguguuu ccuacuuuau gga 23

<210> SEQ ID NO 49
<211> LENGTH: 21
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: miR142 mimic passenger strand
<220> FEATURE:
<221> NAME/KEY: misc_feature
<222> LOCATION: (1)..(2)
<223> OTHER INFORMATION: phosphorothioation
<220> FEATURE:
<221> NAME/KEY: modified_base
<222> LOCATION: (1)..(1)

-continued

<223> OTHER INFORMATION: cm
<220> FEATURE:
<221> NAME/KEY: modified_base
<222> LOCATION: (2)..(2)
<223> OTHER INFORMATION: 2'-O-Methyl-adenosine
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (4)..(6)
<223> OTHER INFORMATION: 2'-O-Methyl-adenosine
<220> FEATURE:
<221> NAME/KEY: modified_base
<222> LOCATION: (7)..(7)
<223> OTHER INFORMATION: 2'-fluoro-guanine
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: 2'-fluoro-adenine
<220> FEATURE:
<221> NAME/KEY: modified_base
<222> LOCATION: (10)..(11)
<223> OTHER INFORMATION: 2'-fluoro-guanine
<220> FEATURE:
<221> NAME/KEY: modified_base
<222> LOCATION: (12)..(14)
<223> OTHER INFORMATION: 2'-O-Methyl-adenosine
<220> FEATURE:
<221> NAME/KEY: modified_base
<222> LOCATION: (15)..(15)
<223> OTHER INFORMATION: cm
<220> FEATURE:
<221> NAME/KEY: modified_base
<222> LOCATION: (16)..(16)
<223> OTHER INFORMATION: 2'-O-Methyl-adenosine
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (18)..(18)
<223> OTHER INFORMATION: um
<220> FEATURE:
<221> NAME/KEY: modified_base
<222> LOCATION: (19)..(19)
<223> OTHER INFORMATION: 2'-O-Methyl-adenosine
<220> FEATURE:
<221> NAME/KEY: modified_base
<222> LOCATION: (20)..(20)
<223> OTHER INFORMATION: cm
<220> FEATURE:
<221> NAME/KEY: modified_base
<222> LOCATION: (21)..(21)
<223> OTHER INFORMATION: 2'-O-Methyl-adenosine

<400> SEQUENCE: 49
cauaaaguag gaaacacuac a 21

MICRORNA AS A THERAPEUTIC AGENT

CROSS-REFERENCE TO RELATED APPLICATIONS

This application claims priority to U.S. Application No. 62/940,723 filed Nov. 26, 2019, the disclosure of which is incorporated by reference herein in its entirety.

STATEMENT AS TO RIGHTS TO INVENTIONS MADE UNDER FEDERALLY SPONSORED RESEARCH AND DEVELOPMENT

This application is a Section 371 US national phase of International Application No. PCT/US2020/062413 filed Nov. 25, 2020, which claims priority to US Application No. 62/940,723 filed Nov. 26, 2019, the disclosure of which is incorporated by reference herein in its entirety.

REFERENCE TO A "SEQUENCE LISTING," A TABLE, OR A COMPUTER PROGRAM LISTING APPENDIX SUBMITTED AS AN ASCII FILE

The Sequence Listing written in file 048440-744001WO_SequenceListing_ST25.txt, created Nov. 23, 2020, 24,598 bytes, machine format IBM-PC, MS Windows operating system, is hereby incorporated by reference.

BACKGROUND

MicroRNAs (miRNAs) are small non-coding RNAs that control gene expression of a broad set of target genes based on sequence complementarity. By binding to the 3' untranslated regions (3'UTR) of target mRNAs, miRNAs regulate gene expression and potentially enable control of multiple gene targets within the same or distinct signaling pathways. (Ref. 1, 2). Many miRNAs are dysregulated in cancer, cardiovascular and autoimmune diseases. (Ref. 3). Genomic mutations, deletion, or changes in the key enzymes in miRNA biogenesis may all lead to alterations in miRNA levels. (Refs. 4, 5). Genome-wide miRNA screening of leukemia-associated loci identified miR146a as major mediator of the chromosome-5q deletion myelodysplastic syndrome, del(5q) MDS, and acute myeloid leukemia (AML). (Refs. 6-8). The reduced miR146a expression contributes to the development of del(5q) MDS and promotes progression to AML through IRAK1- and TRAF6-dependent activation of NF-κB. (Refs. 9, 10). In non-malignant myeloid cells, such as monocytes, decreased miR146a levels result in expression of IL-6 and other proinflammatory mediators implicated in the pathogenesis of autoimmune diseases and cancers. (Refs. 11-13). The miR146a dysregulation and IL-6 elevation in hematopoietic stem/progenitor and myeloid cells is also associated with many autoinflammatory disease such as rheumatoid arthritis, systemic lupus erythematosus, type II diabetes, Sjogren's syndrome and endotoxemia-related cytokine storm. (Ref. 14). While the role of miR146a is yet unclear, the NF-κB-mediated release of IL-6 from monocyte was also shown responsible for cytokine release syndrome (CRS), which is frequent serious adverse effect of CAR T-cell therapies. (Refs. 12, 15). Due to lack of pharmacologic NF-κB inhibitors, the delivery of a synthetic miRNA146a mimic could be an attractive opportunity for immunomodulation or elimination of tumorigenic signaling. However, the effective delivery of miRNA therapeutics remains a challenge, complicated further by safety concerns and potential off-target effects. (Refs. 2, 16). Several types of delivery vehicles, including liposomes, lipid nanoparticles, nanocells, dendrimers or hydrogels were tested for the delivery of functional miRNAs. (Refs. 17-19). Only a few of synthetic miRNA mimics, including anti-fibrotic miR29/Remlarsen targeting TGFβ activity, progressed to initial clinical testing. (Ref. 19).

There is a need in the art to overcome the problems and challenges associated with the in vivo delivery of miRNA. To that end, the present disclosure provides an original approach for the in vivo targeted delivery of chemically-modified miRNA mimics to, for example, non-malignant and neoplastic myeloid cells.

BRIEF SUMMARY

Provided herein are hybridized nucleic acid sequences comprising a miR146a passenger strand sequence hybridized to a miR146a guide strand sequence. Also provided herein are pharmaceutical compositions comprising the hybridized nucleic acid sequences, and the use of the hybridized nucleic acid sequences and pharmaceutical compositions to treat cancer and inflammatory diseases. In embodiments, the hybridized nucleic acid sequences are linked to Toll-like receptor 9-binding nucleic acid sequences.

Provided herein are compounds of comprising a Toll-like receptor 9-binding nucleic acid sequence covalently bonded to a hybridized nucleic acid sequence comprising a microRNA passenger strand sequence hybridized to a microRNA guide strand sequence. In embodiments, the microRNA is miR146a, miR155, miR142, miR125b, miR203b, miR221, miR222, or miR29b. Also provided herein are pharmaceutical compositions comprising the compounds, and the use of the compounds and pharmaceutical compositions to treat cancer and inflammatory diseases. These and other embodiments and embodiments of the disclosure are described herein.

BRIEF DESCRIPTION OF THE DRAWINGS

FIG. 1A shows the design of C-miRNA146a mimic conjugate used throughout the experiments, where the D19 ODN linker is SEQ ID NO:9; the passenger strand miRNA is SEQ ID NO:2; the guide strand miR-146a-5p is SEQ ID NO:7; and each "o" in the linker has the structure:

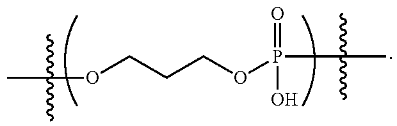

Figure 1A:
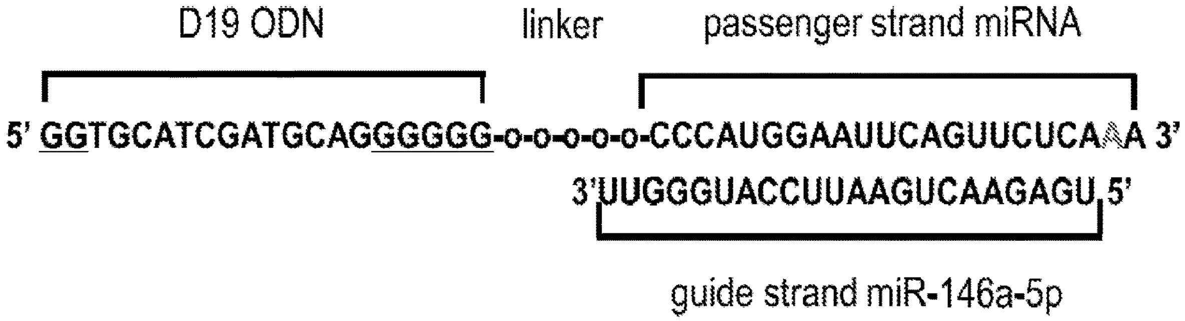
FIGS. 1A-1E show the targeted delivery of miR146a mimic to RISC/Ago2 complexes in myeloid cells.
Figure 1B:
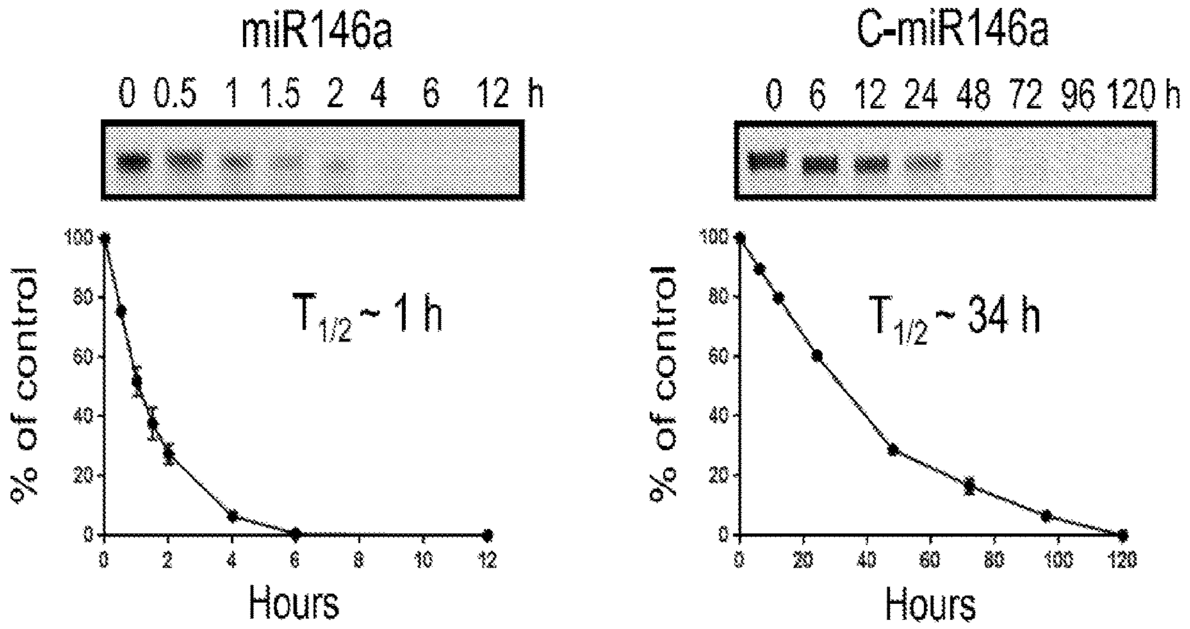
Figure 1C:
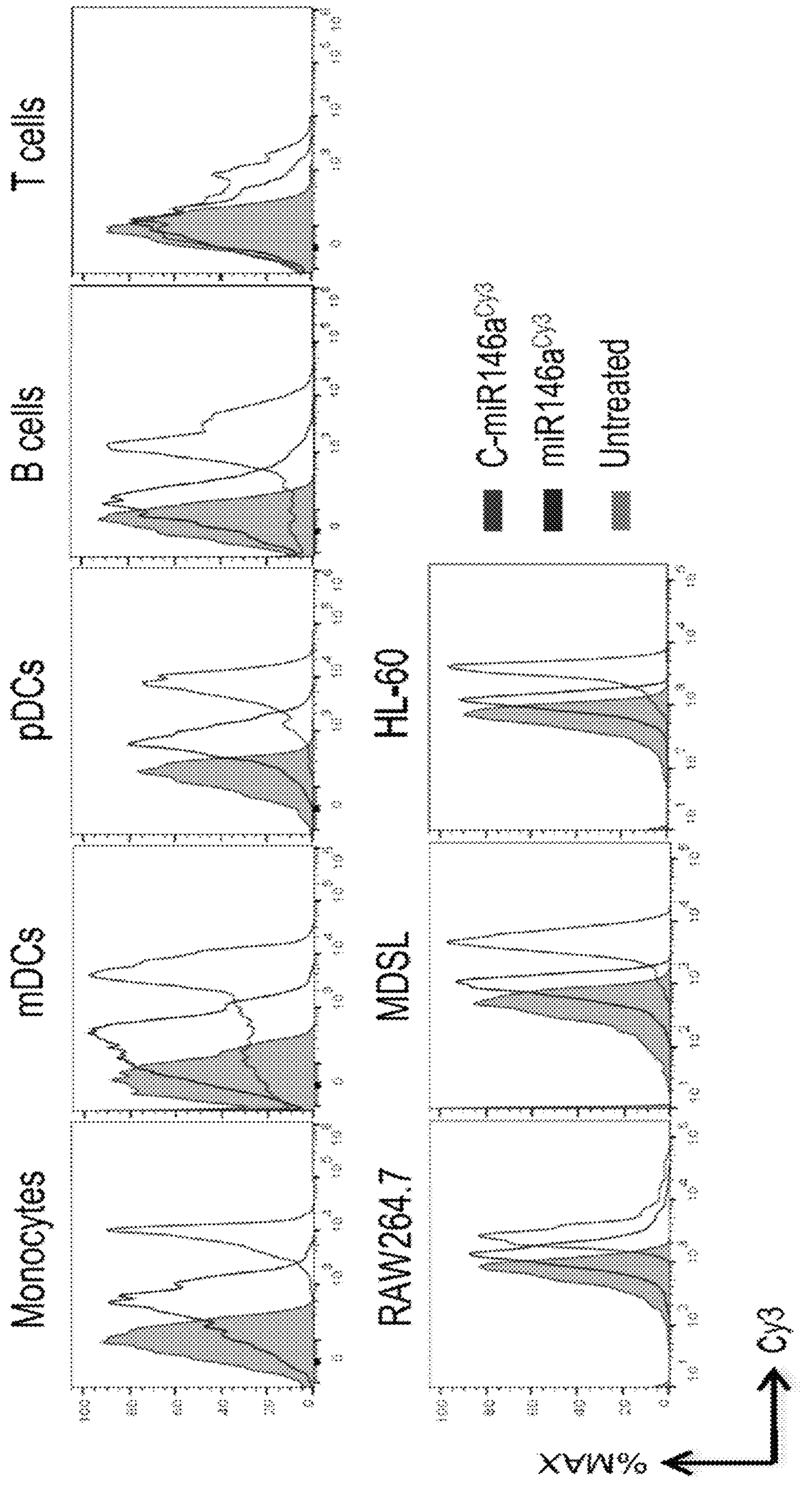
Figure 1D:
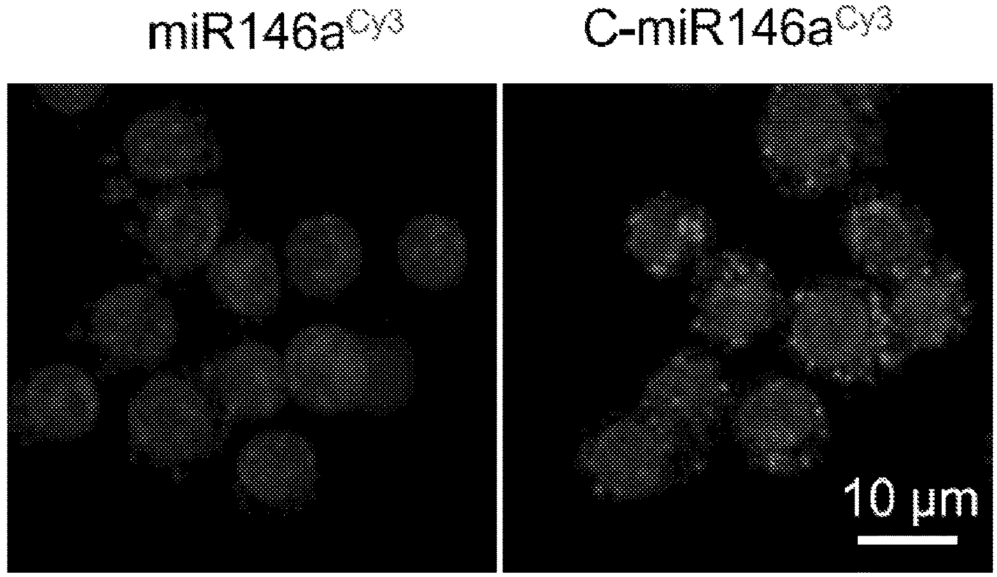
Figure 1E:
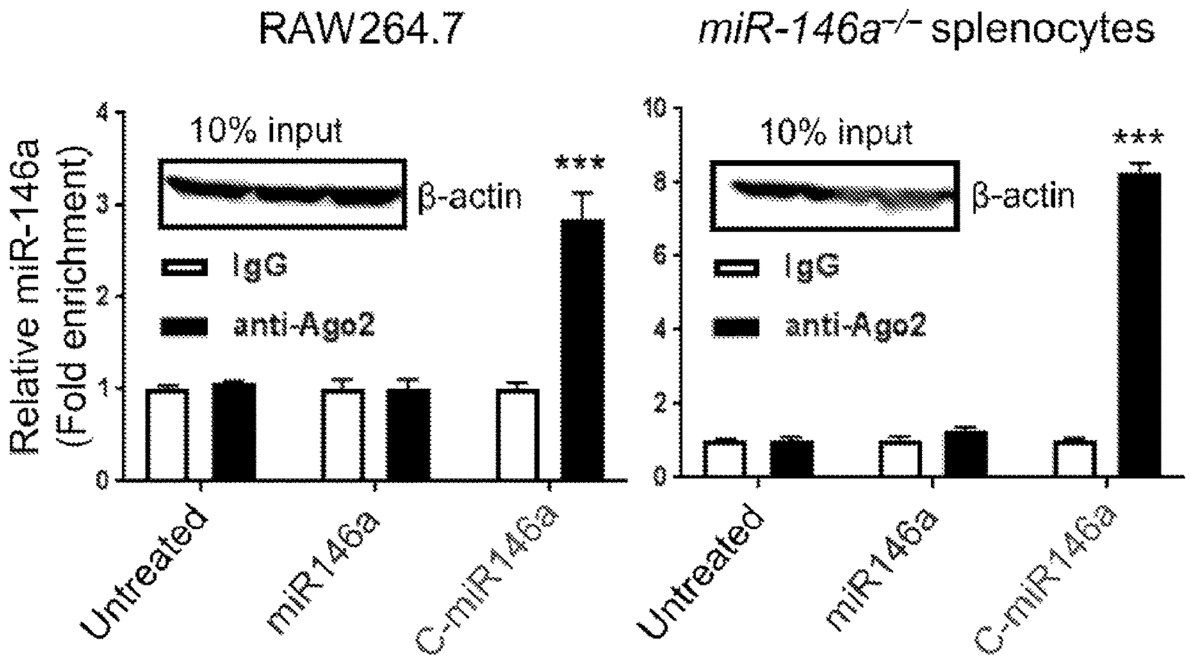

FIG. 1B shows the serum stability of miR146a (left) and C-miR146a (right). Oligonucleotides were incubated in 50% human serum at 37° C. for the indicated times and then resolved on 7.5M urea/15% PAGE gel. Shown is a representative result from one of three independent experiments; the band intensities were quantified and the estimated oligonucleotide half-lives were indicated. FIG. 1C shows the intracellular uptake of C-miR146a$^{Cy3}$ compared to miR146a$^{Cy3}$ alone by primary human immune cells (monocytes: CD14$^{+}$; mDCs: CD1c$^{+}$; pDCs: CD303$^{+}$; B cells: CD19$^{+}$; and T cells: CD3$^{+}$), mouse macrophage RAW264.7 cells, human leukemic cells MDSL and HL-60. Cells were incubated for 1 h with 100 nM C-miR146a$^{Cy3}$ or miR146a$^{Cy3}$ without any transfection reagents, and the uptake was measured using flow cytometry. In FIG. 1C, the left hand peak in each panel is untreated; the middle peak in each panel is miR146a$^{Cy3}$, and the right hand peak is C-miR146a$^{Cy3}$ (i.e., the compound of FIG. TA). FIG. 1D shows the intracellular localization of C-miR146a$^{Cy3}$ or miR146a$^{Cy3}$ oligonucleotides (100 nM/red) as visualized using confocal microscopy in RAW264.7 cells after 1 h incubation. Hoechst33342 (blue) was used for nuclear counterstain. FIG. 1E shows the successful loading of miR146a into RISC/Ago2 by C-miRNA conjugate. RAW264.7 or splenocytes isolated from miR146a mice were incubated for 1 h with 1 μM C-miR146a or miR146a alone. The RNA-protein complexes were immunoprecipitated using anti-Ago2 or control IgG antibodies and the miR146a levels were quantified using qPCR. The equal protein loading was confirmed with Western blotting. The data shown represent results from three independent experiments; shown are means±SEM.

Figure 2A:
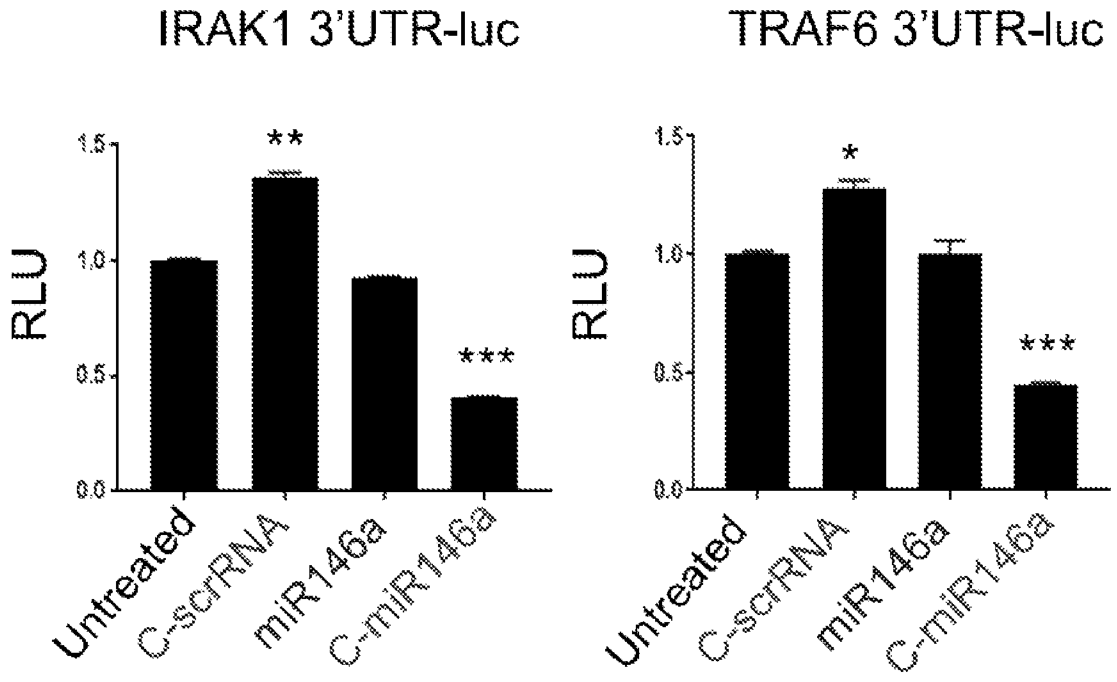
Figure 2B:
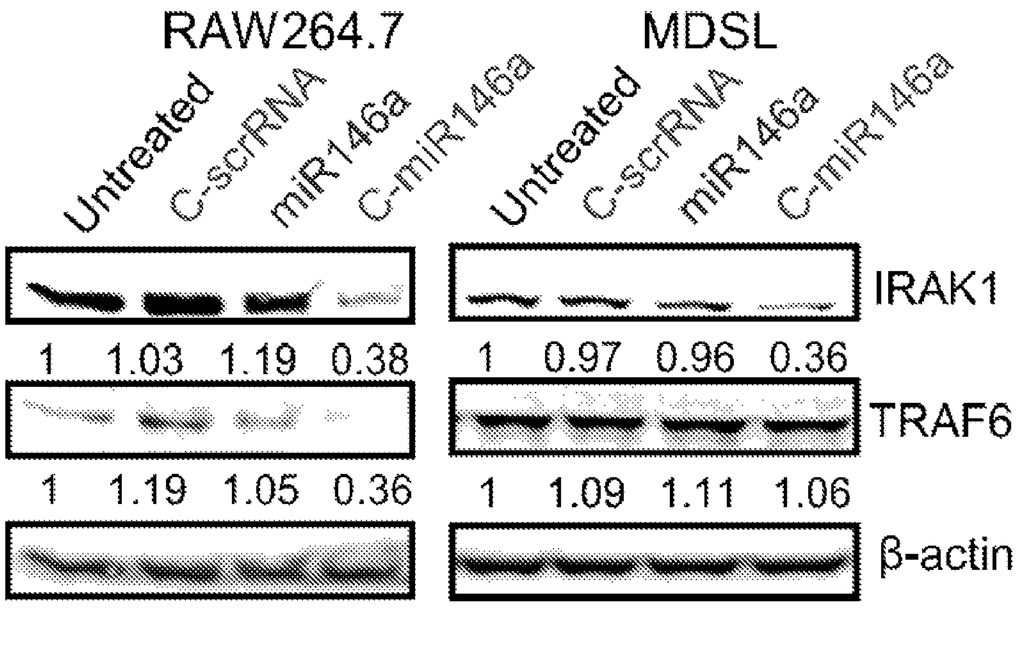
Figure 2C:
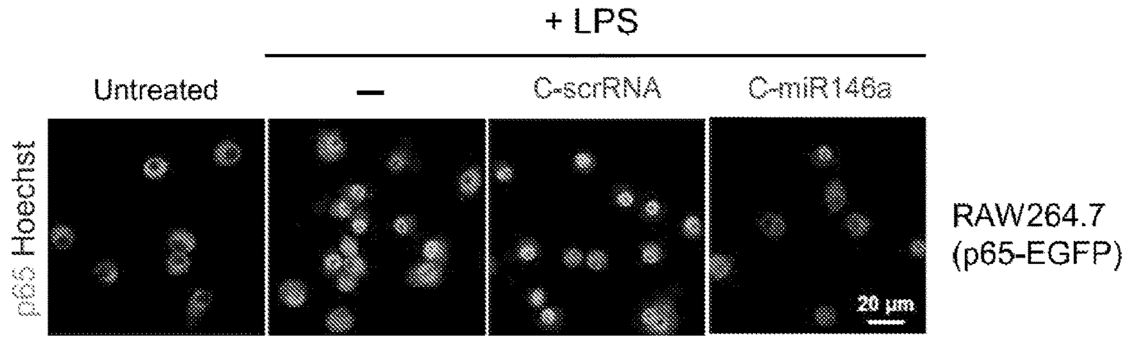
Figure 2D:
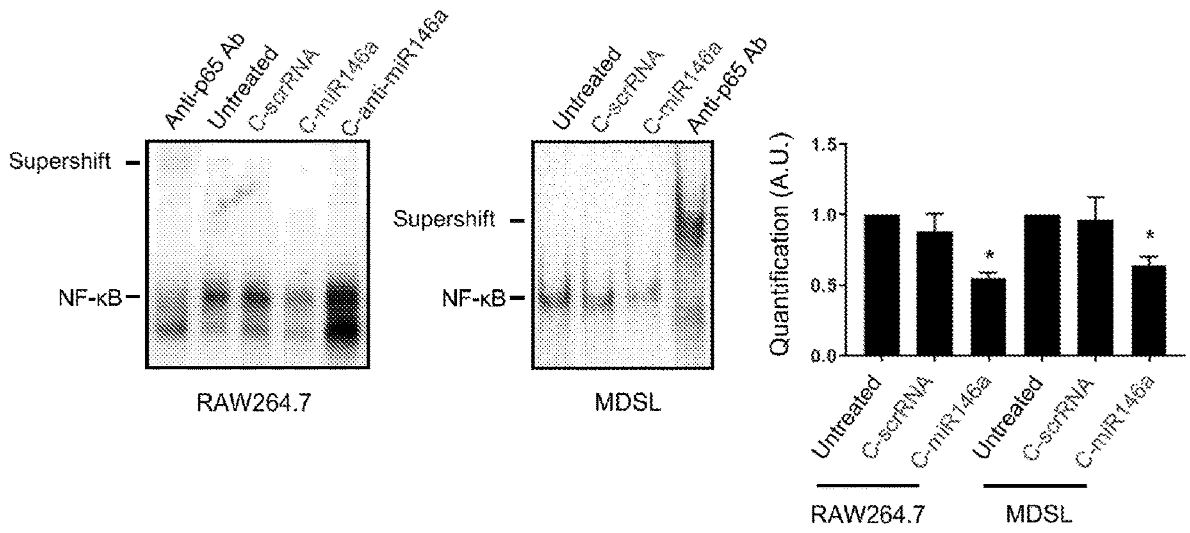
Figure 2E:
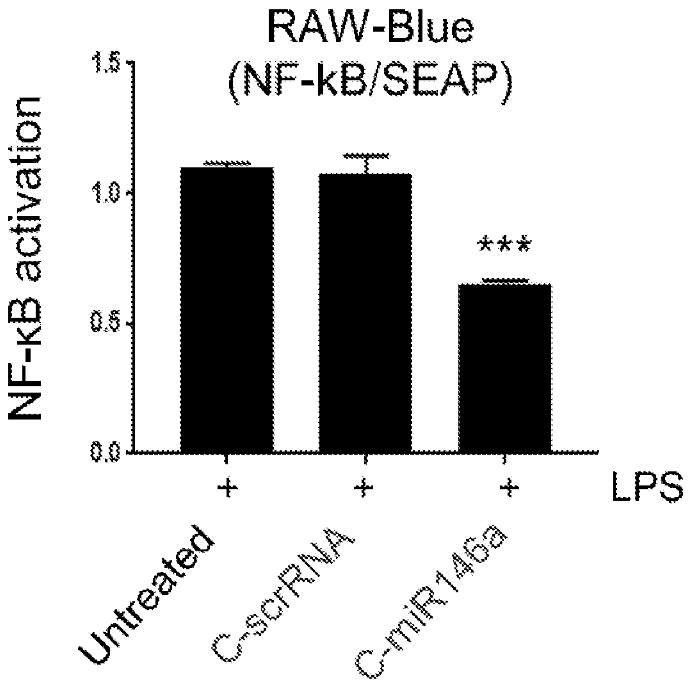
Figure 2F:
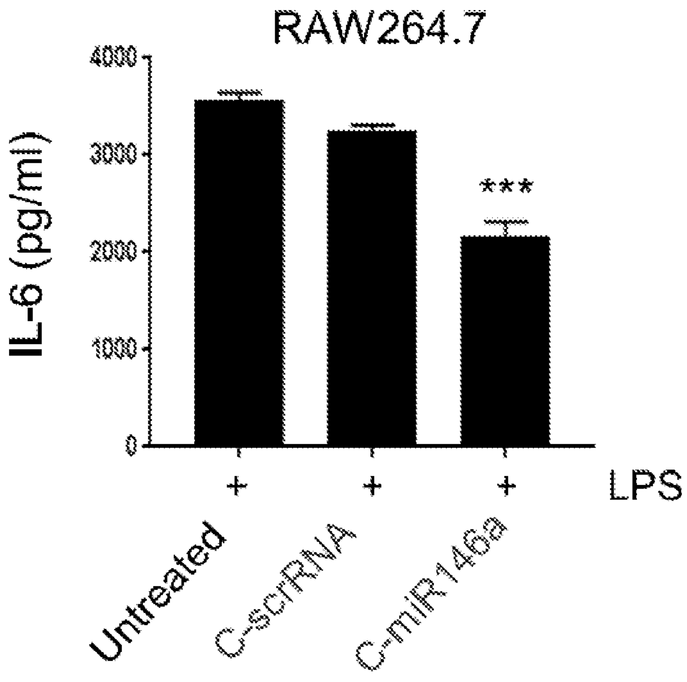

FIGS. 2A-2F show the C-miR146a mimic targets upstream regulators of NF-KB signaling. FIG. 2A shows that C-miR146a inhibits IRAK1 and TRAF6 expression. HEK293T cells transfected with IRAK1 or TRAF6 3'-UTR luciferase reporter and control *Renilla* luciferase plasmids were incubated with 500 nM C-miR146a, control C-scrRNA or miR146a alone. The reporter luciferase activities were evaluated after 48 h. FIG. 2B shows reduced protein levels of IRAK1 and TRAF6 in C-miR146a-treated mouse macrophages and human leukemia cells. IRAK1 and TRAF6 protein levels were assessed using Western blot in RAW264.7 and MDSL cells after 48 h incubation with 500 nM of indicated oligonucleotides. Shown are representative results; band intensities were quantified with normalization to 13-actin as a loading control. FIG. 2C shows that miR146a mimic delivery prevents nuclear translocation of NF-KB. RAW264.7 cells stably expressing p65-eGFP fusion protein were incubated overnight with 500 nM C-miR146a or control C-scrRNA and then stimulated with 100 ng/mL LPS for 4 h. Translocation of NF-KB/p65 (green) into nuclei (blue) was visualized using confocal microscopy. FIG. 2D shows that C-miR146a inhibits NF-κB DNA binding in target myeloid cells, RAW264.7 or MDSL. Cells were incubated with 500 nM C-miR146a, C-anti-miR146a or control C-scrRNA for 48 h. The NF-κB DNA binding was assessed in nuclear extracts and verified using p65-specific antibody supershift. Representative blots (left/middle) and the quantification of band intensities combined from three experiments (right). FIGS. 2E-2F shows that C-miR146a reduces transcriptional activity of NF-KB in macrophages. RAW-Blue (FIG. 2E) or RAW264.7 (FIG. 2F) cells were incubated overnight with 500 nM C-miR146a or control C-scrRNA and then stimulated with 100 ng/mL LPS for 4 h. The expression of the NF-κB-dependent reporter gene (FIG. 2E) or IL-6 secretion (FIG. 2F) were assessed using Quanti-Blue assay or ELISA, respectively. Shown are representative results obtained in three independent experiments; means±SEM.

Figure 3A:
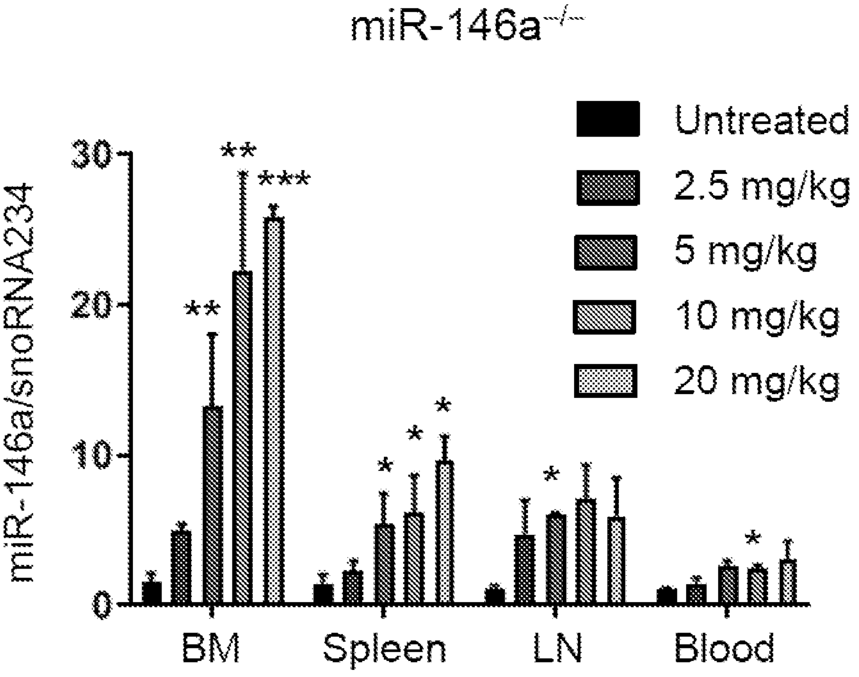
Figure 3B:
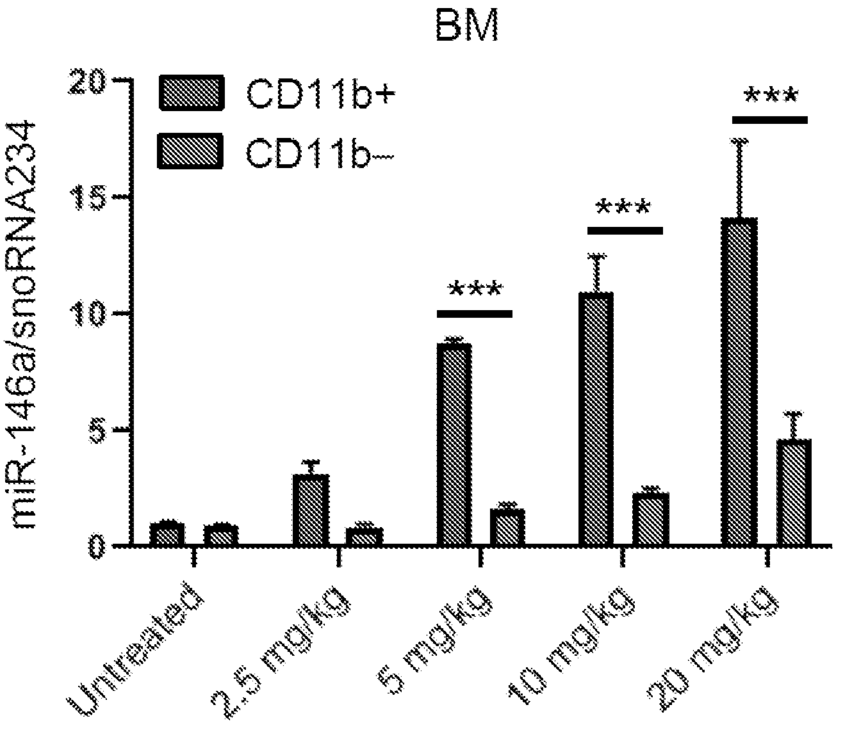
Figure 3C:
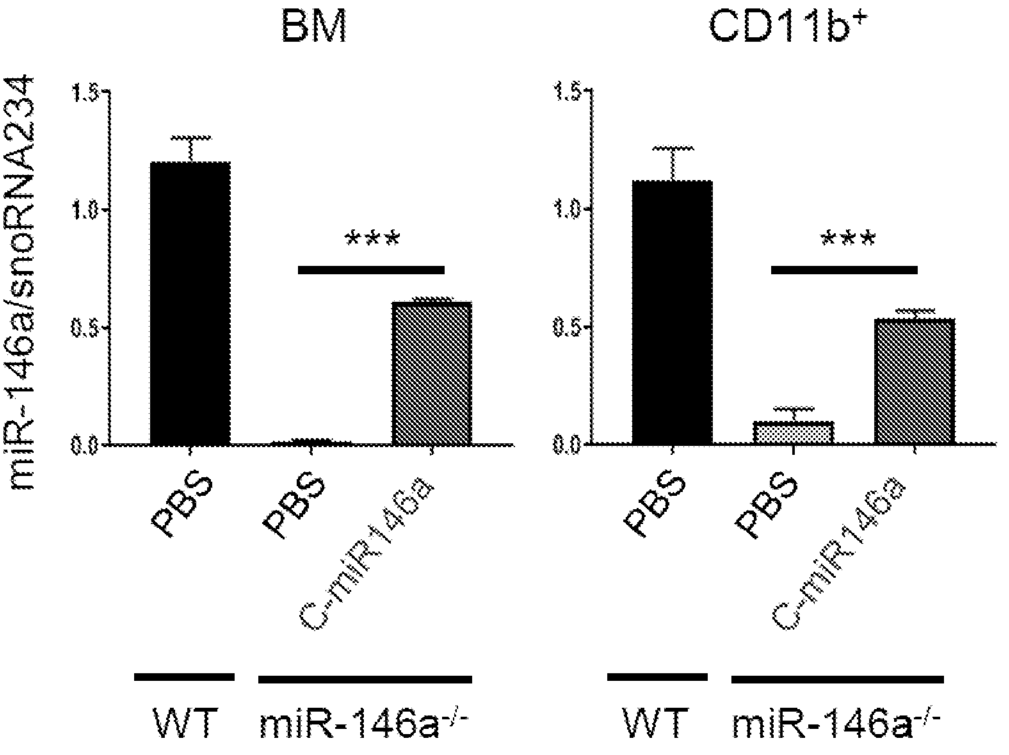
Figure 3D:
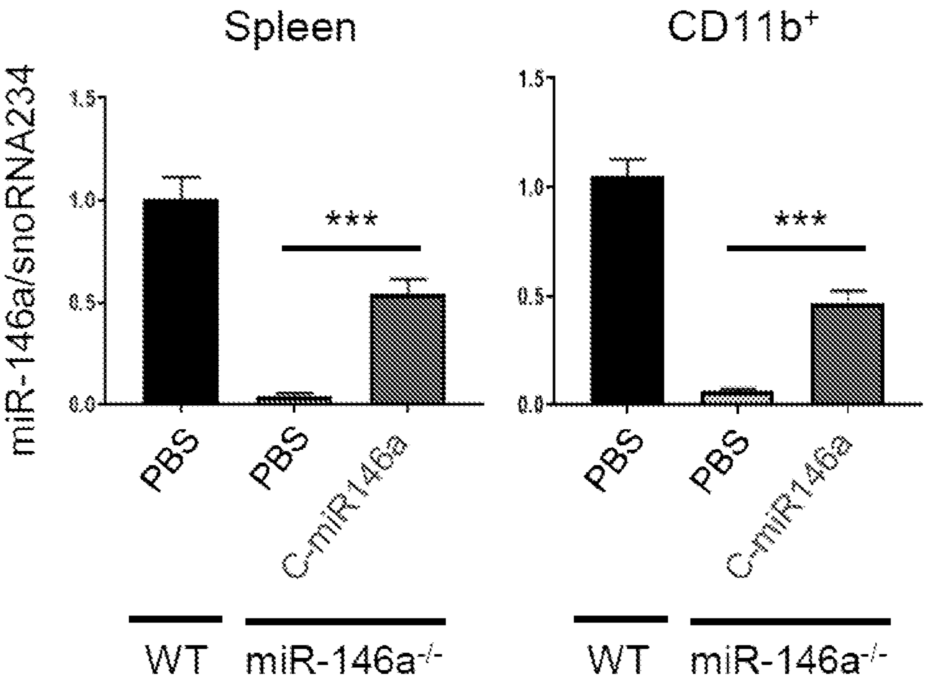
Figure 3E:
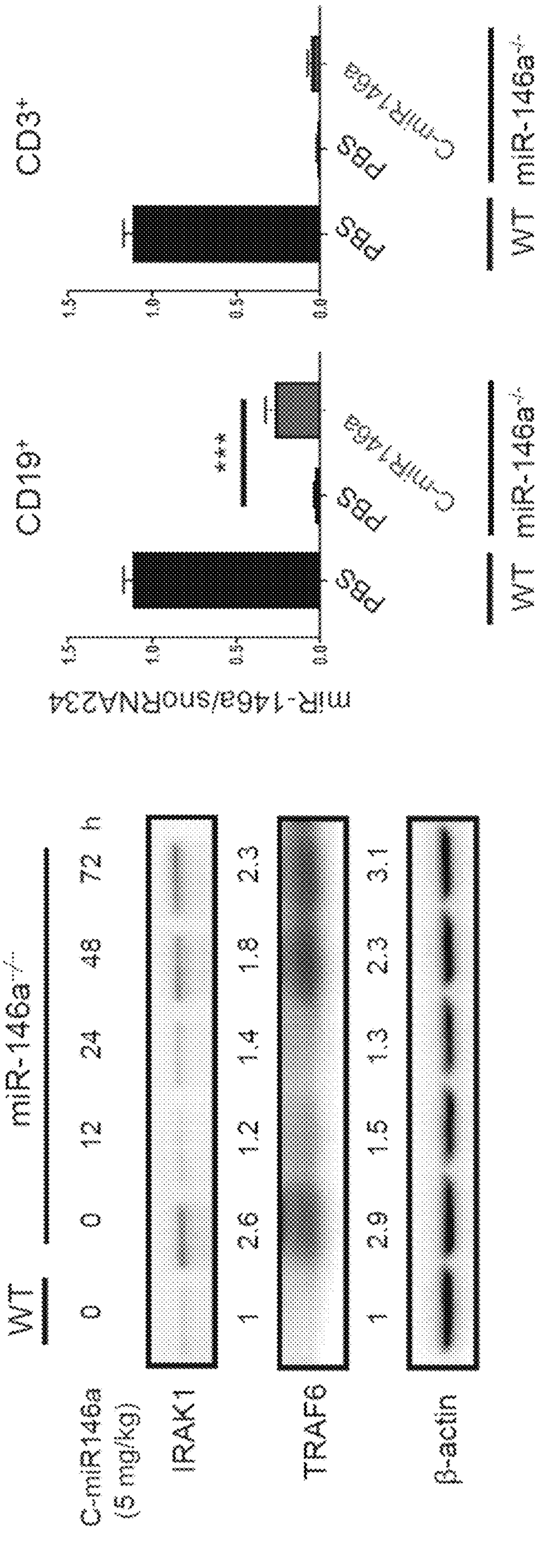

FIGS. 3A-3E shows that C-miR146a targets myeloid cell populations and restores miR146a levels and activity in miR146a mice. FIGS. 3A-3B shows dose-dependent biodistribution of miR146a mimic in organs (FIG. 3A) and in bone-marrow CD11b$^+$ myeloid cells and CD11b$^-$ cells (FIG. 3B) of miR146a-deficient mice. Mice were injected IV using various doses of C-miR146a and euthanized 3 h later to assess miR146a levels in bone marrow (BM), spleen, lymph nodes (LN), blood, and enriched BM CD11b$^+$ myeloid cells and CD11b$^-$ cells using qPCR. FIGS. 3C-3D show myeloid cell-selective delivery of miR146a in vivo. miR146a$^{-/-}$ or WT mice were injected IV with 5 mg/kg C-miR146a and euthanized 3 h later. miR146a levels in BM and splenocytes and enriched CD11b$^+$ myeloid cells, CD19$^+$ B-cells and CD3$^+$ T-cells were assessed using qPCR and compared to the same populations in untreated WT mice. Shown are representative results obtained in three independent experiments; means±SEM (n=3). FIG. 3E shows single injection of C-miR146a$^{-/-}$ results in transient downregulation of IRAK1 and TRAF6 protein levels. miR146a$^{-/-}$ mice were injected IV with 5 mg/kg C-miR146a and euthanized at indicated times. Protein levels of IRAK1 and TRAF6 in bone marrow cells were assessed using Western blot and the quantified band intensities normalized to 13-actin were shown. Shown are results representative for two independent experiments; means±SEM (n=3/group).

Figure 4A:
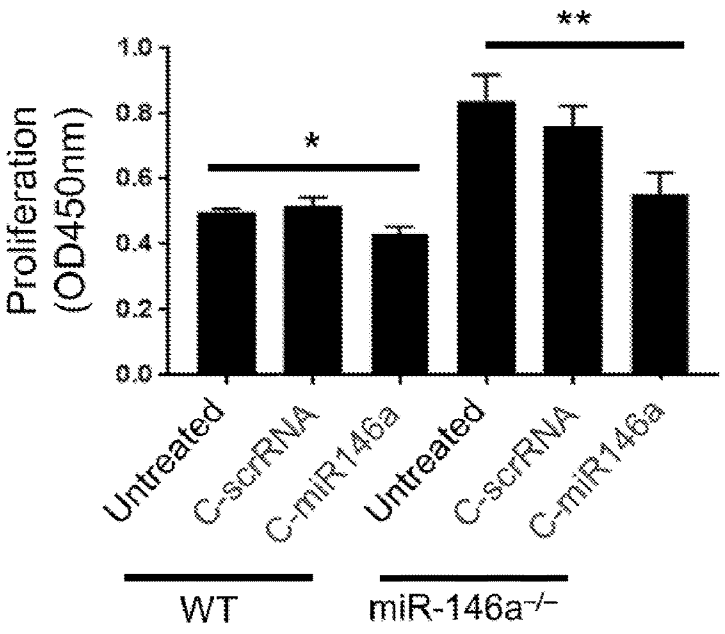
Figure 4B:
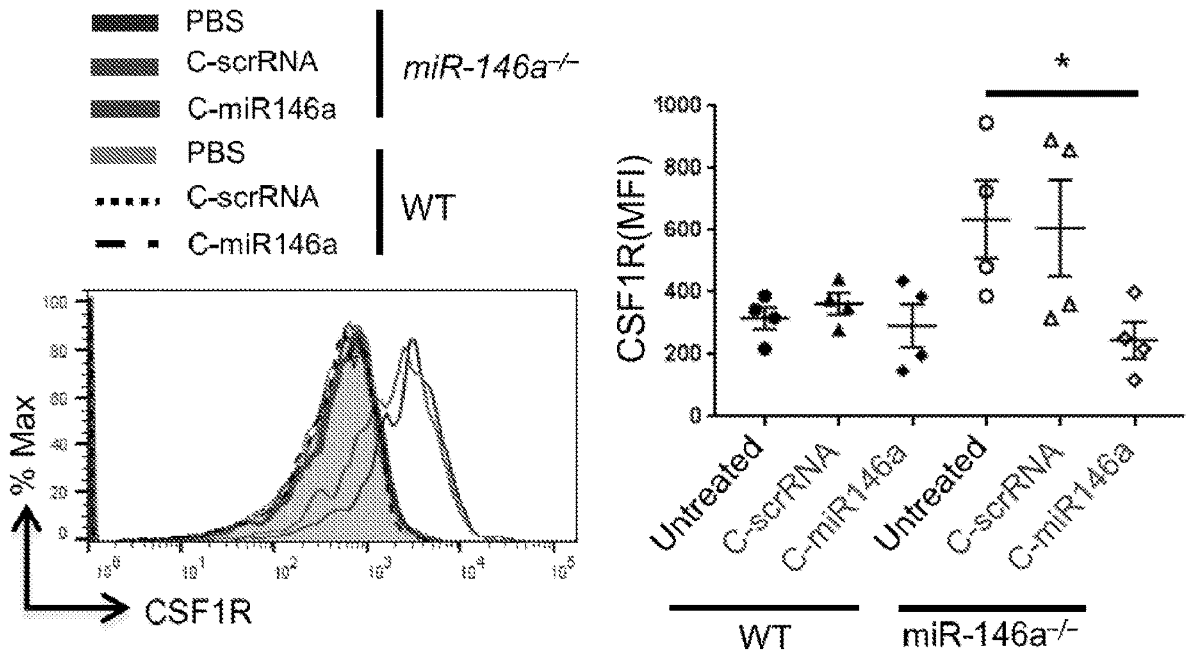
Figure 4C:
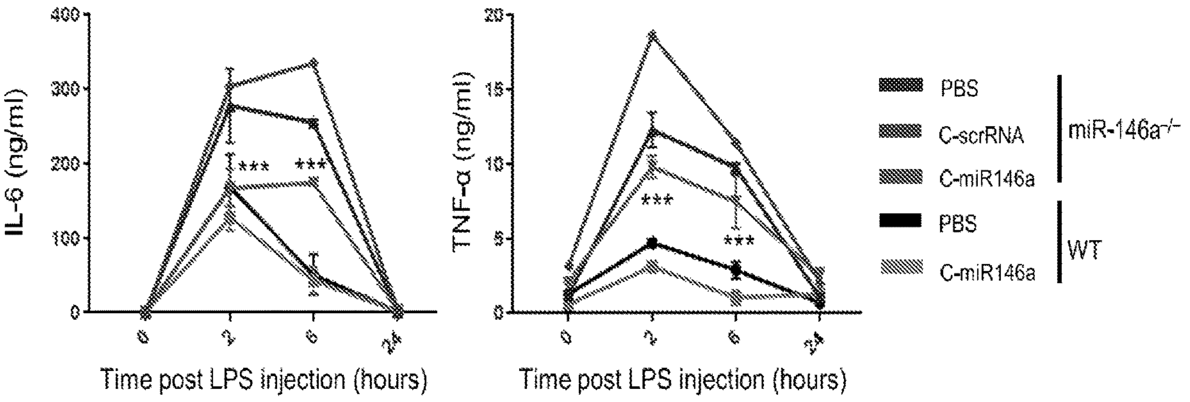

FIGS. 4A-4G show that C-miR146a corrects the aberrant myeloproliferation and inflammatory responses in miR146a-deficient mice. FIGS. 4A-4B show reduced proliferation of miR146a$^{-/-}$ bone marrow-derived macrophages (BMDM) treated with C-miR146a. Bone marrow cells from WT and miR146a$^{-/-}$ mice were cultured in the presence of 50 ng/ml M-CSF for 7 days and treated using 1 μM C-miR146a or C-scrRNA. The cell proliferation (FIG. 4A) was measured using colorimetric XTT assay and the CSF1R expression on CD11b$^+$F4/80$^+$ cells (FIG. 4B) was quantified using flow cytometry. FIG. 4C shows systemic injections of C-miR146a alleviate exaggerated response to endotoxin in miR146a$^{-/-}$ mice. WT or miR146a mice were injected IV with 5 mg/kg C-miR146a$^{-/-}$ or C-scrRNA daily for three days before LPS challenge (IP/1 mg/kg). Blood was collected at the indicated times to analyze IL-6 and TNF-α levels using ELISA. FIGS. 4D-4G show that C-miR146a treatment restored tolerance to *Listeria monocytogenes* infection in mice with myeloid cell-specific miR146a-deletion. WT or miR146a$^{fl/fl}$ mice injected daily IV using 5 mg/kg C-miR146a or C-scrRNA were infected with *L. monocytogenes* on day 3 and euthanized on day 6. The liver bacterial load (FIG. 4D), the percentage of weight loss (FIG. 4E), plasma levels of IL-6 (FIG. 4F) and percentages of various haematopoietic cell populations in circulation were assessed. Representative results from at least two independent experiments are shown; means±SEM (n=5/group).

Figure 5A:
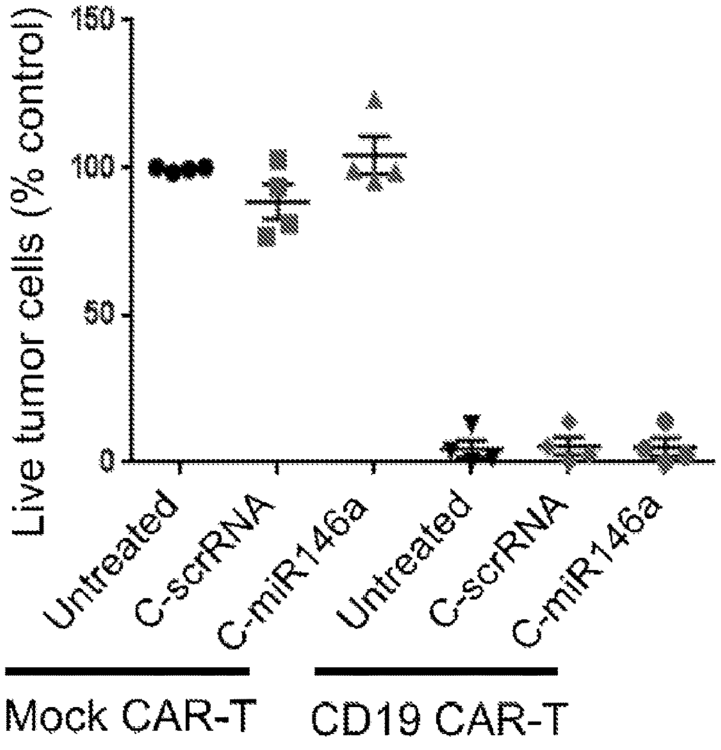
Figure 5B:
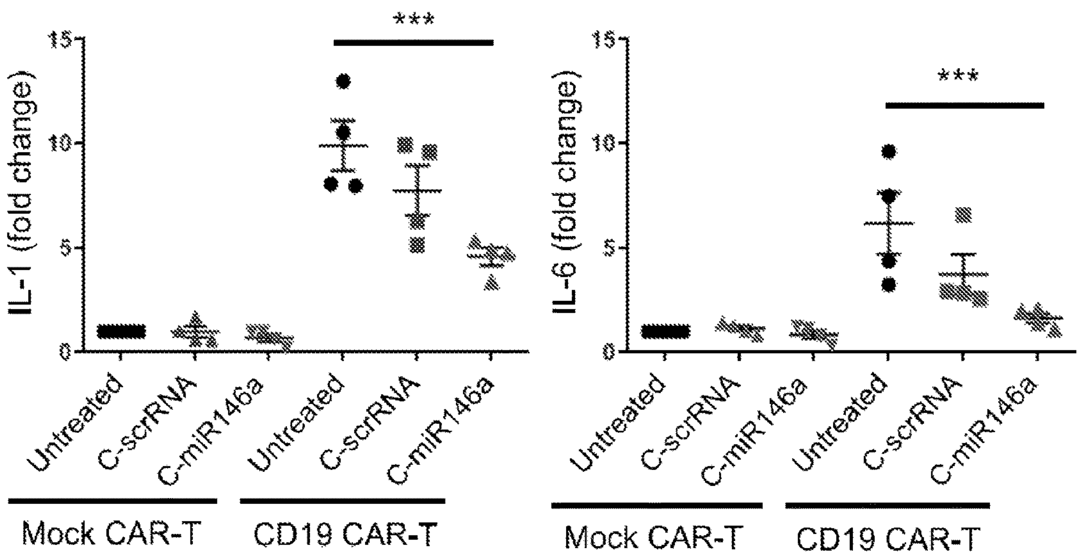
Figure 5C:
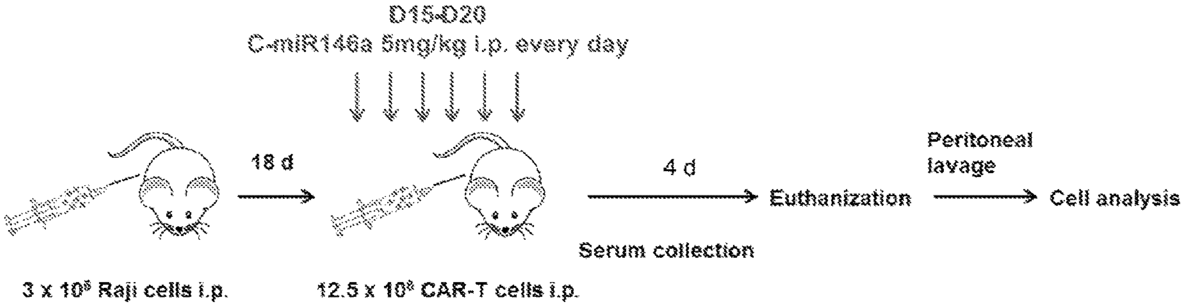
Figure 5D:
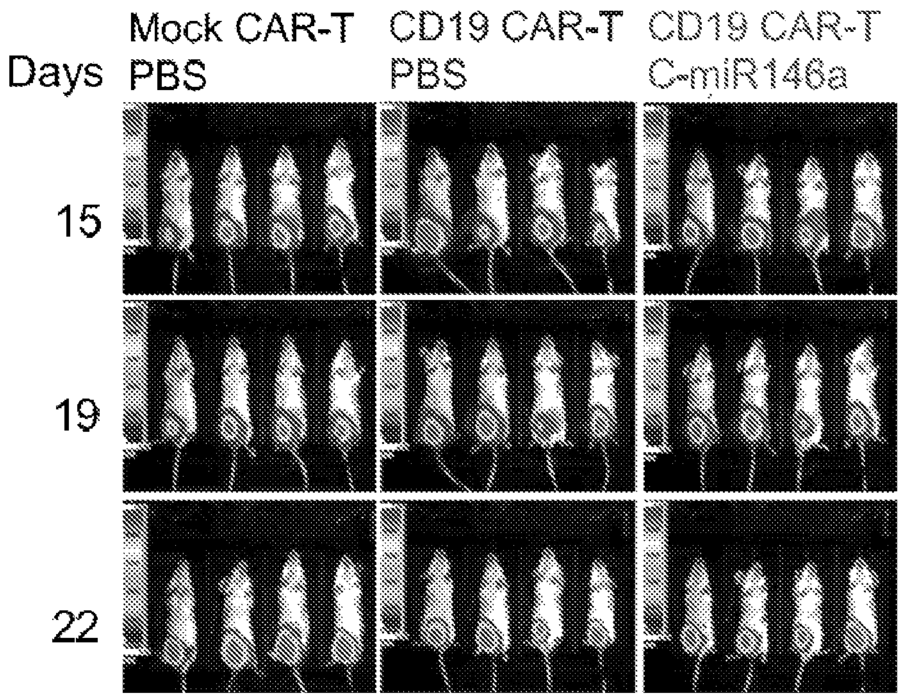
Figure 5E:
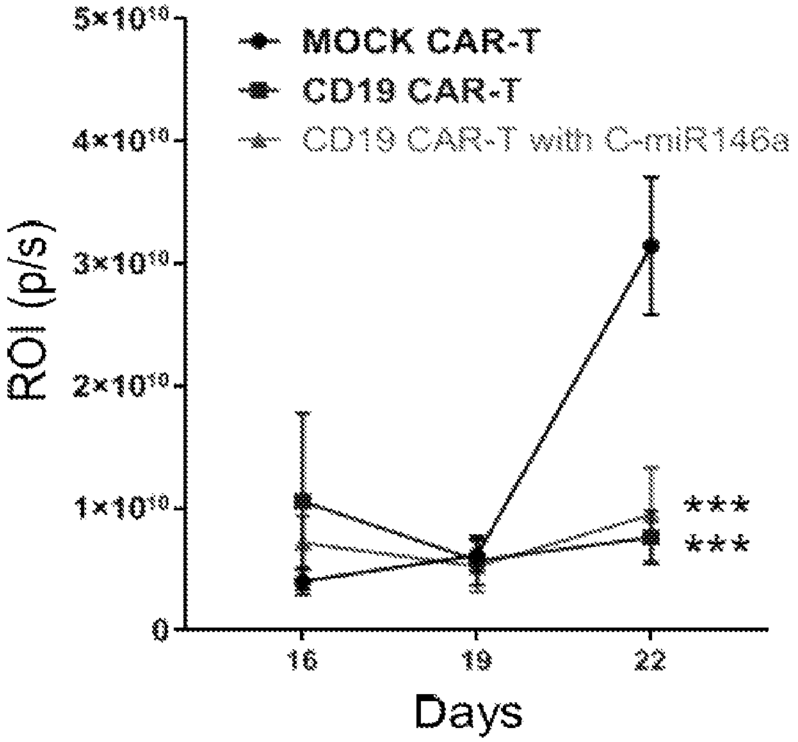
Figure 5F:
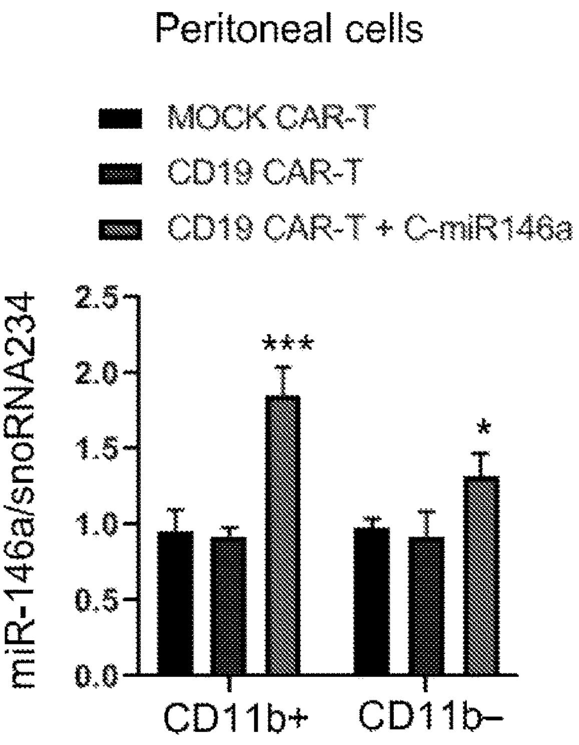
Figure 5G:
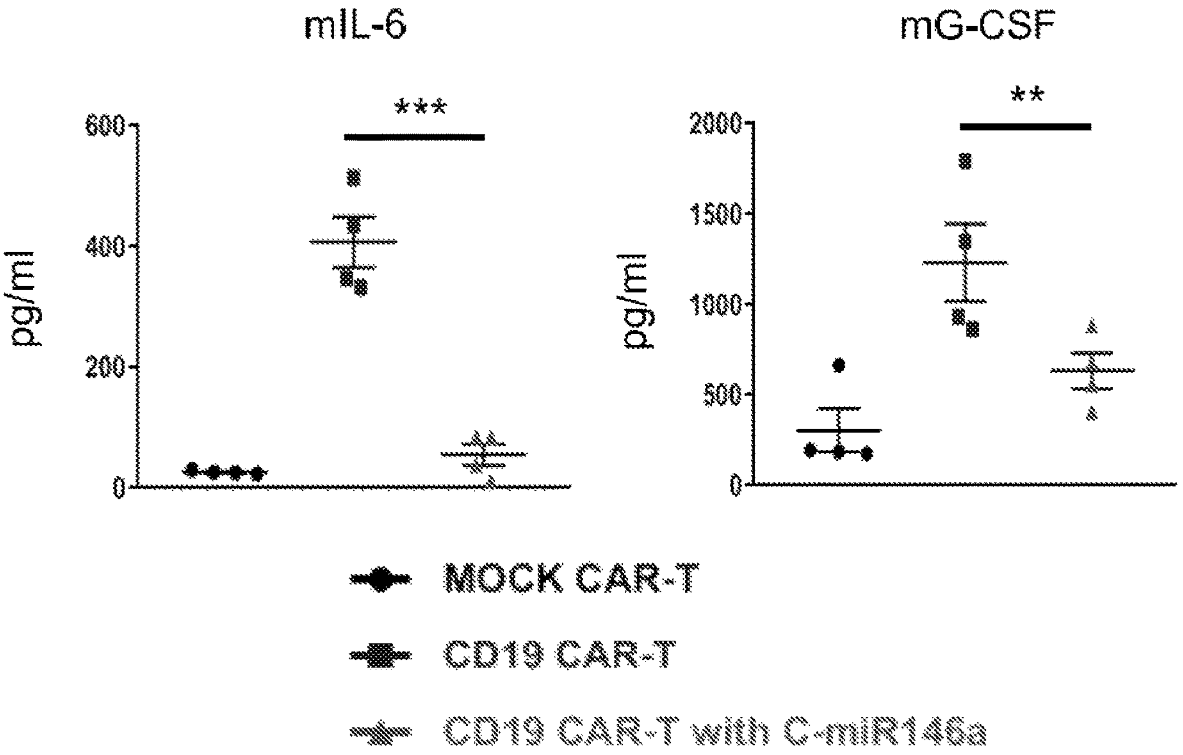

FIGS. 5A-5G show targeting monocytes using C-miR146a mimic alleviates cytokine release syndrome induced by CD19 CAR T-cells without compromising anti-tumor effects. FIGS. 5A-5B show C-miR146a does not affect cytotoxic activity of CD19 CAR T-cells against target leukemia cells. Mock- or CD19 CAR-transduced T cells were co-cultured at a 1:1:1 ratio with donor-matched CD14$^+$ monocytes and target CD19$^+$ Nalm6 B-cell leukemia for 48 h in the presence of 500 nM C-miR146a or control C-scrRNA. Then, the percentages of live target CD19$^+$ cells were assessed using flow cytometry (FIG. 5A), while IL-1 and IL-6 levels in cultured supernatants were measured using ELISA (FIG. 5B). Shown are results combined from four different PBMC donors. FIG. 5C shows the experimental design for in vivo studies on the CAR T-cell-induced CRS using xenotransplanted lymphoma model. SCID-Beige mice were engrafted with luciferase-expressing Raji lymphoma cells (IP) and after two weeks injected daily using 5 mg/kg/IP of C-miR146a or PBS. 12.5×10$^6$ mock or CD19 CAR T-cells were injected IP on day 18 before euthanizing mice on day 22. FIGS. 5D-5E show tumor progression was monitored using bioluminescent imaging (BLI): ROI, regions of interest; p/s, photons per second; means±SEM. FIG. 5F shows the intracellular miR146a levels were measured using qPCR in $CD11b^+$ myeloid and CD11b-non-myeloid cells derived from peritoneal lavage. FIG. 5G shows serum cytokine levels of mouse IL-6 and G-CSF were measured using ELISA after 24 h from CAR T-cell transfer. Representative results from at least two independent experiments were shown as means±SEM (n=4).

Figure 6A:
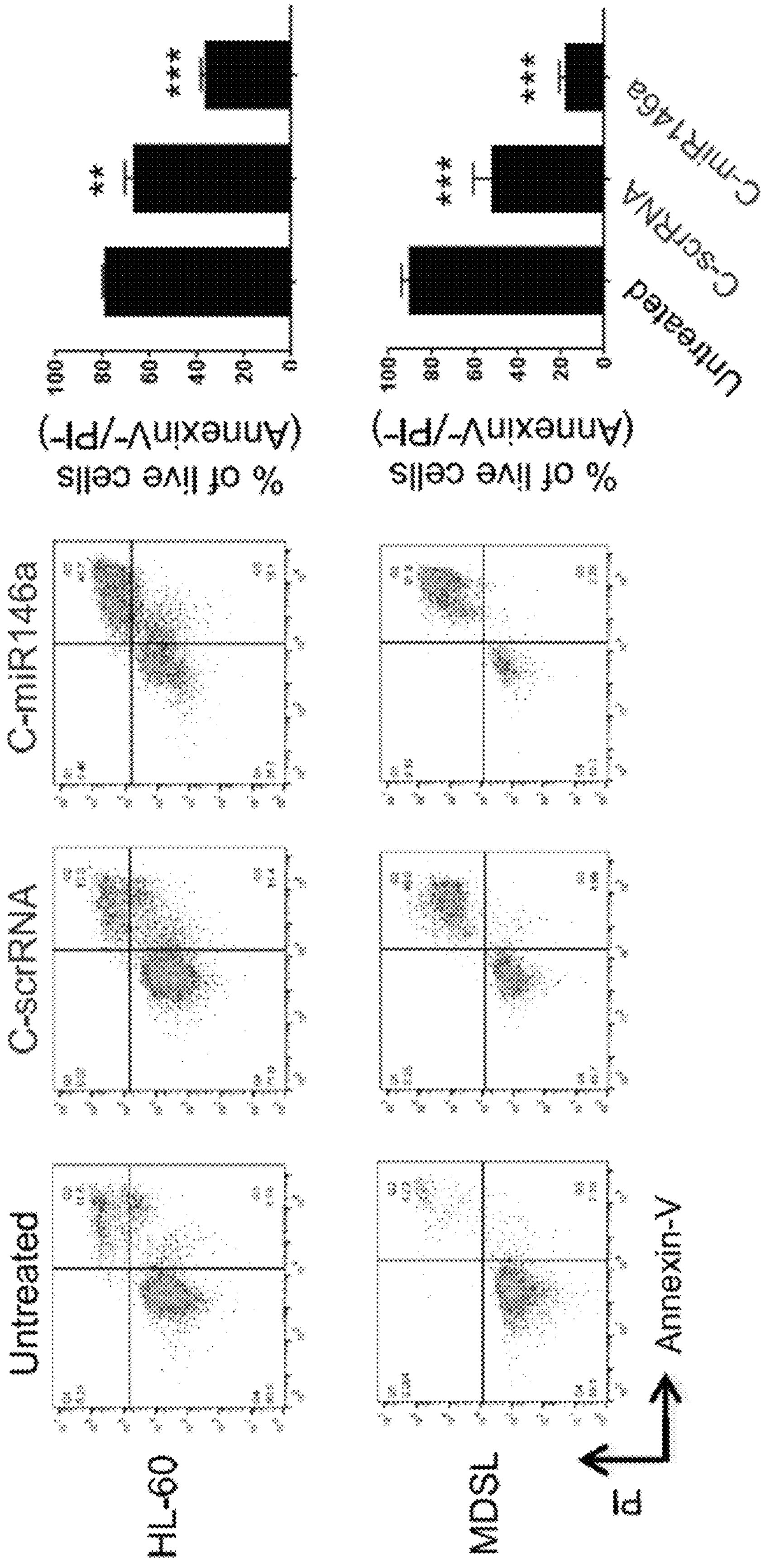
Figure 6B:
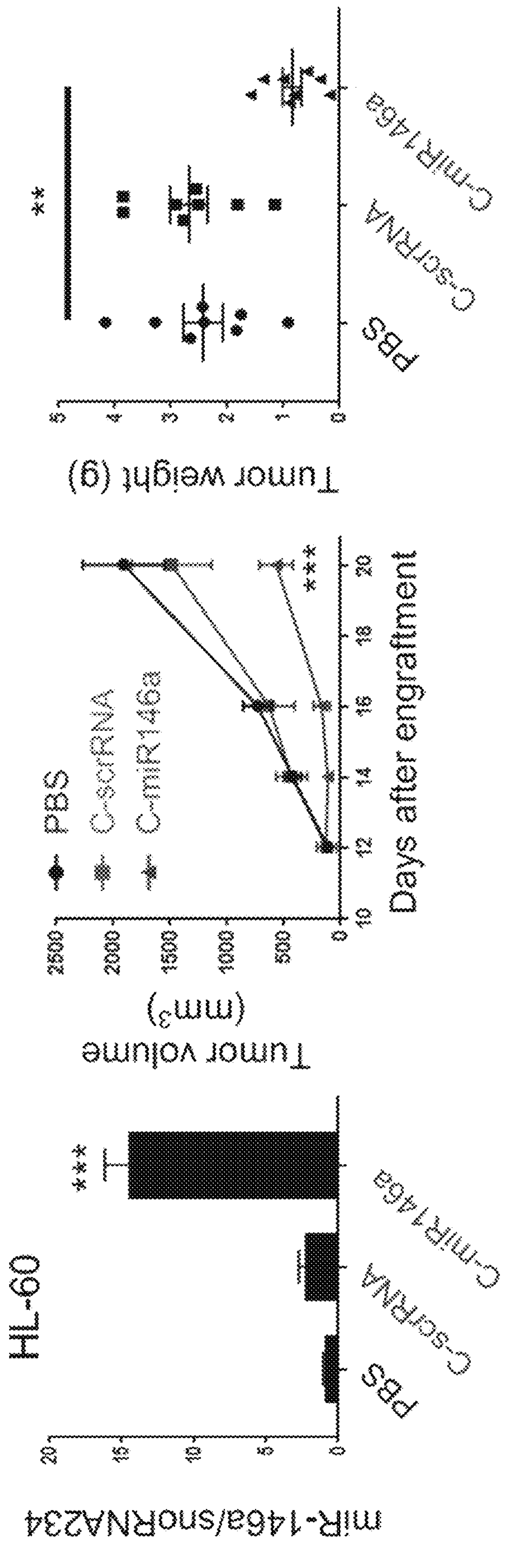
Figure 6C:
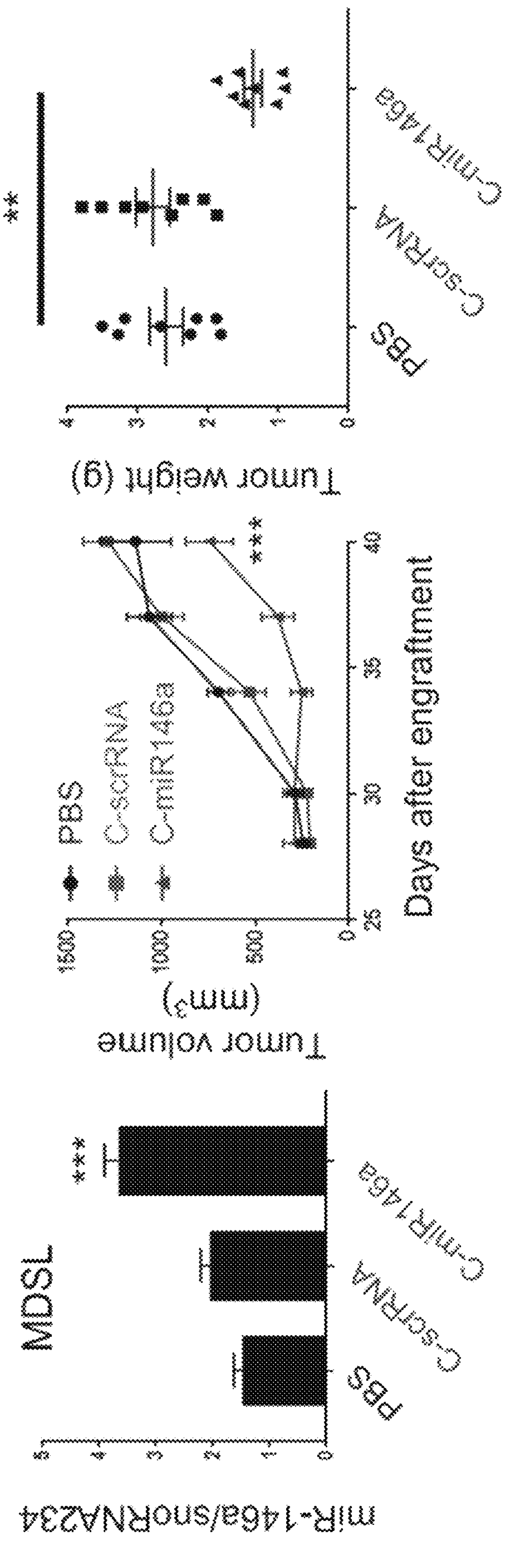
Figure 6D:
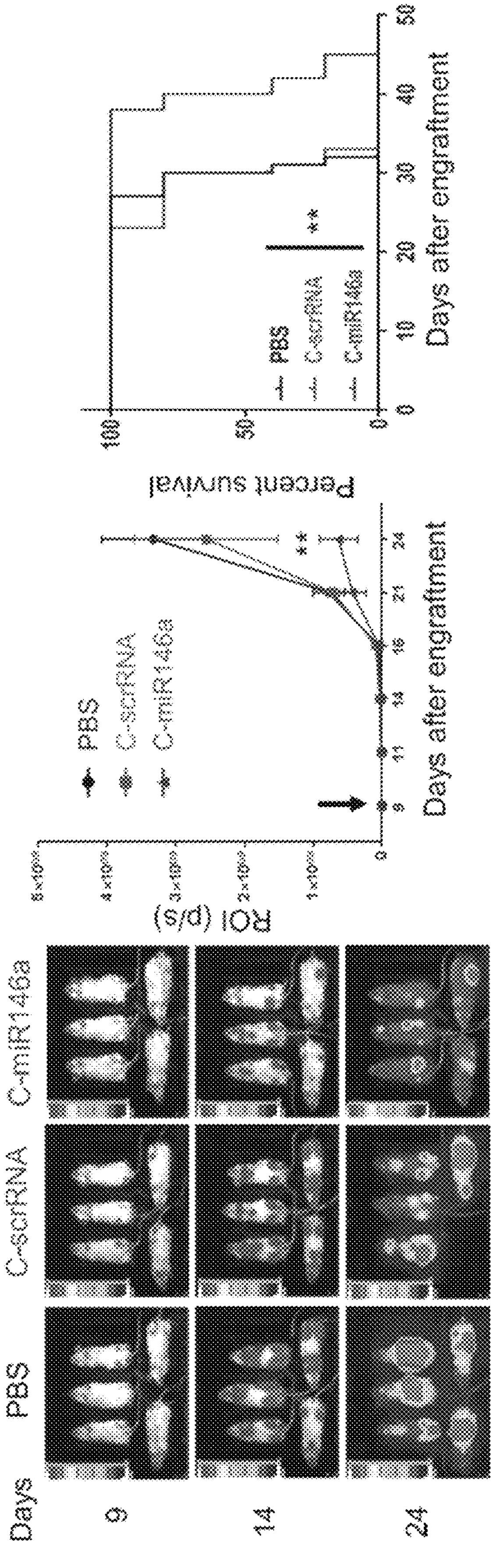

FIGS. 6A-6D show that C-miR146a inhibits progression of del(5q) MDS and AML in vitro and in vivo. In FIG. 6A, Del(5q) HL-60 or MDSL leukemia cells were treated in vitro using 500 nM C-miR146a or C-scrRNA for 6 days and the percentages of live cells were assessed using flow cytometry. Representative results obtained from three independent experiments; means±SEM. In FIGS. 6B-6C, NSG-SGM3 mice were engrafted subcutaneously with HL-60 or MDSL cells, after tumors were established, mice were treated daily using 5 mg/kg C-miR146a or C-scrRNA (IT). Left: intratumoral miR146a levels measured using qPCR at the end of experiment. Tumor growth kinetics (middle) and weight (right); means±SEM (n=8). FIG. 6D shows systemic administration of C-miR146a extended survival of human HL-60 AML-bearing mice. NSG-SGM3 mice engrafted with disseminated HL-60-luc cells were injected daily IV using 10 mg/kg C-miR146a or C-scrRNA and leukemia progression was monitored using BLI (left). Leukemia progression (middle) and the Kaplan-Meier survival curves (right); shown are representative results from at least two independent experiments; means±SEM (n=8).

Figure 7:
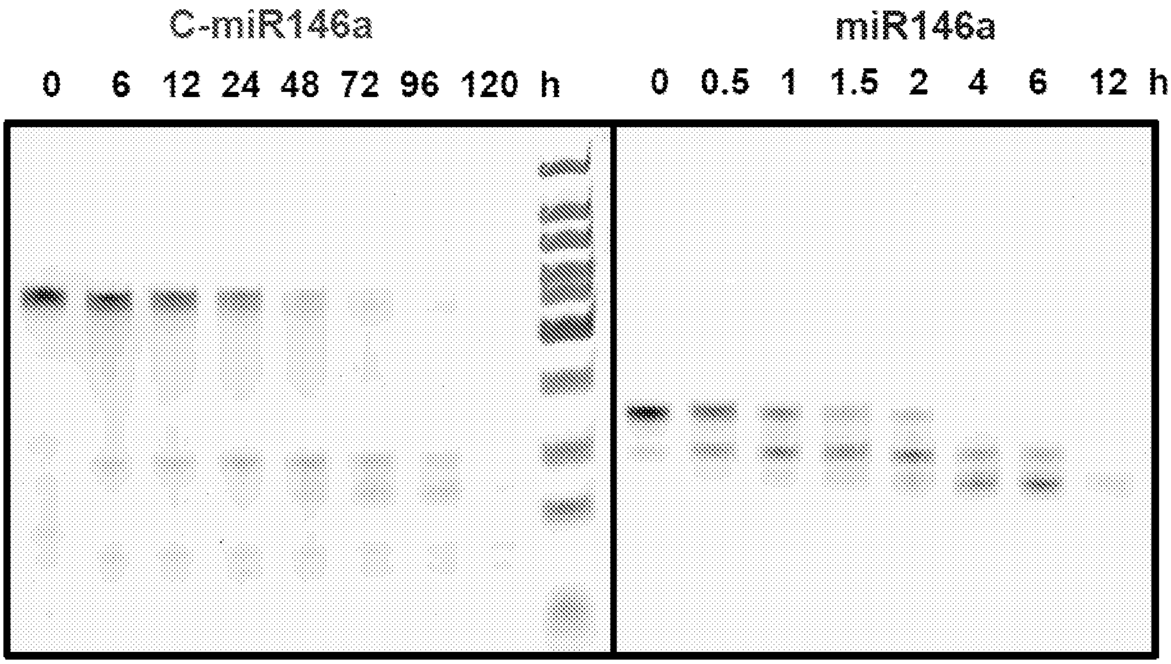

FIG. 7 shows the uncropped, representative gel images corresponding to data in FIG. 1B.

Figure 8:
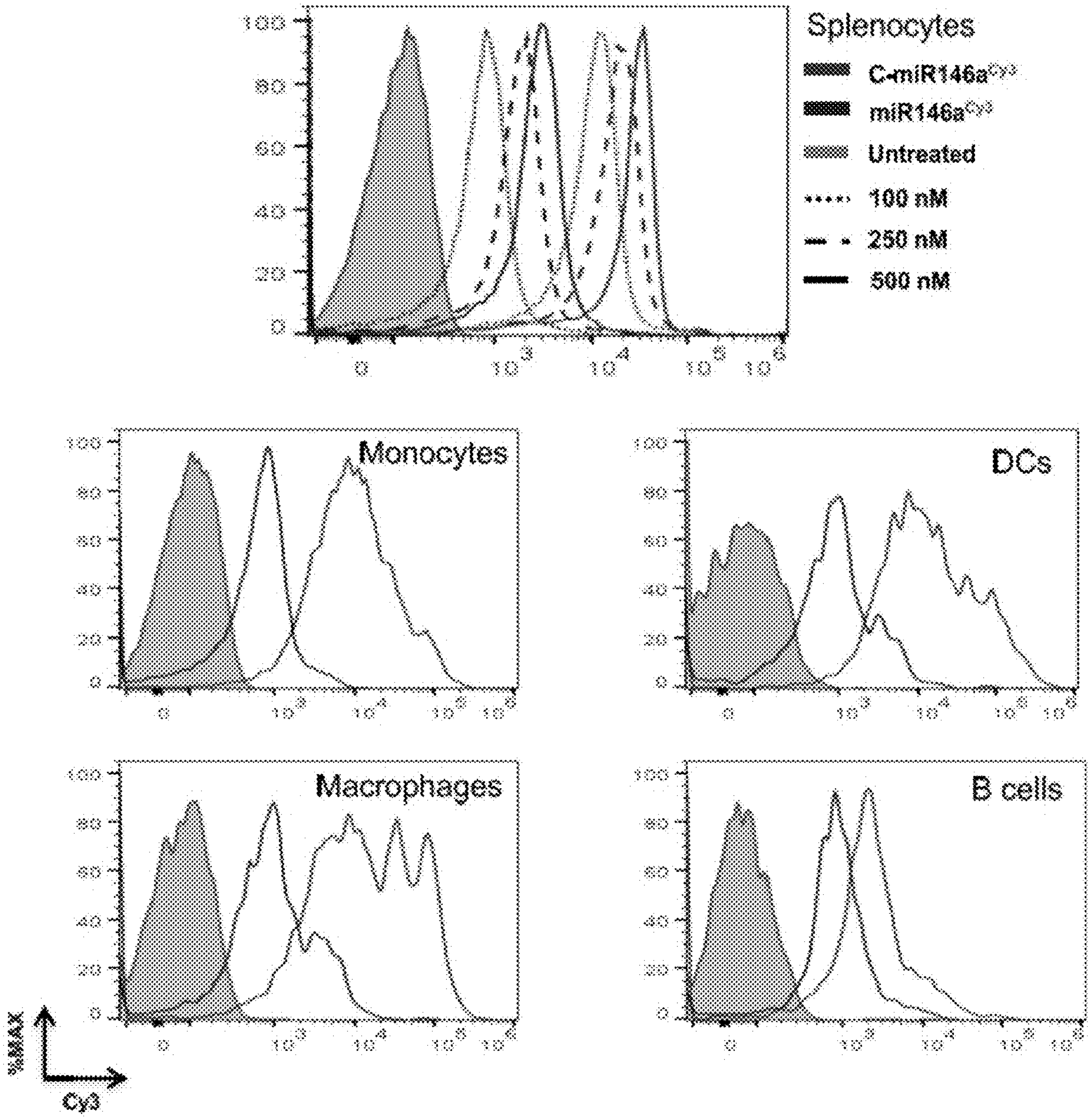

FIG. 8 shows dose-dependent internalization of C-miR146a$^{Cy3}$ by mouse immune cells in vitro. Mouse splenocytes were incubated with the indicated concentrations of C-miR146a$^{Cy3}$ or miR146a$^{Cy3}$ for 1 h, the uptake of the oligonucleotides by monocytes ($CD11b^+CD11c^-$), macrophages ($CD11b^-CD11c^+$), DCs ($CD11b^+CD11c^+$), and B cells ($CD19^+$) were assessed using flow cytometry.

Figure 9:
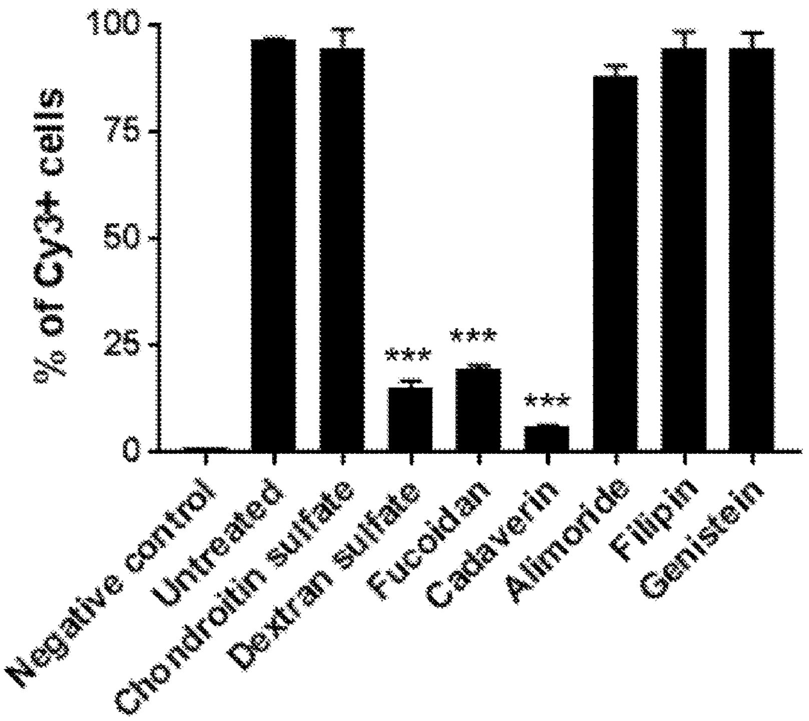

FIG. 9 shows the intracellular uptake of C-miR146a is mediated via scavenger receptor- and clathrin-mediated endocytosis. RAW264.7 cells were incubated with indicated inhibitors of various endocytosis pathways for 1 h and then incubated with 100 nM C-miR146a$^{Cy3}$ for another hour. The percentage of $Cy3^+$ cells was assessed using flow cytometry. Data represented results obtained in three independent experiments, and the quantification results were shown as mean±SEM.

Figure 10A:
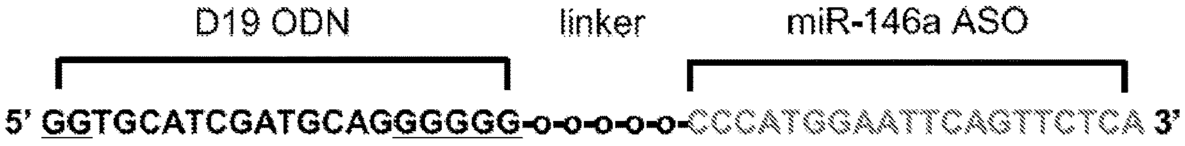

FIGS. 10A-10F shows targeted delivery of anti-miR146a using SR/TLR9 targeted strategy augments NF-KB signaling. FIG. 10A: The design and chemical modifications of C-anti-miR146a oligonucleotide, wherein D19 ODN is SEQ ID NO:9, miR-146a ASO is SEQ ID NO:47, and each "o" in the linking group is:

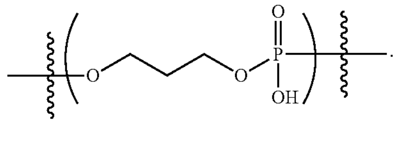

Figure 10B:
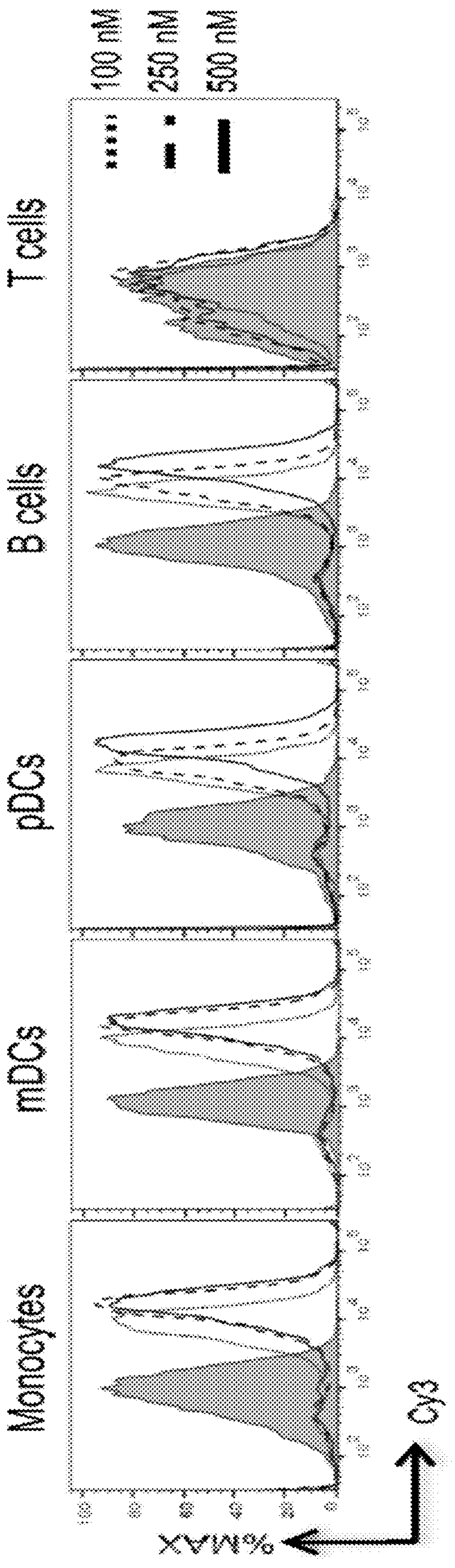
Figure 10C:
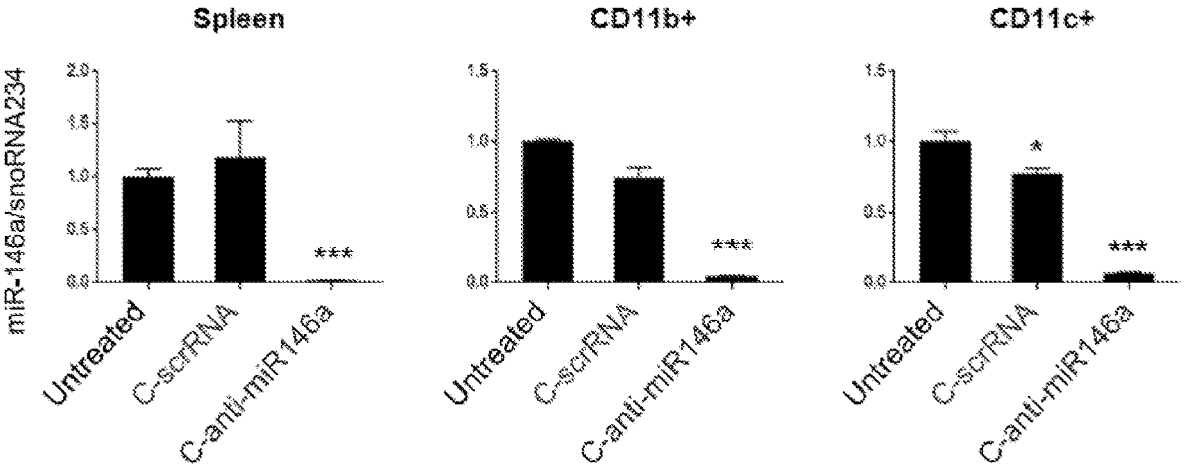
Figure 10D:
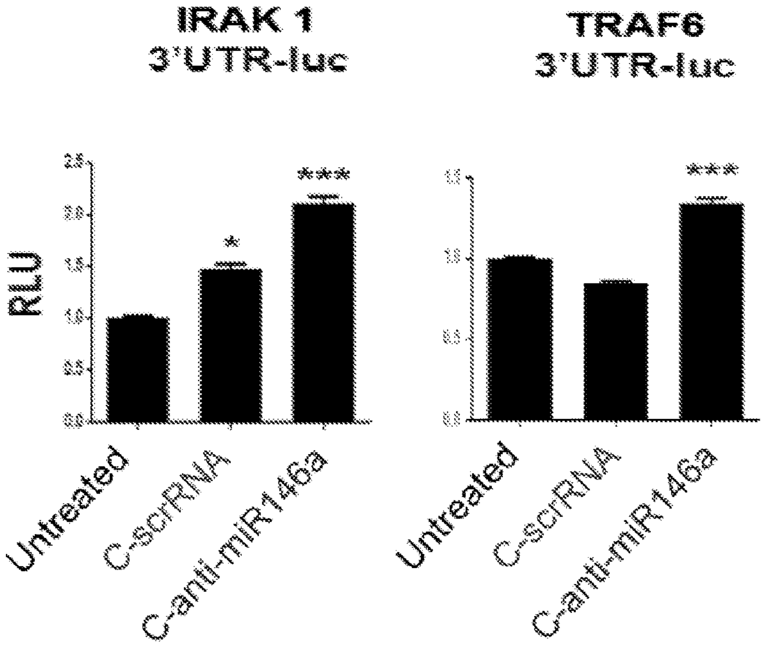
Figure 10E:
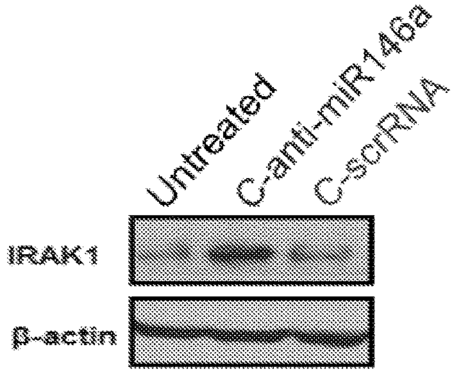
Figure 10F:
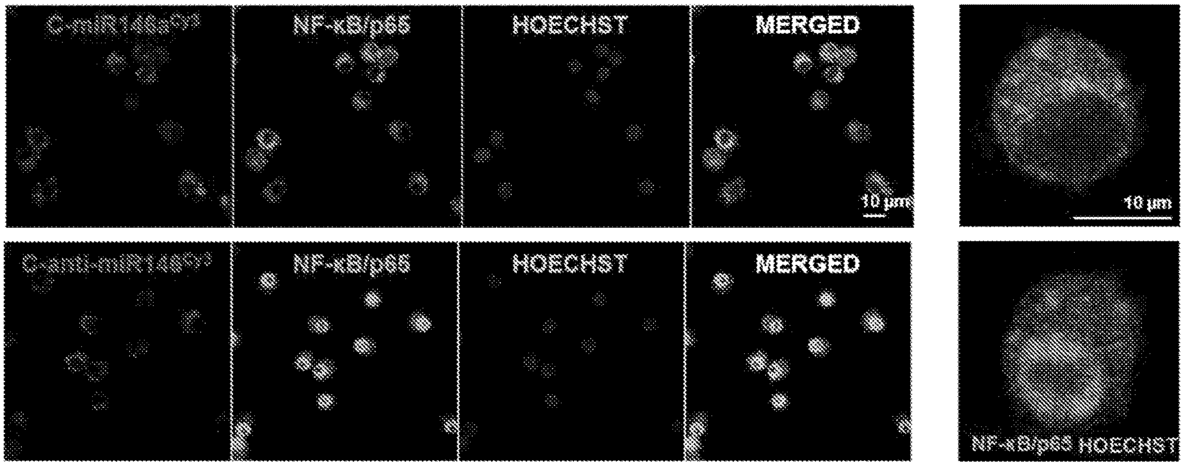

FIG. 10B: The dose-dependent uptake of C-anti-miR146a$^{Cy3}$ by various human immune cells. FIG. 10C: Splenocytes were isolated from C57BL/6 mice and purified $CD11b^+$ and $CD11c^+$ cells were incubated with 500 nM C-anti-miR146a or C-scrRNA for 16 h. miR146a levels were assessed using qPCR. FIG. 10D: HEK293T cells transfected with IRAK1 or TRAF6 3'-UTR luciferase reporter plasmid together with *Renilla*-luciferase plasmid were incubated with 500 nM C-anti-miR146a or C-scrRNA for 48 h. Target gene expression levels were evaluated by measuring dual-luciferase activities. FIG. 10E: Protein expression levels of IRAK1 in RAW264.7 cells were assessed using Western blot after 48 h incubation with 500 nM C-scrRNA or C-anti-miR146a. FIG. 10F: RAW264.7 cells stably expressing p65-eGFP fusion protein were incubated overnight with 500 nM Cy3-labeled C-miR146a mimic or C-anti-miR146a and then stimulated for 4 h with 100 ng/mL LPS. Translocation of NF-κB/p65 (green) into nuclei (blue) was visualized using confocal microscopy. Shown are representative results obtained from three independent experiments.

Figure 11A:
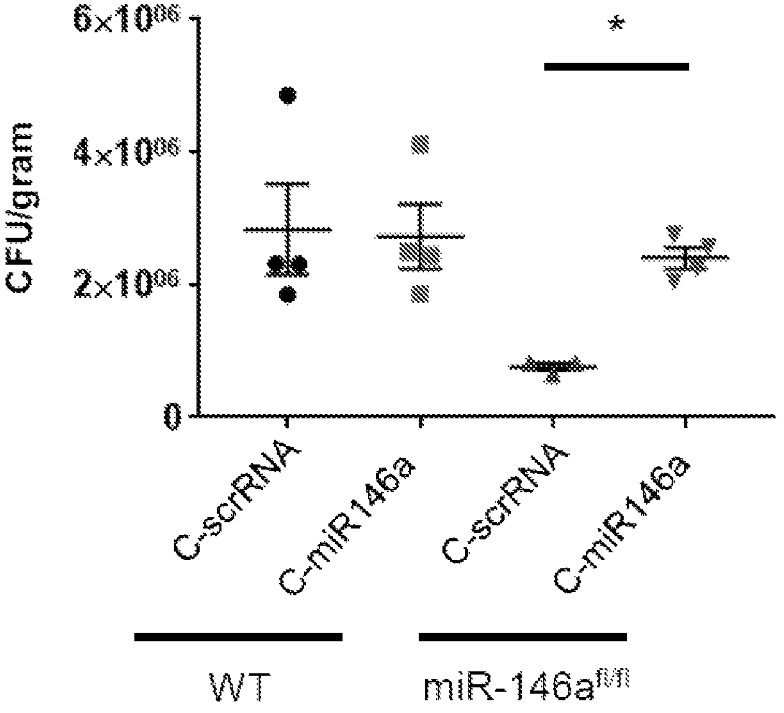
Figure 11B:
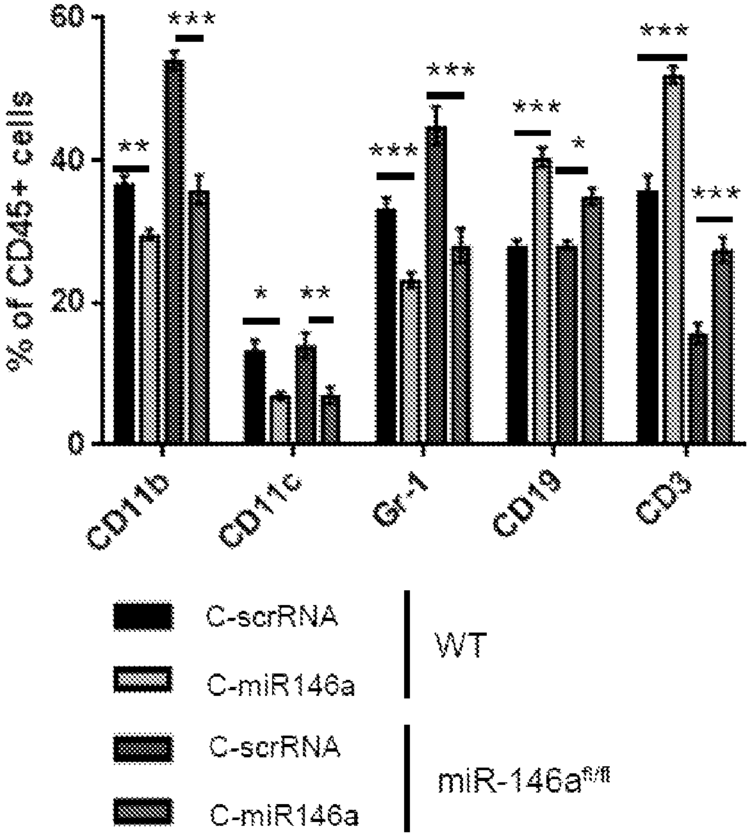

FIGS. 11A-11B show that C-miR146a reduced the antibacterial responses to *Listeria* infection in miR146a$^{fl/fl}$ mice. WT or miR146a$^{fl/fl}$ mice were injected IV with 5 mg/kg C-miR146a or C-scrRNA every day for 6 days. Mice were infected with *Listeria monocytogenes* on day 3 and euthanized on day 6. Spleens were collected to analyze bacterial load and to profile immune cell populations. All data shown were representative of the results obtained in at least two independent experiments using 5 mice per group, and the results are presented as means f SEM.

Figure 12A:
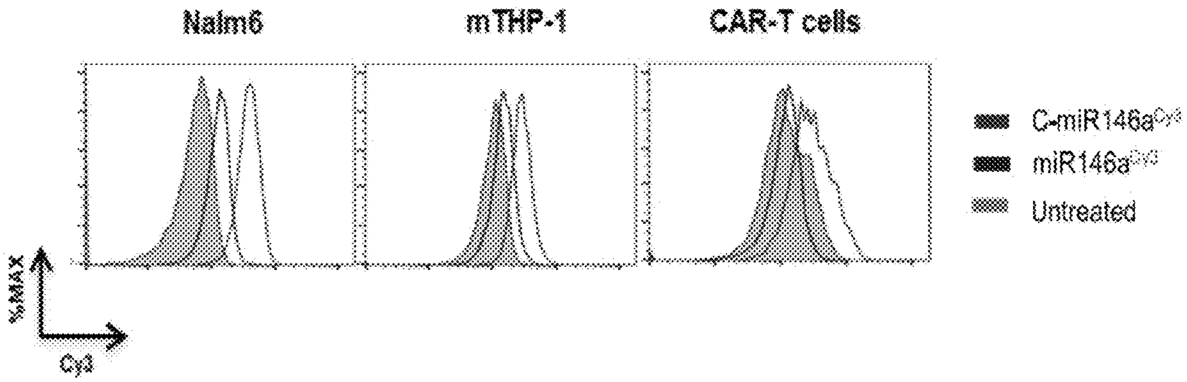
Figure 12B:
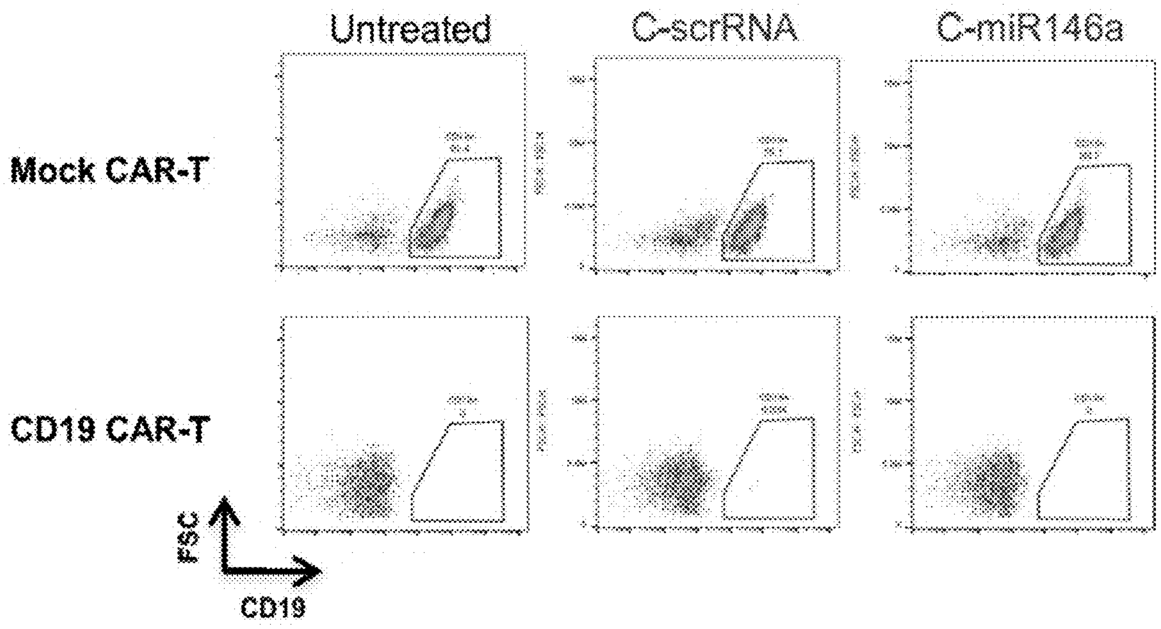
Figure 12C:
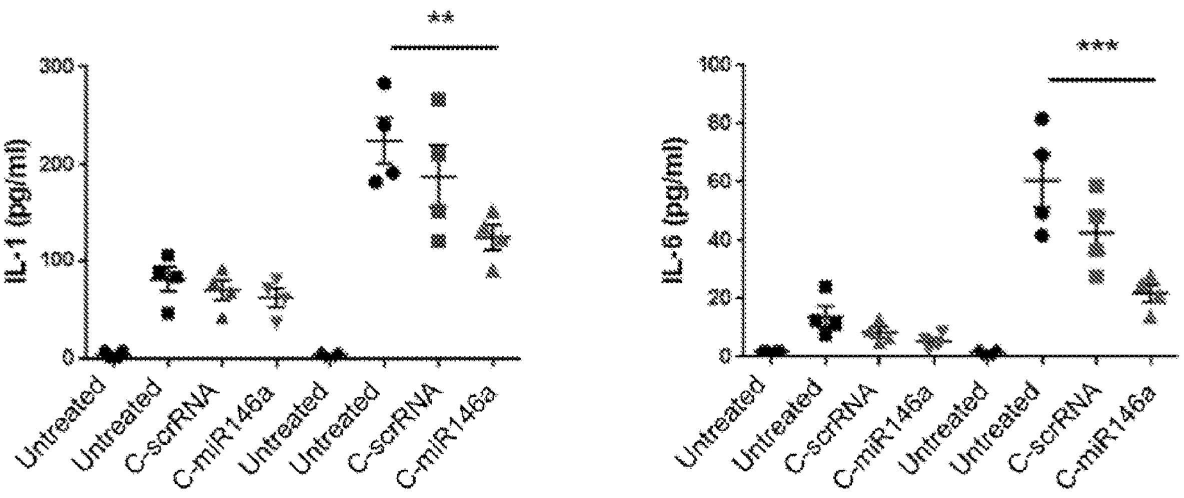

FIGS. 12A-12C show the combination of C-miR146a with CD19 CAR-T abolished CAR-T induced CRS without compromising antitumor efficacy. FIG. 12A: The intracellular uptake of miR146a$^{Cy3}$ or C-miR146a$^{Cy3}$ by Nalm6 leukemia cells, differentiated monocyte-like mTHP-1 cells or CD19 CAR-T cells. Cells were incubated for 1 h with 100 nM miR146a$^{Cy3}$ or C-miR146a$^{Cy3}$, and the percentage of positive cells was measured using flow cytometry. FIG. 12B: Mock or CD19 CAR-T cells were co-cultured for 48 h at a 1:1 effector-to-target ratio with Nalm6 cells in the presence of 500 nM C-miR146a or control C-scrRNA. Percentages of live $CD19^+$ Nalm6 cells were assessed using flow, where the percentages on the top row, left to right, are 81.4, 76,1, and 80.7, and the percentages on the bottom row, left to right, are 0, 0.34, and 0. FIG. 12C: Mock or CD19 CAR-T cells were co-cultured with Nalm6 cells with or without mTHP-1 for 48 h at a 1:1:1 ratio. 500 nM C-scrRNA or C-miR146a were added every 24 h. Supernatant were collected and levels of IL-1 and IL-6 were measured using ELISA. Shown are results combined from four different, individual donors; means±SEM.

Figure 13A:
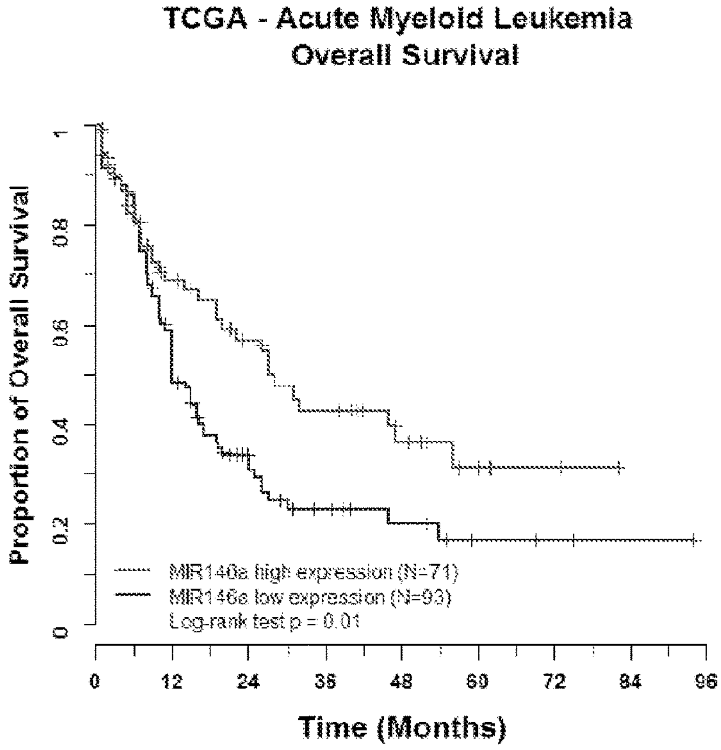
Figure 13B:
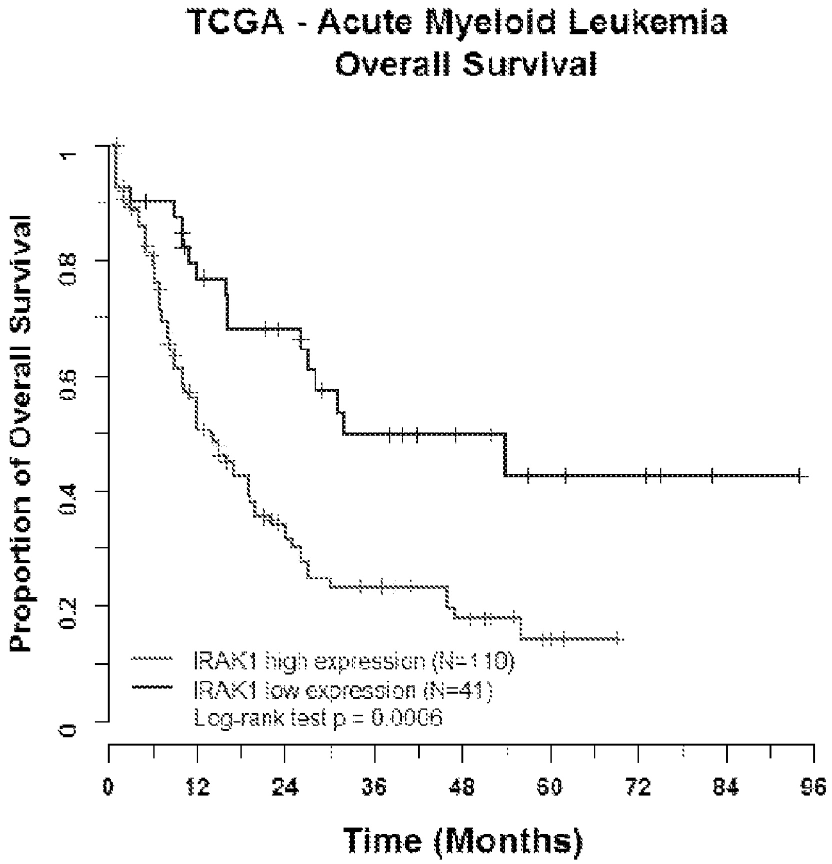

FIGS. 13A-13B show the overall survival analyses with the expression level of miR146a and IRAK1 using TCGA Acute Myeloid Leukemia (LAML) datasets. TCGA level 3 RNA-Seq (Illumina HiSeq) and miRNA-Seq (Illumina GA) gene expression data, along with patient clinical information, were applied to this analysis. Patients having both gene expression and overall survival data were recruited with the exclusion of those having a follow-up time or time-to-death less than or equal to 0 days (n=176 for miRNA-Seq and n=162 for RNA-Seq). Log-rank statistics were applied to identify the optimal cut-point for transforming the continuous variable of gene expression into categorical high and low expression groups in a survfit model. Kaplan-Meier curves are plotted for patient groups based on the expression of miR146a (FIG. 13A) and IRAK1 (FIG. 13B). Log-rank test p-values are shown for each plot.

Figure 14A:
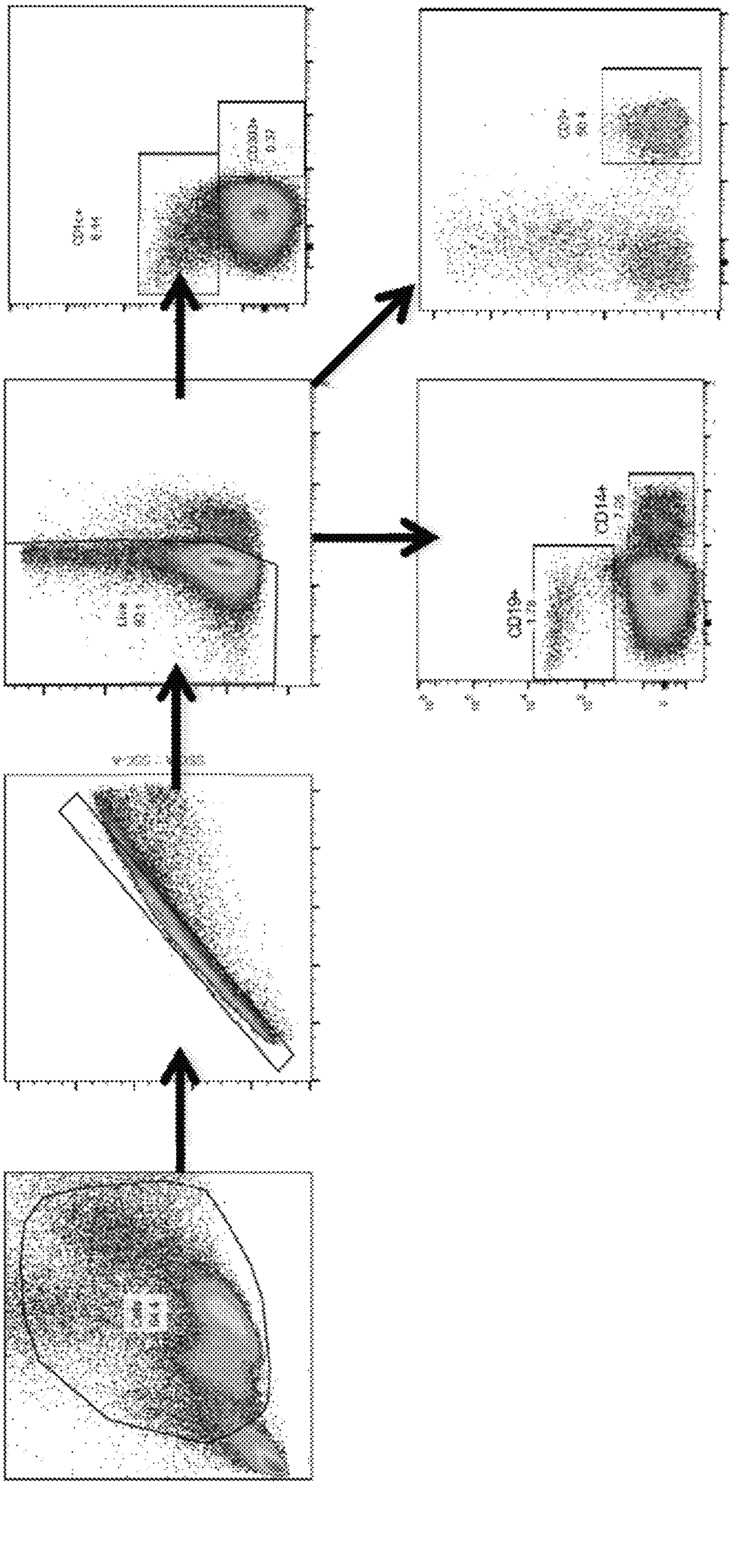
Figure 14B:
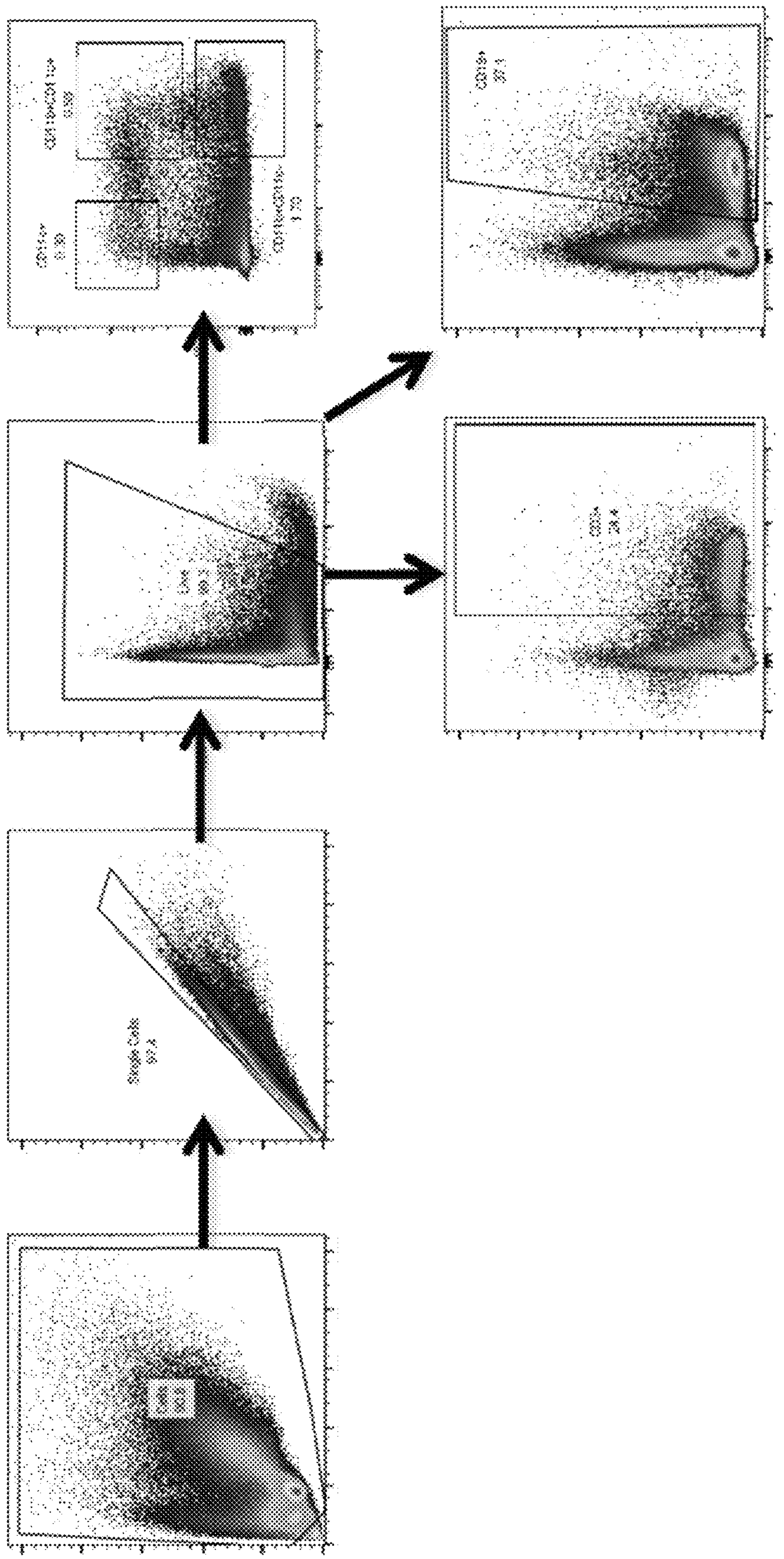

FIGS. 14A-14B show gating strategies for the characterization of immune cell populations. Gating strategies for detection of immune cells among human PBMCs (FIG. 14A), in mouse bone marrow or spleen (FIG. 14B) are indicated.

Figure 15:
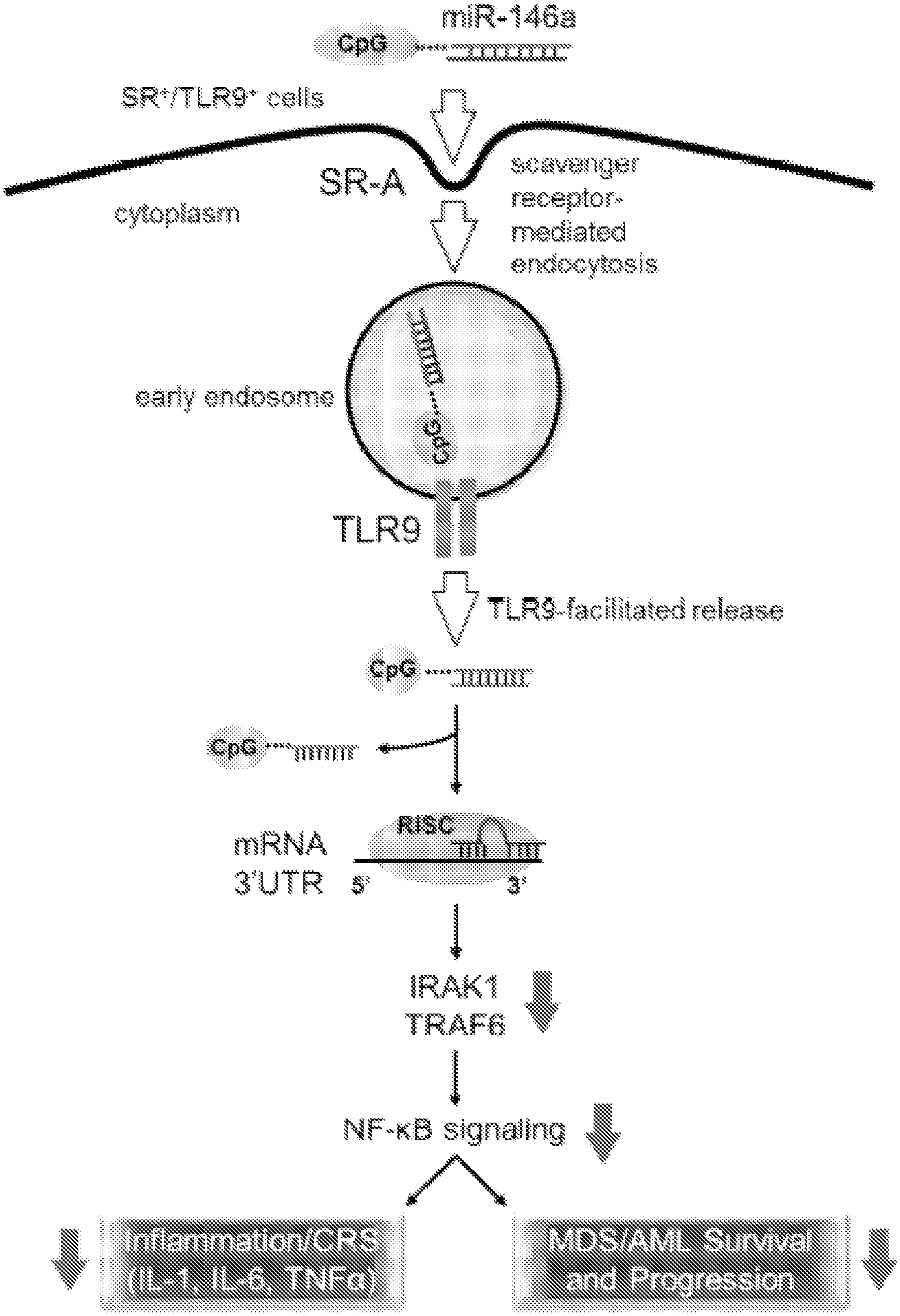

FIG. 15 shows the intracelluar mode of action of C-miR146a. The C-miR146a oligonucleotide is recognized by scavenger receptors on the target cell surface and actively internalized through endocytosis. In early endosomes, C-miR146a triggers TLR9 activation, thereby facilitating the release of C-miR146a into cytoplasm. The C-miR146a becomes incorporated into the RNA-induced silencing complex (RISC) and processed by Argonaute (AGO) proteins. Following unwinding and strand selection, the mature guide strand miR-146a-5p is capable for target recognition through sequence complementarity to IRAK1 and TRAF6 3'UTRs. Downregulation of IRAK1 and TRAF6 results in the inhibition of NF-kB signaling, thereby reducing inflammatory and/or tumorigenic signaling.

Figure 16A:
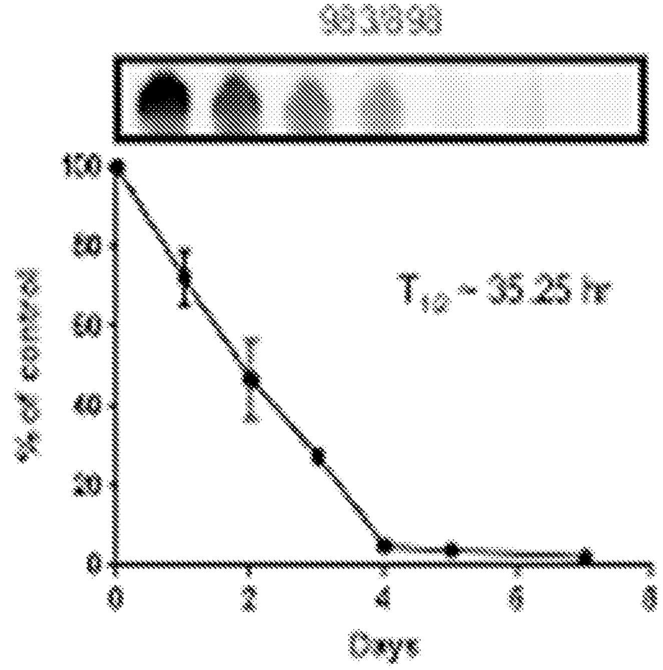
Figure 16B:
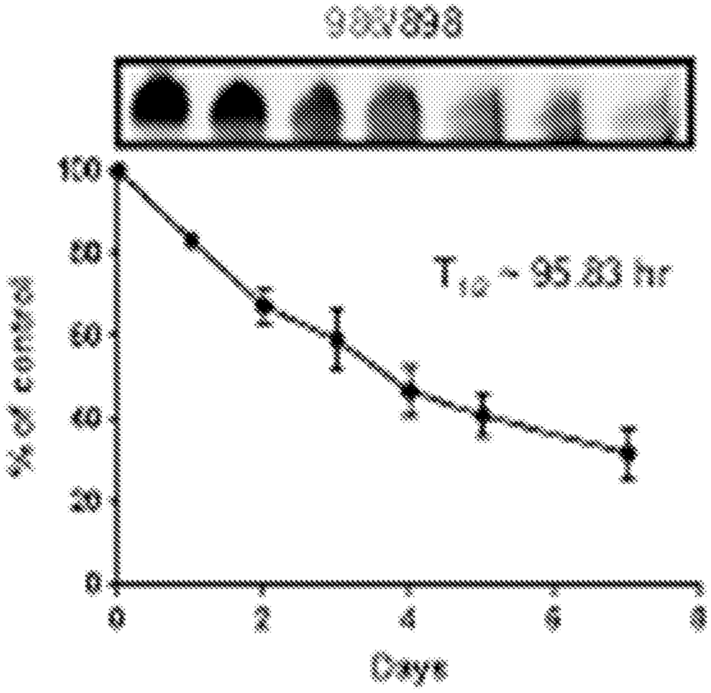
Figure 16C:
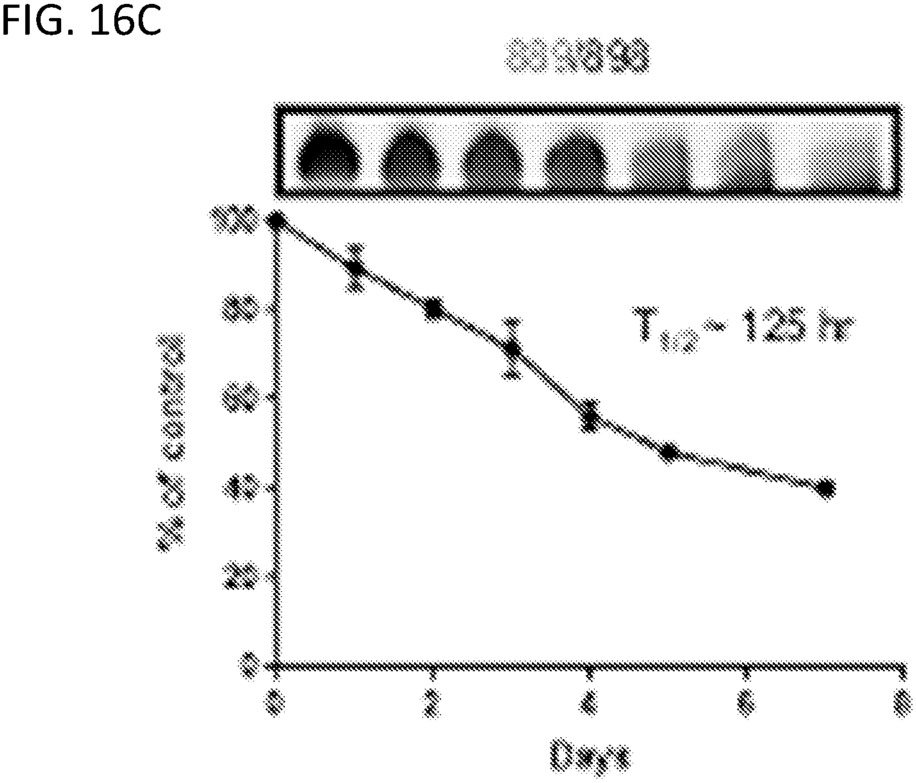
Figure 16D:
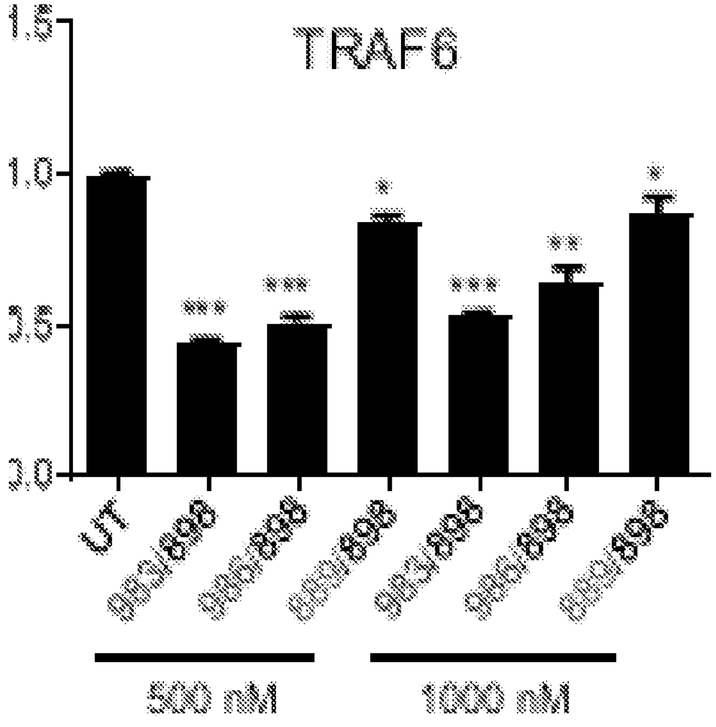
Figure 16E:
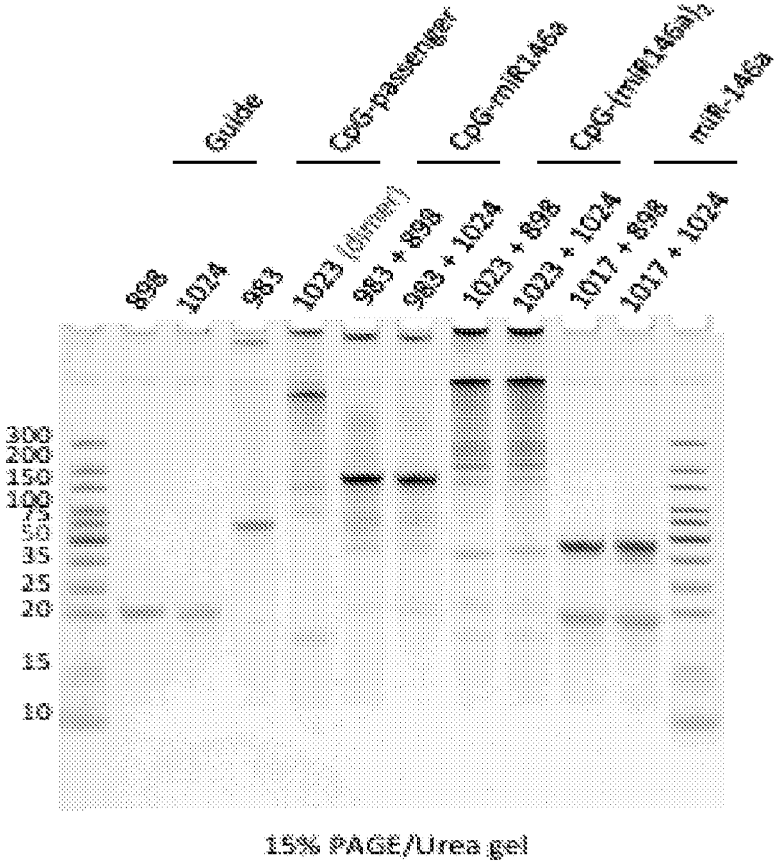

FIGS. 16A-16E show the activity of C-miR146a mimic conjugates. FIGS. 16A-16C show the stability of C-miR146a variants in human serum. FIG. 16D shows the efficacy of target gene silencing by various C-miR146a mimics. FIG. 16E shows the resolution of C-miR146a variants on 16% PAGE/Urea gel. In FIGS. 16A-16D, "983/898" refers to Compound A, and "986/898" refers to Compound C. In FIG. 16E, "898" refers to SEQ ID NO:7; "1024" refers to SEQ ID NO:8; "983" refers to Compound J; "1023" refers to Compound E; "983+898" refers to Compound A; "1023+1024" refers to Compound G; and "1017+898" refers to SEQ ID NO:2 hybridized to SEQ ID NO:7.

Figure 17A:
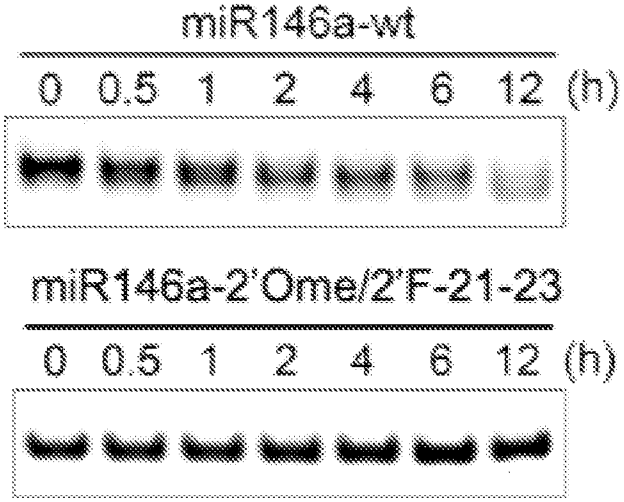
Figure 17B:
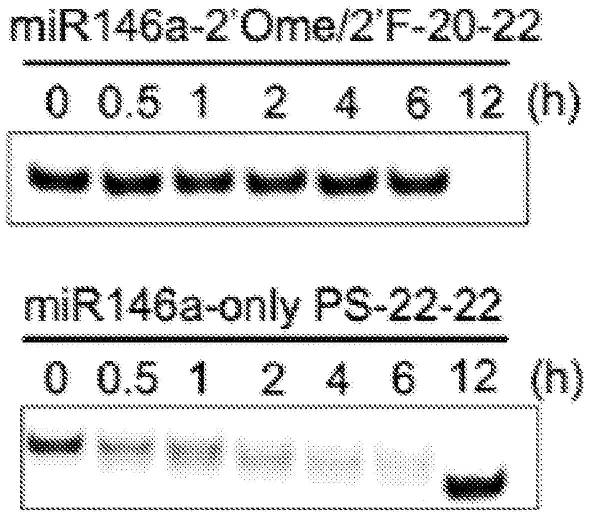

FIGS. 17A-17B show that the 20-22 variant (i.e., SEQ ID NO:38 hybridized to SEQ ID NO:39) and 21-23 variant (SEQ ID NO:36 hybridized to SEQ ID NO:37) of the chemically modified miR146a mimic have improved resistance to human serum nucleases. Extensively (FIG. 17B) or minimally modified (wt) (FIG. 17A) oligonucleotides were incubated in 50% human serum for 24 hours and then resolved on the 15% polyacrylamide gel to assess oligonucleotide stability at 0.5, 1, 2, 4, 6, and 12 hours.

Figure 18A:
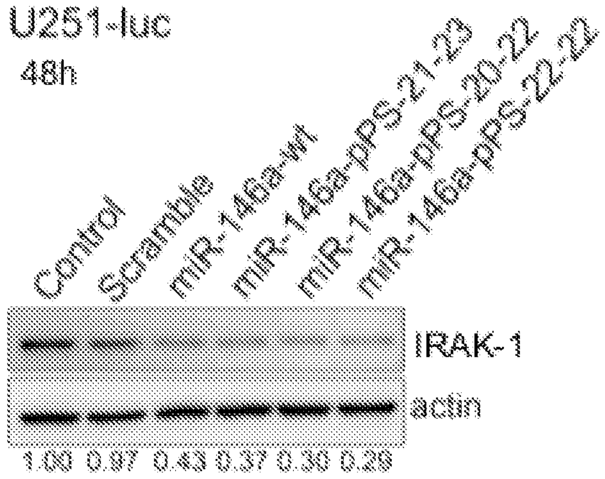
Figure 18B:
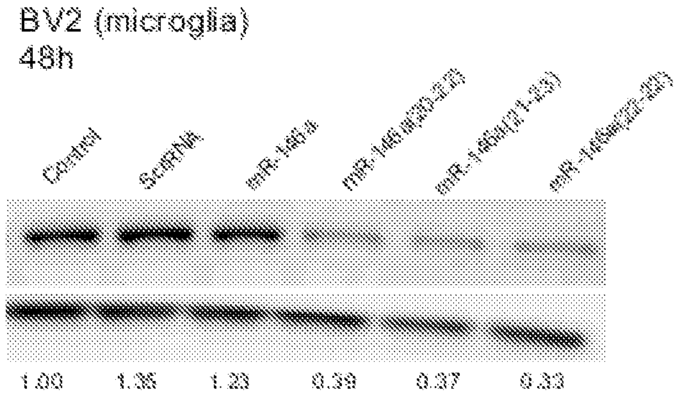

FIGS. 18A-18B show that the 20-22 variant (i.e., SEQ ID NO:38 hybridized to SEQ ID NO:39) and 21-23 variant (SEQ ID NO:36 hybridized to SEQ ID NO:37) of the chemically 2'F-/2'O-methyl-modified miR146a mimic retain activity to reduce protein levels of IRAK1. miR146a mimic oligonucleotides were transfected into U251 glioma cells (FIG. 18A) or BV2 microglial cells (FIG. 18B). Two days later cell were lysed and analyzed using Western blotting for IRAK1 levels and actin used as a loading control.

Figure 19A:
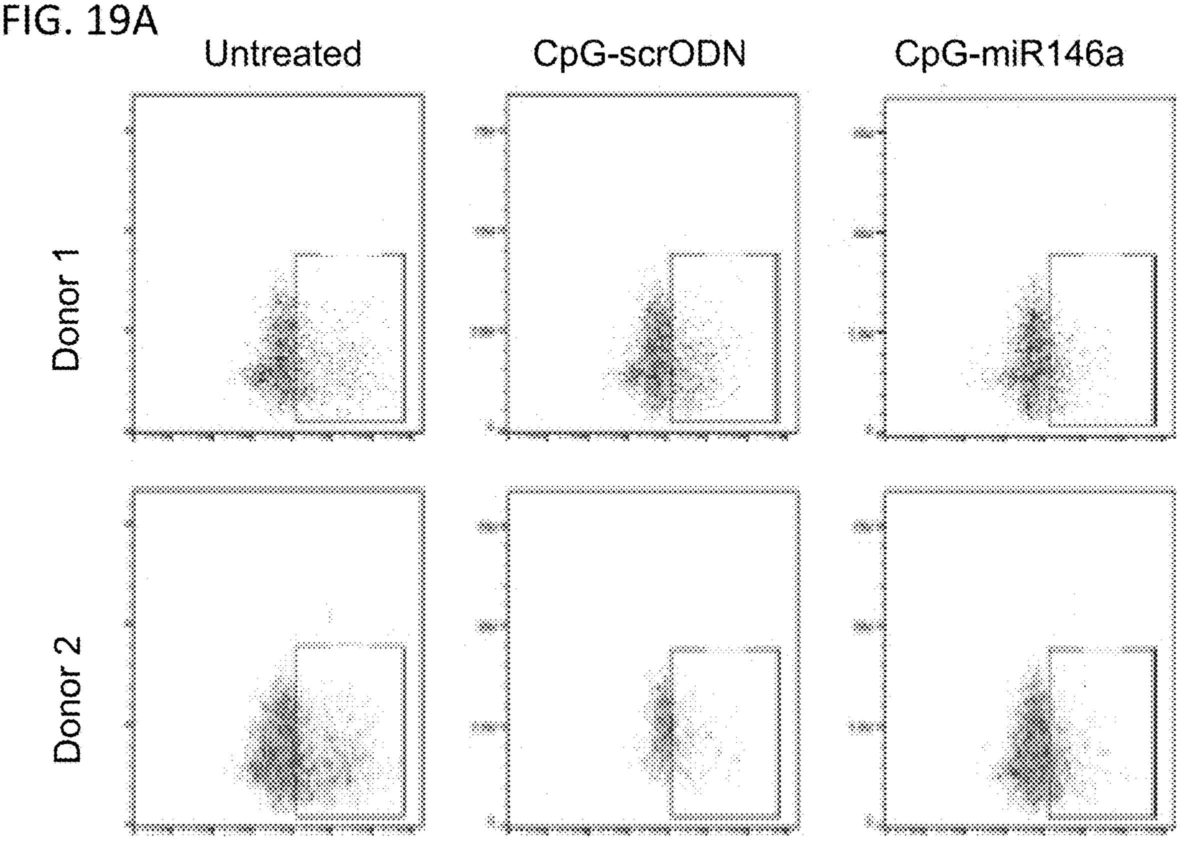
Figure 19B:
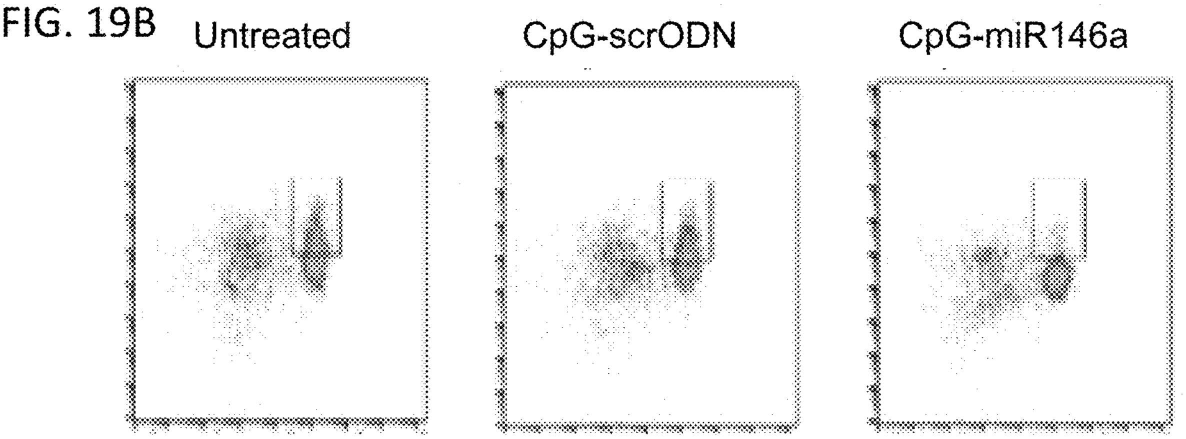

FIGS. 19A-19B show that the CpG-miR146 mimic inhibits NETosis by cultured human PBMCs. Formation of neutrophil extracellular traps (NETs) induced by PMA stimulation in cultured human PBMCs (FIG. 19A) and in the enriched CD15+ neutrophils (FIG. 19B) is inhibited by pre-incubation overnight in 1 μM CpG-miR146a mimic oligonucleotides. Shown are results of flow cytometry using Sytox NETosis assay (Life Technologies). The CpG-scrODN and CpG-miR146a are set forth in the Methods in the Examples section of the disclosure.

Figure 20A:
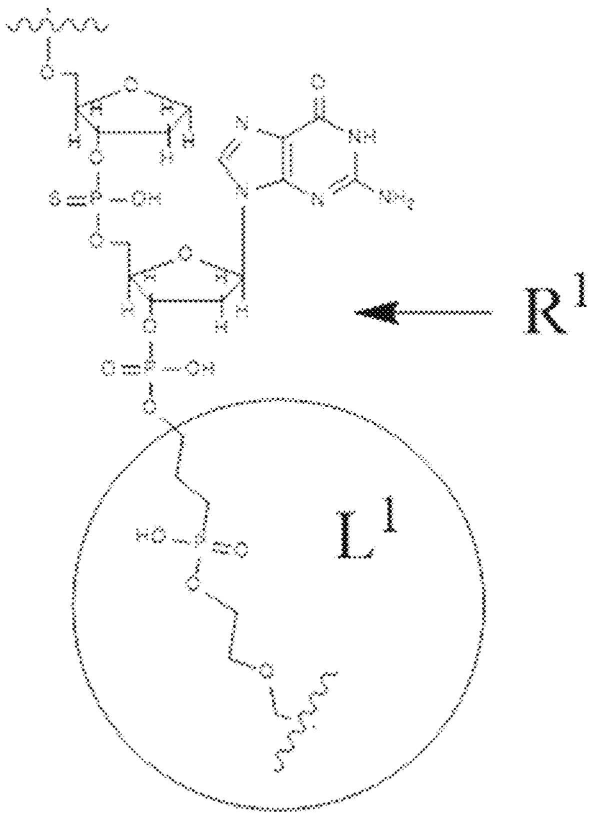
Figure 20B:
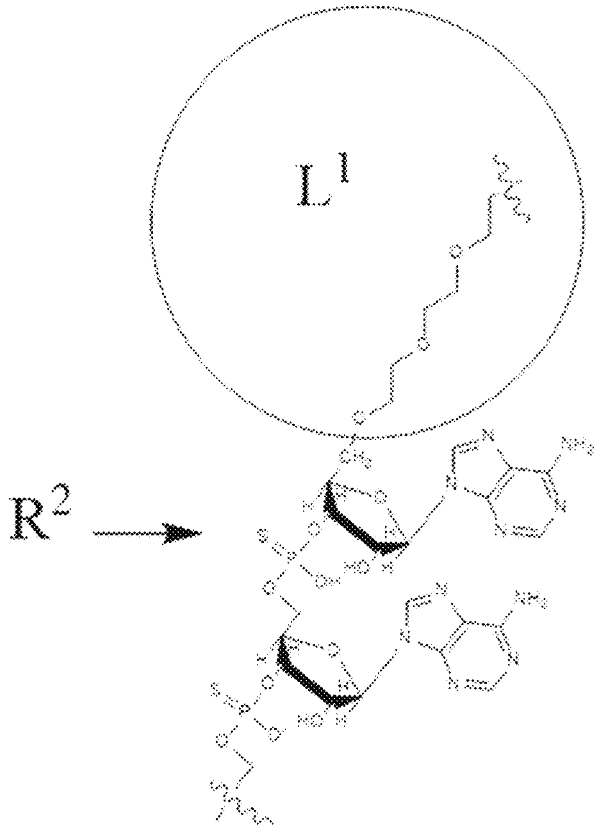

FIGS. 20A-20B are graphics showing the points of attachment of the claimed compounds. FIG. 20A shows the point of attachment between the CpG ODN of $R^1$ and the linking group $L^1$. FIG. 20B shows the point of attachment between the linking group $L^1$ and the nucleotide on the miR146a passenger strand sequence of $R^2$.

DETAILED DESCRIPTION

Definitions

Unless defined otherwise, technical and scientific terms used herein have the same meaning as commonly understood by a person of ordinary skill in the art. See, e.g., Singleton et al., Dictionary of Microbiology and Molecular Biology, 2nd ed., J. Wiley & Sons (New York, NY 1994); Sambrook et al., Molecular Cloning, A Laboratory Manual, Cold Springs Harbor Press (Cold Springs Harbor, N Y 1989). Any methods, devices and materials similar or equivalent to those described herein can be used in the practice of this disclosure. The following definitions are provided to facilitate understanding of certain terms used frequently herein and are not meant to limit the scope of the present disclosure.

A "microRNA," "microRNA nucleic acid sequence," "miR," "miRNA" as used herein, refers to a nucleic acid that functions in RNA silencing and post-transcriptional regulation of gene expression. The term includes all forms of a miRNA, such as the pri-, pre-, and mature forms of the miRNA. In embodiments, microRNAs (miRNAs) are short (20-24 nt) non-coding RNAs that are involved in post-transcriptional regulation of gene expression in multicellular organisms by affecting both the stability and translation of mRNAs. miRNAs are transcribed by RNA polymerase II as part of capped and polyadenylated primary transcripts (pri-miRNAs) that can be either protein-coding or non-coding. The primary transcript is cleaved by the Drosha ribonuclease III enzyme to produce an approximately 70-nt stem-loop precursor miRNA (pre-miRNA), which is further cleaved by the cytoplasmic Dicer ribonuclease to generate the mature miRNA and antisense miRNA star (miRNA*) products. The mature miRNA is incorporated into a RNA-induced silencing complex (RISC), which recognizes target mRNAs through imperfect base pairing with the miRNA and most commonly results in translational inhibition or destabilization of the target mRNA. In embodiments, a miRNA nucleic acid sequence is about 2 to 50 nucleotides in length. In embodiments, a miRNA nucleic acid sequence is about 10 to 30 nucleotides in length. In embodiments, a miRNA nucleic acid sequence is about 15 to 25 nucleotides in length.

The term "microRNA-mimic (miRNA-mimic)" or "miRNA-mimic nucleic acid sequence" is used according to its plain and ordinary meaning and refers to single, double or triple stranded oligonucleotide that is capable of effecting a biological function similar to a microRNA. In embodiments, miRNA-mimic may be non-natural double-stranded miR-like RNA fragments. Such an RNA fragment may be designed to have its 5'-end bearing a partially complementary motif to the selected sequence in the 3'UTR unique to the target gene. Once introduced into cells, this RNA fragment, may mimic an endogenous miRNA, bind specifically to its target gene and produce posttranscriptional repression, more specifically translational inhibition, of the gene. Unlike endogenous miRNAs, miRNA-mimics may act in a gene-specific fashion. In embodiments, the miRNA-mimic is a double stranded oligomer of 10 to 30 bases. In embodiments, the miRNA-mimic is a triple stranded oligomer of 10-30 bases. In embodiments, the miRNA-mimic has a 2'-chemical modification. In embodiments, the miRNA-mimic has serum stability-enhancing chemical modification, e.g., a phosphorothioate internucleotide linkage, a 2'-O-methyl ribonucleotide, a 2'-deoxy-2'-fluoro ribonucleotide, a 2'-deoxy ribonucleotide, a universal base nucleotide, a 5-C methyl nucleotide, an inverted deoxybasic residue incorporation, or a locked nucleic acid.

The term "miR146a" or "miR146 nucleic acid sequence" includes all forms of miR146a including the pri-, pre-, and mature forms of miR146a, as well as variants, homologues, modifications, and derivatives thereof (e.g., within at least 50%, 80%, 90%, 95%, 96%, 97%, 98%, 99% or 100% activity compared to the native miR146a). In embodiments, the variants or homologues or derivatives have at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to a naturally occurring form. In embodiments, the miR146a is the miRNA as identified by NCBI Reference Sequence: NR_029701.1.

The term "miR146a-mimic" or "miR146a-mimic nucleic acid sequence" refers to an oligonucleotide that is structurally substantially similar to miR146a and is capable of effecting a biological function similar to miR146a. In embodiments, the miR146a-mimic has at least 50%, 80%, 90%, 95%, 96%, 97%, 98%, 99% or 100% activity compared to the native miR146a. In embodiments, the miR146a-mimic has at least 50%, 80%, 85%, 90%, 91%, 92%, 93%, 94%, 95%, 96%, 97%, 98%, 99% or 100% sequence identity across the whole sequence or a portion of the sequence compared to native miR146a.

As used herein, the term "miR155" or "miR155 nucleic acid sequence" includes all forms of miR155 including the pri-, pre-, and mature forms of miR155, as well as variants, homologues, modifications, and derivatives thereof (e.g., within at least 50%, 80%, 90%, 95%, 96%, 97%, 98%, 99% or 100% activity compared to the native miR155). In embodiments, the variants or homologues or derivatives have at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to a naturally occurring form. In embodiments, the miR155 is the miRNA as identified by NCBI Reference Sequence: NR_030784.1.

The term "miR155-mimic" or "miR155-mimic nucleic acid sequence" refers to an oligonucleotide that is structurally substantially similar to miR155 and is capable of effecting a biological function similar to miR155. In embodiments, the miR155-mimic has at least 50%, 80%, 90%, 95%, 96%, 97%, 98%, 99% or 100% activity compared to the native miR155. In embodiments, the miR155-mimic has at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to native miR155.

As used herein, the term "miR142" or "miR142 nucleic acid sequence" includes all forms of miR142 including the pri-, pre-, and mature forms of miR142, as well as variants, homologues, modifications, and derivatives thereof (e.g., within at least 50%, 80%, 90%, 95%, 96%, 97%, 98%, 99% or 100% activity compared to the native miR142). In embodiments, the variants or homologues or derivatives have at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to a naturally occurring form. In embodiments, the miR142 is the miRNA as identified by NCBI Reference Sequence: NR_029683.1.

As used herein, the term "miR142-mimic" or "miR142-mimic nucleic acid sequence" refers to an oligonucleotide that is structurally substantially similar to miR142 and is capable of effecting a biological function similar to miR142. In embodiments, the miR142-mimic has at least 50%, 80%, 90%, 95%, 96%, 97%, 98%, 99% or 100% activity compared to the native miR142. In embodiments, the miR142-mimic has at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to native miR142.

As used herein, the term "miR125b" or "miR125b nucleic acid sequence" includes all forms of miR125b including the pri-, pre-, and mature forms of miR125b, as well as variants, homologues, modifications, and derivatives thereof (e.g., within at least 50%, 80%, 90%, 95%, 96%, 97%, 98%, 99% or 100% activity compared to the native miR125b). In embodiments, the variants or homologues or derivatives have at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to a naturally occurring form. In embodiments, the miR125b is the miRNA as identified by NCBI Reference Sequence: NR_029671.1 or sequence.

As used herein, the term "miR125b-mimic" or "miR125b-mimic nucleic acid sequence" refers to an oligonucleotide that is structurally substantially similar to miR125b and is capable of effecting a biological function similar to miR125b. In embodiments, the miR125b-mimic has at least 50%, 80%, 90%, 95%, 96%, 97%, 98%, 99% or 100% activity compared to the native miR125b. In embodiments, the miR125b-mimic has at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to native miR125b.

As used herein, the term "miR203b" or "miR203b nucleic acid sequence" includes all forms of miR203b including the pri-, pre-, and mature forms of miR125b, as well as variants, homologues, modifications, and derivatives thereof (e.g., within at least 50%, 80%, 90%, 95%, 96%, 97%, 98%, 99% or 100% activity compared to the native miR203b). In embodiments, the variants or homologues or derivatives have at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to a naturally occurring form.

As used herein, the term "miR203b-mimic" or "miR203b-mimic nucleic acid sequence" refers to an oligonucleotide that is structurally substantially similar to miR203b and is capable of effecting a biological function similar to miR203b. In embodiments, the miR203b-mimic has at least 50%, 80%, 90%, 95%, 96%, 97%, 98%, 99% or 100% activity compared to the native miR203b. In embodiments, the miR203b-mimic has at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to native miR203b.

As used herein, the term "miR221" or "miR221 nucleic acid sequence" includes all forms of miR22 including the pri-, pre-, and mature forms of miR221, as well as variants, homologues, modifications, and derivatives thereof (e.g., within at least 50%, 80%, 90%, 95%, 96%, 97%, 98%, 99% or 100% activity compared to the native miR221). In embodiments, the variants or homologues or derivatives have at least 50%, 80%, 85%, 90%, 91%, 92%, 93%, 94%, 95%, 96%, 97%, 98%, 99% or 100% sequence identity across the whole sequence or a portion of the sequence (e.g.

a 10, 15, 20, 25, 30, 40, 45, 50, 55, 60, 65, 70, 75, or 80 continuous nucleotides portion) compared to a naturally occurring form.

As used herein, the term "miR221-mimic" or "miR221-mimic nucleic acid sequence" refers to an oligonucleotide that is structurally substantially similar to miR221 and is capable of effecting a biological function similar to miR221. In embodiments, the miR221-mimic has at least 50%, 80%, 90%, 95%, 96%, 97%, 98%, 99% or 100% activity compared to the native miR221. In embodiments, the miR221-mimic has at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to native miR221.

As used herein, the term "miR222" or "miR222 nucleic acid sequence" includes all forms of miR222 including the pri-, pre-, and mature forms of miR222, as well as variants, homologues, modifications, and derivatives thereof (e.g., within at least 50%, 80%, 90%, 95%, 96%, 97%, 98%, 99% or 100% activity compared to the native miR222). In embodiments, the variants or homologues or derivatives have at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to a naturally occurring form.

As used herein, the term "miR222-mimic" or "miR222-mimic nucleic acid sequence" refers to an oligonucleotide that is structurally substantially similar to miR222 and is capable of effecting a biological function similar to miR222. In embodiments, the miR222-mimic has at least 50%, 80%, 90%, 95%, 96%, 97%, 98%, 99% or 100% activity compared to the native miR222. In embodiments, the miR222-mimic has at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to native miR222.

As used herein, the term "miR29b" or "miR29b nucleic acid sequence" includes all forms of miR29b including the pri-, pre-, and mature forms of miR29b, as well as variants, homologues, modifications, and derivatives thereof (e.g., within at least 50%, 80%, 90%, 95%, 96%, 97%, 98%, 99% or 100% activity compared to the native miR29b). In embodiments, the variants or homologues or derivatives have at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to a naturally occurring form.

As used herein, the term "miR29b-mimic" or "miR29b-mimic nucleic acid sequence" refers to an oligonucleotide that is structurally substantially similar to miR29b and is capable of effecting a biological function similar to miR29b. In embodiments, the miR29b-mimic has at least 50%, 80%, 90%, 95%, 96%, 97%, 98%, 99% or 100% activity compared to the native miR29b. In embodiments, the miR29b-mimic has at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to native miR29b.

The term "phosphorothioated miRNA" and "phosphorothioated miRNA-mimic" refers to a nucleic acid sequence in which one or more of the internucleotide linkages constitute a phosphorothioate linkage. In embodiments, a phosphorothioated miRNA is 5 to 30 bases long, single-stranded, partly, or completely phosphorothioated. In embodiments, phosphorothioated miRNA is 10 to 30 bases long, single-stranded, partly or completely phosphorothioated. In embodiments, phosphorothioated miRNA is 15 to 25 bases long, single-stranded, partly or completely phosphorothioated. In embodiments, the phosphorothioated miRNA is a miRNA in which 1, 2, 3, 4, 5, 6, 7, 8, 9, 10, 11, 12, 13, 14, 15, 16, 17, 18, 19, 20, 21, 22, 23, 24, 25, 26, 27, or 28, internucleotide linkages constitute a phosphorothioate linkage. In embodiments, the phosphorothioated miRNA is a miRNA in which 1 to 10 internucleotide linkages constitute a phosphorothioate linkage. In embodiments, the phosphorothioated miRNA is a miRNA in which 1 to 5 internucleotide linkages constitute a phosphorothioate linkage. In embodiments, the phosphorothioated miRNA is a miRNA in which 1 or 2 internucleotide linkages constitute a phosphorothioate linkage. In embodiments, the phosphorothioated miRNA is a miRNA in which all the internucleotide linkages constitute a phosphorothioate linkage. In embodiments, the 3'terminal nucleic acid in the phosphorothioated miRNA is a phosphorothioated nucleotide, which is encompassed by the term "phosphorothioate linkage."

The term "Toll-like receptor 9" or "TLR9" refers to any of the recombinant or naturally-occurring forms of the TLR9 protein or variants or homologs thereof that maintain TLR9 protein activity (e.g. within at least 50%, 80%, 90%, 95%, 96%, 97%, 98%, 99% or 100% activity compared to the TLR9 receptor). In embodiments, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring TLR9 receptor polypeptide. In embodiments, the TLR9 receptor protein is substantially identical to or identical to the protein identified by UniProtKB reference number Q9NR96, or a variant or homolog having substantial identity thereto.

A "toll-like receptor 9-binding nucleic acid sequence" refers to a nucleic acid capable of binding to toll like receptor 9. Exemplary nucleic acids include CpG oligodeoxynucleotides.

The term "CpG oligodeoxynucleotide" or "CpG ODN" refers to a 5' C nucleotide connected to a 3' G nucleotide through a phosphodiester internucleotide linkage or a phosphodiester derivative internucleotide linkage. In embodiments, a CpG ODN includes a phosphodiester internucleotide linkage. In embodiments, a CpG ODN includes a phosphodiester derivative internucleotide linkage.

The term "phosphorothioated oligodeoxynucleotide (ODN)" refers to a nucleic acid sequence, e.g., "CpG nucleic acid sequence" or "GpC nucleic acid sequence" in which one, some, or all the internucleotide linkages constitute a phosphorothioate linkage. In embodiments, phosphorothioated oligodeoxynucleotide (ODN) is 5 to 30 bases long, single-stranded, partly or completely phosphorothioated. The partly phosphorothioated ODN is an ODN in which 1, 2, 3, 4, 5, 6, 7, 8, 9, 10, 11, 12, 13, 14, 15, 16, 17, 18, 19, 20, 21, 22, 23, 24, 25, 26, 27, or 28, internucleotide linkages constitute a phosphorothioate linkage.

The term "Class A CpG ODN" or "A-class CpG ODN" or "D-type CpG ODN" or "Class A CpG DNA sequence" refers to a CpG motif including oligodeoxynucleotide including one or more of poly-G sequence at the 5', 3', or both ends; an internal palindrome sequence including CpG motif; or one or more phosphodiester derivatives linking deoxynucleotides. In embodiments, a Class A CpG ODN includes poly-G sequence at the 5', 3', or both ends; an internal palindrome sequence including CpG motif; and one or more phosphodiester derivatives linking deoxynucleotides. In embodiments, the phosphodiester derivative is phosphorothioate Examples of Class A CpG ODNs include ODN D19, ODN 1585, ODN 2216, and ODN 2336, the sequences of which are known in the art.

The term "Class B CpG ODN" or "B-class CpG ODN" or "K-type CpG ODN" or "Class B CpG DNA sequence" refers to a CpG motif including oligodeoxynucleotide including one or more of a 6mer motif including a CpG motif; phosphodiester derivatives linking all deoxynucleotides. In embodiments, a Class B CpG ODN includes one or more copies of a 6mer motif including a CpG motif and phosphodiester derivatives linking all deoxynucleotides. In embodiments, the phosphodiester derivative is phosphorothioate. In embodiments, a Class B CpG ODN includes one 6mer motif including a CpG motif. In embodiments, a Class B CpG ODN includes two copies of a 6mer motif including a CpG motif. In embodiments, a Class B CpG ODN includes three copies of a 6mer motif including a CpG motif. In embodiments, a Class B CpG ODN includes four copies of a 6mer motif including a CpG motif. Examples of Class B CpG ODNs include ODN 1668, ODN 1826, ODN 2006, ODN 2007, ODN BW006, and ODN D-SL01, the sequences of which are known in the art.

The term "Class C CpG ODN" or "C-class CpG ODN"" or "C-type CpG DNA sequence" refers to an oligodeoxynucleotide including a palindrome sequence including a CpG motif and phosphodiester derivatives (phosphorothioate) linking all deoxynucleotides. Examples of Class C CpG ODNs include ODN 2395, ODN M362, and ODN D-SL03, the sequences of which are known in the art.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences.

An "antisense nucleic acid" as referred to herein is a nucleic acid (e.g., DNA or RNA molecule) that is complementary to at least a portion of a specific target nucleic acid and is capable of reducing transcription of the target nucleic acid (e.g. mRNA from DNA), reducing the translation of the target nucleic acid (e.g. mRNA), altering transcript splicing (e.g. single stranded morpholino oligo), or interfering with the endogenous activity of the target nucleic acid. See, e.g., Weintraub, Scientific American, 262:40 (1990). Typically, synthetic antisense nucleic acids (e.g. oligonucleotides) are generally between 15 and 25 bases in length. Thus, antisense nucleic acids are capable of hybridizing to (e.g. selectively hybridizing to) a target nucleic acid. In embodiments, the antisense nucleic acid hybridizes to the target nucleic acid in vitro. In embodiments, the antisense nucleic acid hybridizes to the target nucleic acid in a cell. In embodiments, the antisense nucleic acid hybridizes to the target nucleic acid in an organism. In embodiments, the antisense nucleic acid hybridizes to the target nucleic acid under physiological conditions. Antisense nucleic acids may comprise naturally occurring nucleotides or modified nucleotides such as, e.g., phosphorothioate, methylphosphonate, and anomeric sugar-phosphate, backbone-modified nucleotides.

In the cell, the antisense nucleic acids hybridize to the corresponding RNA forming a double-stranded molecule. The antisense nucleic acids interfere with the endogenous behavior of the RNA and inhibit its function relative to the absence of the antisense nucleic acid. Furthermore, the double-stranded molecule may be degraded via the RNAi pathway. The use of antisense methods to inhibit the in vitro translation of genes is well known in the art (Marcus-Sakura, Anal. Biochem, 172:289, (1988)). Further, antisense molecules which bind directly to the DNA may be used. Antisense nucleic acids may be single or double stranded nucleic acids. Non-limiting examples of antisense nucleic acids include siRNAs (including their derivatives or pre-cursors, such as nucleotide analogs), short hairpin RNAs (shRNA), micro RNAs (miRNA), saRNAs (small activating RNAs) and small nucleolar RNAs (snoRNA) or certain of their derivatives or pre-cursors.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

"Nucleic acid" refers to nucleotides (e.g., deoxyribonucleotides or ribonucleotides) and polymers thereof in either single-, double- or multiple-stranded form, or complements thereof; or nucleosides (e.g., deoxyribonucleosides or ribonucleosides). In embodiments, "nucleic acid" does not include nucleosides. The terms "polynucleotide," "oligonucleotide," "oligo" or the like refer, in the usual and customary sense, to a linear sequence of nucleotides. The term "nucleoside" refers, in the usual and customary sense, to a glycosylamine including a nucleobase and a five-carbon sugar (ribose or deoxyribose). Non limiting examples, of nucleosides include, cytidine, uridine, adenosine, guanosine, thymidine and inosine. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g. polynucleotides, contemplated herein include any types of RNA, e.g. mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: A Practical Approach, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

The term "phosphorothioated nucleotide" or "nucleotide with a phosphorthioate moiety" refers to a nucleotide having the structure:

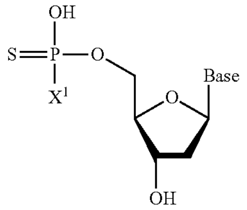

OH where $X^1$ is OH or $O^-$.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism.

The term "complement," as used herein, refers to a nucleotide (e.g., RNA or DNA) or a sequence of nucleotides capable of base pairing with a complementary nucleotide or sequence of nucleotides. As described herein and commonly known in the art the complementary (matching) nucleotide of adenosine is thymidine and the complementary (matching) nucleotide of guanosine is cytosine. Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and a non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence.

As described herein the complementarity of sequences may be partial, in which only some of the nucleic acids match according to base pairing, or complete, where all the nucleic acids match according to base pairing. Thus, two sequences that are complementary to each other, may have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region). In embodiments, the miR146a guide strand sequence has at least 85% sequence identity to the complement of at least 10 consecutive nucleotides of SEQ ID NO:1. In embodiments, the miR146a guide strand sequence has at least 90% sequence identity to the complement of at least 10 consecutive nucleotides of SEQ ID NO:1. In embodiments, the miR146a guide strand sequence has at least 95% sequence identity to the complement of at least 10 consecutive nucleotides of SEQ ID NO:1. In embodiments, the miR146a guide strand sequence has at least 85% sequence identity to the complement of at least 15 consecutive nucleotides of SEQ ID NO: 1. In embodiments, the miR146a guide strand sequence has at least 90% sequence identity to the complement of at least 15 consecutive nucleotides of SEQ ID NO:1. In embodiments, the miR146a guide strand sequence has at least 95% sequence identity to the complement of at least 15 consecutive nucleotides of SEQ ID NO:1. In embodiments, miR146a guide strand sequence has at least 85% sequence identity to the complement of at least 18 consecutive nucleotides of SEQ ID NO:1. In embodiments, the miR146a guide strand sequence has at least 90% sequence identity to the complement of at least 18 consecutive nucleotides of SEQ ID NO: 1. In embodiments, the miR146a guide strand sequence has at least 95% sequence identity to the complement of at least 18 consecutive nucleotides of SEQ ID NO:1. In embodiments, miR146a guide strand sequence has at least 85% sequence identity to the complement of all nucleotides of SEQ ID NO:1. In embodiments, the miR146a guide strand sequence has at least 90% sequence identity to the complement of all nucleotides of SEQ ID NO:1. In embodiments, the miR146a guide strand sequence has at least 95% sequence identity to the complement of all nucleotides of SEQ ID NO: 1. In embodiments, the miR146a guide strand of SEQ ID NO:1 comprises one or more 2'-O-Methyl-modified nucleic acids, one or more 2'-Fluoro-modified nucleic acids, or a combination thereof. In embodiments, the miR146a guide strand of SEQ ID NO:1 comprises one or more 2'-O-Methyl-modified nucleic acids. In embodiments, the miR146a guide strand of SEQ ID NO:1 comprises one or more 2'-Fluoro-modified nucleic acids. In embodiments, the miR146a guide strand of SEQ ID NO:1 comprises one or more phosphorothioate bonds. In embodiments, the miR146a guide strand of SEQ ID NO:1 comprises one or more 2'-O-Methyl-modified nucleic acids, one or more 2'-Fluoro-modified nucleic acids, one or more phosphorothioate bonds, or a combination thereof. In embodiments, the miR146a guide strand of SEQ ID NO:1 comprises one or more 2'-O-Methyl-modified nucleic acids and one or more phosphorothioate bonds. In embodiments, the miR146a guide strand of SEQ ID NO:1 comprises one or more 2'-Fluoro-modified nucleic acids and one or more phosphorothioate bonds.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., siRNA) may be detected by standard PCR or Northern blot methods well known in the art. See, Sambrook et al., 1989 Molecular Cloning: A Laboratory Manual, 18.1-18.88.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. Transgenic cells and plants are those that express a heterologous gene or coding sequence, typically as a result of recombinant methods.

The term "heterologous" when used with reference to portions of a nucleic acid indicates that the nucleic acid including two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein including two or more subsequences that are not found in the same relationship to each other in nature (e.g., a fusion protein).

The phrase "specifically (or selectively) binds" to an antibody or "specifically (or selectively) immunoreactive with," when referring to a protein or peptide (e.g., binding of CpG to TLR9), refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

A "labeled nucleic acid or oligonucleotide" is one that is bound, either covalently, through a linker or a chemical bond, or noncovalently, through ionic, van der Waals, electrostatic, or hydrogen bonds to a label such that the presence of the nucleic acid may be detected by detecting the presence of the detectable label bound to the nucleic acid. Alternatively, a method using high affinity interactions may achieve the same results where one of a pair of binding partners binds to the other, e.g., biotin, streptavidin. In embodiments, the phosphorothioate nucleic acid or phosphorothioate polymer backbone includes a detectable label, as disclosed herein and known in the art.

The terms "isolate" or "isolated", when applied to a nucleic acid, virus, or protein, denotes that the nucleic acid, virus, or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The following eight groups each contain amino acids that are conservative substitutions for one another: (1) Alanine (A), Glycine (G); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); (6) Phenylalanine (F), Tyrosine (Y), Tryptophan (W); (7) Serine (S), Threonine (T); and (8) Cysteine (C), Methionine (M) (see, e.g., Creighton, Proteins (1984)).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (e.g., www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

A "therapeutic agent" as used herein refers to an agent (e.g., nucleic acid, compound, or pharmaceutical composition described herein) that when administered to a subject will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms or the intended therapeutic effect, e.g., treatment or amelioration of an injury, disease, pathology or condition, or their symptoms including any objective or subjective parameter of treatment such as abatement; remission; diminishing of symptoms or making the injury, pathology or condition more tolerable to the patient; slowing in the rate of degeneration or decline; making the final point of degeneration less debilitating; or improving a patient's physical or mental well-being.

"Contacting" is used in accordance with its plain ordinary meaning and refers to the process of allowing at least two distinct species (e.g. chemical compounds including biomolecules or cells) to become sufficiently proximal to react, interact, or physically touch. It should be appreciated; however, the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a nucleic acid as described herein and a cell, protein, or enzyme.

"Control" or "control experiment" is used in accordance with its plain ordinary meaning and refers to an experiment in which the subjects or reagents of the experiment are treated as in a parallel experiment except for omission of a procedure, reagent, or variable of the experiment. In embodiments, the control is used as a standard of comparison in evaluating experimental effects. In embodiments, a control is the measurement of the activity of a protein in the absence of a compound as described herein (including embodiments and examples). One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

A "detectable agent" or "detectable moiety" is a compound or composition detectable by appropriate means such as spectroscopic, photochemical, biochemical, immunochemical, chemical, magnetic resonance imaging, or other physical means. A detectable moiety is a monovalent detectable agent or a detectable agent bound (e.g. covalently and directly or via a linking group) with another compound, e.g., a nucleic acid. Exemplary detectable agents/moieties for use in the present disclosure include an antibody ligand, a peptide, a nucleic acid, radioisotopes, paramagnetic metal ions, fluorophore (e.g. fluorescent dyes), electron-dense reagents, enzymes (e.g., as commonly used in an ELISA), biotin, a biotin-avidin complex, a biotin-streptavidin complex, digoxigenin, magnetic beads (e.g., DYNABEADS® by ThermoFisher, encompassing functionalized magnetic beads such as DYNABEADS® M-270 amine by ThermoFisher), paramagnetic molecules, paramagnetic nanoparticles, ultrasmall superparamagnetic iron oxide nanoparticles, ultrasmall superparamagnetic iron oxide nanoparticle aggregates, superparamagnetic iron oxide nanoparticles, superparamagnetic iron oxide nanoparticle aggregates, monocrystalline iron oxide nanoparticles, monocrystalline iron oxide, nanoparticle contrast agents, liposomes or other delivery vehicles containing Gadolinium chelate molecules, gadolinium, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. In embodiments, the detectable agent is a detectable fluorescent agent. In embodiments, the detectable agent is a detectable phosphorescent agent. In embodiments, the detectable agent is a detectable radioactive agent. In embodiments, the detectable agent is a detectable metalloenzyme. In embodiments, the detectable agent is a detectable colorimetric agent. In embodiments, the detectable agent is a detectable luminescent agent. In embodiments, the detectable agent is a detectable spectrophotometric agent. In embodiments, the detectable agent is a detectable metal-organic framework. In embodiments, the detectable agent is detectable by means other than by spectroscopy. In embodiments, the detectable agent comprises a fluorophore linked to biotin, avidin, or streptavidin. In embodiments, the detectable agent comprises a fluorophore linked to streptavidin. In embodiments, the detectable agent comprises a fluorophore linked to avidin. In embodiments, the detectable agent comprises a fluorophore linked to avidin linked to biotin. In embodiments, the detectable agent comprises a fluorophore linked to streptavidin linked to biotin.

"Fluorophore" refers to compounds that absorb light energy of a specific wavelength and re-emit the light at a lower wavelength. Exemplary fluorophores that may be used herein include xanthenes (e.g., fluorescein, rhodamine, Oregon green, eosin, Texas red); cyanines (e.g., cyanine, indocarbocyanine, oxacarbocyanine, thiacarbocyanine, merocyanine); squaraines (e.g., Seta, Square dyes); squaraine rotaxane (e.g., SeTau® dyes); naphthalenes (e.g., dansyl, prodan); coumarins; oxadiazoles (e.g., pyridyloxazole, nitrobenzoxadiazole, benzooxadiazole); anthracenes (e.g., anthraquinones, DRAQ5®, DRAQ7®, CyTRAK® orange); pyrenes (e.g., cascade blue); oxazines (e.g., Nile red, Nile blue, cresyl violet, oxazine 170); acridines (e.g., proflavin, acridine organge, acridine yellow); arylmethines (e.g., auramine, crystal violet, malachite green); tetrapyrroles (e.g., porphin, phthalocyanine, bilirubin), and the like. In embodiments, "fluorophore" is a fluorophore bound to avidin (e.g., Alexa Fluor® Avidin by ThermoFisher; or Rhodamine Avidin, Fluorescein Avidin, Texas Red® Aavidin all by Vector Laboratories). In embodiments, "fluorophore" is a fluorophore bound to streptavidin (e.g., Alexa Fluor® Streptavidin by ThermoFisher; or DyLight Streptavidin, Cy3 Streptavidin, Fluorescein Streptavidin, Texas Red® Streptavidin all by Vector Laboratories).

Radioactive substances (e.g., radioisotopes) that may be used as imaging and/or labeling agents in accordance with the embodiments of the disclosure include, but are not limited to, $^{18}F$, $^{32}P$, $^{33}P$, $^{45}Ti$, $^{47}Sc$, $^{52}Fe$, $^{59}Fe$, $^{62}Cu$, $^{64}Cu$, $^{67}Cu$, $^{67}Ga$, $^{68}Ga$, $^{77}As$, $^{86}Y$ $^{90}Y$, $^{89}Sr$, $^{89}Zr$, $^{94}Tc$, $^{94}Tc$, $^{99m}Tc$ $^{99}Mo$, $^{105}Pd$, $^{105}Rh$ $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154-1581}Gd$, $^{161}Tb$, $^{166}Dy$, $^{166}Ho$, $^{169}Er$, $^{175}Lu$, $^{177}Lu$, $^{186}Re$, $^{188}Re$, $^{189}Re$, $^{194}Ir$, $^{198}Au$, $^{199}Au$, $^{211}At$, $^{211}Pb$, $^{212}Bi$, $^{212}Pb$, $^{213}Bi$, $^{223}Ra$ and $^{225}Ac$. Paramagnetic ions that may be used as additional imaging agents in accordance with the embodiments of the disclosure include, but are not limited to, ions of transition and lanthanide metals (e.g., metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, $—CH_2CH_2CH_2—$. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable non-cyclic straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—CH_2$, $—S(O)—CH_3$, $—CH_2—CH_2—S(O)_2—CH_3$, $—CH=CHO—CH_3$, $—Si(CH_3)_3$, $—CH_2—CH=N—OCH_3$, $—CH=CH—N(CH_3)—CH_3$, $—O—CH_3$, $—O—CH_2—CH_3$, and —CN. Up to two or three heteroatoms may be consecutive, such as, for example, $—CH_2—NH—OCH_3$ and $—CH_2—O—Si(CH_3)_3$.

The term "heteroalkylene," by itself or as part of another substituent, means, unless otherwise stated, a divalent radical derived from heteroalkyl, as exemplified, but not limited by, $—CH_2—CH_2—S—CH_2—CH_2—$, $—O—CH_2—CH_2—NH—CH_2—$, $—O—(CH_2)_3—O—PO_3—$, $—O—(CH_2)—O—PO_3—$, $—O—(CH_2)_2—O—PO_3—$, $—O—(CH_2)_4—O—PO_3—$, and the like. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $—C(O)_2R'—$ represents both $—C(O)_2R'—$ and $—R'C(O)_2—$. As described above, heteroalkyl groups, as used herein, include those groups that are attached to the remainder of the molecule through a heteroatom, such as —C(O)R', —C(O)NR', —NR'R", —OR', —SR', and/or $—SO_2R'$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic non-aromatic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently (e.g., biphenyl). A fused ring aryl refers to multiple rings fused together wherein at least one of the fused rings is an aryl ring. The term “heteroaryl” refers to aryl groups (or rings) that contain at least one heteroatom such as N, O, or S, wherein the nitrogen and sulfur atoms are optionally oxidized, and the nitrogen atom(s) are optionally quaternized. Thus, the term “heteroaryl” includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An “arylene” and a “heteroarylene,” alone or as part of another substituent, mean a divalent radical derived from an aryl and heteroaryl, respectively. Non-limiting examples of heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

The term “oxo,” as used herein, means an oxygen that is double bonded to a carbon atom.

The term “alkylsulfonyl,” as used herein, means a moiety having the formula —S(O$_2$)—R', where R' is a substituted or unsubstituted alkyl group as defined above. R' may have a specified number of carbons (e.g., “C$_1$-C$_4$ alkylsulfonyl”).

Each of the above terms (e.g., “alkyl,” “heteroalkyl,” “aryl,” and “heteroaryl”) includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C=(O)NR"NR"'R"", —CN, —NO$_2$, in a number ranging from zero to (2m'+1), where m' is the total number of carbon atoms in such radical. R, R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term “alkyl” is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C=(O)NR"NR'R"", —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R"', and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In embodiments, the ring-forming substituents are attached to adjacent members of the base structure. For example, two ring-forming substituents attached to adjacent members of a cyclic base structure create a fused ring structure. In embodiments, the ring-forming substituents are attached to a single member of the base structure. For example, two ring-forming substituents attached to a single member of a cyclic base structure create a spirocyclic structure. In embodiments, the ring-forming substituents are attached to non-adjacent members of the base structure.

Two of the substituents on adjacent atoms of the aryl or heteroaryl ring may optionally form a ring of the formula -T-C(O)—$(CRR')_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-$(CH_2)_r$—B—, wherein A and B are independently —CRR'—, —O—, —NR—, —S—, —S(O)—, —$S(O)_2$—, —$S(O)_2NR'$—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —$(CRR')_s$—X'—$(C''R''R''')_d$—, where s and d are independently integers of from 0 to 3, and X' is —O—, —NR'—, —S—, —S(O)—, —$S(O)_2$—, or —$S(O)_2NR'$—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties: (A) oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$OCF_3$, —$OCHF_2$, —$NHSO_2CH_3$, —$N_3$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from: (i) oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)OH, —NHOH, —$OCF_3$, —$OCHF_2$, —$NHSO_2CH_3$, —$N_3$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from: (a) oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$OCF_3$, —$OCHF_2$, —$NHSO_2CH_3$, —$N_3$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$OCF_3$, —$OCHF_2$, —$NHSO_2CH_3$, —$N_3$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In embodiments, each substituted group described in the compounds herein is substituted with at least one substituent group. More specifically, in embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In embodiments, at least one or all of these groups are substituted with at least one size-limited substituent group. In embodiments, at least one or all of these groups are substituted with at least one lower substituent group.

In embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In embodiments, the compound is a chemical species set forth in the Examples section below.

As defined herein, the term "activation", "activate", "activating", "activator" and the like in reference to a protein-inhibitor interaction means positively affecting (e.g. increasing) the activity or function of the protein relative to the activity or function of the protein in the absence of the activator. In embodiments activation means positively affecting (e.g. increasing) the concentration or levels of the protein relative to the concentration or level of the protein in the absence of the activator. The terms may reference activation, or activating, sensitizing, or up-regulating signal transduction or enzymatic activity or the amount of a protein decreased in a disease. Thus, activation may include, at least in part, partially or totally increasing stimulation, increasing or enabling activation, or activating, sensitizing, or up-regulating signal transduction or enzymatic activity or the amount of a protein associated with a disease (e.g., a protein which is decreased in a disease relative to a non-diseased control). Activation may include, at least in part, partially or totally increasing stimulation, increasing or enabling activation, or activating, sensitizing, or up-regulating signal transduction or enzymatic activity or the amount of a protein The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The term "modulator" refers to a composition that increases or decreases the level of a target molecule or the function of a target molecule or the physical state of the target of the molecule relative to the absence of the modulator.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; or rodent.

Compounds

The disclosure provides a hybridized nucleic acid sequence, where a microRNA passenger strand sequence is hybridized to a microRNA guide strand sequence. In embodiments, the hybridized nucleic acid sequence comprises a miR146a passenger strand sequence hybridized to a miR146a guide strand sequence. In embodiments, the miR146a passenger and guide strand sequences are miR146a-mimic passenger and guide strand sequences. In embodiments, the hybridized nucleic acid sequence comprises miR155 passenger strand sequence hybridized to miR155 guide strand sequence. In embodiments, the miR155 passenger and guide strand sequences are miR155-mimic passenger and guide strand sequences. In embodiments, the hybridized nucleic acid sequence comprises a miR142 passenger strand sequence hybridized to a miR142 guide strand sequence. In embodiments, the miR142 passenger and guide strand sequences are miR142-mimic passenger and guide strand sequences. In embodiments, the hybridized nucleic acid sequence comprises a miR125b passenger strand sequence hybridized to a miR125b guide strand sequence. In embodiments, the miR125b passenger and guide strand sequences are miR142-mimic passenger and guide strand sequences. In embodiments, the hybridized nucleic acid sequence comprises a miR203b passenger strand sequence hybridized to a miR203b guide strand sequence. In embodiments, the miR203b passenger and guide strand sequences are miR203b-mimic passenger and guide strand sequences. In embodiments, the hybridized nucleic acid sequence comprises a miR221 passenger strand sequence hybridized to a miR221 guide strand sequence. In embodiments, the miR221 passenger and guide strand sequences are miR221-mimic passenger and guide strand sequences. In embodiments, the hybridized nucleic acid sequence comprises a miR222 passenger strand sequence hybridized to a miR222 guide strand sequence. In embodiments, the miR222 passenger and guide strand sequences are miR222-mimic passenger and guide strand sequences. In embodiments, the hybridized nucleic acid sequence comprises a miR29b passenger strand sequence hybridized to a miR29b guide strand sequence. In embodiments, the miR129b passenger and guide strand sequences are miR129b-mimic passenger and guide strand sequences. In embodiments, the hybridized nucleic acid sequences are covalently bonded to a Toll-like receptor 9-binding nucleic acid sequence. In embodiments, the microRNA passenger strand sequence is covalently bonded to the Toll-like receptor 9-binding nucleic acid sequence; and the microRNA guide strand sequence is hybridized to the microRNA passenger strand sequence.

The disclosure provides a hybridized nucleic acid sequence, where a miR146a passenger strand sequence is hybridized to a miR146a guide strand sequence. In embodiments, the miR146a passenger strand sequence comprises SEQ ID NO:1 and the miR146a guide strand sequence comprises a complementary nucleic acid sequence. In embodiments, the miR146a passenger strand sequence comprises SEQ ID NO: 1; and the miR146a guide strand sequence comprises SEQ ID NO:6. In embodiments, the miR146a passenger strand sequence comprises SEQ ID NO:1; and the miR146a guide strand sequence comprises SEQ ID NO:7. In embodiments, SEQ ID NO:1 comprises a 2'-O-methyl nucleotide, a 2'-fluoro-nucleotide, a phosphorothioate linkage, or a combination thereof. In embodiments, SEQ ID NO:1 comprises a 2'-O-methyl nucleotide. In embodiments, SEQ ID NO:1 comprises a 2'-fluoro-nucleotide. In embodiments, SEQ ID NO:1 comprises a phosphorothioate linkage. In embodiments, SEQ ID NO:1 comprises a 2'-O-methyl nucleotide and a phosphorothioate linkage. In embodiments, SEQ ID NO:1 comprises a 2'-fluoro-nucleotide and a phosphorothioate linkage. In embodiments, SEQ ID NO:6 comprises a 2'-O-methyl nucleotide, a 2'-fluoro-nucleotide, a phosphorothioate linkage, or a combination thereof. In embodiments, SEQ ID NO:6 comprises a 2'-O-methyl nucleotide, a 2'-fluoro-nucleotide, and a phosphorothioate linkage. In embodiments, SEQ ID NO:6 comprises a 2'-O-methyl nucleotide. In embodiments, SEQ ID NO:6 comprises a 2'-fluoro-nucleotide. In embodiments, SEQ ID NO:6 comprises a 2'-O-methyl nucleotide and a 2'-fluoro-nucleotide. In embodiments, SEQ ID NO:6 comprises a phosphorothioate linkage. In embodiments, SEQ ID NO:6 comprises a 2'-O-methyl nucleotide and a phosphorothioate linkage. In embodiments, SEQ ID NO:6 comprises a 2'-fluoro-nucleotide and a phosphorothioate linkage. In embodiments, SEQ ID NO:7 comprises a 2'-O-methyl nucleotide, a 2'-fluoro-nucleotide, a phosphorothioate linkage, or a combination thereof. In embodiments, SEQ ID NO:7 comprises a 2'-O-methyl nucleotide, a 2'-fluoro-nucleotide, and a phosphorothioate linkage. In embodiments, SEQ ID NO:7 comprises a 2'-O-methyl nucleotide. In embodiments, SEQ ID NO:7 comprises a 2'-fluoro-nucleotide. In embodiments, SEQ ID NO:7 comprises a 2'-O-methyl nucleotide and a 2'-fluoro-nucleotide. In embodiments, SEQ ID NO:7 comprises a phosphorothioate linkage. In embodiments, SEQ ID NO:7 comprises a 2'-O-methyl nucleotide and a phosphorothioate linkage. In embodiments, SEQ ID NO:7 comprises a 2'-fluoro-nucleotide and a phosphorothioate linkage. In embodiments, the hybridized nucleic acid sequences are covalently bonded to a Toll-like receptor 9-binding nucleic acid sequence. In embodiments, the microRNA passenger strand sequence is covalently bonded to the Toll-like receptor 9-binding nucleic acid sequence; and the microRNA guide strand sequence is hybridized to the microRNA passenger strand sequence.

The disclosure provides a hybridized nucleic acid sequence, where a miR146a passenger strand sequence is hybridized to a miR146a guide strand sequence. In embodiments, the miR146a passenger strand sequence comprises SEQ ID NO:1, 2, 3, 4, 5, or 6, and the miR146a guide strand sequence comprises a complementary nucleic acid sequence. In embodiments, the miR146a passenger strand sequence comprises SEQ ID NO:37 or 39, and the miR146a guide strand sequence comprises a complementary nucleic acid sequence. In embodiments, the miR146a passenger strand sequence comprises SEQ ID NO:1, and the miR146a guide strand sequence comprises a complementary nucleic acid sequence. In embodiments, the miR146a passenger strand sequence comprises SEQ ID NO:2, and the miR146a guide strand sequence comprises a complementary nucleic acid sequence. In embodiments, the miR146a passenger strand sequence comprises SEQ ID NO:3, and the miR146a guide strand sequence comprises a complementary nucleic acid sequence. In embodiments, the miR146a passenger strand sequence comprises SEQ ID NO:4, and the miR146a guide strand sequence comprises a complementary nucleic acid sequence. In embodiments, the miR146a passenger strand sequence comprises SEQ ID NO:5, and the miR146a guide strand sequence comprises a complementary nucleic acid sequence. In embodiments, the miR146a passenger strand sequence comprises SEQ ID NO:37, and the miR146a guide strand sequence comprises a complementary nucleic acid sequence. In embodiments, the miR146a passenger strand sequence comprises SEQ ID NO:39, and the miR146a guide strand sequence comprises a complementary nucleic acid sequence. In embodiments, the miR146a guide strand sequence comprises SEQ ID NO: 6, 7, or 8. In embodiments, the miR146a guide strand sequence comprises SEQ ID NO: 6. In embodiments, the miR146a guide strand sequence comprises SEQ ID NO:7. In embodiments, the miR146a guide strand sequence comprises SEQ ID NO: 8. In embodiments, the hybridized nucleic acid sequences are covalently bonded to a Toll-like receptor 9-binding nucleic acid sequence. In embodiments, the miR146a passenger strand sequence is covalently bonded to the Toll-like receptor 9-binding nucleic acid sequence; and the miR146a guide strand sequence is hybridized to the miR146a passenger strand sequence.

The disclosure provides a hybridized nucleic acid sequence, where a miR146a passenger strand sequence is hybridized to a miR146a guide strand sequence. In embodiments, the miR146a guide strand sequence comprises SEQ ID NO:36 or 38. In embodiments, the miR146a guide strand sequence comprises SEQ ID NO:36. In embodiments, the miR146a guide strand sequence comprises SEQ ID NO:38. In embodiments, the miR146a passenger strand sequence comprises SEQ ID NO: 1; and the miR146a guide strand sequence comprises SEQ ID NO:6. In embodiments, the miR146a passenger strand sequence comprises SEQ ID NO:2; and the miR146a guide strand sequence comprises SEQ ID NO:7. In embodiments, the miR146a passenger strand sequence comprises SEQ ID NO:2; and the miR146a guide strand sequence comprises SEQ ID NO:8. In embodiments, the miR146a passenger strand sequence comprises SEQ ID NO:37; and the miR146a guide strand sequence comprises SEQ ID NO:36. In embodiments, the miR146a passenger strand sequence comprises SEQ ID NO: 39; and the miR146a guide strand sequence comprises SEQ ID NO:38. In embodiments, the hybridized nucleic acid sequences are covalently bonded to a Toll-like receptor 9-binding nucleic acid sequence. In embodiments, the miR146a passenger strand sequence is covalently bonded to the Toll-like receptor 9-binding nucleic acid sequence; and the miR146a guide strand sequence is hybridized to the miR146a passenger strand sequence.

The disclosure provides a hybridized nucleic acid sequence, where a miR155 passenger strand sequence is hybridized to a miR155 guide strand sequence. In embodiments, the miR155 passenger strand sequence comprises SEQ ID NO:19, and the miR155 guide strand sequence comprises SEQ ID NO:20. In embodiments, the hybridized nucleic acid sequences are covalently bonded to a Toll-like receptor 9-binding nucleic acid sequence. In embodiments, the miR155 passenger strand sequence is covalently bonded to the Toll-like receptor 9-binding nucleic acid sequence; and the miR155 guide strand sequence is hybridized to the miR155 passenger strand sequence.

The disclosure provides a hybridized nucleic acid sequence, where a miR142 passenger strand sequence is hybridized to a miR142 guide strand sequence. In embodiments, the miR142 passenger strand sequence comprises SEQ ID NO:21, and the miR142 guide strand sequence comprises SEQ ID NO:22. In embodiments, the hybridized nucleic acid sequences are covalently bonded to a Toll-like receptor 9-binding nucleic acid sequence. In embodiments, the miR142 passenger strand sequence is covalently bonded to the Toll-like receptor 9-binding nucleic acid sequence; and the miR142 guide strand sequence is hybridized to the miR142 passenger strand sequence.

The disclosure provides a hybridized nucleic acid sequence, where a miR142 passenger strand sequence is hybridized to a miR142 guide strand sequence. In embodiments, the miR142 passenger strand sequence comprises SEQ ID NO:49, and the miR142 guide strand sequence comprises SEQ ID NO:48. In embodiments, the hybridized nucleic acid sequences are covalently bonded to a Toll-like receptor 9-binding nucleic acid sequence. In embodiments, the miR142 passenger strand sequence is covalently bonded to the Toll-like receptor 9-binding nucleic acid sequence; and the miR142 guide strand sequence is hybridized to the microRNA passenger strand sequence.

The disclosure provides a hybridized nucleic acid sequence, where a miR125b passenger strand sequence is hybridized to a miR125b guide strand sequence. In embodiments, the miR125b passenger strand sequence comprises SEQ ID NO:23, and the miR125b guide strand sequence comprises SEQ ID NO:24. In embodiments, the hybridized nucleic acid sequences are covalently bonded to a Toll-like receptor 9-binding nucleic acid sequence. In embodiments, the miR125b passenger strand sequence is covalently bonded to the Toll-like receptor 9-binding nucleic acid sequence; and the miR125b guide strand sequence is hybridized to the microRNA passenger strand sequence.

The disclosure provides a hybridized nucleic acid sequence, where a miR203b passenger strand sequence is hybridized to a miR203b guide strand sequence. In embodiments, the miR203b passenger strand sequence comprises SEQ ID NO:25, and the miR203b guide strand sequence comprises SEQ ID NO:26. In embodiments, the hybridized nucleic acid sequences are covalently bonded to a Toll-like receptor 9-binding nucleic acid sequence. In embodiments, the miR203b passenger strand sequence is covalently bonded to the Toll-like receptor 9-binding nucleic acid sequence; and the miR203b guide strand sequence is hybridized to the miR203b passenger strand sequence.

The disclosure provides a hybridized nucleic acid sequence, where a miR221 passenger strand sequence is hybridized to a miR221 guide strand sequence. In embodiments, the miR221 passenger strand sequence comprises SEQ ID NO:27, and the miR221 guide strand sequence comprises SEQ ID NO:28. In embodiments, the hybridized nucleic acid sequences are covalently bonded to a Toll-like receptor 9-binding nucleic acid sequence. In embodiments, the miR221 passenger strand sequence is covalently bonded to the Toll-like receptor 9-binding nucleic acid sequence; and the miR221 guide strand sequence is hybridized to the miR221 passenger strand sequence.

The disclosure provides a hybridized nucleic acid sequence, where a miR222 passenger strand sequence is hybridized to a miR222 guide strand sequence. In embodiments, the miR222 passenger strand sequence comprises SEQ ID NO:29, and the miR222 guide strand sequence comprises SEQ ID NO:30. In embodiments, the hybridized nucleic acid sequences are covalently bonded to a Toll-like receptor 9-binding nucleic acid sequence. In embodiments, the miR222 passenger strand sequence is covalently bonded to the Toll-like receptor 9-binding nucleic acid sequence; and the miR222 guide strand sequence is hybridized to the miR222 passenger strand sequence.

The disclosure provides a hybridized nucleic acid sequence, where a miR29b passenger strand sequence is hybridized to a miR29b guide strand sequence. In embodiments, the miR29b passenger strand sequence comprises SEQ ID NO:31, and the miR142 guide strand sequence comprises SEQ ID NO:32. In embodiments, the hybridized nucleic acid sequences are covalently bonded to a Toll-like receptor 9-binding nucleic acid sequence. In embodiments, the miR29b passenger strand sequence is covalently bonded to the Toll-like receptor 9-binding nucleic acid sequence; and the miR29b guide strand sequence is hybridized to the miR29b passenger strand sequence.

The disclosure provides compounds of Formula (I):

$$R^1\text{-}L^1\text{-}R^2 \quad \text{(I);}$$

where $R^1$ is a Toll-like receptor 9-binding nucleic acid sequence; $L^1$ is a linking group; and $R^2$ is a hybridized nucleic acid sequence. In embodiments, the 3' end of $R^1$ is bonded to $L^1$. In embodiments, the 5' end of $R^1$ is bonded to $L^1$. In embodiments of the compound of Formula (I), $R^2$ comprises a miR146a passenger strand sequence hybridized to a miR146a guide strand sequence. In embodiments, the 3' end of the miR146a passenger strand sequence is bonded to $L^1$. In embodiments, the 5' end of the miR146a passenger strand sequence is bonded to $L^1$. In embodiments, the Toll-like receptor 9-binding nucleic acid sequence comprises a phosphorothioate linkage. In embodiments, the miR146a passenger strand sequence comprises SEQ ID NO:1; and the miR146a guide strand sequence comprises SEQ ID NO:6. In embodiments, SEQ ID NO:1 comprises a 2'-O-methyl nucleotide, a 2'-fluoro-nucleotide, a phosphorothioate linkage, or a combination thereof. In embodiments, SEQ ID NO:1 comprises a 2'-O-methyl nucleotide. In embodiments, SEQ ID NO:1 comprises a 2'-fluoro-nucleotide. In embodiments, SEQ ID NO:1 comprises a phosphorothioate linkage. In embodiments, SEQ ID NO:1 comprises a 2'-O-methyl nucleotide and a phosphorothioate linkage. In embodiments, SEQ ID NO:1 comprises a 2'-fluoro-nucleotide and a phosphorothioate linkage. In embodiments, SEQ ID NO:6 comprises a 2'-O-methyl nucleotide, a 2'-fluoro-nucleotide, a phosphorothioate linkage, or a combination thereof. In embodiments, SEQ ID NO:6 comprises a 2'-O-methyl nucleotide. In embodiments, SEQ ID NO:6 comprises a 2'-fluoro-nucleotide. In embodiments, SEQ ID NO:6 comprises a phosphorothioate linkage. In embodiments, SEQ ID NO:6 comprises a 2'-O-methyl nucleotide and a phosphorothioate linkage. In embodiments, SEQ ID NO:6 comprises a 2'-fluoro-nucleotide and a phosphorothioate linkage. In embodiments, the microRNA passenger strand sequence is covalently bonded via the linking group to the Toll-like receptor 9-binding nucleic acid sequence; and the microRNA guide strand sequence is hybridized to the microRNA passenger strand sequence. In embodiments, the 3' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence. In embodiments, the 5' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence.

The disclosure provides compounds of Formula (I):

$$R^1\text{-}L^1\text{-}R^2 \quad \text{(I);}$$

where $R^1$ is a Toll-like receptor 9-binding nucleic acid sequence; $L^1$ is a linking group; and $R^2$ is a hybridized nucleic acid sequence. In embodiments, the 3' end of $R^1$ is bonded to $L^1$. In embodiments, the 5' end of $R^1$ is bonded to $L^1$. In embodiments, $R^2$ comprises a miR146a passenger strand sequence hybridized to a miR146a guide strand sequence. In embodiments, the 3' end of the miR146a passenger strand sequence is bonded to $L^1$. In embodiments, the 5' end of the miR146a passenger strand sequence is bonded to $L^1$. In embodiments, the miR146a passenger strand sequence comprises SEQ ID NO: 1, 2, 3, 4, or 5, and the miR146a guide strand sequence comprises a complementary nucleic acid sequence. In embodiments, the miR146a passenger strand sequence comprises SEQ ID NO: 1, and the miR146a guide strand sequence comprises a complementary nucleic acid sequence. In embodiments, the miR146a passenger strand sequence comprises SEQ ID NO:2, and the miR146a guide strand sequence comprises a complementary nucleic acid sequence. In embodiments, the miR146a passenger strand sequence comprises SEQ ID NO:3, and the miR146a guide strand sequence comprises a complementary nucleic acid sequence. In embodiments, the miR146a passenger strand sequence comprises SEQ ID NO:4, and the miR146a guide strand sequence comprises a complementary nucleic acid sequence. In embodiments, the miR146a passenger strand sequence comprises SEQ ID NO:5, and the miR146a guide strand sequence comprises a complementary nucleic acid sequence. In embodiments, the miR146a guide strand sequence comprises SEQ ID NO:6. In embodiments, the miR146a guide strand sequence comprises SEQ ID NO:7. In embodiments, the miR146a guide strand sequence comprises SEQ ID NO:8. In embodiments, the miR146a passenger strand sequence comprises SEQ ID NO:1; and the miR146a guide strand sequence comprises SEQ ID NO:6. In embodiments, the miR146a passenger strand sequence comprises SEQ ID NO:2; and the miR146a guide strand sequence comprises SEQ ID NO:7. In embodiments, the miR146a passenger strand sequence comprises SEQ ID NO:2; and the miR146a guide strand sequence comprises SEQ ID NO:8. In embodiments, the microRNA passenger strand sequence is covalently bonded via the linking group to the Toll-like receptor 9-binding nucleic acid sequence; and the microRNA guide strand sequence is hybridized to the microRNA passenger strand sequence. In embodiments, the 3' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence. In embodiments, the 5' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence.

In embodiments, $R^2$ comprises a miR146a passenger strand sequence hybridized to a miR146a guide strand sequence. In embodiments, the 3' end of the miR146a passenger strand sequence is bonded to $L^1$. In embodiments, the 5' end of the miR146a passenger strand sequence is bonded to $L^1$. In embodiments, the miR146a passenger strand sequence comprises SEQ ID NO:36 or 38, and the miR146a guide strand sequence comprises a complementary nucleic acid sequence. In embodiments, the miR146a passenger strand sequence comprises SEQ ID NO:37, and the miR146a guide strand sequence comprises a complementary nucleic acid sequence. In embodiments, the miR146a passenger strand sequence comprises SEQ ID NO:39, and the miR146a guide strand sequence comprises a complementary nucleic acid sequence. In embodiments, the miR146a guide strand sequence comprises SEQ ID NO:36 or 38. In embodiments, the miR146a guide strand sequence comprises SEQ ID NO:36. In embodiments, the miR146a guide strand sequence comprises SEQ ID NO:38. In embodiments, the miR146a passenger strand sequence comprises SEQ ID NO:37; and the miR146a guide strand sequence comprises SEQ ID NO:36. In embodiments, the miR146a passenger strand sequence comprises SEQ ID NO:39; and the miR146a guide strand sequence comprises SEQ ID NO:38. In embodiments, the microRNA passenger strand sequence is covalently bonded via the linking group to the Toll-like receptor 9-binding nucleic acid sequence; and the microRNA guide strand sequence is hybridized to the microRNA passenger strand sequence. In embodiments, the 3' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence. In embodiments, the 5' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence.

In embodiments, $R^2$ comprises an miR155 passenger strand sequence hybridized to an miR155 guide strand sequence. In embodiments, the miR155 passenger strand sequence comprises SEQ ID NO: 19, and the miR155 guide strand sequence comprises SEQ ID NO:20. In embodiments, the 3' end of the miR155 passenger strand sequence is bonded to $L^1$. In embodiments, the 5' end of the miR155 passenger strand sequence is bonded to $L^1$. In embodiments, the microRNA passenger strand sequence is covalently bonded via the linking group to the Toll-like receptor 9-binding nucleic acid sequence; and the microRNA guide strand sequence is hybridized to the microRNA passenger strand sequence. In embodiments, the 3' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence. In embodiments, the 5' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence.

In embodiments, $R^2$ comprises a miR142 passenger strand sequence hybridized to a miR142 guide strand sequence. In embodiments, the 3' end of the miR142 passenger strand sequence is bonded to $L^1$. In embodiments, the 5' end of the miR142 passenger strand sequence is bonded to $L^1$. In embodiments, the miR142 passenger strand sequence comprises SEQ ID NO:21, and the miR142 guide strand sequence comprises SEQ ID NO:22. In embodiments, the microRNA passenger strand sequence is covalently bonded via the linking group to the Toll-like receptor 9-binding nucleic acid sequence; and the microRNA guide strand sequence is hybridized to the microRNA passenger strand sequence. In embodiments, the 3' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence. In embodiments, the 5' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence.

In embodiments, $R^2$ comprises a miR142 passenger strand sequence hybridized to a miR142 guide strand sequence. In embodiments, the 3' end of the miR142 passenger strand sequence is bonded to $L^1$. In embodiments, the 5' end of the miR142 passenger strand sequence is bonded to $L^1$. In embodiments, the miR142 passenger strand sequence comprises SEQ ID NO:49, and the miR142 guide strand sequence comprises SEQ ID NO:48. In embodiments, the microRNA passenger strand sequence is covalently bonded via the linking group to the Toll-like receptor 9-binding nucleic acid sequence; and the microRNA guide strand sequence is hybridized to the microRNA passenger strand sequence. In embodiments, the 3' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence. In embodiments, the 5' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence.

In embodiments, $R^2$ comprises a miR125b passenger strand sequence hybridized to a miR125b guide strand sequence. In embodiments, the 3' end of the miR125b passenger strand sequence is bonded to $L^1$. In embodiments, the 5' end of the miR125b passenger strand sequence is bonded to $L^1$. In embodiments, the miR125b passenger strand sequence comprises SEQ ID NO:23, and the miR125b guide strand sequence comprises SEQ ID NO:24. In embodiments, the microRNA passenger strand sequence is covalently bonded via the linking group to the Toll-like receptor 9-binding nucleic acid sequence; and the microRNA guide strand sequence is hybridized to the microRNA passenger strand sequence. In embodiments, the 3' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence. In embodiments, the 5' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence.

In embodiments, $R^2$ comprises a miR203b passenger strand sequence hybridized to a miR203b guide strand sequence. In embodiments, the 3' end of the miR203b passenger strand sequence is bonded to $L^1$. In embodiments, the 5' end of the miR203b passenger strand sequence is bonded to $L^1$. In embodiments, the miR203b passenger strand sequence comprises SEQ ID NO:25, and the miR203b guide strand sequence comprises SEQ ID NO:26. In embodiments, the microRNA passenger strand sequence is covalently bonded via the linking group to the Toll-like receptor 9-binding nucleic acid sequence; and the microRNA guide strand sequence is hybridized to the microRNA passenger strand sequence. In embodiments, the 3' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence. In embodiments, the 5' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence.

In embodiments, $R^2$ comprises a miR221 passenger strand sequence hybridized to a miR221 guide strand sequence. In embodiments, the 3' end of the miR221 passenger strand sequence is bonded to $L^1$. In embodiments, the 5' end of the miR221 passenger strand sequence is bonded to $L^1$. In embodiments, the miR221 passenger strand sequence comprises SEQ ID NO:27, and the miR221 guide strand sequence comprises SEQ ID NO:28. In embodiments, the microRNA passenger strand sequence is covalently bonded via the linking group to the Toll-like receptor 9-binding nucleic acid sequence; and the microRNA guide strand sequence is hybridized to the microRNA passenger strand sequence. In embodiments, the 3' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence. In embodiments, the 5' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence.

In embodiments, $R^2$ comprises a miR222 passenger strand sequence hybridized to a miR222 guide strand sequence. In embodiments, the 3' end of the miR222 passenger strand sequence is bonded to $L^1$. In embodiments, the 5' end of the miR222 passenger strand sequence is bonded to $L^1$. In embodiments, the miR222 passenger strand sequence comprises SEQ ID NO:29, and the miR222 guide strand sequence comprises SEQ ID NO:30. In embodiments, the microRNA passenger strand sequence is covalently bonded via the linking group to the Toll-like receptor 9-binding nucleic acid sequence; and the microRNA guide strand sequence is hybridized to the microRNA passenger strand sequence. In embodiments, the 3' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence. In embodiments, the 5' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence.

In embodiments, $R^2$ comprises a miR29b passenger strand sequence hybridized to a miR29b guide strand sequence. In embodiments, the 3' end of the miR29b passenger strand sequence is bonded to $L^1$. In embodiments, the 5' end of the miR29b passenger strand sequence is bonded to $L^1$. In embodiments, the miR29b passenger strand sequence comprises SEQ ID NO:31, and the miR142 guide strand sequence comprises SEQ ID NO:32. In embodiments, the microRNA passenger strand sequence is covalently bonded via the linking group to the Toll-like receptor 9-binding nucleic acid sequence; and the microRNA guide strand sequence is hybridized to the microRNA passenger strand sequence. In embodiments, the 3' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence. In embodiments, the 5' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence.

The disclosure provides compounds of Formula (II):

(II)

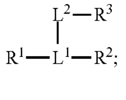

where $R^1$ is a Toll-like receptor 9-binding nucleic acid sequence; $L^1$ and $L^2$ are independently a linking group; and $R^2$ and $R^3$ are independently a hybridized nucleic acid sequence. In embodiments, the 3' end of $R^1$ is bonded to $L^1$. In embodiments, the 5' end of $R^1$ is bonded to $L^1$. In embodiments of the compound of Formula (II), $R^2$ and $R^3$ are independently comprise a passenger strand sequence hybridized to a guide strand sequence.

In embodiments, $R^2$ and $R^3$ are independently comprise a miR146a passenger strand sequence hybridized to a miR146a guide strand sequence. In embodiments, the 3' end of the miR146a passenger strand sequence of $R^2$ is bonded to $L^1$. In embodiments, the 5' end of the miR146a passenger strand sequence of $R^2$ is bonded to $L^1$. In embodiments, the 3' end of the miR146a passenger strand sequence of $R^3$ is bonded to $L^2$. In embodiments, the 5' end of the miR146a passenger strand sequence of $R^3$ is bonded to $L^2$. In embodiments, the Toll-like receptor 9-binding nucleic acid sequence comprises a phosphorothioate linkage. In embodiments, the miR146a passenger strand sequence comprises SEQ ID NO:1; and the miR146a guide strand sequence comprises SEQ ID NO:6. In embodiments, SEQ ID NO:1 comprises a 2'-O-methyl nucleotide, a 2'-fluoro-nucleotide, a phosphorothioate linkage, or a combination thereof. In embodiments, SEQ ID NO:1 comprises a 2'-O-methyl nucleotide. In embodiments, SEQ ID NO:1 comprises a 2'-fluoro-nucleotide. In embodiments, SEQ ID NO:1 comprises a phosphorothioate linkage. In embodiments, SEQ ID NO:1 comprises a 2'-O-methyl nucleotide and a phosphorothioate linkage. In embodiments, SEQ ID NO:1 comprises a 2'-fluoro-nucleotide and a phosphorothioate linkage. In embodiments, SEQ ID NO:6 comprises a 2'-O-methyl nucleotide, a 2'-fluoro-nucleotide, a phosphorothioate linkage, or a combination thereof. In embodiments, SEQ ID NO:6 comprises a 2'-O-methyl nucleotide. In embodiments, SEQ ID NO:6 comprises a 2'-fluoro-nucleotide. In embodiments, SEQ ID NO:6 comprises a phosphorothioate linkage. In embodiments, SEQ ID NO:6 comprises a 2'-O-methyl nucleotide and a phosphorothioate linkage. In embodiments, SEQ ID NO:6 comprises a 2'-fluoro-nucleotide and a phosphorothioate linkage. In embodiments, the microRNA passenger strand sequence is covalently bonded via the linking group to the Toll-like receptor 9-binding nucleic acid sequence; and the microRNA guide strand sequence is hybridized to the microRNA passenger strand sequence. In embodiments, the 3' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence. In embodiments, the 5' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence.

The disclosure provides compounds of Formula (II):

(II)

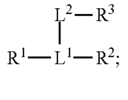

where $R^1$ is a Toll-like receptor 9-binding nucleic acid sequence; $L^1$ and $L^2$ are independently a linking group; and $R^2$ and $R^3$ are independently a hybridized nucleic acid sequence. In embodiments, the 3' end of $R^1$ is bonded to $L^1$. In embodiments, the 5' end of $R^1$ is bonded to $L^1$. In embodiments, $R^2$ and $R^3$ are independently comprise a miR146a passenger strand sequence hybridized to a miR146a guide strand sequence. In embodiments, the 3' end of the miR146a passenger strand sequence of $R^2$ is bonded to $L^1$. In embodiments, the 5' end of the miR146a passenger strand sequence of $R^2$ is bonded to $L^1$. In embodiments, the 3' end of the miR146a passenger strand sequence of $R^3$ is bonded to $L^2$. In embodiments, the 5' end of the miR146a passenger strand sequence of $R^3$ is bonded to $L^2$. In embodiments, the miR146a passenger strand sequence comprises SEQ ID NO: 1, 2, 3, 4, or 5, and the miR146a guide strand sequence comprises a complementary nucleic acid sequence. In embodiments, the miR146a passenger strand sequence comprises SEQ ID NO: 1, and the miR146a guide strand sequence comprises a complementary nucleic acid sequence. In embodiments, the miR146a passenger strand sequence comprises SEQ ID NO:2, and the miR146a guide strand sequence comprises a complementary nucleic acid sequence. In embodiments, the miR146a passenger strand sequence comprises SEQ ID NO:3, and the miR146a guide strand sequence comprises a complementary nucleic acid sequence. In embodiments, the miR146a passenger strand sequence comprises SEQ ID NO:4, and the miR146a guide strand sequence comprises a complementary nucleic acid sequence. In embodiments, the miR146a passenger strand sequence comprises SEQ ID NO:5, and the miR146a guide strand sequence comprises a complementary nucleic acid sequence. In embodiments, the miR146a guide strand sequence comprises SEQ ID NO:6. In embodiments, the miR146a guide strand sequence comprises SEQ ID NO:7. In embodiments, the miR146a guide strand sequence comprises SEQ ID NO:8. In embodiments, the miR146a passenger strand sequence comprises SEQ ID NO:1; and the miR146a guide strand sequence comprises SEQ ID NO:6. In embodiments, the miR146a passenger strand sequence comprises SEQ ID NO:2; and the miR146a guide strand sequence comprises SEQ ID NO:7. In embodiments, the miR146a passenger strand sequence comprises SEQ ID NO:2; and the miR146a guide strand sequence comprises SEQ ID NO:8. In embodiments, the miR146a passenger strand sequence of $R^2$ and $R^3$ are the same. In embodiments, the miR146a passenger strand sequence of $R^2$ and $R^3$ are different. In embodiments, the miR146a guide strand sequence of $R^2$ and $R^3$ are the same. In embodiments, the miR146a guide strand sequence of $R^2$ and $R^3$ are different. In embodiments, the miR146a passenger strand sequence and guide strand sequence of $R^2$ and $R^3$ are the same. In embodiments, $L^2$ is covalently bonded to L. In embodiments, the microRNA passenger strand sequence is covalently bonded via the linking group to the Toll-like receptor 9-binding nucleic acid sequence; and the microRNA guide strand sequence is hybridized to the microRNA passenger strand sequence. In embodiments, the 3' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence. In embodiments, the 5' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence.

In embodiments, the miR146a passenger strand sequence comprises SEQ ID NO:37 or 39, and the miR146a guide strand sequence comprises a complementary nucleic acid sequence. In embodiments, the miR146a passenger strand sequence comprises SEQ ID NO:37, and the miR146a guide strand sequence comprises a complementary nucleic acid sequence. In embodiments, the miR146a passenger strand sequence comprises SEQ ID NO:39, and the miR146a guide strand sequence comprises a complementary nucleic acid sequence. In embodiments, the miR146a guide strand sequence comprises SEQ ID NO:36. In embodiments, the miR146a guide strand sequence comprises SEQ ID NO:38. In embodiments, the miR146a passenger strand sequence comprises SEQ ID NO:37; and the miR146a guide strand sequence comprises SEQ ID NO:36. In embodiments, the miR146a passenger strand sequence comprises SEQ ID NO:39; and the miR146a guide strand sequence comprises SEQ ID NO:38. In embodiments, the miR146a passenger strand sequence of $R^2$ and $R^3$ are the same. In embodiments, the miR146a passenger strand sequence of $R^2$ and $R^3$ are different. In embodiments, the miR146a guide strand sequence of $R^2$ and $R^3$ are the same. In embodiments, the miR146a guide strand sequence of $R^2$ and $R^3$ are different. In embodiments, the miR146a passenger strand sequence and guide strand sequence of $R^2$ and $R^3$ are the same. In embodiments, $L^2$ is covalently bonded to $L^1$. In embodiments, the microRNA passenger strand sequence is covalently bonded via the linking group to the Toll-like receptor 9-binding nucleic acid sequence; and the microRNA guide strand sequence is hybridized to the microRNA passenger strand sequence. In embodiments, the 3' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence. In embodiments, the 5' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence.

In embodiments, $R^2$ and $R^3$ independently comprise an miR155 passenger strand sequence hybridized to an miR155 guide strand sequence. In embodiments, the miR155 passenger strand sequence comprises SEQ ID NO: 19, and the miR155 guide strand sequence comprises SEQ ID NO:20. In embodiments, the 3' end of the miR155 passenger strand sequence of $R^2$ is bonded to $L^1$. In embodiments, the 5' end of the miR155 passenger strand sequence of $R^2$ is bonded to $L^1$. In embodiments, the 3' end of the miR155 passenger strand sequence of $R^3$ is bonded to $L^2$. In embodiments, the 5' end of the miR155 passenger strand sequence of $R^3$ is bonded to $L^2$. In embodiments, $L^2$ is covalently bonded to $L^1$. In embodiments, the microRNA passenger strand sequence is covalently bonded via the linking group to the Toll-like receptor 9-binding nucleic acid sequence; and the microRNA guide strand sequence is hybridized to the microRNA passenger strand sequence. In embodiments, the 3' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence. In embodiments, the 5' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence.

In embodiments, $R^2$ and $R^3$ are independently comprise a miR142 passenger strand sequence hybridized to a miR142 guide strand sequence. In embodiments, the miR142 passenger strand sequence comprises SEQ ID NO:21, and the miR142 guide strand sequence comprises SEQ ID NO:22. In embodiments, the miR142 passenger strand sequence comprises SEQ ID NO:49, and the miR142 guide strand sequence comprises SEQ ID NO:48. In embodiments, the 3' end of the miR142 passenger strand sequence of $R^2$ is bonded to $L^1$. In embodiments, the 5' end of the miR142 passenger strand sequence of $R^2$ is bonded to $L^1$. In embodiments, the 3' end of the miR142 passenger strand sequence of $R^3$ is bonded to $L^2$. In embodiments, the 5' end of the miR142 passenger strand sequence of $R^3$ is bonded to $L^2$. In embodiments, $L^2$ is covalently bonded to $L^1$. In embodiments, the microRNA passenger strand sequence is covalently bonded via the linking group to the Toll-like receptor 9-binding nucleic acid sequence; and the microRNA guide strand sequence is hybridized to the microRNA passenger strand sequence. In embodiments, the 3' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence. In embodiments, the 5' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence.

In embodiments, $R^2$ and $R^3$ are independently comprise a miR125b passenger strand sequence hybridized to a miR125b guide strand sequence. In embodiments, the miR125b passenger strand sequence comprises SEQ ID NO:23, and the miR125b guide strand sequence comprises SEQ ID NO:24. In embodiments, the 3' end of the miR125b passenger strand sequence of $R^2$ is bonded to $L^1$. In embodiments, the 5' end of the miR125b passenger strand sequence of $R^2$ is bonded to $L^1$. In embodiments, the 3' end of the miR125b passenger strand sequence of $R^3$ is bonded to $L^2$. In embodiments, the 5' end of the miR125b passenger strand sequence of $R^3$ is bonded to $L^2$. In embodiments, $L^2$ is covalently bonded to $L^1$. In embodiments, the microRNA passenger strand sequence is covalently bonded via the linking group to the Toll-like receptor 9-binding nucleic acid sequence; and the microRNA guide strand sequence is hybridized to the microRNA passenger strand sequence. In embodiments, the 3' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence. In embodiments, the 5' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence.

In embodiments, $R^2$ and $R^3$ are independently comprise a miR203b passenger strand sequence hybridized to a miR203b guide strand sequence. In embodiments, the miR203b passenger strand sequence comprises SEQ ID NO:25, and the miR203b guide strand sequence comprises SEQ ID NO:26. In embodiments, the 3' end of the miR203b passenger strand sequence of $R^2$ is bonded to $L^1$. In embodiments, the 5' end of the miR203b passenger strand sequence of $R^2$ is bonded to $L^1$. In embodiments, the 3' end of the miR203b passenger strand sequence of $R^3$ is bonded to $L^2$. In embodiments, the 5' end of the miR203b passenger strand sequence of $R^3$ is bonded to $L^2$. In embodiments, $L^2$ is covalently bonded to $L^1$. In embodiments, the microRNA passenger strand sequence is covalently bonded via the linking group to the Toll-like receptor 9-binding nucleic acid sequence; and the microRNA guide strand sequence is hybridized to the microRNA passenger strand sequence. In embodiments, the 3' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence. In embodiments, the 5' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence.

In embodiments, $R^2$ and $R^3$ are independently comprise a miR221 passenger strand sequence hybridized to a miR221 guide strand sequence. In embodiments, the miR221 passenger strand sequence comprises SEQ ID NO:27, and the miR221 guide strand sequence comprises SEQ ID NO:28. In embodiments, the 3' end of the miR221 passenger strand sequence of $R^2$ is bonded to $L^1$. In embodiments, the 5' end of the miR221 passenger strand sequence of $R^2$ is bonded to $L^1$. In embodiments, the 3' end of the miR221 passenger strand sequence of $R^3$ is bonded to $L^2$. In embodiments, the 5' end of the miR221 passenger strand sequence of $R^3$ is bonded to $L^2$. In embodiments, $L^2$ is covalently bonded to $L^1$. In embodiments, the microRNA passenger strand sequence is covalently bonded via the linking group to the Toll-like receptor 9-binding nucleic acid sequence; and the microRNA guide strand sequence is hybridized to the microRNA passenger strand sequence. In embodiments, the 3' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence. In embodiments, the 5' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence.

In embodiments, $R^2$ and $R^3$ are independently comprise a miR222 passenger strand sequence hybridized to a miR222 guide strand sequence. In embodiments, the miR222 passenger strand sequence comprises SEQ ID NO:29, and the miR222 guide strand sequence comprises SEQ ID NO:30. In embodiments, the 3' end of the miR222 passenger strand sequence of $R^2$ is bonded to $L^1$. In embodiments, the 5' end of the miR222 passenger strand sequence of $R^2$ is bonded to $L^1$. In embodiments, the 3' end of the miR222 passenger strand sequence of $R^3$ is bonded to $L^2$. In embodiments, the 5' end of the miR222 passenger strand sequence of $R^3$ is bonded to $L^2$. In embodiments, $L^2$ is covalently bonded to $L^1$. In embodiments, the microRNA passenger strand sequence is covalently bonded via the linking group to the Toll-like receptor 9-binding nucleic acid sequence; and the microRNA guide strand sequence is hybridized to the microRNA passenger strand sequence. In embodiments, the 3' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence. In embodiments, the 5' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence.

In embodiments, $R^2$ and $R^3$ are independently comprise a miR29b passenger strand sequence hybridized to a miR29b guide strand sequence. In embodiments, the miR29b passenger strand sequence comprises SEQ ID NO:31, and the miR142 guide strand sequence comprises SEQ ID NO:32. In embodiments, the 3' end of the miR29b passenger strand sequence of $R^2$ is bonded to $L^1$. In embodiments, the 5' end of the miR29b passenger strand sequence of $R^2$ is bonded to $L^1$. In embodiments, the 3' end of the miR29b passenger strand sequence of $R^3$ is bonded to $L^2$. In embodiments, the 5' end of the miR29b passenger strand sequence of $R^3$ is bonded to $L^2$. In embodiments, $L^2$ is covalently bonded to $L^1$. In embodiments, the microRNA passenger strand sequence is covalently bonded via the linking group to the Toll-like receptor 9-binding nucleic acid sequence; and the microRNA guide strand sequence is hybridized to the microRNA passenger strand sequence. In embodiments, the 3' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence. In embodiments, the 5' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence.

In embodiments, $R^2$ and $R^3$ comprise different hybridized microRNA. In embodiments, $R^2$ comprises a microRNA passenger strand sequence hybridized to a microRNA guide strand sequence, wherein the microRNA is miR146, miR155, miR142, miR125b, miR203b, miR221, miR222, miR29b; and $R^3$ comprises a microRNA passenger strand sequence hybridized to a microRNA guide strand sequence, wherein the microRNA is miR146, miR155, miR142, miR125b, miR203b, miR221, miR222, miR29b; wherein the microRNA is $R^2$ and $R^3$ are different. In embodiments, the miR146a passenger strand sequence comprises SEQ ID NO:1, 2, 3, 4, or 5, and the miR146a guide strand sequence comprises SEQ ID NO:6, 7, or 8. In embodiments, the miR146a passenger strand sequence comprises SEQ ID NO:1, and the miR146a guide strand sequence comprises SEQ ID NO:6. In embodiments, the miR146a passenger strand sequence comprises SEQ ID NO:2, and the miR146a guide strand sequence comprises SEQ ID NO:7. In embodiments, the miR146a passenger strand sequence comprises SEQ ID NO:2, and the miR146a guide strand sequence comprises SEQ ID NO:8. In embodiments, the miR146a passenger strand sequence comprises SEQ ID NO:37, and the miR146a guide strand sequence comprises SEQ ID NO:36. In embodiments, the miR146a passenger strand sequence comprises SEQ ID NO:39, and the miR146a guide strand sequence comprises SEQ ID NO:38. In embodiments, the miR155 passenger strand sequence comprises SEQ ID NO:19, and the miR155 guide strand sequence comprises SEQ ID NO:20. In embodiments, the miR142 passenger strand sequence comprises SEQ ID NO:21, and the miR142 guide strand sequence comprises SEQ ID NO:22. In embodiments, the miR142 passenger strand sequence comprises SEQ ID NO:49, and the miR142 guide strand sequence comprises SEQ ID NO:48. In embodiments, the miR125b passenger strand sequence comprises SEQ ID NO:23, and the miR125b guide strand sequence comprises SEQ ID NO:24. In embodiments, the miR203b passenger strand sequence comprises SEQ ID NO:25, and the miR203b guide strand sequence comprises SEQ ID NO:26. In embodiments, the miR221 passenger strand sequence comprises SEQ ID NO:27, and the miR221 guide strand sequence comprises SEQ ID NO:28. In embodiments, the miR222 passenger strand sequence comprises SEQ ID NO:29, and the miR222 guide strand sequence comprises SEQ ID NO:30. In embodiments, the miR29b passenger strand sequence comprises SEQ ID NO:31, and the miR142 guide strand sequence comprises SEQ ID NO:32. In embodiments, the 3' end of the microRNA passenger strand sequence of $R^2$ is bonded to $L^1$. In embodiments, the 5' end of the microRNA passenger strand sequence of $R^2$ is bonded to $L^1$. In embodiments, the 3' end of the microRNA passenger strand sequence of $R^3$ is bonded to $L^2$. In embodiments, the 5' end of the microRNA passenger strand sequence of $R^3$ is bonded to $L^2$. In embodiments, $R^2$ comprises a miR146a passenger strand sequence hybridized to a miR146a guide strand sequence; and $R^3$ comprises an miR155 passenger strand sequence hybridized to an miR155 guide strand sequence. In embodiments, the 3' end of the miR146a passenger strand sequence of $R^2$ is bonded to $L^1$. In embodiments, the 5' end of the miR146a passenger strand sequence of $R^2$ is bonded to $L^1$. In embodiments, the 3' end of the miR155 passenger strand sequence of $R^3$ is bonded to $L^2$. In embodiments, the 5' end of the miR155 passenger strand sequence of $R^3$ is bonded to $L^2$. In embodiments, $R^2$ comprises a miR146a passenger strand sequence hybridized to a miR146a guide strand sequence; and $R^3$ comprises a miR142 passenger strand sequence hybridized to a miR142 guide strand sequence. In embodiments, the 3' end of the miR146a passenger strand sequence of $R^2$ is bonded to $L^1$. In embodiments, the 5' end of the miR146a passenger strand sequence of $R^2$ is bonded to $L^1$. In embodiments, the 3' end of the miR142 passenger strand sequence of $R^3$ is bonded to $L^2$. In embodiments, the 5' end of the miR141 passenger strand sequence of $R^3$ is bonded to $L^2$. In embodiments, $R^2$ comprises a miR146a passenger strand sequence hybridized to a miR146a guide strand sequence; and $R^3$ comprises a miR125b passenger strand sequence hybridized to a miR125b guide strand sequence. In embodiments, the 3' end of the miR146a passenger strand sequence of $R^2$ is bonded to $L^1$. In embodiments, the 5' end of the miR146a passenger strand sequence of $R^2$ is bonded to $L^1$. In embodiments, the 3' end of the miR125b passenger strand sequence of $R^3$ is bonded to $L^2$. In embodiments, the 5' end of the miR125b passenger strand sequence of $R^3$ is bonded to $L^2$. In embodiments, $R^2$ comprises a miR146a passenger strand sequence hybridized to a miR146a guide strand sequence; and $R^3$ comprises a miR203b passenger strand sequence hybridized to a miR203b guide strand sequence. In embodiments, the 3' end of the miR146a passenger strand sequence of $R^2$ is bonded to $L^1$. In embodiments, the 5' end of the miR146a passenger strand sequence of $R^2$ is bonded to $L^1$. In embodiments, the 3' end of the miR203b passenger strand sequence of $R^3$ is bonded to $L^2$. In embodiments, the 5' end of the miR203b passenger strand sequence of $R^3$ is bonded to $L^2$. In embodiments, $R^2$ comprises a miR146a passenger strand sequence hybridized to a miR146a guide strand sequence; and $R^3$ comprises a miR221 passenger strand sequence hybridized to a miR221 guide strand sequence. In embodiments, the 3' end of the miR146a passenger strand sequence of $R^2$ is bonded to $L^1$. In embodiments, the 5' end of the miR146a passenger strand sequence of $R^2$ is bonded to $L^1$. In embodiments, the 3' end of the miR221 passenger strand sequence of $R^3$ is bonded to $L^2$. In embodiments, the 5' end of the miR221 passenger strand sequence of $R^3$ is bonded to $L^2$. In embodiments, $R^2$ comprises a miR146a passenger strand sequence hybridized to a miR146a guide strand sequence; and $R^3$ comprises a miR222 passenger strand sequence hybridized to a miR222 guide strand sequence. In embodiments, the 3' end of the miR146a passenger strand sequence of $R^2$ is bonded to $L^1$. In embodiments, the 5' end of the miR146a passenger strand sequence of $R^2$ is bonded to $L^1$. In embodiments, the 3' end of the miR222 passenger strand sequence of $R^3$ is bonded to $L^2$. In embodiments, the 5' end of the miR222 passenger strand sequence of $R^3$ is bonded to $L^2$. In embodiments, $R^2$ comprises a miR146a passenger strand sequence hybridized to a miR146a guide strand sequence; and $R^3$ comprises a miR29b passenger strand sequence hybridized to a miR29b guide strand sequence. In embodiments, the 3' end of the miR146a passenger strand sequence of $R^2$ is bonded to $L^1$. In embodiments, the 5' end of the miR146a passenger strand sequence of $R^2$ is bonded to $L^1$. In embodiments, the 3' end of the miR29b passenger strand sequence of $R^3$ is bonded to $L^2$. In embodiments, the 5' end of the miR29b passenger strand sequence of $R^3$ is bonded to $L^2$.

The disclosure provides a compound of Formula (III):

(III)

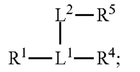

where $R^1$ is a Toll-like receptor 9-binding nucleic acid sequence; $L^1$ and $L^2$ are independently a linking group; and $R^4$ and $R^5$ are independently a microRNA passenger strand sequence. In embodiments, the microRNA passenger strand sequence is a miR146a passenger strand sequence. In embodiments, the microRNA passenger strand sequence is miR155 passenger strand sequence. In embodiments, the microRNA passenger strand sequence is a miR142 passenger strand sequence. In embodiments, the microRNA passenger strand sequence is a miR125b passenger strand sequence. In embodiments, the microRNA passenger strand sequence is a miR203b passenger strand sequence. In embodiments, the microRNA passenger strand sequence is a miR221 passenger strand sequence. In embodiments, the microRNA passenger strand sequence is a miR222 passenger strand sequence. In embodiments, the microRNA passenger strand sequence is a miR29b passenger strand sequence. In embodiments, the miR146a passenger strand sequence comprises SEQ ID NO:1. In embodiments, one or more nucleotides in SEQ ID NO:1 are modified with 2'-O-Methyl, 2'-Fluoro, a phosphorothioate linkage, or a combination thereof. In embodiments, the miR146a passenger strand sequence comprises SEQ ID NO:2. In embodiments, the miR146a passenger strand sequence comprises SEQ ID NO:3. In embodiments, the miR146a passenger strand sequence comprises SEQ ID NO:4. In embodiments, the miR146a passenger strand sequence comprises SEQ ID NO:5. In embodiments, the miR146a passenger strand sequence comprises SEQ ID NO: 37. In embodiments, the miR146a passenger strand sequence comprises SEQ ID NO:39. In embodiments, the miR155 passenger strand sequence comprises SEQ ID NO:19. In embodiments, the miR142 passenger strand sequence comprises SEQ ID NO:21. In embodiments, the miR142 passenger strand sequence comprises SEQ ID NO:49. In embodiments, the miR125b passenger strand sequence comprises SEQ ID NO:23. In embodiments, the miR203b passenger strand sequence comprises SEQ ID NO:25. In embodiments, the miR221 passenger strand sequence comprises SEQ ID NO:27. In embodiments, the miR222 passenger strand sequence comprises SEQ ID NO:29. In embodiments, the miR29b passenger strand sequence comprises SEQ ID NO:31. In embodiments, the 3' end of the microRNA passenger strand sequence of $R^4$ is bonded to $L^1$. In embodiments, the 5' end of the microRNA passenger strand sequence of $R^4$ is bonded to $L^1$. In embodiments, the 3' end of the microRNA passenger strand sequence of $R^5$ is bonded to $L^2$. In embodiments, the 5' end of the microRNA passenger strand sequence of $R^5$ is bonded to $L^2$. In embodiments, $L^2$ is covalently bonded to $L^1$. In embodiments, the microRNA passenger strand sequence is covalently bonded via the linking group to the Toll-like receptor 9-binding nucleic acid sequence; and the microRNA guide strand sequence is hybridized to the microRNA passenger strand sequence. In embodiments, the 3' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence. In embodiments, the 5' end of the microRNA passenger strand sequence is covalently bonded via the linking group to the 3' end of the Toll-like receptor 9-binding nucleic acid sequence; and the microRNA guide strand sequence is hybridized to the microRNA passenger strand sequence.

In embodiments, $R^4$ and $R^5$ comprise different hybridized microRNA. In embodiments, $R^4$ comprises a miR146a passenger strand sequence hybridized to a miR146a guide strand sequence; and $R^5$ comprises an miR155 passenger strand sequence hybridized to an miR155 guide strand sequence. In embodiments, the 3' end of the miR146a passenger strand sequence of $R^4$ is bonded to $L^1$. In embodiments, the 5' end of the miR146a passenger strand sequence of $R^4$ is bonded to $L^1$. In embodiments, the 3' end of the miR155 passenger strand sequence of $R^5$ is bonded to $L^2$. In embodiments, the 5' end of the miR155 passenger strand sequence of $R^5$ is bonded to $L^2$. In embodiments, the miR146a passenger and guide strand sequences are as described herein, including embodiments thereof. In embodiments, the miR155 passenger and guide strand sequences are as described herein, including embodiments thereof.

In embodiments, $R^4$ comprises a miR146a passenger strand sequence hybridized to a miR146a guide strand sequence; and $R^5$ comprises a miR142 passenger strand sequence hybridized to a miR142 guide strand sequence. In embodiments, the 3' end of the miR146a passenger strand sequence of $R^4$ is bonded to $L^1$. In embodiments, the 5' end of the miR146a passenger strand sequence of $R^4$ is bonded to $L^1$. In embodiments, the 3' end of the miR142 passenger strand sequence of $R^5$ is bonded to $L^2$. In embodiments, the 5' end of the miR142 passenger strand sequence of $R^5$ is bonded to $L^2$. In embodiments, the miR146a passenger and guide strand sequences are as described herein, including embodiments thereof. In embodiments, the miR142 passenger and guide strand sequences are as described herein, including embodiments thereof.

In embodiments, $R^4$ comprises a miR146a passenger strand sequence hybridized to a miR146a guide strand sequence; and $R^5$ comprises a miR125b passenger strand sequence hybridized to a miR125b guide strand sequence. In embodiments, the 3' end of the miR146a passenger strand sequence of $R^4$ is bonded to $L^1$. In embodiments, the 5' end of the miR146a passenger strand sequence of $R^5$ is bonded to $L^1$. In embodiments, the 3' end of the miR125b passenger strand sequence of $R^5$ is bonded to $L^2$. In embodiments, the 5' end of the miR125b passenger strand sequence of $R^5$ is bonded to $L^2$. In embodiments, the miR146a passenger and guide strand sequences are as described herein, including embodiments thereof. In embodiments, the miR125b passenger and guide strand sequences are as described herein, including embodiments thereof.

In embodiments, $R^4$ comprises a miR146a passenger strand sequence hybridized to a miR146a guide strand sequence; and $R^5$ comprises a miR203b passenger strand sequence hybridized to a miR203b guide strand sequence. In embodiments, the 3' end of the miR146a passenger strand sequence of $R^4$ is bonded to $L^1$. In embodiments, the 5' end of the miR146a passenger strand sequence of $R^4$ is bonded to $L^1$. In embodiments, the 3' end of the miR203b passenger strand sequence of $R^5$ is bonded to $L^2$. In embodiments, the 5' end of the miR203b passenger strand sequence of $R^5$ is bonded to $L^2$. In embodiments, the miR146a passenger and guide strand sequences are as described herein, including embodiments thereof. In embodiments, the miR203b passenger and guide strand sequences are as described herein, including embodiments thereof.

In embodiments, $R^4$ comprises a miR146a passenger strand sequence hybridized to a miR146a guide strand sequence; and $R^5$ comprises a miR221 passenger strand sequence hybridized to a miR221 guide strand sequence. In embodiments, the 3' end of the miR146a passenger strand sequence of $R^4$ is bonded to $L^1$. In embodiments, the 5' end of the miR146a passenger strand sequence of $R^4$ is bonded to $L^1$. In embodiments, the 3' end of the miR221 passenger strand sequence of $R^5$ is bonded to $L^2$. In embodiments, the 5' end of the miR221 passenger strand sequence of $R^5$ is bonded to $L^2$. In embodiments, the miR146a passenger and guide strand sequences are as described herein, including embodiments thereof. In embodiments, the miR221 passenger and guide strand sequences are as described herein, including embodiments thereof.

In embodiments, $R^4$ comprises a miR146a passenger strand sequence hybridized to a miR146a guide strand sequence; and $R^5$ comprises a miR222 passenger strand sequence hybridized to a miR222 guide strand sequence. In embodiments, the 3' end of the miR146a passenger strand sequence of $R^4$ is bonded to $L^1$. In embodiments, the 5' end of the miR146a passenger strand sequence of $R^4$ is bonded to $L^1$. In embodiments, the 3' end of the miR222 passenger strand sequence of $R^5$ is bonded to $L^2$. In embodiments, the 5' end of the miR222 passenger strand sequence of $R^5$ is bonded to $L^2$. In embodiments, the miR146a passenger and guide strand sequences are as described herein, including embodiments thereof. In embodiments, the miR222 passenger and guide strand sequences are as described herein, including embodiments thereof.

In embodiments, $R^4$ comprises a miR146a passenger strand sequence hybridized to a miR146a guide strand sequence; and $R^5$ comprises a miR29b passenger strand sequence hybridized to a miR29b guide strand sequence. In embodiments, the 3' end of the miR146a passenger strand sequence of $R^4$ is bonded to $L^1$. In embodiments, the 5' end of the miR146a passenger strand sequence of $R^4$ is bonded to $L^1$. In embodiments, the 3' end of the miR29b passenger strand sequence of $R^5$ is bonded to $L^2$. In embodiments, the 5' end of the miR29b passenger strand sequence of $R^5$ is bonded to $L^2$. In embodiments, the miR146a passenger and guide strand sequences are as described herein, including embodiments thereof. In embodiments, the miR29b passenger and guide strand sequences are as described herein, including embodiments thereof.

In embodiments of all the compounds described herein, the microRNA passenger strand sequence further comprises from 1 to 10 nucleotides on the 3' end, the '5 end, or both the 3' and 5' end; wherein 1 to 10 nucleotides are modified with 2'-O-Methyl, 2'-Fluoro, a phosphorothioate linkage, or a combination thereof. In embodiments, the microRNA passenger strand sequence further comprises from 1 to 8 nucleotides on the 3' end, the '5 end, or both the 3' and 5' end; wherein 1 to 8 nucleotides are modified with 2'-O-Methyl, 2'-Fluoro, a phosphorothioate linkage, or a combination thereof. In embodiments, the microRNA passenger strand sequence further comprises from 1 to 6 nucleotides on the 3' end, the '5 end, or both the 3' and 5' end; wherein 1 to 6 nucleotides are modified with 2'-O-Methyl, 2'-Fluoro, a phosphorothioate linkage, or a combination thereof. In embodiments, the microRNA passenger strand sequence further comprises from 1 to 5 nucleotides on the 3' end, the '5 end, or both the 3' and 5' end; wherein 1 to 5 nucleotides are modified with 2'-O-Methyl, 2'-Fluoro, a phosphorothioate linkage, or a combination thereof. In embodiments, the microRNA passenger strand sequence further comprises from 1 to 4 nucleotides on the 3' end, the '5 end, or both the 3' and 5' end; wherein 1 to 4 nucleotides are modified with 2'-O-Methyl, 2'-Fluoro, a phosphorothioate linkage, or a combination thereof. In embodiments, the microRNA passenger strand sequence further comprises from 1 to 3 nucleotides on the 3' end, the '5 end, or both the 3' and 5' end; wherein 1 to 3 nucleotides are modified with 2'-O-Methyl, 2'-Fluoro, a phosphorothioate linkage, or a combination thereof. In embodiments, the microRNA passenger strand sequence further comprises from 1 to 2 nucleotides on the 3' end, the '5 end, or both the 3' and 5' end; wherein 1 to 2 nucleotides are modified with 2'-O-Methyl, 2'-Fluoro, a phosphorothioate linkage, or a combination thereof. In embodiments, the microRNA passenger strand sequence is miR-146a, miR155, miR142, miR125b, miR203b, miR221, miR222, or miR29b. In embodiments, the microRNA passenger strand sequence is miR-146a. In embodiments, the microRNA passenger strand sequence is anti-miR-155. In embodiments, the microRNA passenger strand sequence is miR-142. In embodiments, the microRNA passenger strand sequence is miR-125b. In embodiments, the microRNA passenger strand sequence is miR-203b. In embodiments, the microRNA passenger strand sequence is miR-221. In embodiments, the microRNA passenger strand sequence is miR-222. In embodiments, the microRNA passenger strand sequence is miR-29b.

In embodiments of all the compounds described herein, SEQ ID NO:1 further comprises from 1 to 10 nucleotides on the 3' end, the '5 end, or both the 3' and 5' end; wherein 1 to 10 nucleotides are modified with 2'-O-Methyl, 2'-Fluoro, a phosphorothioate linkage, or a combination thereof. In embodiments, SEQ ID NO:1 further comprises from 1 to 8 nucleotides on the 3' end, the '5 end, or both the 3' and 5' end; wherein 1 to 8 nucleotides are modified with 2'-O-Methyl, 2'-Fluoro, a phosphorothioate linkage, or a combination thereof. In embodiments, SEQ ID NO:1 further comprises from 1 to 6 nucleotides on the 3' end, the '5 end, or both the 3' and 5' end; wherein 1 to 6 nucleotides are modified with 2'-O-Methyl, 2'-Fluoro, a phosphorothioate linkage, or a combination thereof. In embodiments, SEQ ID NO:1 further comprises from 1 to 5 nucleotides on the 3' end, the '5 end, or both the 3' and 5' end; wherein 1 to 5 nucleotides are modified with 2'-O-Methyl, 2'-Fluoro, a phosphorothioate linkage, or a combination thereof. In embodiments, SEQ ID NO:1 further comprises from 1 to 4 nucleotides on the 3' end, the '5 end, or both the 3' and 5' end; wherein 1 to 4 nucleotides are modified with 2'-O-Methyl, 2'-Fluoro, a phosphorothioate linkage, or a combination thereof. In embodiments, SEQ ID NO:1 further comprises from 1 to 3 nucleotides on the 3' end, the '5 end, or both the 3' and 5' end; wherein 1 to 3 nucleotides are modified with 2'-O-Methyl, 2'-Fluoro, a phosphorothioate linkage, or a combination thereof. In embodiments, SEQ ID NO:1 further comprises 1 or 2 nucleotides on the 3' end, the '5 end, or both the 3' and 5' end; wherein 1 or 2 nucleotides are modified with 2'-O-Methyl, 2'-Fluoro, a phosphorothioate linkage, or a combination thereof. In embodiments, 1 or more of the additional nucleotides on the 3' end of SEQ ID NO:1 are modified with 2'-O-Methyl, 2'-Fluoro, a phosphorothioate linkage, or a combination thereof. In embodiments, 1 or more of the additional nucleotides on the 5' end of SEQ ID NO:1 are modified with 2'-O-Methyl, 2'-Fluoro, a phosphorothioate linkage, or a combination thereof. In embodiments, 1 or more of the additional nucleotides on both the 3' end and the 5' end of SEQ ID NO:1 are modified with 2'-O-Methyl, 2'-Fluoro, a phosphorothioate linkage, or a combination thereof. In embodiments, SEQ ID NO:1 is further modified in a manner to produce SEQ ID NO:2 or SEQ ID NO:3. In embodiments, SEQ ID NO:1 is further modified in a manner to produce SEQ ID NO:2, 3, 4 or 5. In embodiments, SEQ ID NO:1 is further modified in a manner to produce SEQ ID NO:2. In embodiments, SEQ ID NO:1 is further modified in a manner to produce SEQ ID NO: 3. In embodiments, SEQ ID NO:1 is further modified in a manner to produce SEQ ID NO:4 In embodiments, SEQ ID NO:1 is further modified in a manner to produce SEQ ID NO: 5. In embodiments, SEQ ID NO:1 is further modified in a manner to produce SEQ ID NO:37 or SEQ ID NO:39. In embodiments, SEQ ID NO:1 is further modified in a manner to produce SEQ ID NO: 37. In embodiments, SEQ ID NO:1 is further modified in a manner to produce SEQ ID NO:39. In embodiments, SEQ ID NO:1 is further modified in a manner to produce SEQ ID NO:2, SEQ ID NO:3, SEQ ID NO:4, SEQ ID NO:5, SEQ ID NO:37, or SEQ ID NO:39.

In embodiments of all the compounds described herein, SEQ ID NO:6 further comprises from 1 to 10 nucleotides on the 3' end, the '5 end, or both the 3' and 5' end; wherein 1 to 10 nucleotides are optionally modified with 2'-O-Methyl, 2'-Fluoro, a phosphorothioate linkage, or a combination thereof. In embodiments, SEQ ID NO:6 further comprises from 1 to 8 nucleotides on the 3' end, the '5 end, or both the 3' and 5' end; wherein 1 to 8 nucleotides are optionally modified with 2'-O-Methyl, 2'-Fluoro, a phosphorothioate linkage, or a combination thereof. In embodiments, SEQ ID NO:6 further comprises from 1 to 6 nucleotides on the 3' end, the '5 end, or both the 3' and 5' end; wherein 1 to 6 nucleotides are optionally modified with 2'-O-Methyl, 2'-Fluoro, a phosphorothioate linkage, or a combination thereof. In embodiments, SEQ ID NO:6 further comprises from 1 to 5 nucleotides on the 3' end, the '5 end, or both the 3' and 5' end; wherein 1 to 5 nucleotides are optionally modified with 2'-O-Methyl, 2'-Fluoro, a phosphorothioate linkage, or a combination thereof. In embodiments, SEQ ID NO:6 further comprises from 1 to 4 nucleotides on the 3' end, the '5 end, or both the 3' and 5' end; wherein 1 to 4 nucleotides are optionally modified with 2'-O-Methyl, 2'-Fluoro, a phosphorothioate linkage, or a combination thereof. In embodiments, SEQ ID NO:6 further comprises from 1 to 3 nucleotides on the 3' end, the '5 end, or both the 3' and 5' end; wherein 1 to 3 nucleotides are optionally modified with 2'-O-Methyl, 2'-Fluoro, a phosphorothioate linkage, or a combination thereof. In embodiments, SEQ ID NO:6 further comprises 1 or 2 nucleotides on the 3' end, the '5 end, or both the 3' and 5' end; wherein 1 or 2 nucleotides are optionally modified with 2'-O-Methyl, 2'-Fluoro, a phosphorothioate linkage, or a combination thereof. In embodiments, 1 or more of the additional nucleotides on the 3' end of SEQ ID NO:6 are optionally modified with 2'-O-Methyl, 2'-Fluoro, a phosphorothioate linkage, or a combination thereof. In embodiments, 1 or more of the additional nucleotides on the 5' end of SEQ ID NO:6 are modified with 2'-O-Methyl, 2'-Fluoro, a phosphorothioate linkage, or a combination thereof. In embodiments, 1 or more of the additional nucleotides on both the 3' end and the 5' end of SEQ ID NO:6 are optionally modified with 2'-O-Methyl, 2'-Fluoro, a phosphorothioate linkage, or a combination thereof. In embodiments, SEQ ID NO:6 is further modified to provide SEQ ID NO:7 or SEQ ID NO:8. In embodiments, SEQ ID NO:6 is further modified to provide SEQ ID NO:7. In embodiments, SEQ ID NO:6 is further modified to provide SEQ ID NO:8. In embodiments, SEQ ID NO:6 is further modified to provide SEQ ID NO:36 or SEQ ID NO:38. In embodiments, SEQ ID NO:6 is further modified to provide SEQ ID NO:36. In embodiments, SEQ ID NO:6 is further modified to provide SEQ ID NO:38. In embodiments, SEQ ID NO:6 is further modified to provide SEQ ID NO:7, SEQ ID NO: 8, SEQ ID NO:36, or SEQ ID NO:38.

$R^1$ comprises a Toll-like receptor 9-binding nucleic acid sequence. In embodiments, the Toll-like receptor 9-binding nucleic acid sequence comprises a CpG oligodeoxynucleotide (ODN). In embodiments, the CpG ODN is a CpG-A ODN, a CpG-B ODN, a CpG-C ODN, or a combination of two or more thereof. In embodiments, the CpG ODN is a CpG-A ODN. In embodiments, the CpG ODN is a CpG-B ODN. In embodiments, the CpG ODN is a CpG-C ODN. In embodiments, the CpG ODN is CpG ODN D19, CpG ODN 1585, CpG ODN 2216, CpG ODN 2336, CpG ODN 1668, CpG ODN 1826, CpG ODN 2006, CpG ODN 2007, CpG ODN BW006, CpG ODN D-SL01, CpG ODN 2395, CpG ODN M362, CpG ODN D-SL03, or a combination of two or more thereof. In embodiments, the CpG ODN is CpG ODN D19. In embodiments, the CpG ODN is CpG ODN 1585. In embodiments, the CpG ODN is CpG ODN 2216. In embodiments, the CpG ODN is CpG ODN 2336. In embodiments, the CpG ODN is CpG ODN 1668. In embodiments, the CpG ODN is CpG ODN 1826. In embodiments, the CpG ODN is CpG ODN 2006. In embodiments, the CpG ODN is CpG ODN 2007. In embodiments, the CpG ODN is CpG ODN BW006. In embodiments, the CpG ODN is CpG ODN D-SL01. In embodiments, the CpG ODN is CpG ODN 2395. In embodiments, the CpG ODN is CpG ODN CpG ODN M362. In embodiments, the CpG ODN is CpG ODN D-SL03. In embodiments, the CpG oligodeoxynucleotide comprises one or more phosphorothioate linkages.

In embodiments, $R^1$ comprises a CpG-ODN nucleic acid sequence listed in Table 1.

TABLE 1

| NAME | SEQ ID NO: | SEQUENCE 5'-3' (* = phosphorothioate linkage) |
|---|---|---|
| CpG(A)-ODN | 9 | G*G*TGCATCGATGCAGG*G *G*G*G* |
| GpC(A)-ODN | 10 | G*G*T GCA TGC ATG CA G G*G*G*G*G |
| D19-PS | 11 | G*G*T*G*C*A*T*C*G*A* T*G*C*A*G*G*G*G*G |
| CpG(B)-ODN | 12 | T*C*C*A*T*G*A*C*G*T* T*C*C*T*G*A*T*G*C*T |

TABLE 1-continued

| NAME | SEQ ID NO: | SEQUENCE 5'-3' (* = phosphorothioate linkage) |
|---|---|---|
| ODN 1585 | 13 | G*G*GGTCAACGTTGAG*G* G*G*G*G |
| ODN 1585 | 14 | G*GGGTCAACGTTGAG*G*G *G*G*G |
| ODN 2216 | 15 | G*G*GGGACGATCGTCG*G* G*G*G*G |
| ODN 2216 | 16 | G*GGGGACGATCGTCG*G*G *G*G*G |
| ODN D19 | 17 | G*G*TGCATCGATGCAGG*G *G*G*G |
| ODN D19 | 18 | G*GTGCATCGATGCAGG*G* G*G*G* |
| ODN 2336 | 33 | G*G*G*GACGACGTCGTGG* G*G*G*G*G |
| ODN 2336 | 34 | G*G*GGACGACGTCGTGG*G *G*G*G*G |
| ODN 1668 | 35 | T*C*C*A*T*G*A*C*G*T* T*C*C*T*G*A*T*G*C*T |
| ODN 1826 | 40 | T*C*C*A*T*G*A*C*G*T* T*C*C*T*G*A*C*G*T*T |
| ODN 2006 | 41 | T*C*G*T*C*G*T*T*T*T* G*T*C*G*T*T*T*T*G*T* C*G*T*T |
| ODN 2007 | 42 | T*C*G*T*C*G*T*T*G*T* C*G*T*T*T*T*G*T*C*G* T*T |
| ODN 2395 | 43 | T*C*G*T*C*G*T*T*T*T* C*G*G*C*G*C*G*C*G*C* C*G |
| ODN M362 | 44 | T*C*G*T*C*G*T*C*G*T* T*C*G*A*A*C*G*A*C*G* T*T*G*A*T |

In embodiments, $R^1$ comprises any one of SEQ ID NOS: 9-18, 33-35, and 40-44. In embodiments, $R^1$ comprises SEQ ID NO:9. In embodiments, $R^1$ comprises SEQ ID NO:10. In embodiments, $R^1$ comprises SEQ ID NO: 11. In embodiments, $R^1$ comprises SEQ ID NO: 12. In embodiments, $R^1$ comprises SEQ ID NO: 13. In embodiments, $R^1$ comprises SEQ ID NO: 14. In embodiments, $R^1$ comprises SEQ ID NO: 15. In embodiments, $R^1$ comprises SEQ ID NO: 16. In embodiments, $R^1$ comprises SEQ ID NO: 17. In embodiments, $R^1$ comprises SEQ ID NO: 18. In embodiments, $R^1$ comprises SEQ ID NO:33. In embodiments, $R^1$ comprises SEQ ID NO:34. In embodiments, $R^1$ comprises SEQ ID NO:35. In embodiments, $R^1$ comprises SEQ ID NO:40. In embodiments, $R^1$ comprises SEQ ID NO:41. In embodiments, $R^1$ comprises SEQ ID NO:42. In embodiments, $R^1$ comprises SEQ ID NO:43. In embodiments, $R^1$ comprises SEQ ID NO:44. In embodiments, $R^1$ comprises SEQ ID NO:9 or SEQ ID NO:17. In embodiments, $R^1$ comprises SEQ ID NO:9, SEQ ID NO: 10, SEQ ID NO:17, or SEQ ID NO:18.

In embodiments of all the compounds described herein, $R^2$ is a miR146a passenger strand sequence hybridized to a complement miR146a guide strand sequence. In embodiments, $R^2$ is a miR146a passenger strand sequence comprising SEQ ID NO: 1, SEQ ID NO:2, SEQ ID NO:3, SEQ ID NO:4, SEQ ID NO:5, SEQ ID NO:37, or SEQ ID NO:39 hybridized to a complement miR146a guide strand sequence. In embodiments, $R^2$ is a miR146a passenger strand sequence comprising SEQ ID NO:1 hybridized to a complement miR146a guide strand sequence. In embodiments, $R^2$ is a miR146a passenger strand sequence comprising SEQ ID NO:2 hybridized to a complement miR146a guide strand sequence. In embodiments, $R^2$ is a miR146a passenger strand sequence comprising SEQ ID NO:1 hybridized to a miR146a guide strand sequence comprising SEQ ID NO:6. In embodiments, $R^2$ is a miR146a passenger strand sequence comprising SEQ ID NO:2 hybridized to a miR146a guide strand sequence comprising SEQ ID NO:7. In embodiments, $R^2$ is a miR146a passenger strand sequence comprising SEQ ID NO:37 or SEQ ID NO:39 hybridized to a complement miR146a guide strand sequence. In embodiments, $R^2$ is a hybridized nucleic acid sequence, the hybridized nucleic acid sequence comprising a miR146a passenger strand sequence hybridized to a miR146a guide strand sequence, wherein the miR146a passenger strand sequence comprises SEQ ID NO:1; and the miR146a guide strand sequence comprises SEQ ID NO:6; wherein SEQ ID NO:1 and SEQ ID NO:6 comprise nucleic acids that are independently and optionally modified with 2'-O-Methyl, 2'-Fluoro, or a phosphorothioate linkage. In embodiments, $R^2$ is a hybridized nucleic acid sequence, the hybridized nucleic acid sequence comprising a miR146a passenger strand sequence hybridized to a miR146a guide strand sequence, wherein the miR146a passenger strand sequence comprises SEQ ID NO:1, 2, 3, 4, or 5; and the miR146a guide strand sequence comprises SEQ ID NO:6, 7, or 8. In embodiments, $R^2$ is a hybridized nucleic acid sequence, the hybridized nucleic acid sequence comprising a miR146a passenger strand sequence hybridized to a miR146a guide strand sequence, wherein the miR146a passenger strand sequence comprises SEQ ID NO:1; and the miR146a guide strand sequence comprises SEQ ID NO:6. In embodiments, $R^2$ is a hybridized nucleic acid sequence, the hybridized nucleic acid sequence comprising a miR146a passenger strand sequence hybridized to a miR146a guide strand sequence, wherein the miR146a passenger strand sequence comprises SEQ ID NO:2; and the miR146a guide strand sequence comprises SEQ ID NO:7. In embodiments, $R^2$ is a hybridized nucleic acid sequence, the hybridized nucleic acid sequence comprising a miR146a passenger strand sequence hybridized to a miR146a guide strand sequence, wherein the miR146a passenger strand sequence comprises SEQ ID NO:2; and the miR146a guide strand sequence comprises SEQ ID NO:8. In embodiments, $R^2$ is a hybridized nucleic acid sequence, the hybridized nucleic acid sequence comprising a miR146a passenger strand sequence hybridized to a miR146a guide strand sequence, wherein the miR146a passenger strand sequence comprises SEQ ID NO:37 or 39; and the miR146a guide strand sequence comprises SEQ ID NO:36 or 38.

In embodiments of all the compounds described herein, $R^3$ is a miR146a passenger strand sequence hybridized to a complement miR146a guide strand sequence. In embodiments, $R^3$ is a miR146a passenger strand sequence comprising SEQ ID NO: 1, SEQ ID NO:2, SEQ ID NO:3, SEQ ID NO:4, SEQ ID NO:5, SEQ ID NO:37, or SEQ ID NO:39 hybridized to a complement miR146a guide strand sequence. In embodiments, $R^3$ is a miR146a passenger strand sequence comprising SEQ ID NO:1 hybridized to a complement miR146a guide strand sequence. In embodiments, $R^3$ is a miR146a passenger strand sequence comprising SEQ ID NO:2 hybridized to a complement miR146a guide strand sequence. In embodiments, $R^3$ is a miR146a passenger strand sequence comprising SEQ ID NO:1 hybridized to a miR146a guide strand sequence comprising SEQ ID NO:6. In embodiments, $R^3$ is a miR146a passenger strand sequence comprising SEQ ID NO:2 hybridized to a miR146a guide strand sequence comprising SEQ ID NO:7. In embodiments, $R^3$ is a miR146a passenger strand sequence comprising SEQ ID NO:37 or SEQ ID NO:39 hybridized to a complement miR146a guide strand sequence. In embodiments, $R^3$ is a hybridized nucleic acid sequence, the hybridized nucleic acid sequence comprising a miR146a passenger strand sequence hybridized to a miR146a guide strand sequence, wherein the miR146a passenger strand sequence comprises SEQ ID NO:1; and the miR146a guide strand sequence comprises SEQ ID NO:6; wherein SEQ ID NO:1 and SEQ ID NO:6 comprise nucleic acids that are independently and optionally modified with 2'-O-Methyl, 2'-Fluoro, or a phosphorothioate linkage. In embodiments, $R^3$ is a hybridized nucleic acid sequence, the hybridized nucleic acid sequence comprising a miR146a passenger strand sequence hybridized to a miR146a guide strand sequence, wherein the miR146a passenger strand sequence comprises SEQ ID NO:1, 2, 3, 4, or 5; and the miR146a guide strand sequence comprises SEQ ID NO:6, 7, or 8. In embodiments, $R^3$ is a hybridized nucleic acid sequence, the hybridized nucleic acid sequence comprising a miR146a passenger strand sequence hybridized to a miR146a guide strand sequence, wherein the miR146a passenger strand sequence comprises SEQ ID NO:1; and the miR146a guide strand sequence comprises SEQ ID NO:6. In embodiments, $R^3$ is a hybridized nucleic acid sequence, the hybridized nucleic acid sequence comprising a miR146a passenger strand sequence hybridized to a miR146a guide strand sequence, wherein the miR146a passenger strand sequence comprises SEQ ID NO:2; and the miR146a guide strand sequence comprises SEQ ID NO:7. In embodiments, $R^3$ is a hybridized nucleic acid sequence, the hybridized nucleic acid sequence comprising a miR146a passenger strand sequence hybridized to a miR146a guide strand sequence, wherein the miR146a passenger strand sequence comprises SEQ ID NO:2; and the miR146a guide strand sequence comprises SEQ ID NO:8. In embodiments, $R^3$ is a hybridized nucleic acid sequence, the hybridized nucleic acid sequence comprising a miR146a passenger strand sequence hybridized to a miR146a guide strand sequence, wherein the miR146a passenger strand sequence comprises SEQ ID NO:37 or 39; and the miR146a guide strand sequence comprises SEQ ID NO:36 or 38.

$L^1$ and $L^2$ are independently a bond, a nucleic acid sequence, a DNA sequence, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or a combination of two or more thereof. In embodiments, $L^1$ and $L^2$ are independently a bond, a nucleic acid sequence, unsubstituted alkylene, unsubstituted heteroalkylene, or a combination of two or more thereof. In embodiments, $L^1$ and $L^2$ are independently a covalent bond. In embodiments, $L^1$ and $L^2$ are independently a nucleic acid sequence. In embodiments, $L^1$ and $L^2$ are independently a nucleic acid sequence and a substituted or unsubstituted alkylene. In embodiments, $L^1$ and $L^2$ are independently a nucleic acid sequence and an unsubstituted alkylene. In embodiments, $L^1$ and $L^2$ are independently a nucleic acid sequence and a substituted or unsubstituted heteroalkylene. In embodiments, $L^1$ and $L^2$ are independently a nucleic acid sequence and an unsubstituted heteroalkylene. In embodiments, $L^1$ and $L^2$ are independently a substituted or unsubstituted heteroalkylene. In embodiments, $L^1$ and $L^2$ are independently unsubstituted heteroalkylene. In embodiments, $L^1$ and $L^2$ are independently a substituted or unsubstituted alkylene. In embodiments, $L^1$ and $L^2$ are independently a substituted alkylene. In embodiments, $L^1$ and $L^2$ are independently unsubstituted alkylene.

In embodiments, $L^1$ and $L^2$ are independently substituted heteroalkylene. In embodiments, $L^1$ and $L^2$ are independently substituted 6 to 60 membered heteroalkylene. In embodiments, $L^1$ and $L^2$ are independently substituted 6 to 54 membered heteroalkylene. In embodiments, $L^1$ and $L^2$ are independently substituted 12 to 48 membered heteroalkylene. In embodiments, $L^1$ and $L^2$ are independently substituted 18 to 42 membered heteroalkylene. In embodiments, $L^1$ and $L^2$ are independently substituted 24 to 36 membered heteroalkylene. In embodiments, $L^1$ and $L^2$ are independently substituted 30 membered heteroalkylene. In embodiments, the heteroalkylene comprises an oxygen atom, a phosphorous atom, or a combination thereof. In embodiments, the substituents on the substituted heteroalkylene comprise oxo, —OH, —O—, or a combination of two or more thereof. In embodiments, $L^1$ and $L^2$ are independently substituted 18 to 42 membered heteroalkylene; wherein the heteroalkylene comprises an oxygen atom, a phosphorous atom, or a combination thereof; and wherein the substituents are independently selected from the group consisting of oxo, —OH, and —O—.

In embodiments, $L^1$ and $L^2$ are independently:

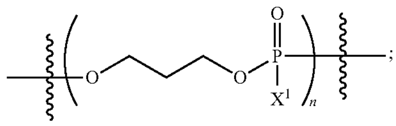
;

wherein $X^1$ is independently —OH or —O—, and n is an integer from 1 to 10. In embodiments, each $X^1$ is —OH. In embodiments, each $X^1$ is —O—. In embodiments, n is an integer from 2 to 10. In embodiments, n is an integer from 2 to 8. In embodiments, n is an integer from 3 to 7. In embodiments, n is an integer from 4 to 6. In embodiments, n is 1. In embodiments, n is 2. In embodiments, n is 3. In embodiments, n is 4. In embodiments, n is 5. In embodiments, n is 6. In embodiments, n is 7. In embodiments, n is 8. In embodiments, n is 9. In embodiments, n is 10.

In embodiments, $L^1$ and $L^2$ are independently substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or a combination of two or more thereof. In embodiments, $L^1$ and $L^2$ are independently a combination of two or three of substituted or unsubstituted alkylene, substituted or unsubstituted heteroalkylene, substituted or unsubstituted cycloalkylene, substituted or unsubstituted heterocycloalkylene, substituted or unsubstituted arylene, and substituted or unsubstituted heteroarylene.

In embodiments, $L^1$ and $L^2$ are independently substituted or unsubstituted heteroalkylene, substituted or unsubstituted heterocycloalkylene, substituted or unsubstituted heteroarylene, or a combination of two or more thereof. In embodiments, $L^1$ and $L^2$ are independently a combination of substituted or unsubstituted heteroalkylene, substituted or unsubstituted heterocycloalkylene, and substituted or unsubstituted heteroarylene.

In embodiments, $L^1$ and $L^2$ are substituted or unsubstituted heteroalkylene, wherein the substituted or unsubstituted heteroalkylene comprises —$(CH_2CH_2O)$—.

In embodiments, $L^1$ and $L^2$ are independently a 5 or 6 membered substituted or unsubstituted heteroarylene. In embodiments, $L^1$ and $L^2$ are independently a 5 or 6 membered substituted or unsubstituted heteroarylene comprising one or two nitrogen atoms. In embodiments, $L^1$ and $L^2$ are independently a 5 or 6 membered substituted or unsubstituted heterocycloalkylene. In embodiments, $L^1$ and $L^2$ are independently a 5 or 6 membered substituted or unsubstituted heterocycloalkylene comprising an oxygen atom, a nitrogen atom, or a combination thereof.

In embodiments, $L^1$ and $L^2$ are independently a combination of two or more of (a) a 5 or 6 membered substituted or unsubstituted heteroarylene comprising one or two nitrogen atoms; (b) a 5 or 6 membered substituted or unsubstituted heterocycloalkylene comprising an oxygen atom, a nitrogen atom, or a combination thereof; and (c) substituted or unsubstituted heteroalkylene, wherein the substituted or unsubstituted heteroalkylene comprises —$(CH_2CH_2O)$—

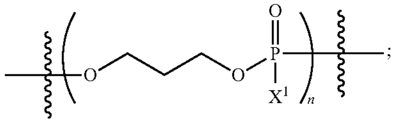

wherein $X^1$ is independently —OH or —O—, and n is an integer from 1 to 10; or a combination thereof.

In embodiments, $L^1$ and $L^2$ are independently one of the following structures:

(a)

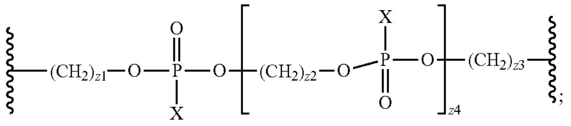

(b)

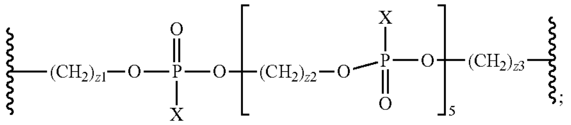

(c)

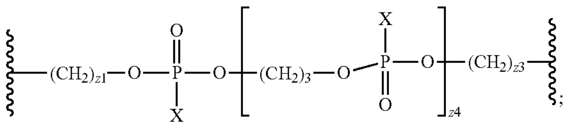

-continued (d)

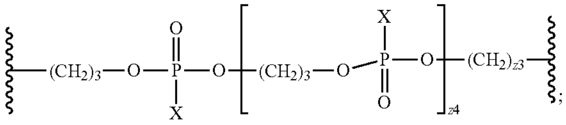

(e)

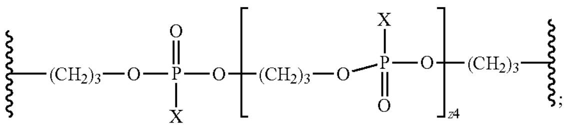

(f)

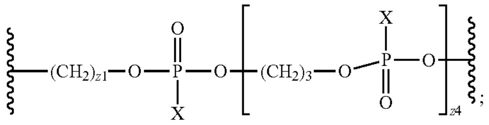

(g)

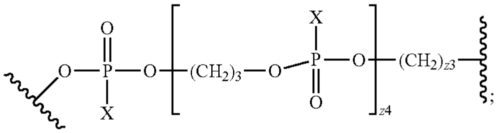

or (h)

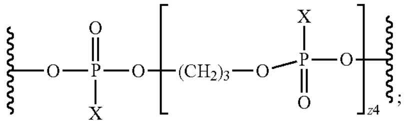

wherein z1, z2, z3 and z4 are independently integers from 0 to 20; and each X is independently —OH or —O—. In embodiments, z1 is an integer from 0 to 5. In embodiments, z1 is an integer from 2 to 4. In embodiments, z2 is an integer from 0 to 5. In embodiments, z2 is an integer from 2 to 4. In embodiments, z3 is an integer from 0 to 5. In embodiments, z1 is an integer from 2 to 4. In embodiments, z4 is an integer from 3 to 7. In embodiments, z4 is an integer from 4 to 6. In embodiments, each X is —OH. In embodiments, each X is —O—. In embodiments, $L^1$ is (a). In embodiments, $L^1$ is (b). In embodiments, $L^1$ is (c). In embodiments, $L^1$ is (d). In embodiments, $L^1$ is (e). In embodiments, $L^1$ is (f). In embodiments, $L^1$ is (g). In embodiments, $L^1$ is (h). In embodiments, $L^2$ is (a). In embodiments, $L^2$ is (b). In embodiments, $L^2$ is (c). In embodiments, $L^2$ is (d). In embodiments, $L^2$ is (e). In embodiments, $L^2$ is (f). In embodiments, $L^2$ is (g). In embodiments, $L^2$ is (h).

In embodiments, the compound of Formula (II) is the compound of Formula (IIA):

(IIA)

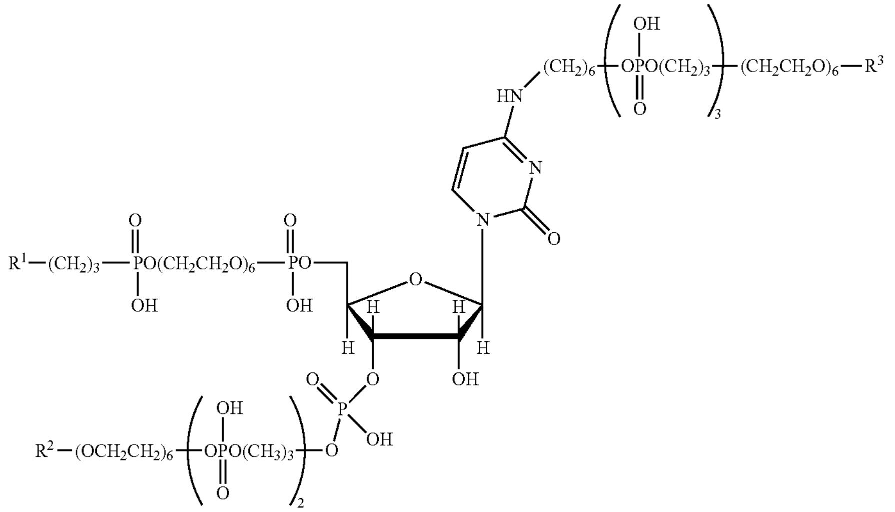

wherein $R^1$, $R^2$, and $R^3$ are as defined herein. The skilled artisan will appreciate that the $L^1$ and $L^2$ linking groups represented above can be appropriately varied and need not be limited to this specific structure. In embodiments, $R^1$ is CpG-A ODN. In embodiments, $R^1$ is CpG ODN D19. In embodiments, $R^2$ is a hybridized nucleic acid comprising a miR146a passenger strand sequence hybridized to a miR146a guide strand sequence; and $R^3$ is a hybridized nucleic acid comprising an miR155 passenger strand sequence hybridized to an miR155 guide strand sequence. In embodiments, the 3' end of the CpG ODN is bound to the linking group, and the 3' ends of the miR146a passenger strand sequence and the miR155 passenger strand sequence are bound to the linking group. In embodiments, $R^1$ is ODN D19; $R^2$ and $R^3$ are independently a hybridized nucleic acid comprising a miR146a passenger strand sequence hybridized to a miR146a guide strand sequence. In embodiments, the 3' end of the CpG ODN is bound to the linking group, and the 3' ends of the miR146a passenger strand sequences are bound to the linking group. For the sake of clarity, FIG. 20A shows the point of attachment between the CpG ODN of $R^1$ and the linking group $L^1$. Similarly, FIG. 20B shows the point of attachment between the linking group $L^1$ and the nucleotide on the miR146a passenger strand sequence of $R^2$.

In embodiments, the compound of Formula (II) is the compound of Formula (IIB):

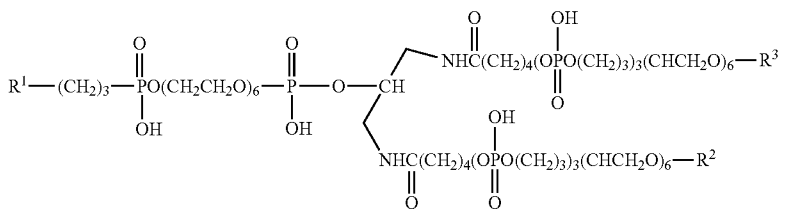

wherein $R^1$, $R^2$, and $R^3$ are as defined herein. The skilled artisan will appreciate that the $L^1$ and $L^2$ linking groups represented above can be appropriately varied and need not be limited to this specific structure. In embodiments, $R^1$ is CpG-A ODN. In embodiments, $R^1$ is CpG ODN D19. In embodiments, $R^2$ is a hybridized nucleic acid comprising a miR146a passenger strand sequence hybridized to a miR146a guide strand sequence; and $R^3$ is a hybridized nucleic acid comprising an miR155 passenger strand sequence hybridized to an miR155 guide strand sequence. In embodiments, the 3' end of the CpG ODN is bound to the linking group, and the 3' ends of the miR146a passenger strand sequence and the miR155 passenger strand sequence are bound to the linking group. In embodiments, $R^1$ is ODN D19; $R^2$ and $R^3$ are independently a hybridized nucleic acid comprising a miR146a passenger strand sequence hybridized to a miR146a guide strand sequence. In embodiments, the 3' end of the CpG ODN is bound to the linking group, and the 3' ends of the miR146a passenger strand sequences are bound to the linking group.

In embodiments, the compound of Formula (I) is a compound of Formula (IA):

$$R^1\text{-}(x)_p\text{-}R^2 \quad \text{(IA);}$$

wherein $R^1$, $R^2$, x, and p are as defined herein. In embodiments, $R^1$ is a CpG-A ODN and $R^2$ is a hybridized nucleic acid sequence, the hybridized nucleic acid sequence comprising a miR146a passenger strand sequence hybridized to a miR146a guide strand sequence, wherein the miR146a passenger strand sequence comprises SEQ ID NO:1, SEQ ID NO:2, SEQ ID NO:3, SEQ ID NO:4, or SEQ ID NO:5; and the miR146a guide strand sequence comprises SEQ ID NO:6, SEQ ID NO:7, or SEQ ID NO: 8. In embodiments, $R^1$ is a CpG-A ODN and $R^2$ is a hybridized nucleic acid sequence, the hybridized nucleic acid sequence comprising a miR146a passenger strand sequence hybridized to a miR146a guide strand sequence, wherein the miR146a passenger strand sequence comprises SEQ ID NO:1 or SEQ ID NO:2; and the miR146a guide strand sequence comprises SEQ ID NO:6, SEQ ID NO:7, or SEQ ID NO: 8. In embodiments, R is CpG ODN D19 and $R^2$ a miR146 passenger strand comprising SEQ ID NO:1 hybridized to a miR146a guide strand comprising SEQ ID NO:6. In embodiments, $R^1$ is CpG ODN comprising the sequence of any one of SEQ ID NOS:40-57; and $R^2$ a miR146 passenger strand comprising SEQ ID NO:1 hybridized to a miR146a guide strand comprising SEQ ID NO:6. In embodiments, $R^1$ is CpG ODN comprising the sequence of any one of SEQ ID NOS:40-57; and $R^2$ a miR146 passenger strand comprising SEQ ID NO:1 hybridized to a miR146a guide strand comprising SEQ ID NO:6; wherein one or more nucleic acids in SEQ ID NO:1 and/or SEQ ID NO:6 are independently modified with 2'-O-Methyl, 2'-Fluoro, or a phosphorothioate linkage. In embodiments, $R^1$ is CpG ODN comprising the sequence of any one of SEQ ID NOS:40-57; and $R^2$ a miR146 passenger strand comprising SEQ ID NO:2 hybridized to a miR146a guide strand comprising SEQ ID NO:7. In embodiments, $R^1$ is CpG ODN D19 and $R^2$ a miR146 passenger strand comprising SEQ ID NO:2 hybridized to a miR146a guide strand comprising SEQ ID NO:7. In embodiments, $R^1$ is CpG ODN D19 and $R^2$ a miR146 passenger strand comprising SEQ ID NO:2 hybridized to a miR146a guide strand comprising SEQ ID NO:8 In embodiments, R is CpG ODN 1585 and $R^2$ a miR146 passenger strand comprising SEQ ID NO:1 hybridized to a miR146a guide strand comprising SEQ ID NO:6. In embodiments, R is CpG ODN 1585 and $R^2$ a miR146 passenger strand comprising SEQ ID NO:2 hybridized to a miR146a guide strand comprising SEQ ID NO:7. In embodiments, R is CpG ODN 1585 and $R^2$ a miR146 passenger strand sequence comprising SEQ ID NO:2 hybridized to a miR146a guide strand comprising SEQ ID NO: 8. In embodiments, $R^1$ is CpG ODN 2216 and $R^2$ a miR146 passenger strand comprising SEQ ID NO:1 hybridized to a miR146a guide strand comprising SEQ ID NO: 6. In embodiments, R is CpG ODN 2216 and $R^2$ a miR146 passenger strand comprising SEQ ID NO:2 hybridized to a miR146a guide strand comprising SEQ ID NO:7. In embodiments, $R^1$ is CpG ODN 2216 and $R^2$ a miR146 passenger strand comprising SEQ ID NO:2 hybridized to a miR146a guide strand comprising SEQ ID NO: 8. In embodiments, R is CpG ODN 2336 and $R^2$ a miR146 passenger strand comprising SEQ ID NO:1 hybridized to a miR146a guide strand comprising SEQ ID NO:6. In embodiments, $R^1$ is CpG ODN 2336 and $R^2$ a miR146 passenger strand comprising SEQ ID NO:2 hybridized to a miR146a guide strand comprising SEQ ID NO:7. In embodiments, R is CpG ODN 2336 and $R^2$ a miR146 passenger strand comprising SEQ ID NO:2 hybridized to a miR146a guide strand comprising SEQ ID NO:8. In embodiments, $R^1$ is a CpG-A ODN and $R^2$ is a hybridized nucleic acid sequence, the hybridized nucleic acid sequence comprising a miR146a passenger strand sequence hybridized to a miR146a guide strand sequence, wherein the miR146a passenger strand sequence comprises SEQ ID NO:37 or SEQ ID NO:39; and the miR146a guide strand sequence comprises SEQ ID NO:36 or SEQ ID NO:38. In embodiments, $R^1$ is covalently bonded to “x” at the 3' end, and the miR146 passenger strand sequence of $R^2$ is covalently bonded to “x” at the 5' end. In embodiments, $R^1$ is covalently bonded to “x” at the 5' end, and the miR146 passenger strand sequence of $R^2$ is covalently bonded to “x” at the 3' end.

In embodiments, the compound of Formula (II) is a compound of Formula (IIC):

(IIC)

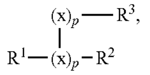

wherein $R^1$, $R^2$, $R^3$, x and p are as defined herein. In embodiments, $R^1$ is a CpG-A ODN and $R^2$ and $R^3$ are independently a hybridized nucleic acid sequence, the hybridized nucleic acid sequence comprising a miR146a passenger strand sequence hybridized to a miR146a guide strand sequence, wherein the miR146a passenger strand sequence comprises SEQ ID NO:1, SEQ ID NO:2, SEQ ID NO:3, SEQ ID NO:4, or SEQ ID NO:5; and the miR146a guide strand sequence comprises SEQ ID NO:6, SEQ ID NO:7, or SEQ ID NO: 8. In embodiments, $R^1$ is a CpG-A ODN and $R^2$ and $R^3$ are independently a hybridized nucleic acid sequence, the hybridized nucleic acid sequence comprising a miR146a passenger strand sequence hybridized to a miR146a guide strand sequence, wherein the miR146a passenger strand sequence comprises SEQ ID NO:1 or SEQ ID NO:2; and the miR146a guide strand sequence comprises SEQ ID NO:6, SEQ ID NO:7, or SEQ ID NO:8. In embodiments, $R^1$ is CpG ODN D19 and $R^2$ and $R^3$ are independently a miR146 passenger strand comprising SEQ ID NO:1 hybridized to a miR146a guide strand comprising SEQ ID NO:6. In embodiments, $R^1$ is CpG ODN D19 and $R^2$ and $R^3$ are independently a miR146 passenger strand comprising SEQ ID NO:1 hybridized to a miR146a guide strand comprising SEQ ID NO:6; wherein one or more nucleic acids in SEQ ID NO:1 and/or SEQ ID NO:6 are independently modified with 2'-O-Methyl, 2'-Fluoro, or a phosphorothioate linkage. In embodiments, $R^1$ is CpG ODN D19 and $R^2$ and $R^3$ are independently a miR146 passenger strand comprising SEQ ID NO:2 hybridized to a miR146a guide strand comprising SEQ ID NO:7. In embodiments, $R^1$ is CpG ODN D19 and $R^2$ and $R^3$ are independently a miR146 passenger strand comprising SEQ ID NO:2 hybridized to a miR146a guide strand comprising SEQ ID NO:8. In embodiments, $R^1$ is CpG ODN 1585 and $R^2$ and $R^3$ are independently a miR146 passenger strand comprising SEQ ID NO:1 hybridized to a miR146a guide strand comprising SEQ ID NO:6. In embodiments, $R^1$ is CpG ODN 1585 and $R^2$ and $R^3$ are independently a miR146 passenger strand comprising SEQ ID NO:2 hybridized to a miR146a guide strand comprising SEQ ID NO:7. In embodiments, $R^1$ is CpG ODN 1585 and $R^2$ and $R^3$ are independently a miR146 passenger strand comprising SEQ ID NO:2 hybridized to a miR146a guide strand comprising SEQ ID NO:8. In embodiments, $R^1$ is CpG ODN 2216 and $R^2$ and $R^3$ are independently a miR146 passenger strand comprising SEQ ID NO:1 hybridized to a miR146a guide strand comprising SEQ ID NO:6. In embodiments, $R^1$ is CpG ODN 2216 and $R^2$ and $R^3$ are independently a miR146 passenger strand comprising SEQ ID NO:2 hybridized to a miR146a guide strand comprising SEQ ID NO:7. In embodiments, $R^1$ is CpG ODN 2216 and $R^2$ and $R^3$ are independently a miR146 passenger strand comprising SEQ ID NO:2 hybridized to a miR146a guide strand comprising SEQ ID NO:8. In embodiments, $R^1$ is CpG ODN 2336 and $R^2$ and $R^3$ are independently a miR146 passenger strand comprising SEQ ID NO:1 hybridized to a miR146a guide strand comprising SEQ ID NO:6. In embodiments, $R^1$ is CpG ODN 2336 and $R^2$ and $R^3$ are independently a miR146 passenger strand comprising SEQ ID NO:2 hybridized to a miR146a guide strand comprising SEQ ID NO:7. In embodiments, $R^1$ is CpG ODN 2336 and $R^2$ and $R^3$ are independently a miR146 passenger strand comprising SEQ ID NO:2 hybridized to a miR146a guide strand comprising SEQ ID NO:8. In embodiments, $R^1$ is a CpG-A ODN and $R^2$ and $R^3$ are independently a hybridized nucleic acid sequence, the hybridized nucleic acid sequence comprising a miR146a passenger strand sequence hybridized to a miR146a guide strand sequence, wherein the miR146a passenger strand sequence comprises SEQ ID NO:37 or SEQ ID NO:39; and the miR146a guide strand sequence comprises SEQ ID NO:36 or SEQ ID NO:38. In embodiments, $R^1$ is covalently bonded to "x" at the 3' end, and the miR146 passenger strand sequence of $R^2$ and $R^3$ are covalently bonded to "x" at the 5' end. In embodiments, $R^1$ is covalently bonded to "x" at the 5' end, and the miR146 passenger strand sequence of $R^2$ and $R^3$ are covalently bonded to "x" at the 3' end.

In embodiments, the compound of Formula (III) is a compound of Formula (IIIA):

(III)

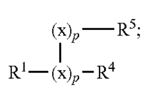

wherein $R^1$, $R^4$, $R^5$, x and p are as defined herein. In embodiments, $R^1$ is a CpG-A ODN and $R^4$ and $R^5$ are independently a miR146a passenger strand sequence comprising SEQ ID NO:1, SEQ ID NO:2, SEQ ID NO:3, SEQ ID NO:4, or SEQ ID NO:5. In embodiments, $R^1$ is a CpG-A ODN and $R^4$ and $R^5$ are independently a miR146a passenger strand sequence comprising SEQ ID NO:1 or SEQ ID NO:2. In embodiments, $R^1$ is CpG ODN D19 and $R^4$ and $R^5$ are independently a miR146 passenger strand comprising SEQ ID NO:1. In embodiments, $R^1$ is CpG ODN D19 and $R^4$ and $R^5$ are independently a miR146 passenger strand comprising SEQ ID NO:2. In embodiments, $R^1$ is CpG ODN 1585 and $R^2$ and $R^3$ are independently a miR146 passenger strand comprising SEQ ID NO:1. In embodiments, $R^1$ is CpG ODN 1585 and $R^2$ and $R^3$ are independently a miR146 passenger strand comprising SEQ ID NO:2. In embodiments, $R^1$ is CpG ODN 2216 and $R^2$ and $R^3$ are independently a miR146 passenger strand comprising SEQ ID NO:1. In embodiments, R is CpG ODN 2216 and $R^2$ and $R^3$ are independently a miR146 passenger strand comprising SEQ ID NO:2. In embodiments, $R^1$ is CpG ODN 2336 and $R^2$ and $R^3$ are independently a miR146 passenger strand comprising SEQ ID NO: 1. In embodiments, R is CpG ODN 2336 and $R^2$ and $R^3$ are independently a miR146 passenger strand comprising SEQ ID NO:2. In embodiments, $R^1$ is a CpG-A ODN and $R^4$ and $R^5$ are independently a miR146a passenger strand sequence comprising SEQ ID NO:37 or SEQ ID NO:39.

In embodiments, "x" is

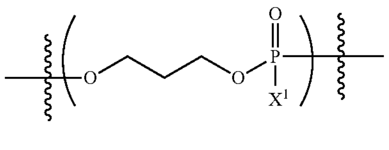

wherein $X^1$ is independently —OH or —O—.

In embodiments, "x" is

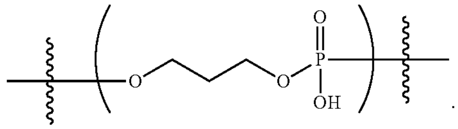

p is independently an integer from 1 to 10. In embodiments, p is independently an integer from 2 to 10. In embodiments, p is independently an integer from 2 to 8. In embodiments, p is independently an integer from 3 to 7. In embodiments, p is independently an integer from 4 to 6. In embodiments, p is 1. In embodiments, p is 2. In embodiments, p is 3. In embodiments, p is 4. In embodiments, p is 5. In embodiments, p is 6. In embodiments, p is 7. In embodiments, p is 8. In embodiments, p is 9. In embodiments, p is 10.

In embodiments, the nucleic acids described herein (e.g., Toll-like receptor 9-binding nucleic acid sequences, miR146a passenger strand sequences, miR146a guide strand sequences) comprises a terminal C3 spacer modification on the 5'-terminus, the 3'-terminus, or both the 5' and 3'-terminus. In embodiments, the nucleic acids described herein comprise a terminal C3 spacer modification on the 5'-terminus. In embodiments, the nucleic acids described herein comprise a terminal C3 spacer modification on the 3'-terminus. In embodiments, the nucleic acids described herein comprise a terminal C3 spacer modification on both the 5'-terminus and the 3'-terminus. The term "terminal C3 unit" or "terminal C3 spacer modification" refers to a moiety of the following structure:

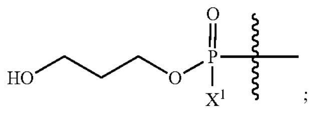

;

$X^1$ is —OH or $O^-$.

In embodiments, the disclosure provides Compound A. In embodiments, the disclosure provides a pharmaceutical composition comprising Compound A and a pharmaceutically acceptable excipient. Compound A refers to SEQ ID NO:9 covalently bonded via a linking group to SEQ ID NO:2 which is hybridized to SEQ ID NO:7, wherein the linking group is:

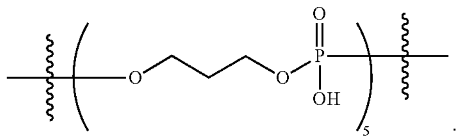

In embodiments, the disclosure provides Compound A1. In embodiments, the disclosure provides a pharmaceutical composition comprising Compound A1 and a pharmaceutically acceptable excipient. Compound A refers to SEQ ID NO:17 covalently bonded via a linking group to SEQ ID NO:2 which is hybridized to SEQ ID NO:7, wherein the linking group is:

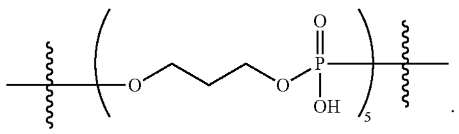

In embodiments, the disclosure provides Compound B. In embodiments, the disclosure provides a pharmaceutical composition comprising Compound B and a pharmaceutically acceptable excipient. Compound B refers to SEQ ID NO:9 covalently bonded via a linking group to SEQ ID NO:2 which is hybridized to SEQ ID NO:8, wherein the linking group is:

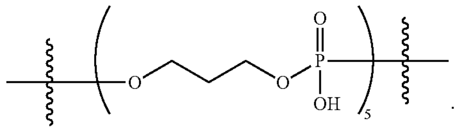

In embodiments, the disclosure provides Compound B1. In embodiments, the disclosure provides a pharmaceutical composition comprising Compound B1 and a pharmaceutically acceptable excipient. Compound B1 refers to SEQ ID NO: 17 covalently bonded via a linking group to SEQ ID NO:2 which is hybridized to SEQ ID NO:8, wherein the linking group is:

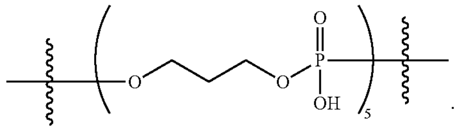

In embodiments, the disclosure provides Compound C. In embodiments, the disclosure provides a pharmaceutical composition comprising Compound C and a pharmaceutically acceptable excipient. Compound C refers to SEQ ID NO:9 covalently bonded via a linking group to SEQ ID NO:4 which is hybridized to SEQ ID NO:7, wherein the linking group is:

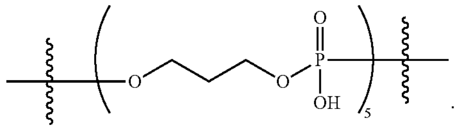

In embodiments, the disclosure provides Compound C1. In embodiments, the disclosure provides a pharmaceutical composition comprising Compound C1 and a pharmaceutically acceptable excipient. Compound C1 refers to SEQ ID NO: 17 covalently bonded via a linking group to SEQ ID NO:4 which is hybridized to SEQ ID NO:7, wherein the linking group is:

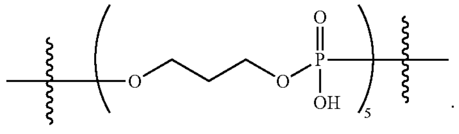

In embodiments, the disclosure provides Compound D. In embodiments, the disclosure provides a pharmaceutical composition comprising Compound D and a pharmaceutically acceptable excipient. Compound D refers to SEQ ID NO:9 covalently bonded via a linking group to SEQ ID NO:5 which is hybridized to SEQ ID NO:6, wherein the linking group is:

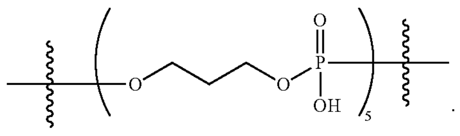

In embodiments, the disclosure provides Compound D1. In embodiments, the disclosure provides a pharmaceutical composition comprising Compound D1 and a pharmaceutically acceptable excipient. Compound D1 refers to S SEQ ID NO:17 covalently bonded via a linking group to SEQ ID NO:5 which is hybridized to SEQ ID NO:6, wherein the linking group is:

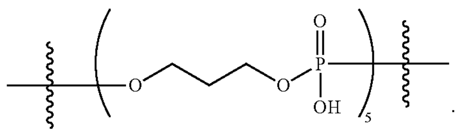

In embodiments, the disclosure provides Compound E. In embodiments, the disclosure provides a pharmaceutical composition comprising Compound E and a pharmaceutically acceptable excipient. Compound E refers to a compound of Formula (IIA), wherein $R^1$ is SEQ ID NO:9; $R^2$ is SEQ ID NO:3, and $R^3$ is SEQ ID NO:3, wherein the 3' end of SEQ ID NO:3 is covalently bonded to the linking group in Formula (IIA).

In embodiments, the disclosure provides Compound E1. In embodiments, the disclosure provides a pharmaceutical composition comprising Compound E1 and a pharmaceutically acceptable excipient. Compound E1 refers to a compound of Formula (IIA), wherein $R^1$ is SEQ ID NO:17; $R^2$ is SEQ ID NO:3, and $R^3$ is SEQ ID NO:3, wherein the 3' end of SEQ ID NO:3 is covalently bonded to the linking group in Formula (IIA).

In embodiments, the disclosure provides Compound F. In embodiments, the disclosure provides a pharmaceutical composition comprising Compound F and a pharmaceutically acceptable excipient. Compound F refers to a compound of Formula (IIB), wherein $R^1$ is SEQ ID NO:9 or SEQ ID NO: 17; $R^2$ is SEQ ID NO:3, and $R^3$ is SEQ ID NO:3. In embodiments, $R^1$ is SEQ ID NO:9. In embodiments, $R^1$ is SEQ ID NO: 17.

In embodiments, the disclosure provides Compound G. In embodiments, the disclosure provides a pharmaceutical composition comprising Compound G and a pharmaceutically acceptable excipient. Compound G refers to a compound of Formula (IIA), wherein $R^1$ is SEQ ID NO:9, $R^2$ is SEQ ID NO:3 hybridized to SEQ ID NO:8, and $R^3$ is SEQ ID NO:3 hybridized to SEQ ID NO: 8, wherein the 3' end of SEQ ID NO:3 is covalently bonded to the linking group in Formula (IIA).

In embodiments, the disclosure provides Compound G1. In embodiments, the disclosure provides a pharmaceutical composition comprising Compound G1 and a pharmaceutically acceptable excipient. Compound G1 refers to a compound of Formula (IIA), wherein $R^1$ is SEQ ID NO:17, $R^2$ is SEQ ID NO:3 hybridized to SEQ ID NO:8, and $R^3$ is SEQ ID NO:3 hybridized to SEQ ID NO:8, wherein the 3' end of SEQ ID NO:3 is covalently bonded to the linking group in Formula (IIA).

In embodiments, the disclosure provides Compound H. In embodiments, the disclosure provides a pharmaceutical composition comprising Compound H and a pharmaceutically acceptable excipient. Compound H refers to a compound of Formula (IIB), wherein $R^1$ is SEQ ID NO:9 or SEQ ID NO: 17, $R^2$ is SEQ ID NO:3 hybridized to SEQ ID NO:7, and $R^3$ is SEQ ID NO:3 hybridized to SEQ ID NO:7. In embodiments, $R^1$ is SEQ ID NO:9. In embodiments, $R^1$ is SEQ ID NO: 17.

In embodiments, the disclosure provides Compound J. In embodiments, the disclosure provides a pharmaceutical composition comprising Compound J and a pharmaceutically acceptable excipient. Compound J refers to SEQ ID NO:9 covalently bonded via a linking group to SEQ ID NO:2, wherein the linking group is:

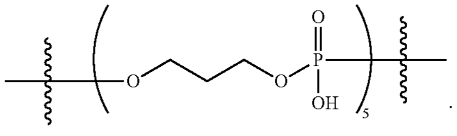

In embodiments, the disclosure provides Compound J1. In embodiments, the disclosure provides a pharmaceutical composition comprising Compound J1 and a pharmaceutically acceptable excipient. Compound J1 refers to SEQ ID NO:17 covalently bonded via a linking group to SEQ ID NO:2, wherein the linking group is:

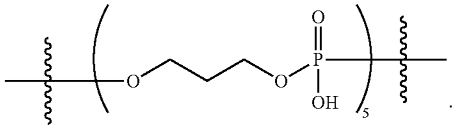

In embodiments, the disclosure provides Compound K. In embodiments, the disclosure provides a pharmaceutical composition comprising Compound K and a pharmaceutically acceptable excipient. Compound K refers to SEQ ID NO:9 covalently bonded via a linking group to SEQ ID NO:4, wherein the linking group is:

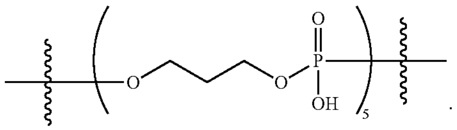

In embodiments, the disclosure provides Compound K1. In embodiments, the disclosure provides a pharmaceutical composition comprising Compound KI and a pharmaceutically acceptable excipient. Compound KI refers to SEQ ID NO:17 covalently bonded via a linking group to SEQ ID NO:4, wherein the linking group is:

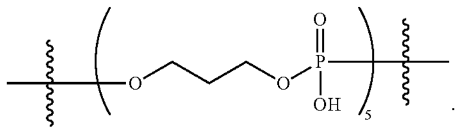

In embodiments, the disclosure provides Compound L. In embodiments, the disclosure provides a pharmaceutical composition comprising Compound L and a pharmaceutically acceptable excipient. Compound L refers to SEQ ID NO:9 covalently bonded via a linking group to SEQ ID NO:45, wherein the linking group is:

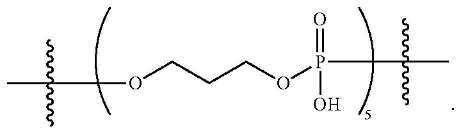

In embodiments, SEQ ID NO:9 is covalently bonded via a linking group to SEQ ID NO:45. In embodiments, SEQ ID NO:17 is covalently bonded via a linking group to SEQ ID NO:45.

In embodiments, the disclosure provides Compound M. In embodiments, the disclosure provides a pharmaceutical composition comprising Compound M and a pharmaceutically acceptable excipient. Compound M refers to SEQ ID NO:9 covalently bonded via a linking group to SEQ ID NO:4 which is hybridized to SEQ ID NO:6, wherein the linking group is:

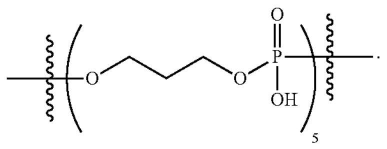

In embodiments, the disclosure provides Compound M1. In embodiments, the disclosure provides a pharmaceutical composition comprising Compound M1 and a pharmaceutically acceptable excipient. Compound M1 refers to SEQ ID NO:17 covalently bonded via a linking group to SEQ ID NO:4 which is hybridized to SEQ ID NO:6, wherein the linking group is:

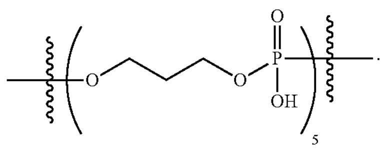

In embodiments, the disclosure provides Compound N. In embodiments, the disclosure provides a pharmaceutical composition comprising Compound N and a pharmaceutically acceptable excipient. Compound N refers to SEQ ID NO:17 covalently bonded via a linking group to SEQ ID NO:49 which is hybridized to SEQ ID NO:48, wherein the linking group is:

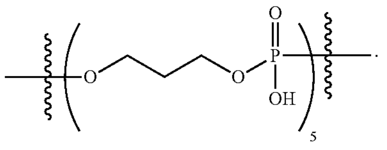

In embodiments, the disclosure provides Compound N1. In embodiments, the disclosure provides a pharmaceutical composition comprising Compound N1 and a pharmaceutically acceptable excipient. Compound N refers to SEQ ID NO:9 covalently bonded via a linking group to SEQ ID NO:49 which is hybridized to SEQ ID NO:48, wherein the linking group is:

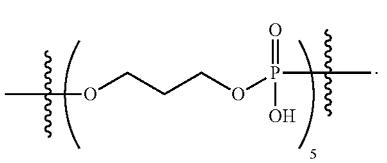

In embodiments, the compound further comprises a detectable moiety. The detectable moiety can be any known in the art and described herein. In embodiments, the detectable moiety is an enzyme, biotin, digoxigenin, a paramagnetic molecule, a contrast agent, gadolinium, a radioisotope, radionuclide, fluorodeoxyglucose, barium sulfate, thorium dioxide, gold, a fluorophore, a hapten, a protein, a fluorescent moiety, or a combination of two or more thereof. In embodiments, the contrast agent is a magnetic resonance imaging contrast agent, an X-ray contrast agent, or an iodinated contrast agent. In embodiments, the detectable agent is a fluorophore (e.g., fluorescein, rhodamine, coumarin, cyanine, or analogs thereof). In embodiments, the detectable agent is a chemiluminescent agent. In embodiments, the detectable agent is a radionuclide. In embodiments, the detectable agent is a radioisotope. In embodiments, the detectable agent is a paramagnetic molecule or a paramagnetic nanoparticle. The detectable moiety can be bonded to $R^1$, $R^2$, $R^3$, $R^4$, $R^5$, $L^1$, $L^2$, any nucleic acid described herein (e.g., Toll-like receptor 9-binding nucleic acid sequences, miR146a passenger strand sequences, miR146a guide strand sequences), or any combination of two or more thereof.

Pharmaceutical Compositions

In embodiments, the disclosure provides pharmaceutical compositions comprising a pharmaceutically acceptable excipient and an effective amount of the compounds described herein, including all embodiments and embodiments thereof. In embodiments, the disclosure provides pharmaceutical compositions comprising a pharmaceutically acceptable excipient and a therapeutically effective amount of the hybridized nucleic acids, as described herein, including all embodiments and embodiments thereof.

A "effective amount" is an amount sufficient for a compound of the disclosure to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

For any compound described herein, the therapeutically effective amount can be initially determined from cell culture assays. Target concentrations will be those concentrations of active compound (e.g., neural stem cells, vesicles) that are capable of achieving the methods described herein, as measured using the methods described herein or known in the art.

As is known in the art, therapeutically effective amounts for use in humans can also be determined from animal models. For example, a dose for humans can be formulated to achieve a concentration that has been found to be effective in animals. The dosage in humans can be adjusted by monitoring the effectiveness of the compositions, neural stem cells, and vesicles described herein, and adjusting the dosage upwards or downwards. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent (e.g., compounds, hybridized nucleic acids) sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound used. The dose administered to a patient should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intra-tumoral, intravenous, intramuscular, intra-arteriole, intradermal, subcutaneous, intraperitoneal, intraventricular, and intracranial. In embodiments, the neural stem cells, vesicles or pharmaceutical compositions described herein are parenterally administered to a patient. In embodiments, the neural stem cells, vesicles or pharmaceutical compositions described herein are administered intra-tumorally to a patient. Other modes of delivery include, but are not limited to, the use of liposomal formulations, intravenous infusion, transdermal patches, etc. In embodiments, the administering does not include administration of any active agent other than the recited active agent.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

Dose and Dosing Regimens

The dosage and frequency (single or multiple doses) of the active agents described herein, including all embodiments thereof, administered to a subject can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer and severity of such symptoms), kind of concurrent treatment, complications from the disease being treated or other health-related problems. Other therapeutic regimens or agents can be used in conjunction with the methods described herein. Adjustment and manipulation of established dosages (e.g., frequency and duration) are well within the ability of those skilled in the art.

For any active agents described herein, the effective amount can be initially determined from cell culture assays. Target concentrations will be those concentrations of active agents that are capable of achieving the methods described herein, as measured using the methods described herein or known in the art. As is known in the art, effective amounts of active agents for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

Dosages of the active agents may be varied depending upon the requirements of the patient. The dose administered to a patient should be sufficient to affect a beneficial therapeutic response in the patient over time. The size of the dose also will be determined by the existence, nature, and extent of any adverse side-effects. Determination of the proper dosage for a particular situation is within the skill of the art. Generally, treatment is initiated with smaller dosages which are less than the optimum dose of the active agents. Thereafter, the dosage is increased by small increments until the optimum effect under circumstances is reached. Dosage amounts and intervals can be adjusted individually to provide levels of the active agents effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active agents by considering factors such as compound potency, relative bioavailability, patient body weight, presence and severity of adverse side effects.

In embodiments, the active agent is administered to a patient at an amount of about 0.01 mg/kg to about 500 mg/kg. In aspects, the active agent is administered to a patient in an amount of about 0.1 mg/kg, 0.5 mg/kg, 1 mg/kg, 2 mg/kg, 3 mg/kg, 4 mg/kg, 5 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 200 mg/kg, or 300 mg/kg. It is understood that where the amount is referred to as "mg/kg," the amount is milligram per kilogram body weight of the subject being administered with the active agents. In aspects, the active agent is administered to a patient in an amount from about 0.1 mg to about 1,000 mg per day, as a single dose, or in a dose administered two or three times per day.

Methods of Treatment

In embodiments, the disclosure provides methods of treating an inflammatory disease in a patient in need thereof by administering to the patient in an effective amount of the compounds described herein, including all embodiments and embodiments thereof. In embodiments, the disclosure provides methods of treating an inflammatory disease in a patient in need thereof by administering to the patient in an effective amount of a pharmaceutical composition comprising a pharmaceutically acceptable excipient and the compounds described herein, including all embodiments and embodiments thereof.

In embodiments, the disclosure provides methods of treating an inflammatory disease in a patient in need thereof by administering to the patient in an effective amount of the nucleic acids described herein, including all embodiments and embodiments thereof. In embodiments, the disclosure provides methods of treating an inflammatory disease in a patient in need thereof by administering to the patient in an effective amount of a pharmaceutical composition comprising the nucleic acids described herein, including all embodiments and embodiments thereof.

The term "inflammatory disease" refers to a disease or condition characterized by aberrant inflammation (e.g. an increased level of inflammation compared to a control such as a healthy person not suffering from a disease). Examples of inflammatory diseases include cytokine release syndrome, hypercytokinemia (e.g., cytokine storm), multisystem inflammatory syndrome (MIS-C), sepsis, enterocolitis (e.g., necrotizing enterocolitis), autoimmune diseases, arthritis, rheumatoid arthritis, psoriatic arthritis, juvenile idiopathic arthritis, multiple sclerosis, systemic lupus erythematosus, myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, thromboembolism (e.g., deep vein thrombosis, venous thrombosis), cardiac inflammation (e.g., endocarditis, myocarditis, pericarditis), atherosclerosis, scleroderma, and atopic dermatitis. In embodiments, the inflammatory disease is hypercytokinemia. In embodiments, the inflammatory disease is multisystem inflammatory syndrome. In embodiments, the inflammatory disease is multisystem inflammatory syndrome in children (e.g., people under 18 years old). In embodiments, the inflammatory disease is thromboembolism. In embodiments, the inflammatory disease is deep vein thrombosis. In embodiments, the inflammatory disease is venous thrombosis. In embodiments, the inflammatory disease is cardiac inflammation. In embodiments, the inflammatory disease is endocarditis. In embodiments, the inflammatory disease is myocarditis. In embodiments, the inflammatory disease is pericarditis.

In embodiments, the inflammatory disease is cytokine release syndrome. Cytokine release syndrome is a systemic inflammatory response that can occur after immunotherapy treatment, e.g., treatment with monoclonal antibodies, chimeric antigen receptor (CAR) T cells, or non-protein-based cancer drugs, Cytokine release syndrome is caused by a large, rapid release of cytokines into the blood from immune cells affected by the immunotherapy. In embodiments, the cytokine release syndrome is chimeric antigen receptor T-cell-induced cytokine release syndrome.

In embodiments, the inflammatory disease is sepsis. Sepsis is also known as systemic inflammatory response syndrome after microbial infection. During sepsis, microbial infection or necrotic tissue release high levels of harmful substances, resulting in the activation of systemic immune response and excessive activation of immune cells. The excessive release of cytokines plays a destructive effect. TLR-4 activation is important in inflammatory response triggering because of TLR-4 expressed in G-bacteria outer membrane, and TLR-4 is able to form a receptor complex with CD14 and MD2 to mediate lipopolysaccharide (LPS) recognition, thus triggering an inflammatory response In embodiments, the disclosure provides methods of treating cancer in a patient in need thereof by administering to the patient in an effective amount of the compounds described herein, including all embodiments and embodiments thereof. In embodiments, the disclosure provides methods of treating cancer in a patient in need thereof by administering to the patient in an effective amount of a pharmaceutical composition comprising a pharmaceutically acceptable excipient and the compounds described herein, including all embodiments and embodiments thereof.

In embodiments, the disclosure provides methods of treating cancer in a patient in need thereof by administering to the patient in an effective amount of the nucleic acids described herein, including all embodiments and embodiments thereof. In embodiments, the disclosure provides methods of treating cancer in a patient in need thereof by administering to the patient in an effective amount of a pharmaceutical composition comprising a pharmaceutically acceptable excipient and the nucleic acids described herein.

The term "cancer" refers to all types of cancer, neoplasm or malignant tumors found in mammals (e.g. humans), including leukemias, lymphomas, carcinomas and sarcomas. Exemplary cancers that may be treated with compounds, nucleic acids, and pharmaceutical compositions described herein include leukemia (e.g., acute myeloid leukemia ("AML") or chronic myeloid leukemia ("CML")) brain cancer, glioma, glioblastoma, neuroblastoma, prostate cancer, colorectal cancer, pancreatic cancer, medulloblastoma, melanoma, cervical cancer, gastric cancer, ovarian cancer, lung cancer, cancer of the head, Hodgkin's disease, and Non-Hodgkin's lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute myeloid leukemia, chronic myeloid leukemia, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "lymphoma" refers to a group of cancers affecting hematopoietic and lymphoid tissues. It begins in lymphocytes, the blood cells that are found primarily in lymph nodes, spleen, thymus, and bone marrow. Two main types of lymphoma are non-Hodgkin lymphoma and Hodgkin's disease. Hodgkin's disease represents approximately 15% of all diagnosed lymphomas. This is a cancer associated with Reed-Sternberg malignant B lymphocytes. Non-Hodgkin's lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas that may be treated with a compound or method provided herein include, but are not limited to, small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. Exemplary T-cell lymphomas that may be treated with a compound or method provided herein include, but are not limited to, cunateous T-cell lymphoma, peripheral T-cell lymphoma, anaplastic large cell lymphoma, mycosis fungoides, and precursor T-lymphoblastic lymphoma.

The terms "metastasis," "metastatic," and "metastatic cancer" can be used interchangeably and refer to the spread of a proliferative disease or disorder, e.g., cancer, from one organ or another non-adjacent organ or body part. "Metastatic cancer" is also called "Stage IV cancer." Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms, fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In embodiments, chronic administration may be required. For example, the compositions are administered to the subject in an amount and for a duration sufficient to treat the patient. In embodiments, the treating or treatment is no prophylactic treatment.

The term "prevent" refers to a decrease in the occurrence of disease symptoms in a patient. As indicated above, the prevention may be complete (no detectable symptoms) or partial, such that fewer symptoms are observed than would likely occur absent treatment.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, and other non-mammalian animals. In embodiments, a patient is human.

Cancer model organism, as used herein, is an organism exhibiting a phenotype indicative of cancer, or the activity of cancer causing elements, within the organism. The term cancer is defined above. A wide variety of organisms may serve as cancer model organisms, and include for example, cancer cells and mammalian organisms such as rodents (e.g. mouse or rat) and primates (such as humans). Cancer cell lines are widely understood by those skilled in the art as cells exhibiting phenotypes or genotypes similar to in vivo cancers. Cancer cell lines as used herein includes cell lines from animals (e.g. mice) and from humans.

"Coadminister" means that compounds, nucleic acids, or pharmaceutical composition described herein is administered at the same time, just prior to, or just after the administration of one or more additional anti-inflammatory agents, anti-cancer agents and/or radiation treatment. The compounds provided herein can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation).

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. Exemplary anti-cancer agents include antibodies, small molecules, large molecules, and combinations thereof. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds or platinum containing agents (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole;

isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras famesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or $rIL_2$), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, erbulozole (i.e. R-55104), dolastatin 10 (i.e. DLS-10 and NSC-376128), mivobulin isethionate (i.e. as CI-980), vincristine, NSC-639829, Discodermolide (i.e. as NVP-XX-A-296), ABT-751 (Abbott, i.e. E-7010), altorhyrtins (e.g. Altorhyrtin A and Altorhyrtin C), spongistatins (e.g. spongistatin 1, spongistatin 2, spongistatin 3, spongistatin 4, spongistatin 5, spongistatin 6, spongistatin 7, spongistatin 8, and Spongistatin 9), cemadotin hydrochloride (i.e. LU-103793 and NSC-D-669356), epothilones (e.g. Epothilone A, Epothilone B, Epothilone C (i.e. desoxyepothilone A or dEpoA), epothilone D (i.e. KOS-862, dEpoB, and desoxyepothilone B), epothilone E, epothilone F, epothilone B N-oxide, epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), soblidotin (i.e. TZT-1027), vincristine sulfate, cryptophycin 52 (i.e. LY-355703), vitilevuamide, tubulysin A, canadensol, centaureidin (i.e. NSC-106969), Oncocidin A1 (i.e. BTO-956 and DIME), fijianolide B, laulimalide, narcosine (also known as NSC-5366), nascapine, hemiasterlin, vanadocene acetylacetonate, monsatrol, lnanocine (i.e. NSC-698666), eleutherobins (such as desmethyleleutherobin, desaetyleleutherobin, lsoeleutherobin A, and Z-Eleutherobin), caribaeoside, caribaeolin, halichondrin B, diazonamide A, taccalonolide A, diozostatin, (−)-phenylahistin (i.e. NSCL-96F037), myoseverin B, resverastatin phosphate sodium, steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{11}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, innotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™) panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, hormonal therapies, or the like.

The singular terms "a", "an", and "the" include the plural reference unless the context clearly indicates otherwise.

The term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Embodiments

Embodiment 1. A compound of Formula (I) or Formula (II): $R^1$-$L^1$-$R^2$ (I) or (II)

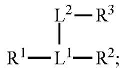

wherein: $R^1$ is a CpG oligodeoxynucleotide (ODN); $L^1$ and $L^2$ are independently a linking group; $R^2$ and $R^3$ are independently a hybridized nucleic acid sequence, the hybridized nucleic acid sequence comprising a microRNA passenger strand sequence hybridized to a microRNA guide strand sequence; wherein (i) the microRNA is miR146a, wherein the miR146a passenger strand sequence comprises SEQ ID NO:1, and the miR146a guide strand sequence comprises SEQ ID NO:6; (ii) the microRNA is anti-miR155, wherein the anti-miR155 passenger strand sequence comprises SEQ ID NO:19, and the anti-miR155 guide strand sequence comprises SEQ ID NO:20; (iii) the microRNA is miR142, wherein the miR142 passenger strand sequence comprises SEQ ID NO:21, and the miR142 guide strand sequence comprises SEQ ID NO:22; (iv) the microRNA is miR125b, wherein the miR125b passenger strand sequence comprises SEQ ID NO:23, and the miR125b guide strand sequence comprises SEQ ID NO:24; (v) the microRNA is miR203b, wherein the miR203b passenger strand sequence comprises SEQ ID NO:25, and the miR203b guide strand sequence comprises SEQ ID NO:26; (vi) the microRNA is miR221, wherein the miR221 passenger strand sequence comprises SEQ ID NO:27, and the miR221 guide strand sequence comprises SEQ ID NO:28; (vii) the microRNA is miR222, wherein the miR222 passenger strand sequence comprises SEQ ID NO: 29, and the miR222 guide strand sequence comprises SEQ ID NO:30; or (viii) the microRNA is miR29b, wherein the miR29b passenger strand sequence comprises SEQ ID NO:31, and the miR142 guide strand sequence comprises SEQ ID NO:32.

Embodiment 2. The compound of Embodiment 1, wherein the microRNA is miR146a, wherein the miR146a passenger strand sequence comprises SEQ ID NO:1, and the miR146a guide strand sequence comprises SEQ ID NO:6.

Embodiment 3. The compound of Embodiment 1 or 2, wherein one or more nucleotides in the microRNA passenger strand sequence are modified with 2'-O-Methyl, 2'-Fluoro, or a combination thereof.

Embodiment 4. The compound of any one of Embodiments 1 to 3, wherein the miR146a passenger strand sequence comprises SEQ ID NO:2.

Embodiment 5. The compound of any one of Embodiments 1 to 4, wherein the miR146a guide strand sequence comprises SEQ ID NO:7.

Embodiment 6. The compound of any one of Embodiments 1 to 5, wherein the miR146a guide strand sequence comprises SEQ ID NO:8.

Embodiment 7. The compound of any one of Embodiments 1 to 6, wherein one or more nucleotides in the microRNA guide strand sequence are modified with 2'-O-Methyl, 2'-Fluoro, or a combination thereof.

Embodiment 8. The compound of any one of Embodiments 1 to 7, wherein the 3' end of $R^1$ is covalently bonded to $L^1$.

Embodiment 9. The compound of any one of Embodiments 1 to 8, wherein the CpG ODN is a CpG-A ODN.

Embodiment 10. The compound of Embodiment 9, wherein the CpG-A ODN is CpG ODN D19.

Embodiment 11. The compound of Embodiment 9, wherein the CpG-A ODN is CpG ODN 1585.

Embodiment 12. The compound of Embodiment 9, wherein the CpG-A ODN is CpG ODN 2216.

Embodiment 13. The compound of Embodiment 9, wherein the CpG-A ODN is CpG ODN 2336.

Embodiment 14. The compound of any one of Embodiments 1 to 8, wherein the CpG ODN is a CpG-A ODN, a CpG-B ODN, a CpG-C ODN, or a combination of two or more thereof.

Embodiment 15. The compound of any one of Embodiments 1 to 8, wherein the CpG ODN is CpG ODN 19, CpG ODN 1585, CpG ODN 2216, CpG ODN 2336, CpG ODN 1668, CpG ODN 1826, CpG ODN 2006, CpG ODN 2007, CpG ODN BW006, CpG ODN D-SL01, CpG ODN 2395, CpG ODN M362, CpG ODN D-SL03, or a combination of two or more thereof.

Embodiment 16. The compound of any one of Embodiments 1 to 15, wherein $L^1$ and L2 are independently a bond, a nucleic acid sequence, a DNA sequence, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or a combination of two or more thereof.

Embodiment 17. The compound of Embodiment 16, wherein $L^1$ and $L^2$ are independently a bond, a nucleic acid sequence, substituted or unsubstituted alkylene, a substituted or unsubstituted heteroalkylene, or a combination of two or more thereof.

Embodiment 18. The compound of any one of Embodiments 1 to 15, wherein $L^1$ and L2 are independently a substituted 6 to 60 membered heteroalkylene.

Embodiment 19. The compound of any one of Embodiments 1 to 15, wherein $L^1$ and L2 are independently a substituted 18 to 42 membered heteroalkylene; wherein the heteroalkylene comprises an oxygen atom, a phosphorous atom, or a combination thereof; and wherein the substituents are independently selected from the group consisting of =O, —OH, and —O—.

Embodiment 20. The compound of any one of Embodiments 1 to 15, wherein $L^1$ and $L^2$ are independently:

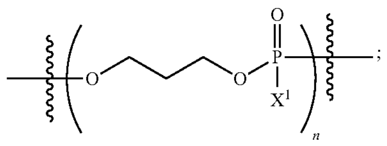

wherein $X^1$ is independently —OH or —O—, and n is an integer from 1 to 10.

Embodiment 21. The compound of Embodiment 20, wherein n is an integer from 2 to 8.

Embodiment 22. The compound of Embodiment 21, wherein n is an integer from 4 to 6.

Embodiment 23. The compound of Embodiment 21, wherein n is 5.

Embodiment 24. The compound of Embodiment 16, wherein $L^1$ and $L^2$ are independently substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or a combination of two or more thereof.

Embodiment 25. The compound of Embodiment 24, wherein $L^1$ and $L^2$ are independently substituted or unsubstituted heteroalkylene, substituted or unsubstituted heterocycloalkylene, substituted or unsubstituted heteroarylene, or a combination of two or more thereof.

Embodiment 26. The compound of Embodiment 25, wherein the substituted or unsubstituted heteroalkylene comprises $-(CH_2CH_2O)-$.

Embodiment 27. The compound of Embodiment 25 or 26, wherein the substituted or unsubstituted heteroalkylene comprises:

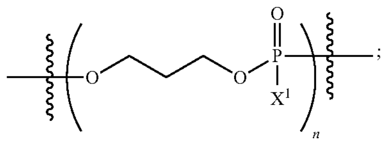

wherein $X^1$ is independently —OH or —O—, and n is an integer from 1 to 10.

Embodiment 28. The method of any one of Embodiments 24 to 27, wherein the substituted or unsubstituted heteroarylene is a 5 or 6 membered substituted or unsubstituted heteroarylene comprising one or two nitrogen atoms.

Embodiment 29. The method of any one of Embodiments 24 to 28, wherein the substituted or unsubstituted heterocycloalkylene is a 5 or 6 membered substituted or unsubstituted heterocycloalkylene comprising an oxygen atom, a nitrogen atom, or a combination thereof.

Embodiment 30. The compound of any one of Embodiments 1 to 29, wherein the compound is of formula (I).

Embodiment 31. The compound of Embodiment 30, wherein the 5' end of the microRNA passenger strand sequence is covalently bonded to $L^1$.

Embodiment 32. The compound of Embodiment 30, wherein the 3' end of the microRNA passenger strand sequence is covalently bonded to $L^1$.

Embodiment 33. The compound of Embodiment 30, wherein the microRNA is miR146a, and (i) the 3' end of $R^1$ is bonded to $L^1$; (ii) $R^2$ is the hybridized nucleic acid sequence; wherein the 5' end of the miR146a passenger strand sequence is covalently bonded to $L^1$; and wherein the miR146a passenger strand sequence comprises SEQ ID NO:2 and the miR146a guide strand sequence comprises SEQ ID NO:7 or SEQ ID NO:8; and (iii) $L^1$ is

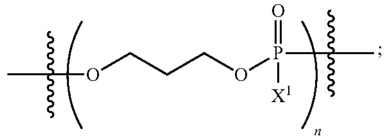

wherein $X^1$ is independently —OH or —O—, and n is an integer from 4 to 6.

Embodiment 34. The compound of Embodiment 33, wherein n is 5.

Embodiment 35. The compound of Embodiment 33 or 34, wherein $R^1$ is CpG ODN D19.

Embodiment 36. The compound of any one of Embodiments 1 to 29, wherein the compound is of formula (II).

Embodiment 37. The compound of Embodiment 36, wherein the microRNA is miR146a, and (i) the 3' end of $R^1$ is bonded to $L^1$; (ii) $R^2$ is the hybridized nucleic acid sequence; wherein the 5' end of the miR146a passenger strand sequence is covalently bonded to $L^1$; the miR146a passenger strand sequence comprises SEQ ID NO:2 and the miR146a guide strand sequence comprises SEQ ID NO:6 or SEQ ID NO:7; (iii) $R^3$ is the hybridized nucleic acid sequence; wherein the 5' end of the miR146a passenger strand sequence is covalently bonded to $L^2$; wherein the miR146a passenger strand sequence comprises SEQ ID NO:2 and the miR146a guide strand sequence comprises SEQ ID NO:7 or SEQ ID NO:8; and (iv) $L^1$ and $L^2$ are independently: (a) substituted or unsubstituted heteroalkylene; (b) 5 or 6 membered substituted or unsubstituted heteroarylene comprising one or two nitrogen atoms; (c) 5 or 6 membered substituted or unsubstituted heterocycloalkylene comprising an oxygen atom, a nitrogen atom, or a combination thereof; or (d) a combination of two or more of the foregoing.

Embodiment 38. The compound of Embodiment 37, wherein $R^1$ is CpG ODN D19.

Embodiment 39. Compound A.

Embodiment 40. Compound B.

Embodiment 41. Compound C.

Embodiment 42. Compound D.

Embodiment 43. Compound E.

Embodiment 44. Compound G.

Embodiment 45. Compound G.

Embodiment 46. Compound H.

Embodiment 47. Compound J.

Embodiment 48. Compound K.

Embodiment 49. Compound L.

Embodiment 50. A pharmaceutical composition comprising the compound of any one of Embodiments 1 to 49 and a pharmaceutically acceptable excipient.

Embodiment 51. A method of treating cancer in a patient in need thereof, the method comprising administering to the patient an effective amount of the compound of any one of Embodiments 1 to 49, or the pharmaceutical composition of Embodiment 50.

Embodiment 52. The method of Embodiment 51, wherein the cancer is leukemia.

Embodiment 53. The method of Embodiment 52, wherein the leukemia is myeloid leukemia.

Embodiment 54. The method of Embodiment 51, wherein the cancer is lymphoma.

Embodiment 55. The method of Embodiment 54, wherein the lymphoma is B-cell lymphoma.

Embodiment 56. A method of treating an inflammatory disease in a patient in need thereof, the method comprising administering to the patient an effective amount of the compound of any one of Embodiments 1 to 49, or the pharmaceutical composition of Embodiment 50.

Embodiment 57. The method of Embodiment 56, wherein the inflammatory disease is cytokine release syndrome or sepsis.

Embodiment 58. A hybridized nucleic acid sequence, the hybridized nucleic acid sequence comprising a microRNA passenger strand sequence hybridized to a microRNA guide strand sequence; wherein (i) the microRNA is miR146a, wherein the miR146a passenger strand sequence comprises SEQ ID NO: 1, and the miR146a guide strand sequence comprises SEQ ID NO:6; (ii) the microRNA is anti-miR155, wherein the anti-miR155 passenger strand sequence comprises SEQ ID NO: 19, and the anti-miR155 guide strand sequence comprises SEQ ID NO:20; (iii) the microRNA is miR142, wherein the miR142 passenger strand sequence comprises SEQ ID NO:21, and the miR142 guide strand sequence comprises SEQ ID NO:22; (iv) The microRNA is miR125b, wherein the miR125b passenger strand sequence comprises SEQ ID NO:23, and the miR125b guide strand sequence comprises SEQ ID NO:24; (v) the microRNA is miR203b, wherein the miR203b passenger strand sequence comprises SEQ ID NO:25, and the miR203b guide strand sequence comprises SEQ ID NO:26; (vi) the microRNA is miR221, wherein the miR221 passenger strand sequence comprises SEQ ID NO:27, and the miR221 guide strand sequence comprises SEQ ID NO:28; (vii) the microRNA is miR222, wherein the miR222 passenger strand sequence comprises SEQ ID NO:29, and the miR222 guide strand sequence comprises SEQ ID NO:30; or (viii) the microRNA is miR29b, wherein the miR29b passenger strand sequence comprises SEQ ID NO:31, and the miR142 guide strand sequence comprises SEQ ID NO:32.

Embodiment 59. The hybridized nucleic acid sequence of Embodiment 58, wherein the microRNA is miR146a, wherein the miR146a passenger strand sequence comprises SEQ ID NO:1, and the miR146a guide strand sequence comprises SEQ ID NO:6.

Embodiment 60. The hybridized nucleic acid sequence of Embodiment 58 or 59, wherein one or more nucleotides in the microRNA passenger strand sequence are modified with 2'-O-Methyl, 2'-Fluoro, or a combination thereof.

Embodiment 61. The hybridized nucleic acid sequence of any one of Embodiments 58 to 60, wherein the miR146a passenger strand sequence comprises SEQ ID NO:2.

Embodiment 62. The hybridized nucleic acid sequence of any one of Embodiments 58 to 12, wherein the miR146a guide strand sequence comprises SEQ ID NO:7.

Embodiment 63. The hybridized nucleic acid sequence of any one of Embodiments 58 to 62, wherein one or more nucleotides in the microRNA guide strand sequence are modified with 2'-O-Methyl, 2'-Fluoro, or a combination thereof.

Embodiment 64. A pharmaceutical composition comprising the hybridized nucleic acid of any one of Embodiments 58 to 63 and a pharmaceutically acceptable excipient.

Embodiment 65. A method of treating cancer in a patient in need thereof, the method comprising administering to the patient an effective amount of the hybridized nucleic acid of any one of Embodiments 58 to 63 or the pharmaceutical composition of Embodiment 64.

Embodiment 66. The method of Embodiment 65, wherein the cancer is leukemia or lymphoma.

Embodiment 67. The method of Embodiment 66, wherein the cancer is myeloid leukemia or B-cell lymphoma.

Embodiment 68. A method of treating an inflammatory disease in a patient in need thereof, the method comprising administering to the patient an effective amount of the hybridized nucleic acid of any one of Embodiments 58 to 63 or the pharmaceutical composition of Embodiment 64.

Embodiment 69. The method of Embodiment 68, wherein the inflammatory disease is cytokine release syndrome or sepsis.

Embodiment 70. A compound of Formula (III):

(III)

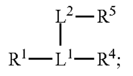

wherein: $R^1$ is a CpG oligodeoxynucleotide (ODN); $L^1$ and $L^2$ are independently a linking group; $R^4$ and $R^5$ are independently a miR146a passenger strand sequence which comprises SEQ ID NO:1; anti-miR155 passenger strand sequence which comprises SEQ ID NO: 19; a miR142 passenger strand sequence which comprises SEQ ID NO:21; a miR125b passenger strand sequence which comprises SEQ ID NO:23; a miR203b passenger strand sequence which comprises SEQ ID NO:25; a miR221 passenger strand sequence which comprises SEQ ID NO:27; a miR222 passenger strand sequence which comprises SEQ ID NO:29; or a miR29b passenger strand sequence which comprises SEQ ID NO:31.

Embodiment 71. The compound of Embodiment 70, wherein $R^4$ and $R^5$ are independently a miR146a passenger strand sequence which comprises SEQ ID NO:1

Embodiment 72. The compound of Embodiment 71, wherein one or more nucleotides in the passenger strand sequence are modified with 2'-O-Methyl, 2'-Fluoro, or a combination thereof.

Embodiment 73. The compound of Embodiments 71, wherein the miR146a passenger strand sequence comprises SEQ ID NO:2.

EXAMPLE

It is understood that the example described herein is for illustrative purposes only and that various modifications or changes in light thereof will be suggested to persons skilled in the art and are to be included within the spirit and purview of this application and scope of the appended claims.

NF-KB is a key regulator of inflammation and cancer progression, with an important role in leukemogenesis. Despite therapeutic potential, targeting NF-KB proved challenging for pharmacologic inhibitors. Here, Applicant describes a myeloid cell-selective NF-KB inhibitor using miR146a mimic oligonucleotide conjugated to scavenger receptors (SR)/Toll-like receptor 9 (TLR9) agonist (C-miR146a). Unlike an unconjugated miR146a, C-miR146a was rapidly internalized and delivered to cytoplasm of target myeloid cells and leukemic cells. C-miR146a reduced expression of classic miR146a targets, IRAK1 and TRAF6, thereby blocking NF-KB activation in target cells. Intravenous injections of C-miR146a mimic to miR146-deficient mice prevented excessive NF-KB activation in myeloid cells, thereby alleviating myeloproliferation and mice hypersensitivity to bacterial challenge. Importantly, C-miR146a showed efficacy in dampening severe inflammation in clinically relevant models of chimeric antigen receptor (CAR) T-cell-induced cytokine release syndrome (CRS). Systemic administration of C-miR146a oligonucleotide alleviated human monocyte-dependent release of IL-1 and IL-6 in xenotransplanted B-cell lymphoma model without affecting CD19-specific CAR T-cell antitumor activity. Beyond anti-inflammatory functions, miR146a is a known tumor suppressor commonly deleted in human myeloid leukemia. Correspondingly, C-miR146a induced cytotoxic effects in human MDSL and HL-60 leukemia cells in vitro. The repeated intravenous administration of C-miR146a thwarted progression of both leukemia models in vivo. These results demonstrate that myeloid cell-selective miR146a mimics are useful for treating inflammatory and myeloproliferative disorders.

Methods

Mice. All animal experiments were following institutional guidance and approved protocols from the institutional animal care and use committee (COH). C57BL/6 mice, aged between 6-8 weeks, were purchased from the National Cancer Institute. Female C.B-Igh-1b/GbmsTac-Prkdc$^{scid}$-Lyst$^{b}$g N7 (SCID-Beige) mice were purchased from Taconic. NOD/SCID/IL-2RgKO (NSG) and NSG Tg(CMV-IL3,CSF2,KITLG)1 Eav/MloySzJ (SGM3) mice from Jackson Laboratory. miR146a$^{-/-}$ and LyzM-Cre/miR146a$^{fl/fl}$ mice were described before[9,20] and were bred and housed in Caltech Office of Laboratory Animal Resources facility with approved protocols.

C-miR146a design and synthesis. The C-miR146a conjugates were synthesized in the DNA/RNA Synthesis Core (COH) by linking CpG-D19 ODN to miR146a passenger strands as described.[21] The resulting conjugates were hybridized with complementary guide strands of mature miR146a sequence to create chimeric C-miR146a mimic constructs. For internalization studies, the miR146a guide strand was labeled on 3' ends using Cy3 fluorochrome. The sequences of single stranded constructs are listed below (x=a single C3 unit; asterisks=phosphorothioation sites; underline=2'O-methylated nucleotide):

C-miR146a passenger strand is SEQ ID NO:17 covalently bonded via a linking group to SEQ ID NO:2, wherein the linking group is

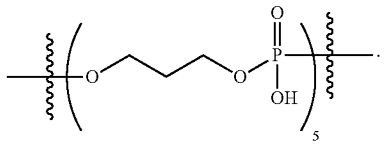

miR146a guide strand is SEQ ID NO:7.

C-scrRNA passenger strand is SEQ ID NO: 17 covalently bonded via a linking group to SEQ ID NO:45, wherein the linking group is

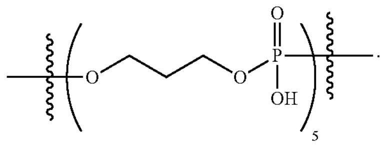

scrRNA guide strand is SEQ ID NO:46.

RNA-binding protein immunoprecipitation. The RNA-binding protein immunoprecipitation (RIP) was performed using *Magna* RIP kit (Millipore) according to manufacturer's instructions.

In vivo bio-distribution. miR146a$^{-/-}$ mice were injected retro-orbitally with 2.5-20 mg/kg C-miR146a. After 3 h, mice were euthanized and organs were collected for qPCR or Western blot analysis. For the CD11b$^+$, CD11c$^+$, CD19$^+$ and CD3$^+$ populations, cells were selected using EasySep PE-positive selection kit (Stemcell Technologies) following manufacturer's instructions.

*Listeria monocytogenes* infection. *Listeria monocytogenes* (strain 10,403/serotype 1) were grown in brain heart infusion media. A total bacterial load of 10E5 c.f.u. were injected to each WT C57BL/6 or LyzM-Cre/miR146a$^{fl/fl}$ mice using retro-orbital injections. Mice were treated every day using 5 mg/kg C-miR146a or C-scrRNA (negative control) for three days before infection and three days after infection. Three days after infection, the mice were euthanized, liver, blood and spleen tissues were collected for bacterial load quantification, hematopoietic cell frequencies and IL-6 serum levels.

In Vivo cytokine release syndrome models. 6-8 week old female SCID-Beige mice were injected intraperitoneally using 3'10$^6$ Raji$^{GFP/Luc}$ cells, and tumor burden was evaluated using in vivo bioluminescent imaging. Mice were injected intraperitoneally with C-miR146a (5 mg/kg) or PBS every day for three days before CAR-T-cell transfer. On day 18, mice were injected intraperitoneally using 12.5'10$^6$ mock-transfected or CD19-specific CAR-T-cells. Plasma was collected before and 6, 18, 24, 30, 54 h after CAR-T-cell transfer. Mouse IL-6 and G-CSF levels were analyzed using ELISA (Thermo Fisher). Mice were euthanized 72 h after CAR-T-cell transfer, and peritoneal myeloid cells were collected and analyzed for miR146a levels.

In vivo tumor models. MDSL or HL-60 cells (1×10$^6$ cells) were injected subcutaneously (SC) to SGM3 mice and the tumor sizes were measured every other day. Once tumors reached –200 mm$^3$, mice were injected intratumorally every day using 5 mg/kg C-miR146a or C-scrRNA. The mice were euthanized when untreated tumors reached –2000 mm$^3$ size and tumors were collected. For the systemic leukemia xenograft models, SGM3 mice were injected intravenously with 2×10$^6$ of HL-60$^{LUC}$ cells. Tumor progression was monitored using bioluminescent imaging on AmiX (Spectral Instruments). Starts from day 9, mice were injected retro-orbitally with 10 mg/kg of C-miR146a or C-scrRNA every other day.

Statistics. Unpaired t test was used to calculate two-tailed P value to estimate statistical significance of differences between two treatment groups. One- or two-way ANOVA plus Bonfeerroni post-test were applied to assess differences between multiple groups or in tumor growth kinetics experiments, respectively. Statistically significant P values were indicated in figures as *, P<0.001; , P<0.01 and *, P<0.05 compared to untreated or PBS groups. Data analyzed using Prism software v.7 (GraphPad).

Results

Targeted Delivery of Functional miR146a Mimic into Myeloid Cells and B-Cells

To overcome challenges in the efficient and cell-selective delivery of miR146a, Applicant modified the scavenger receptor (SR)/Toll-like receptor 9 (TLR9)-targeting platform originally developed for transfer of 25/27-mer Dicer-substrate siRNA. (Ref. 21). The double-stranded miR146a was conjugated through 5' end of the passenger strand to the 3' end of a single-stranded and partly phosphorothioated oligodeoxynucleotide (CpG ODN) using a synthetic carbon linker. The specific type-A CpG ODN sequence of the conjugate was selected for monocytes/myeloid cell specificity and poor ability to activate NF-KB and its downstream IL-6 and IL-10 targets. (Refs. 22, 23). To ensure the maximum activity and target specificity, the miR146a was chemically modified for nuclease resistance by a 2'O-methyl-modification in the 3' end of passenger strand (FIG. 1A). This design significantly improved serum stability of the miR146a conjugate without impacting its activity. Compared to miR146a (T1/2~1 h), the conjugated C-miR146a had 34 h half-life in human serum (FIG. 1B and Supplemental FIG. S1). The C-miR146a$^{C}$y$^3$ was rapidly internalized by primary human immune cells and mouse RAW264.7 macrophages (FIG. 1C) or splenocytes (FIG. 8) within an hour of incubation, without any transfection reagents. Compared to the unconjugated miR146a$^{C}$y$^3$, C-miR146a$^{C}$y$^3$ was also efficiently taken up by human leukemic cells, such as MDSL or HL60 (FIG. 1C). The uptake of C-miR146a depended on the scavenger receptor A- and clathrin-mediated endocytosis, as verified using internalization inhibitors, specifically dextran sulfate, fucoidan and cadaverine (FIG. 9). Confocal microscopy images showed C-miR146a localized to the cytosol of target cells within 1 h, while miR146a alone was undetectable (FIG. 1D). To inhibit target mRNAs, the miRNA guide strand must bind Argonaute-2 (Ago2) protein within the RNA-induced silencing complex (RISC). To assess whether the guide strand of C-miR146a was successfully loaded onto the RISC, we performed RNA-binding protein immunoprecipitation (RIP) using Ago2-specific antibodies (FIG. 1E). In fact, the level of Ago2-bound miR146a guide strand increased several fold in mouse RAW264.7 macrophages incubated with the C-miR146a but not with miR146a. This effect was even more prominent in primary mouse splenocytes derived from miR146a$^{-/-}$ mice (FIG. 1E). These results indicated that the C-miR146a allows for the delivery of functional miR146a to human and mouse myeloid target cells.

C-miR146a Mimic Targets Upstream Regulators of NF-KB Signaling

MiR-146a targets IRAK1 and TRAF6, the critical upstream regulators of NF-κB signaling. (Ref. 10). Applicant used 3'-UTR-luciferase reporter assays to verify whether C-miR146a can alter IRAK1 and TRAF6 expression. As shown in FIG. 2A, C-miR146a, but not miR146a alone, significantly reduced IRAK1 and TRAF6 3'-UTR-luciferase reporter activities in treated cells. In contrast, cells treated with negative control scrambled RNA conjugate (C-scrRNA) showed weak upregulation of IRAK1 and TRAF6 3'-UTR luciferase levels (FIG. 2A). Moreover, C-miR146a, but not the control oligonucleotides, reduced protein levels of IRAK and TRAF6 in mouse RAW264.7 macrophages and IRAK1 in human MDSL cells (FIG. 2B). Activated NF-κB translocates to the nucleus, thus Applicant examined the effect of C-miR146a on the localization of NF-κB in LPS-treated RAW264.7 cells expressing NF-κB/p65-eGFP fusion protein.[24] Confocal microscopy confirmed that C-miR146a, but not C-scrRNA, efficiently blocked the nuclear translocation of NF-κB (FIG. 2C). Correspondingly, the C-miR146a reduced the NF-κB DNA-binding activity in nuclear extracts from RAW264.7 and MDSL cells as measured using electrophoretic mobility shift assays (EMSA; FIG. 2D). These inhibitory effects of the C-miR146a resulted in reduced transcriptional NF-κB activity as shown using NF-κB-regulated promoter in LPS-treated RAW-Blue macrophages (FIG. 2E) and by the reduced secretion of IL-6 cytokine by parental RAW264.7 cells (FIG. 2F).

For an additional verification that the observed effects were specific for the miRNA sequence within the conjugate, Applicant used analogical approach to deliver antisense-targeting miR146a, C-anti-miR146a (FIG. 10A). (Ref. 25). While C-anti-miR146a showed similar cell-selective internalization pattern as the C-miR146a mimic (FIG. 10B), it had opposite biological activity. C-anti-miR146a abrogated miR146a expression in primary mouse splenocytes and myeloid cells (FIG. 10C), thereby upregulating IRAK1 and TRAF6 3' UTR activities (FIG. 10D-10E) and augmenting NF-KB DNA-binding (FIG. 10D) and nuclear translocation (FIG. 10F). Taken together, the presence of CpG ODN moiety did not interfere with activity of miR146a mimic or anti-miR146a. The flexibility of this oligonucleotide strategy permits positive and negative regulation of NF-κB activity using miR146a mimic and antisense delivery.

Systemic C-miR146a Mimic Delivery Restored Control Over IRAK1 and TRAF6 in miR146a-Deficient Myeloid Cells In Vivo Treatment of NF-κB-related disorders requires efficient delivery of miR146a mimics to target myeloid cells in various organs. To directly quantify the biodistribution of C-miR146a mimic, Applicant used the real-time qPCR to detect miR146a guide-strand in various organs of miR146a-deficient mice. (Ref. 9). The results showed dose-dependent increase of miR146a guide-strand levels in bone-marrow, spleens and to lesser extent in lymph nodes from miR146a$^{-/-}$ mice after intravenous injections of various doses of C-miR146a (FIG. 3A). At 5-20 mg/kg dosing, C-miR146a significantly upregulated the levels of miR146a-5p guide-strand in miR146a$^{-/-}$CD1b$^{+}$ myeloid cells compared to the rest of non-targeted (CD11b$^{-}$) cells from bone-marrow (FIG. 3B). Next, Applicant compared the miR146a expression levels in oligonucleotide-treated miR146a$^{-/-}$ mice to the untreated wild-type (WT) mice to quantify the relative restoration of miR146a in various cell populations. As shown in the FIGS. 3C-3D, the single injection of 5 mg/kg C-miR146a replaced −61% and −53% of WT miR146a levels in bone marrows and in spleens, respectively. CD11b$^{+}$ myeloid cells isolated from bone-marrow or spleen of miR146a$^{-/-}$ mice showed −54% or −47% of WT miR146a levels, respectively. The miR146a levels were restored to −28% and to −5% in CD19$^{+}$ B cells and CD3$^{+}$ T cells, respectively (FIG. 3D), consistently with earlier in vitro results underscoring myeloid cell specificity of the strategy (FIG. 1). Finally, Applicant tested whether partial restoration of miR146a had sufficient biological activity to inhibit target IRAK1 and TRAF6 proteins. In fact, within 12-24 h after a single IV injection C-miR146a (5 mg/kg), both IRAK1 and TRAF6 were reduced close to the WT levels, returning to the baseline after 2-3 days (FIG. 3E). These results indicate that systemic delivery of C-miR146a using relatively low dosing can transiently restore levels and full biological activity of miR146a in target myeloid cells in vivo.

C-miR146a Abrogates Myeloproliferation and Exaggerated Inflammatory Responses in miR146a-Deficient Mice Expansion of myeloid cells is one of the critical phenotypic features of the miR146a-deficient mice. (Ref. 26). Compared to WT mice, bone marrow-derived macrophages (BMDMs) from miR146a-deficient mice show enhanced proliferation accompanied by elevated expression of colony-stimulating factor receptor-1 (CSF1R). (Ref. 27). Therefore, Applicant examined whether delivery of C-miR146a mimic to miR146a$^{-/-}$ BMDMs can prevent the aberrant myeloproliferation. In fact, the C-miR146a but not C-scrRNA treatment reduced proliferative rate of miR146a$^{-/-}$ BMDMs close to the proliferation rate of WT BMDMs (FIG. 4A).

Consistently with the reduced proliferation, the elevated cell surface levels of CSF1R on miR146a$^{-/-}$ BMDMs were reduced by C-miR146a to baseline levels similar as in WT BMDMs (FIG. 4B).

Figure 4D:
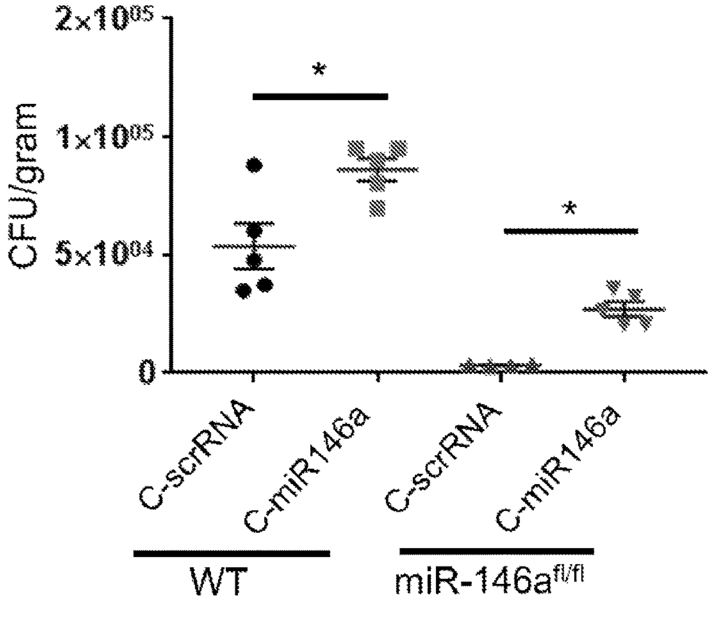
Figure 4E:
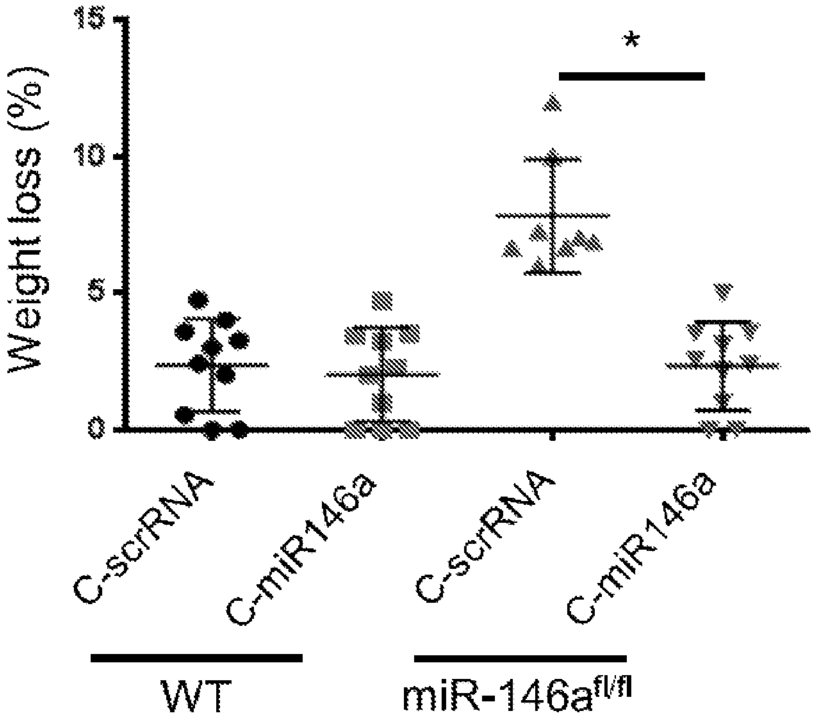
Figure 4F:
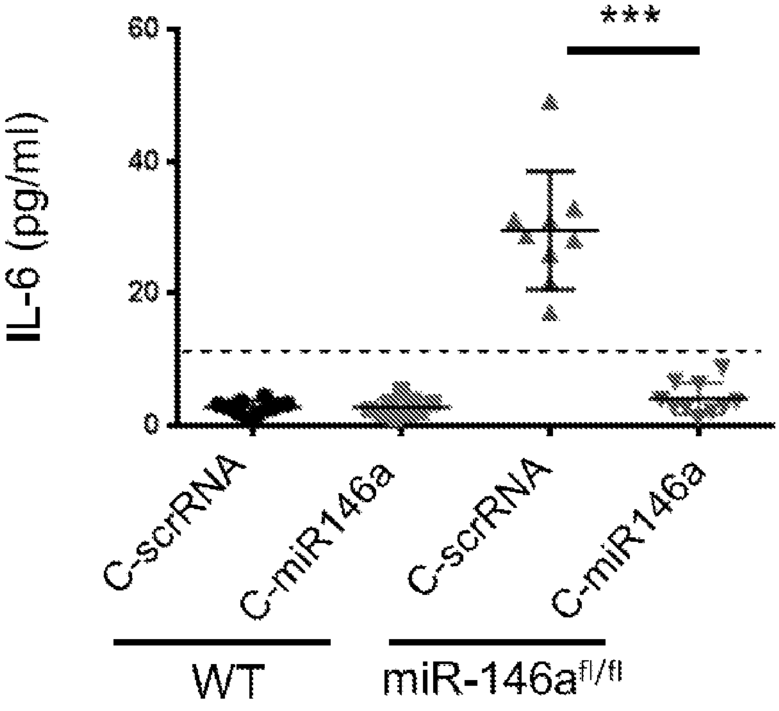
Figure 4G:
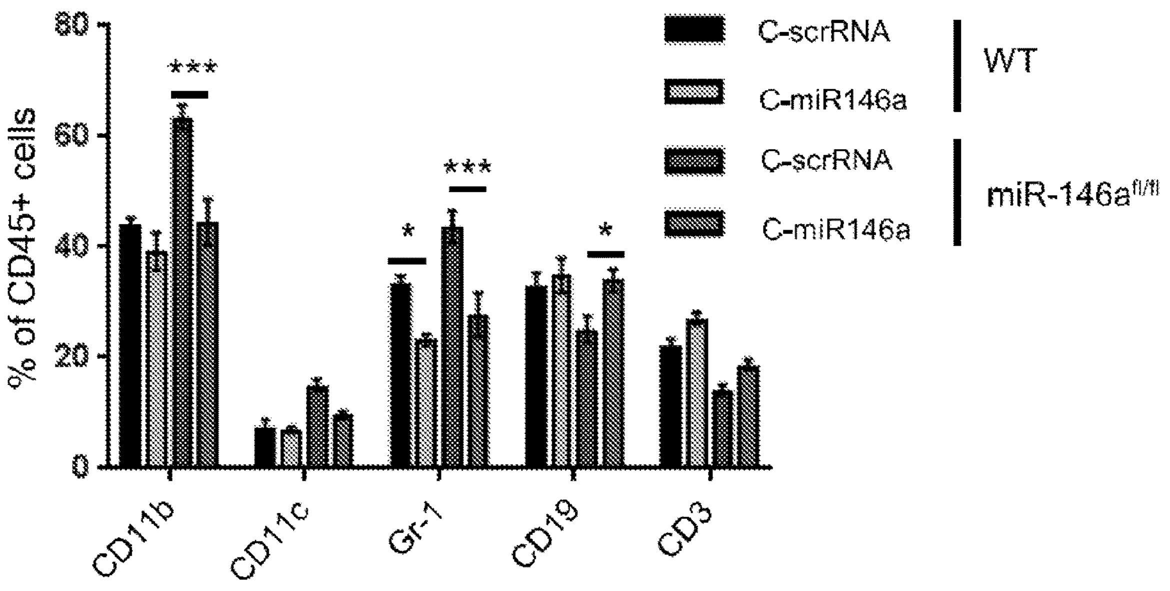

Next, Applicant examined whether miR146a mimic delivery can attenuate the exaggerated inflammatory response to a systemic bacterial endotoxin challenge resulting from the miR146a ablation. (Ref. 27). Age- and gender-matched WT and miR146a$^{-/-}$ mice were injected with a sub-lethal dose of LPS, and the plasma levels of pro-inflammatory cytokines, such as IL-6 and TNF-α, were measured using ELISA. As expected, LPS induced a higher and more prolonged cytokine response in miR146a$^{-/-}$ mice than in WT mice, peaking at 26 h before returning to baseline at 24 h. In contrast, C-miR146a treatment reduced IL-6 and TNF-α upregulation in miR146a$^{-/-}$ mice at both 2 and 6 h compared to control treatment with C-scrRNA (FIG. 4C). The effect of C-miR146a on the inflammatory cytokine secretion in WT mice was minimal, indicating the adequate negative control of cytokine production by the endogenous miR146a. Following on these results, Applicant used mice with the myeloid cell-specific miR146a ablation (LyzM-Cre/miR146a$^{fl/fl}$) to assess the effect of miR146a restoration on the IL-6-controlled response to a bacterial infection with *Listeria monocytogenes*. (Ref. 20, 28, 29). Both WT and miR146a$^{fl/fl}$ mice were injected daily with C-miR146a or control C-scrRNA (5 mg/kg) starting 3 days prior to the sublethal infection with an attenuated strain of *L. monocytogenes* (strain 10,403/serotype-1,10$^{5}$c.f.u.). Mice were euthanized at the expected time of the maximal innate response (72 h) for further analysis. The C-miR146a treatment interfered with the bacterial clearance in miR146a-deficient and also in WT mice resulting in significantly higher bacterial burden in liver and spleen (FIG. 4D and FIG. 5A). The reduced bacterial load in control-treated miR146afl/fl mice correlated with increased weight loss (FIG. 4E) and elevated plasma levels of IL-6 (FIG. 4F). All these effects of miR146a loss were completely eliminated in miR146a$^{fl/fl}$ mice treated using C-miR146a, which did not differ from WT mice. Finally, miR146a restoration decreased the expansion of CD11b myeloid cells, including Grl$^{+}$ granulocytes, observed in blood and spleen of control miR146a$^{fl/fl}$ mice (FIG. 4G and FIG. 5B). Taken together, the results indicate that myeloid cell-selective miR146a restoration using C-miRNA mimic is effective in reversing the key phenotypic features of miR146a-deletion in vivo, both the expansion of myeloid cells and the augmented inflammatory responses to bacterial challenge.

Monocyte-Selective miR146a Delivery Alleviates Cytokine Release Syndrome Triggered by CD19 CAR T-Cells without Compromising Antitumor Effects CAR T-cell immunotherapy has emerged as a revolutionary treatment for various hematologic cancers but many patients experience severe side effects known as cytokine release syndrome (CRS). (Ref. 30, 31). Recent studies linked CRS to CAR T-cell-dependent activation of CD40 signaling in monocytes/macrophages, thereby inducing secretion of IL-1 and IL-6, the key cytokine storm mediators. While CD40 triggers canonical and non-canonical NF-KB signaling, it does not increase miR146a levels. (Ref. 26). Thus, Applicant tested whether delivery of miR146a mimic will dampen pro-inflammatory effects of human monocytes induced by the CD19-specific CAR T cells. As verified in initial tests in vitro, internalization of fluorescently-labeled C-miR146a$^{Cy3}$ by CD19 CAR T-cells was low compared to monocytes (FIG. 12A) and it did not affect CAR T-cell cytotoxicity against target CD19' Nalm6 leukemia (FIG. 5A and FIG. 12B). Next, Applicant tested C-miR146a in a 3-component CRS model co-culturing in vitro: $CD19^+$ Nalm6 cells with CD19-specific CAR T-cells (generated from four different donors' PBMCs) and donor-matched $CD14^+$ monocytes (FIG. 5B). As expected, the upregulation of IL-1 and IL-6 depended on the presence of monocytes and was induced only by $CD19^+$ leukemia-specific and not mock-transfected CAR T-cells (FIG. 5B). Importantly, C-miR146a reduced IL-1 secretion by half, while bringing IL-6 levels close to baseline compared to control treatments. Similar results were obtained from assays using differentiated THP-1 monocyte-like cells instead of primary monocytes (FIG. 12C).

To further confirm that the combination of C-miR146a with CD19 CAR T-cells has therapeutic potential for alleviating CRS-related toxicities, Applicant adopted a model of CAR T-cell-induced CRS in human $CD19^+$ Raji B-cell lymphoma in partly immunodeficient SCID-Beige mice. (Ref. 15). Mice with heavy intraperitoneal lymphoma burden develop CRS and acute inflammation within 3 days after CD19 CAR T-cell injection (FIG. 5C). Mice were treated using C-miR146a or control vehicle 3 days before CAR T-cell transfer. As shown in FIGS. 5D-5E, the C-miR146a did not interfere with the CAR T-cell mediated inhibition of lymphoma progression. However, the C-miR146a mimic doubled the amount of endogenous miR146a in target peritoneal myeloid cells (FIG. 5F). As a result, Applicant observed that C-miR146a dramatically reduced major CRS-related cytokines, IL-6 and G-CSF, likely derived from mouse monocytes in this model as suggested by others (FIG. 5G). (Ref. 15). These findings underscore the use of C-miR146a mimic to alleviate adverse effects of CD19 CAR T-cell therapy without impeding on-target therapeutic effects.

C-miR146a Inhibits Del (5q) Leukemia Tumor Progression

Low expression of miR146a located on chromosome 5q has been reported in both MDS and AML since chromosome 5q deletions are common in high-risk leukemia. (Ref. 7). In a survival analysis of the TCGA-derived AML patients, Applicant observed that low miR146a expression and elevated IRAK1 expression are both significantly associated with worse clinical outcome (FIG. 13). Therefore, Applicant tested the cytotoxic effect of in vitro miR146a mimic delivery to HL-60 and MDSL del(5q) AML and MDS. C-miR146a treatment showed increased cytotoxicity against miR146a-deficient MDSL and HL-60 leukemia cells (FIG. 6A). To assess antitumor effects of C-miR146a, mice with subcutaneously implanted MDSL or HL-60 leukemia were injected intratumorally using 5 mg/kg C-miR146a, C-scrRNA, or PBS. The delivery of miR146a mimic effectively inhibited growth of both HL-60 (FIG. 6B) and MDSL (FIG. 6C). Finally, Applicant examined the efficacy of systemic C-miR146a administration (10 mg/kg) against disseminated HL-60 leukemia. As shown in FIG. 6D, compared to the rapid tumor progression in PBS and C-scrRNA treated groups, C-miR146a reduced AML progression, and thereby prolonged mice survival. Altogether, these results demonstrate the direct antitumor effect of C-miR146a both in vitro and in vivo, against miR146a deficient MDS and AML.

DISCUSSION

In this study, Applicant demonstrated the feasibility of systemic delivery of therapeutic miRNA mimic specifically to human and mouse myeloid cells to modulate their immune activity or neoplastic growth. The C-miR146a conjugates injected intravenously restored miR146a-5p in target myeloid cells to the levels sufficient for complete elimination of exacerbated NF-KB activity in $miR146a^{-/-}$ mice, thereby preventing the exaggerated inflammatory responses and aberrant myeloproliferation. This miR146a mimic delivery strategy also proved effective in human models of NF-KB-driven autoinflammatory disorder and myeloid neoplasms (MDS/AML). Importantly, unlike standard anti-inflammatory strategies, such as steroid hormones, the myeloid cell-specific miR146a mimic delivery proved effective without interfering with antitumor activity of CAR T-cells or any signs of toxicity.

Despite broad clinical potential, only few miRNA therapeutics entered clinical trials and the majority represented antisense molecules (anti-miRs or antagomirs), which as single-stranded oligonucleotides proved easier to optimize for in vivo use. (Refs. 19, 32). One of the best examples is targeting lymphoma cell addiction to oncogenic miR155. (Ref. 33). In contrast, the therapeutic replacement/restoration of tumor suppressor miRNAs proved challenging. The chemical modification of miRNA to ensure nuclease-resistance can interfere with intracellular processing, RISC loading and/or mRNA targeting. Pharmacologic formulation of miRNA mimics for systemic administration can result in severe immune toxicities. (Ref. 34). Cell-selective delivery of chemically-stabilized, naked miRNA mimics is gaining attention with a success of siRNA delivery using hepatocyte-specific GalNAc-conjugates and a recent study revisiting folate as targeting moiety to miRNA delivery to breast and lung cancer cells. (Refs. 35, 36).

The inventors' previous studies focused on myeloid cell-selective delivery of oligonucleotides to disrupt immunosuppression in the tumor microenvironment. The conjugation of CpG ODNs with inhibitors of STAT3, a master immune checkpoint regulator, resulted in potent antitumor immune responses. While it seems counterintuitive, the SR/TLR9-mediated delivery strategy can be adapted for dampening excessive immune activity of myeloid cells in autoinflammatory diseases or myeloid malignancies. Unlike CpG-B ODN sequences, CpG-A ODNs are poor activators of NF-KB signaling and cytokines such as IL-6 and IL-10. (Ref. 37). Recent study showed that injections of CpG-A alleviated severity of sepsis in mice by reducing blood clotting. (Ref. 38). Despite these findings, the control CpG-A-scrRNA used in Applicant's experiments did not induce significant anti-inflammatory activity. The reduction of myeloid cell proliferation and cytokine production required the presence of functional miR146a-5p guide strand in the CpG conjugate. The more extensive chemical modifications of miR146a guide strand negatively impacted its activity likely interfering with the required unwinding of the duplex while in RISC. (Ref. 39). Importantly, even partial restoration of miR146a-5p levels in target immune cells in vivo was sufficient for near complete and durable inhibition of the specific gene targets, IRAK1 and TRAF6. The systemic administration of C-miR146a mimic effectively reversed key features of the miR146a deletion related to excessive NF-KB signaling both in vitro and in vivo. Importantly, Applicant's results indicate that myeloid cell-specific miR146a mimic has potent anti-inflammatory activity also in human immune system, thereby preventing systemic inflammatory response to cytotoxic CAR T-cell activity. Cytokine storm and CRS occur in response to a variety of conditions, such as bacterial infections, antibody-based therapies or immunomodulatory drugs. In context of CAR T-cell cancer therapies, especially CD19-specific CAR T-cells, CRS constitutes one of the most severe and common adverse effects with potential fatalities. The lower incidence of CRS correlates with prolonged survival with patients received CAR-T therapy. (Ref. 40). Despite the routine use of the IL-6 receptor antagonist (tocilizumab), high dose steroid hormones are frequently required to control severe CRS but at the same time potentially curbing antitumor efficacy of CAR T-cells. (Refs. 40, 41). Therefore, there is need for more precise immunomodulatory strategies addressing complexity of immune responses. Myeloid cell-selective miR146a mimic acts at the nodal point of immune cell network, preventing release of cytokines driving CRS from monocytes and macrophages without interfering with CAR T-cell activity. (Refs. 12, 15).

The simplicity and flexibility of the C-miRNA mimic design, adaptable to delivery of both miRNA mimics as well as anti-miRs, provides an opportunity for the development of miRNA therapeutics for immunomodulation and/or therapy of myeloproliferative disorders or leukemia. The pleiotropic effect of single miRNA on multiple protein targets can benefit their potency and reduce development of drug resistance, while the myeloid cell selective delivery can limit concerns about safety of miRNA therapeutics. The growing list of myeloid cell-specific anti-inflammatory miRNAs extends beyond miR146a, including recently described miR125b and miR203b or tolerance-inducing miR221 and miR222. (Refs. 42, 43). In addition to the immunoregulatory role, the miR146a is well established tumor suppressor and the genetic loss of miR146a is common in MDS patients and in AML. (Ref. 44). MiR-146a replacement using SR/TLR9-targeted delivery provides therapeutic opportunity in this group of patients. However, given the genetic instability of AML, C-miR146a therapy could likely benefit from combination with targeting additional oncogenic or tumor suppressor miRNAs. (Ref. 44). miR155 is one of the most upregulated oncogenic miRNAs in FMS-like tyrosine kinase 3 internal tandem duplication (FLT3-ITD)-associated AML. (Ref. 45). Noteworthy, miR155 can also antagonize the immunoregulatory effects of miR146a on NF-KB in mouse myeloid cells. (Ref 20). It is not known whether miR155 plays similar role inhibiting tumor suppressive effect of miR146a in human leukemia but Applicant's strategy can be easily adapted to delivery of anti-miRNA to AML cells, including leukemia stem cells. (Ref. 46). Further studies should explore the possibility of personalizing miRNA mimic/antisense combinations to an AML patient-specific miRNA profile using the same SR/TLR9 delivery platform. The emerging CAR T-cell strategies for AML, such as CD123-specific CAR design underscore the potential to combine AML-specific CAR T-cells with C-miR146a, thereby alleviating potential immunotoxicities as well as reducing AML cell survival. (Ref. 47).

Supplemental Methods

Cell lines. Healthy donors' PBMCs were collected according to Declaration of Helsinki under the institutional review board (IRB) protocol 13378 (City of Hope; COH). Human HEK293T, THP-1, HL-60, Nalm6, Raji and mouse RAW264.7 cells were purchased from ATCC. RAW264.7 cells expressing p65-eGFP were provided by Dr. lain Fraser (NIH). CD19-specific CAR T-cells were generated as described. (Ref. 21). Human MDS cell line MDSL was developed by Dr. Kaoru Tohyama (Kawasaki Medical School) and cultured in RPMI with 10% fetal bovine serum (FBS) and 30 ng/mL human recombinant IL-3. (Ref. 22). HL-60 cells were cultured in IMDM/20% FBS; HEK293T and RAW264.7 cells were cultured in DMEM/10% FBS; and Nalm6, Raji, and THP-1 cells were cultured in RPMI/10% FBS. $Raji^{LUC}$ and $HL\text{-}60^{LUC}$ cells were generated by transducing parental cells with GFP/luciferase-expressing lentiviruses followed by flow cytometry sorting.

Serum stability assay. C-miR146a and miR146a were incubated in 50% human serum (H4522, Sigma-Aldrich, St. Louis, MO) for up to 5 days. Samples collected at different time points were then resolved on 7.5M Urea/15% PAGE gel and stained using ethidium bromide. The gels were scanned and the intensities of bands representing intact conjugates were quantified using ImageJ software.

Flow cytometry analysis. Human PBMCs were analyzed using the following fluorochrome-labeled antibodies: CD14, CD1c, CD303, CD19, and CD3 (eBioscience). For mouse samples, single-cell suspensions were prepared by mechanic dispersion and enzymatic digestion of organs and tumor tissues. Extracellular staining was performed using fluorochrome-labeled antibodies to CD11b, CD11c, CD19, F4/80, CSF1R or CD3 after anti-FcγIII/IIRBlock (eBioscience) using gating strategy shown in FIG. 14. For assessment of apoptosis, MDSL, and HL-60 cells were seeded in triplicate at a concentration of $5\times10^4$ cells/well in 24-well plates and treated with 0.5 μM C-miR146a or C-scrRNA every other day for 7 days. Cells were stained with Annexin V and PI using an Apoptosis detection kit (BD Biosciences) according to manufacturer's instructions and analyzed using flow cytometry. All samples were analyzed on BD LSRFortessa, AccuriC6 (BD Bioscience) or Attune NxT (Thermo Fisher) flow cytometers using FlowJo software (TreeStar, Ashland, OR).

Confocal microscopy. RAW264.7 cells were seeded on 24-well plates on top of coverslips for overnight, and then incubated with 100 nM $C\text{-}miR146a^{Cy3}$ or $miR146a^{Cy3}$ for 1 h. For the p65 localization experiment, RAW264.7 cells expressing p65-eGFP were seeded on 24-well plates on top of coverslips, once attached, cells were incubated with 500 nM C-miR146a or C-scrRNA overnight. Next day, the cells were then incubated with 100 ng/mL LPS for 1 h. The coverslips were fixed in 2% paraformaldehyde (EMS), incubated with Hoechst, and then mounted in Vectashield Hard-Set medium (Vector Laboratories). Next day the slides were visualized on an LSM880 confocal microscope (Zeiss) and analyzed using LSM ImageBrowser (v.4.2.0.121; Zeiss).

RNA-binding protein immunoprecipitation. The RNA-binding protein immunoprecipitation (RIP) was performed using *Magna* RIP kit (Millipore) according to manufacturer's instructions. $20\times10^6$ RAW264.7 cells or splenocytes from miR146a-mice plated and incubated for 1 h with 1p M C-miR146a or miR146a. Cells were resuspended in complete RIP lysis buffer, incubated with AGO2-specific antibody or normal rabbit IgG conjugated magnetic beads and incubated overnight. RNA-protein complexes were eluted using proteinase K digestion at 55° C. for 30 minutes, and RNA was purified and analyzed as described. 10% of the input samples were subjected to Western Blot as a loading control.

3' UTR reporter assay. The IRAK1 and TRAF6 3'UTR luciferase reporter constructs were provided by Dr. Mark Boldin (COH). pMIR-REPORT vector was used as a control. HEK293T cells were plated in 48-well culture dishes and transfected using Lipofectamine 2000 reagent (Thermo Fisher) with 20 ng IRAK1, TRAF6 plasmid or empty vector together with 10 ng *Renilla* luciferase reporter plasmid (pRL-SV40; Promega). Cells were treated with 0.5 μM C-miR146a, miR146a or C-scrRNA every 24 h. 48 h later, cell lysates were prepared, and the luciferase activities were measured using a Dual Luciferase Reporter assay system (Promega).

EMSA. Electrophoretic mobility shift assays (EMSAs) to detect NF-KB DNA-binding activity were performed as described previously. Briefly, 10 μg of nuclear extracts were incubated with $^{32}$P-labeled oligonucleotide probes specific for NF-KB. Supershift control was performed using anti-p65 or antibody (Santa Cruz Biotechnology). Protein-DNA complexes were resolved on 5% nondenaturing polyacrylamide gel electrophoresis and detected by autoradiography.

NF-KB-dependent secreted embryonic alkaline phosphatase (SEAP) reporter assay RAW-Blue cells carrying a SEAP reporter construct inducible by NF-KB were purchased from InvivoGen (San Diego, CA). Cells were incubated with 0.5 μM C-miR146a or C-scrRNA for overnight then incubated with 0.1 μg/ml LPS for 4 h. Cell supernatant were collected for SEAP assay according to manufacturer's protocol using Quanti-Blue SEAP detection medium.

Quantitative real-time PCR. Total RNA with enhanced miRNA enrichment was extracted from cultured or in vivo cells using the Maxwell RSC miRNA tissue kit in combination with the Maxwell system (Promega). The RNA was then transcribed into cDNAs using iScript cDNA Synthesis kit (Bio-Rad) or Taqman microRNA reverse transcription kit. The qPCR was carried out using Taqman microRNA assays for miR146a and snoRNA234 as an internal control (Thermo Fisher) on CFX96 Real-Time PCR Detection System (Bio-Rad).

Western blot. Total cellular lysates were prepared as previously described (Ref. 24) and analyzed using antibodies specific to IRAK1 (Cell Signaling), TRAF6 (Santa Cruz), and β-actin (Sigma).

ELISA. Plasma samples or cell supernatants collected from in vitro treated RAW264.7 cells or in vivo were assayed for IL-6, TNFα and/or G-CSF cytokine levels using uncoated ELISA kits (Thermo Fisher) according to the manufacturer's instructions. Absolute cytokine levels were quantified by comparison to a standard curve produced using recombinant proteins.

BMDM proliferation assay. Bone marrow cells from age, gender and weight matched WT C57BL/6 and miR146a$^{-/-}$ mice were collected and plated in triplicate in 48-well plates at a concentration of $5\times10^4$ cells/well in BMM medium (RPMI/20% FBS/50 ng/ml M-CSF). The BMM medium was completely replaced on day 4. Cells were treated with 1 μM C-miR146a or C-scrRNA every other day. On day 7, proliferation was assayed in triplicates using cell-counting kit-8 (Sigma-Aldrich, St. Louis, MO) according to the manufacturer's protocol. On the same day, the expression levels of CD11b, F4/80, and CSF1R were assessed cytofluorimetrically.

In vitro Cytokine Release Syndrome Assays. For in vitro studies, mock or CD19 CAR T cells from four donors were cultured with target Nalm6 cancer cells with or without mTHP1 cells or primary monocytes CD14+ cells enriched from same donor PBMC. mTHP1 monocyte-like cell was induced from THP1 cells through 48 h of 50 nM PMA. The co-cultured cells were treated with C-miR146a or C-scrRNA (500 nM) every day for 2 days. After 48 h, supernatants were collected and IL-1 and IL-6 levels were analyzed using ELISA kits (Thermo Fisher) according to the manufacturer's instructions.

REFERENCES (1) Mehta A, Baltimore D. *Nat Rev Immunol.* 2016; 16(5):279-294. (2) Garzon R, Marcucci G, Croce C M. *Nat Rev Drug Discov.* 2010; 9(10):775-789. (3) Nejad C, Stunden H J, Gantier M P. *FEBS J.* 2018; 285(20):3695-3716. (4) Kasinski A L, Slack F J. *Nat Rev Cancer.* 2011; 11(12):849-864. (5) Nicoloso et al, *Nat Rev Cancer.* 2009; 9(4):293-302. (6) Wallace J A, O'Connell R M. *Blood.* 2017; 130(11): 1290. (7) Starczynowski, et al. *Blood.* 2011; 117(2):595-607. (8) Starczynowski, et al. *Nat Med.* 2010; 16(1):49-58. (9) Boldin, et al. *J Exp Med.* 2011; 208(6):1189-1201. (10) Zhao et al, *Proc Natl Acad Sci USA.* 2011; 108(22):9184-9189. (11) Boldin M P, Baltimore D. *Immunol Rev.* 2012; 246(1):205-220. (12) Norelli, et al. *Nat Med.* 2018; 24(6): 739-748. (13) Halkein, et al. *J Clin Invest.* 2013; 123(5): 2143-2154. (14) O'Connell R M, Rao D S, Baltimore D. *Annu Rev Immunol.* 2012; 30:295-312. (15) Giavridis et al, *Nat Med.* 2018; 24(6):731-738. (16) Lieberman J. *Nat Struct Mol Biol.* 2018; 25(5):357-364. (17) Ling H, Fabbri M, Calin G A. *Nature Reviews Drug Discovery.* 2013; 12:847. (180 Chen Y, Gao D Y, Huang L. *Adv Drug Deliv Rev.* 2015; 81:128-141. (19) Rupaimoole R, Slack F J. *Nat Rev Drug Discov.* 2017; 16(3):203-222. (20) Mann M, Mehta A, Zhao J L, et al. *Nat Commun.* 2017; 8(1):851. (21) Kortylewski, et al. *Nat Biotechnol.* 2009; 27(10):925-932. (22) Verthelyi et al, *J Immunol.* 2001; 166(4):2372-2377. (23) Zhang, et al. *Blood.* 2013; 121(8):1304-1315. (24) Sakai A, et al. *Sci Rep.* 2017; 7(1):1428. (25) Su Y L, Swiderski P, Marcucci G, Kortylewski M. *Methods Mol Biol.* 2019; 1974:141-150. (26) Taganov K D, Boldin M P, Baltimore D. *Immunity.* 2007; 26(2):133-137. (27) Magilnick et al. *Proc Natl Acad Sci USA.* 2017; 114(34):E7140-E7149. (28) Lucke K, Yan I, Krohn S, et al. *PLoS One.* 2018; 13(8):e0203395. (29) Cho S, Lee H M, Yu I S, et al. *Nat Commun.* 2018; 9(1):2757. (30) Wang, et al. *Blood.* 2016; 127(24):2980-2990. (31) Sterner R M, Sakemura R, Cox M J, et al. *Blood.* 2018. (32) Setten R L, Rossi J J, Han S P. *Nat Rev Drug Discov.* 2019. (33) Cheng, et al. *Nature.* 2015; 518(7537):107-110. (34) Beg, et al. *Invest New Drugs.* 2017; 35(2):180188. (35) Springer A D, Dowdy S F. *Nucleic Acid Ther.* 2018; 28(3): 109-118. (36) *Orellana* et al, *Sci Transl Med.* 2017; 9(401). (37) Vollmer J, Krieg A M. *Adv Drug Deliv Rev.* 2009; 61(3):195-204. (38) Yamamoto, et al. *Front Immunol.* 2017; 8:1049. (39) Adams et al, *J Clin Invest.* 2017; 127(3):761-771. (40) Neelapu et al. *Nat Rev Clin Oncol.* 2018; 15(1): 47-62. (41) Park et al. *N Engl J Med.* 2018; 378(5):449-459. (42) Sisti et al. *Sci Signal.* 2018; 11(528). (43) Seeley et al. *Nature.* 2018; 559(7712):114-119. (44) Wallace J A, O'Connell R M. *Blood.* 2017; 130(11):1290-1301. (45) Gerloff et al. *Leukemia.* 2015; 29(3):535-547. (46) Zhang et al. *Nat Med.* 2018; 24(4):450-462. (47) Mardiros et al. *Blood.* 2013; 122(18):3138-3148.

Informal Sequence Listing

In the sequence listings, * is phosphorothioation; a double quote after the nucleic acid (e.g., U") means the nucleic acid is modified with 2'-O-methyl, and a single quote after the nucleic acid (e.g., U') means that the nucleic acid is modified with 2'-fluoro; and $U^P$ means that the nucleic acid has a single phosphate group.

```
(miR146a passenger strand)
                                        SEQ ID NO: 1
5'CCCAUGGAAUUCAGUUCUCA 3'

(miR146a passenger strand)
                                        SEQ ID NO: 2
5' CCCAUGGAAUUCAGUUCUCAA"A 3'

(miR146a passenger strand)
                                        SEQ ID NO: 3
5' CCCAUGGAAUUCAGUUCUCAA"A* 3'
```

-continued (miR146a passenger strand)

SEQ ID NO: 4

5' C'C'C'AU'GGAAU'U'C'AGU'U'C'U'C'AAA 3'

(miR146a passenger strand)

SEQ ID NO: 5

5' C"*C"*C"*A"*U"*G"*G"*A"*A"*U"*U"*C"*A"

*G"*U"*U"*C"*U"*C"*A"*A"*A"* 3', (miR146a guide strand)

SEQ ID NO: 6

5' UGAGAACUGAAUUCCAUGGG 3'

(miR146a guide strand)(898)

SEQ ID NO: 7

5' UGAGAACUGAAUUCCAUGGGUU 3'

(miR146a guide strand) (1024)

SEQ ID NO: 8

5' $U^{P}$GAGAACUGAAUUCCAUGGGU"U* 3'

SEQ ID NO: 9

5' G*G*TGCATCGATGCAGG*G*G*G*G* 3'

SEQ ID NO: 10

5' G*G*T GCA TGC ATG CAG G*G*G*G*G 3'

SEQ ID NO: 11

5' g*G*T*G*C*A*T*C*G*A*T*G*C*A*G*G*G*G*G*G 3'

SEQ ID NO: 12

5' T*C*C*A*T*G*A*C*G*T*T*C*C*T*G*A*T*G*C*T 3'

SEQ ID NO: 13

5' G*G*GGTCAACGTTGAG*G*G*G*G*G 3'

SEQ ID NO: 14

5' G*GGGTCAACGTTGAG*G*G*G*G*G 3'

SEQ ID NO: 15

5' G*G*GGGACGA:TCGTCG*G*G*G*G*G 3'

SEQ ID NO: 16

5' G*GGGGACGA:TCGTCG*G*G*G*G*G 3'

SEQ ID NO: 17

5' G*G*TGCATCGATGCAGG*G*G*G*G 3'

SEQ ID NO: 18

5' G*GTGCATCGATGCAGG*G*G*G*G* 3' anti-miR155 passenger strand sequence

SEQ ID NO: 19

5'ACCCCUAUCACAAUUAGCAUUAA3* anti-miR155 guide strand sequence

SEQ ID NO: 20

5' UUAAUGCUAAUUGUGAUAGGGGU3' miR142 passenger strand sequence

SEQ ID NO: 21

5' UCCAUAAAGUAGGAAACACUACA 3' miR142 guide strand sequence

SEQ ID NO: 22

5' UGUAGUGUUUCCUACUUUAUGGA3' miR125b passenger strand sequence

SEQ ID NO: 23

5' UCACAAGUUAGGGUCUCAGGGA 3' miR-125b (or miR125-5p) guide strand sequence

SEQ ID NO: 24

5' UCCCUGAGACCCUAACUUGUGA 3' miR203b passenger strand sequence

SEQ ID NO: 25

5' UGUGAAAUGUUUAGGACCACUA 3' mir203b (or miR203b-5p) guide strand sequence

SEQ ID NO: 26

5' UAGUGGUCCUAAACAUUUCACA 3' mir221 passenger strand sequence

SEQ ID NO: 27

5' GAAACCCAGCAGACAAUGUAGCU 3' mir221 (or miR221-3p) guide strand sequence

SEQ ID NO: 28

5' AGCUACAUUGUCUGCUGGGUUUC 3' miR222 passenger strand sequence

SEQ ID NIO: 29

5' ACCCAGUAGCCAGAUGUAGCU 3' miR222 (or miR222-3p) guide strand sequence

SEQ ID NO: 30

5' AGCUACAUCUGGCUACUGGGU 3' miR29b passenger strand sequence

SEQ ID NO: 31

5' UCUAAACCACCAUAUGAAACCAGC 3' miR29b (or miR29b-5p) guide strand sequence

SEQ ID NO: 32

5' GCUGGUUUCAUAUGGUGGUUUAGA 3'

SEQ ID NO: 33

5' G*G*G*GACGAC:GTCGTGG*G*G*G*G*G 3'

SEQ ID NO: 34

5' G*G*GGACGAC:GTCGTGG*G*G*G*G*G 3'

SEQ ID NO: 35

5' T*C*C*A*T*G*A*C*G*T*T*C*C*T*G*A*T*G*C*T 3' miR-146a-2OMe-2F-pPS-21-23-guide

SEQ ID NO: 36

5' U"*U'*G"A"G"A'A"C"U"G"A"A"U"U'C"C'A"U"

G"G"G"*U"*U"

miR-146a-2OMe-2F-pPS-21-23-passenger

SEQ ID NO: 37

5' C"*C"*C"A"U"G"G'A"A'U'U'C"A"G"U"U"C"U"C"A"A"

miR-146a-2OMe-2F-pPS-20-22-guide

SEQ ID NO: 38

5' U"*G'*A"G"A"A'C"U"G"A"A"U"U"C'C"A'U"

G"G"G"*U"*U"

miR-146a-2OMe-2F-pPS-20-22-passenger

SEQ ID NO: 39

5' C"*C"*C"A"U"G'G"A'A'U'U"C"A"G"U"U"C"U"C"A"

SEQ ID NO: 40

5' T*C*C*A*T*G*A*C*G*T*T*C*C*T*G*A*C*G*T*T 3'

SEQ ID NO: 41

5' T*C*G*T*C*G*T*T*T*T*G*T*C*G*T*T*T*T*

G*T*C*G*T*T 3'

SEQ ID NO: 42

5' T*C*G*T*C*G*T*T*G*T*C*G*T*T*T*T*G*

T*C*G*T*T 3'

SEQ ID NO: 43

5' T*C*G*T*C*G*T*T*T*T*C*G*G*C*G*C*G*C*

G*C*C*G 3'

SEQ ID NO: 44

5' T*C*G*T*C*G*T*C*G*T*T*C*G*A*A*C*G*A*C*

G*T*T*G*A*T 3'

-continued

SEQ ID NO: 45
5' AUUUAGCCUUAAUACACGCCA"A 3'

SEQ ID NO: 46
5' GGCGUGUAUUAAGGCUAAAUCU 3'

(Mir-146A ASO)
SEQ ID NO: 47
5' C"C"C"A"T"G"G"A"A"T"T"C"A"G"T"T"C"T"C"A" 3'

(miR142 mimic guide strand)

-continued

SEQ ID NO: 48
5' U"*G'*U"A"G"U'G"U"U"U"C"C"U"A'C"U'U"U"

A"U"G"*G"*A"3'

(miR142 mimic passenger strand)
SEQ ID NO: 49
5' C"*A"*U"A"A"A"G'U"A'G'G'A"A"A"C"A"

C"U"A"C"A"3'

What is claimed is:

1. A compound of Formula (I): (1) or Formula (II):

$R^1$-L1-$R^2$ (I) or

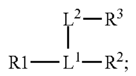

(II)

wherein:

$R^1$ is a CpG oligodeoxynucleotide (ODN);

$L^1$ and $L^2$ are independently a linking group;

$R^2$ and $R^3$ are independently a hybridized nucleic acid comprising a miR146a passenger strand hybridized to a miR146a guide strand; wherein the miR146a passenger strand has a sequence comprising SEQ ID NO:2, 3, 4, 5, 37, or 39, and the miR146a guide strand has a sequence comprising SEQ ID NO:7, 8, 36, or 38.

2. The compound of claim 1, wherein the miR146a passenger strand sequence comprises SEQ ID NO:2, 3, 4, or 5, and the miR146a guide strand sequence comprises SEQ ID NO:7 or 8.

3. The compound of claim 1, wherein the 3' end of $R^1$ is covalently bonded to $L^1$.

4. The compound of claim 1, wherein the microRNA passenger strand sequence is covalently bonded to the linking group; and wherein the microRNA guide strand sequence is hybridized to the microRNA passenger strand sequence.

5. The compound of claim 1, wherein the CpG ODN is a CpG-A ODN, a CpG-B ODN, a CpG-C ODN, or a combination of two or more thereof.

6. The compound claim 1, wherein the CpG ODN is CpG ODN 19, CpG ODN 1585, CpG ODN 2216, CpG ODN 2336, CpG ODN 1668, CpG ODN 1826, CpG ODN 2006, CpG ODN 2007, CpG ODN BW006, CpG ODN D-SL01, CpG ODN 2395, CpG ODN M362, CpG ODN D-SL03, or a combination of two or more thereof.

7. The compound of claim 1, wherein $R^1$ comprises the sequence of any one of SEQ ID NOS: 9-18, 33-35, and 40-44.

8. The compound of claim 1, wherein $L^1$ and $L^2$ are independently a bond, a nucleic acid sequence, a DNA sequence, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or a combination of two or more thereof.

9. The compound of claim 1, wherein $L^1$ and $L^2$ are independently is a substituted 6 to 60 membered heteroalkylene.

10. The compound of claim 1, wherein $L^1$ and $L^2$ are independently:

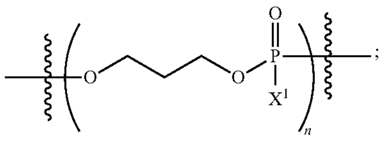

;

wherein $X^1$ is independently —OH or —$O^-$, and n is an integer from 1 to 10.

11. The compound of claim 1, wherein $L^1$ and $L^2$ are independently is —($CH_2CH_2O$)—; a 5 or 6 membered substituted or unsubstituted heteroarylene comprising one or two nitrogen atoms; or a 5 or 6 membered substituted or unsubstituted heterocycloalkylene comprising an oxygen atom, a nitrogen atom, or a combination thereof.

12. The compound of claim 1, wherein the 5' end of the microRNA passenger strand sequence is covalently bonded to $L^1$.

13. The compound of claim 1, wherein in the compound of Formula (I):

(i) the 3' end of $R^1$ is bonded to $L^1$;

(ii) $R^2$ is the hybridized nucleic acid sequence; wherein the 5' end of the miR146a passenger strand sequence is covalently bonded to $L^1$; and wherein the miR146a passenger strand sequence comprises SEQ ID NO:2 and the miR146a guide strand sequence comprises SEQ ID NO:7 or SEQ ID NO:8; and (iii) $L^1$ is

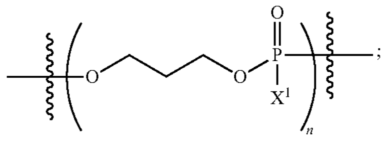

;

wherein $X^1$ is independently —OH or —$O^-$, and n is an integer from 4 to 6.

14. The compound of claim 13, wherein $R^1$ comprises SEQ ID NO:9, SEQ ID NO: 10, SEQ ID NO:17, or SEQ ID NO: 18.

15. The compound of claim 1, wherein the miR146a passenger strand has a sequence comprising SEQ ID NO:2, and the miR146a guide strand has a sequence comprising SEQ ID NO:7 or SEQ ID NO:8.

16. The compound of claim 1, wherein the miR146a passenger strand has a sequence comprising SEQ ID NO:37, and the miR146a guide strand has a sequence comprising SEQ ID NO:36.

17. The compound of claim 1, wherein the miR146a passenger strand has a sequence comprising SEQ ID NO:39, and the miR146a guide strand has a sequence comprising SEQ ID NO:38.

18. The compound of claim 1, wherein in the compound of Formula (II):

(i) the 3' end of $R^1$ is bonded to $L^1$;

(ii) $R^2$ is the hybridized nucleic acid sequence; wherein the 5' end of the miR146a passenger strand sequence is covalently bonded to $L^1$; the miR146a passenger strand sequence comprises SEQ ID NO:2 and the miR146a guide strand sequence comprises SEQ ID NO:6 or SEQ ID NO:7;

(iii) $R^3$ is the hybridized nucleic acid sequence; wherein the 5' end of the miR146a passenger strand sequence is covalently bonded to $L^2$; wherein the miR146a passenger strand sequence comprises SEQ ID NO:2 and the miR146a guide strand sequence comprises SEQ ID NO:7 or SEQ ID NO:8; and (iv) $L^1$ and $L^2$ are independently:

(a) substituted or unsubstituted heteroalkylene;

(b) 5 or 6 membered substituted or unsubstituted heteroarylene comprising one or two nitrogen atoms;

(c) 5 or 6 membered substituted or unsubstituted heterocycloalkylene comprising an oxygen atom, a nitrogen atom, or a combination thereof; or (d) a combination of two or more of the foregoing.

19. A pharmaceutical composition comprising the compound of claim 1 and a pharmaceutically acceptable excipient.

20. A method of treating cancer or an inflammatory disease in a patient in need thereof, the method comprising administering to the patient an effective amount of the compound of claim 1.

21. A method of treating cytokine release syndrome, sepsis, acute myeloid leukemia, B-cell lymphoma, or myelodysplastic syndrome in a patient in need thereof, the method comprising administering to the patient an effective amount of the compound of claim 1.

* * * * *